United States Patent
Levin et al.

(10) Patent No.: US 6,225,311 B1
(45) Date of Patent: May 1, 2001

(54) ACETYLENIC α-AMINO ACID-BASED SULFONAMIDE HYDROXAMIC ACID TACE INHIBITORS

(75) Inventors: Jeremy I. Levin, New City, NY (US); James M. Chen, Bedminister, NJ (US); Derek C. Cole, New City, NY (US); Mila T. Du, Suffern, NY (US); Leif M. Laakso, New City, NY (US)

(73) Assignee: American Cyanamid Company, Madison, NJ (US)

(*) Notice: Subject to any disclaimer, the term of this patent is extended or adjusted under 35 U.S.C. 154(b) by 0 days.

(21) Appl. No.: 09/492,691

(22) Filed: Jan. 27, 2000

Related U.S. Application Data

(60) Provisional application No. 60/155,249, filed on Jan. 27, 1999.

(51) Int. Cl.[7] .................. A61K 31/54; A61K 31/5375; C07D 279/10; C07D 279/12

(52) U.S. Cl. .................. 514/227.5; 514/575; 544/59; 544/58.1

(58) Field of Search .................. 514/227.5, 575; 544/59, 58.1

(56) References Cited

U.S. PATENT DOCUMENTS

| | | | |
|---|---|---|---|
| 5,413,905 | * 5/1995 | Lok et al. .................. | 430/600 |
| 5,455,258 | 10/1995 | MacPherson et al. .................. | 514/357 |
| 5,506,242 | 4/1996 | MacPherson et al. .................. | 514/336 |
| 5,552,419 | 9/1996 | MacPherson et al. .................. | 514/357 |
| 5,753,653 | 5/1998 | Bender et al. .................. | 514/227.5 |
| 5,770,624 | 6/1998 | Parker .................. | 514/575 |
| 5,804,593 | 9/1998 | Warpechoski et al. .................. | 514/419 |
| 5,817,822 | 10/1998 | Nantermet et al. .................. | 546/194 |
| 5,929,097 | 7/1999 | Levin et al. .................. | 514/351 |

FOREIGN PATENT DOCUMENTS

| | | |
|---|---|---|
| 19542189 | 5/1997 | (DE) . |
| 606046 | 12/1993 | (EP) . |
| 757037 | 7/1996 | (EP) . |
| 757984 | 8/1996 | (EP) . |
| 803505 | 4/1997 | (EP) . |
| WO9535275 | 12/1995 | (WO) . |
| WO9535276 | 12/1995 | (WO) . |
| WO9600214 | 1/1996 | (WO) . |
| WO9627583 | 9/1996 | (WO) . |
| 9633172 | * 10/1996 | (WO) . |
| 9808825 | * 10/1996 | (WO) . |
| WO9718194 | 5/1997 | (WO) . |
| WO9719068 | 5/1997 | (WO) . |
| WO9720824 | 6/1997 | (WO) . |
| WO9722587 | 6/1997 | (WO) . |
| WO9727174 | 7/1997 | (WO) . |
| WO9745402 | 12/1997 | (WO) . |
| WO9803166 | 1/1998 | (WO) . |
| WO9807697 | 2/1998 | (WO) . |
| 9808815 | * 3/1998 | (WO) . |
| WO9808815 | 3/1998 | (WO) . |
| WO9808822 | 3/1998 | (WO) . |
| WO9808823 | 3/1998 | (WO) . |
| WO9808825 | 3/1998 | (WO) . |
| WO9808827 | 3/1998 | (WO) . |
| WO9808853 | 3/1998 | (WO) . |
| WO9816503 | 4/1998 | (WO) . |
| WO9816506 | 4/1998 | (WO) . |
| WO9816514 | 4/1998 | (WO) . |
| WO9816520 | 4/1998 | (WO) . |
| WO9827069 | 6/1998 | (WO) . |
| WO9831664 | 7/1998 | (WO) . |
| WO9833768 | 8/1998 | (WO) . |
| WO9834918 | 8/1998 | (WO) . |
| WO9839313 | 9/1998 | (WO) . |
| WO9839329 | 9/1998 | (WO) . |
| WO9842659 | 10/1998 | (WO) . |
| WO9843963 | 10/1998 | (WO) . |

OTHER PUBLICATIONS

J.I.Levin et al. "The Syn. & Biol.Act.of Novel series of . . . MMP Inhi.",Bior.&Med.Chem. L.8,2657/98, Jun. 1998.*
M.G. Shire et al. "TNF–alpha inhibitore & rheum. arthritis", Exp.Opin.Ther.Patent 8(5),53191998) Jun. 1998.*
Shire, M.G., Exp. Opin. Ther. Patents 8(5), 531 (1998).
Grossman, J.M., Women's Health, 6(6), 627 (1997).
Isomaki, P.J., Ann. Med., 29, 499 (1997).
Camussi, G., Drugs, 55(5), 613 (1998).
Mathison et al., J. Clin. Invest., 81, 1925, (1988).
Miethke et al., J. Exp. Med., 175, 91 (1992).
Piquet, P. F., J. Exp. Med. 166, 1280 (1987).
Beuther, B., Ann Rev., Biochem, 57, 505 (1988).
Ksontini, R., Arch, Surg., 133, 558, (1998).
Packer, M., Circulation, 92(6), 1379 (1995).
Ferrari, R., et al., Circulation 92(6), 1479 (1995).
Hotamisligil, G.S. et al., Science, 259, 87 (1993).
Peterson, P.K. et al., J. Clin. Invest., 89, 574 (1992).
Pallares–Trujillo et al., Med. Res. Reviews, 15(6), 533 (1995).
Old, L., Science, 230, 630 (1985).
Rankin, E.C. et al., Br. J. Rheumatol., 34, 334 (1995).
Pharmaprojects, Therapeutic Updates 17 (Oct.) au 197, M2Z (1996).

(List continued on next page.)

*Primary Examiner*—Mukund J. Shah
*Assistant Examiner*—Sudhaker B. Patel
(74) *Attorney, Agent, or Firm*—Rebecca R. Barrett

(57) ABSTRACT

Compounds of the formula:

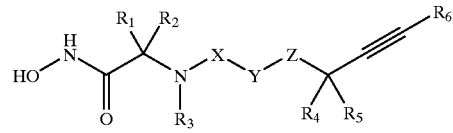

are useful in treating disease conditions mediated by TNF-α, such as rheumatoid arthritis, osteoarthritis, sepsis, AIDS, ulcerative colitis, multiple sclerosis, Crohn's disease and degenerative cartilage loss.

13 Claims, No Drawings

OTHER PUBLICATIONS

McGheehan et al, Current Pharmaceutical Design, 2, 662 (1996).
Script 20, 2349 (1998).
MacPherson et al., J. Med. Chem., 40, 2525 (1997).
Tamura et al., J. Med. Chem. 41, 640 (1998).
Levin et al., Bioorg. & Med. Chem. Letters, 8, 2657 (1998).
Pikul et al., J. Med. Chem., 41, 3568 (1998).

* cited by examiner

ACETYLENIC α-AMINO ACID-BASED SULFONAMIDE HYDROXAMIC ACID TACE INHIBITORS

This application claims the benefit of U.S. Provisional Application Ser. No. 60/155,249, filed Jan. 27, 1999.

FIELD OF INVENTION

This invention relates to acetylenic aryl sulfonamide hydroxamic acids which act as inhibitors of TNF-α converting enzyme (TACE). The compounds of the present invention are useful in disease conditions mediated by TNF-α, such as rheumatoid arthritis, osteoarthritis, sepsis, AIDS, ulcerative colitis, multiple sclerosis, Crohn's disease and degenerative cartilage loss.

BACKGROUND OF THE INVENTION

TNF-α converting enzyme (TACE) catalyzes the formation of TNF-α from membrane bound TNF-α precursor protein. TNF-α is a pro-inflammatory cytokine that is believed to have a role in rheumatoid arthritis [Shire, M. G.; Muller, G. W. *Exp. Opin. Ther. Patents* 1998, 8(5), 531; Grossman, J. M.; Brahn, E. *J. Women's Health* 1997, 6(6), 627; Isomaki, P.; Punnonen, J. *Ann. Med.* 1997, 29, 499; Camussi, G.; Lupia, E. *Drugs*, 1998, 55(5), 613.] septic shock [Mathison, et. al. *J. Clin. Invest.* 1988, 81, 1925; Miethke, et. al. *J. Exp. Med.* 1992, 175, 91.], graft rejection [Piguet, P. F.; Grau, G. E.; et. al. *J. Exp. Med.* 1987, 166, 1280.], cachexia [Beutler, B.; Cerami, A. *Ann. Rev. Biochem.* 1988, 57, 505.], anorexia, inflammation [Ksontini, R,; MacKay, S. L. D.; Moldawer, L. L. *Arch. Surg.* 1998, 133, 558.], congestive heart failure [Packer, M. *Circulation,* 1995, 92(6), 1379; Ferrari, R.; Bachetti, T.; et. al. *Circulation,* 1995, 92(6), 1479.], post-ischaemic reperfusion injury, inflammatory disease of the central nervous system, inflammatory bowel disease, insulin resistance [Hotamisligil, G. S.; Shargill, N. S.; Spiegelman, B. M.; et. al. *Science,* 1993, 259, 87.] and HIV infection [Peterson, P. K.; Gekker, G.; et. al. *J. Clin. Invest.* 1992, 89, 574; Pallares-Trujillo, J.; Lopez-Soriano, F. J. Argiles, J. M. *Med. Res. Reviews,* 1995, 15(6), 533.]], in addition to its well-documented antitumor properties [Old, L. *Science,* 1985, 230, 630.]. For example, research with anti-TNF-α ntibodies and transgenic animals has demonstrated that blocking the formation of TNF-α inhibits the progression of arthritis [Rankin, E. C.; Choy, E. H.; Kassimos, D.; Kingsley, G. H.; Sopwith, A. M.; Isenberg, D. A; Panayi, G. S. *Br. J. Rheumatol.* 1995, 34, 334; *Pharmaprojects,* 1996, Therapeutic Updates 17 (October), au197-M2Z.]. This observation has recently been extended to humans as well as described in "TNF-α in Human Diseases", *Current Pharmaceutical Design,* 1996, 2, 662.

It is expected that small molecule inhibitors of TACE would have the potential for treating a variety of disease states. Although a variety of TACE inhibitors are known, many of these molecules are peptidic and peptide-like which suffer from bioavailability and pharmacokinetic problems. In addition, many of these molecules are non-selective, being potent inhibitors of matrix metalloproteinases and, in particular, MMP-1. Inhibition of MMP-1 (collagenase 1) has been postulated to cause joint pain in clinical trials of MMP inhibitors [*Scrip,* 1998, 2349, 20] Long acting, selective, orally bioavailable non-peptide inhibitors of TACE would thus be highly desirable for the treatment of the disease states discussed above.

U.S. Pat. Nos. 5,455,258, 5,506,242, 5,552,419, 5,770, 624, 5,804,593, and 5,817,822 as well as European patent application EP606,046A1 and WIPO international publications WO9600214 and WO9722587 disclose non-peptide inhibitors of matrix metalloproteinases and/or TACE of which the aryl sulfonamide hydroxamic acid shown below is representative. Additional publications disclosing sulfonamide based MMP inhibitors which are variants of the sulfonamide-hydroxamate shown below, or the analogous sulfonamide-carboxylates, are European patent applications EP-757037-A1 and EP-757984-A1 and WIPO international publications WO9535275, WO9535276, WO9627583, WO9719068, WO9727174, WO9745402, WO9807697, WO9831664, WO9833768, WO9839313, WO9839329, WO9842659 and WO9843963. The discovery of this type of MMP inhibitor is further detailed by MacPherson, et. al. in *J. Med. Chem.,* 1997, 40, 2525 and Tamura, et. al. in *J. Med. Chem.* 1998, 41, 640.

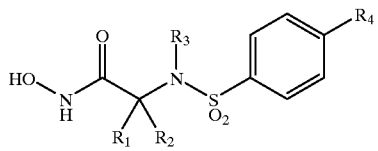

Publications disclosing β-sulfonamide-hydroxamate inhibitors of MMPs and/or TACE in which the carbon alpha to the hydroxamic acid has been joined in a ring to the sulfonamide nitrogen, as shown below, include U.S. Pat. No. 5,753,653, WIPO international publications WO9633172, WO9720824, WO9827069, WO9808815, WO9808822, WO9808823, WO9808825, WO9834918, WO9808827, Levin, et. al. *Bioorg. & Med. Chem. Letters* 1998, 8, 2657 and Pikul, et. al. *J. Med. Chem.* 1998, 41, 3568.

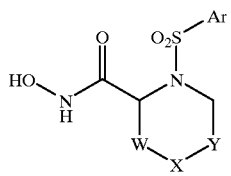

The patent applications DE19,542,189-A1, WO9718194, and EP803505 disclose additional examples of cyclic sulfonamides as MMP and/or TACE inhibitors. In this case the sulfonamide-containing ring is fused to a aromatic or heteroaromatic ring.

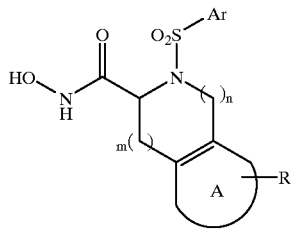

Examples of sulfonamide hydroxamic acid MMP/TACE inhibitors in which a 2 carbon chain separates the hydroxanic acid and the sulfonamide nitrogen, as shown below, are disclosed in WIPO international publications WO9816503, WO9816506, WO9816514 and WO9816520 and U.S. Pat. No. 5,776,961.

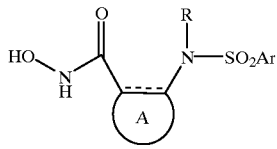

Analogous to the sulfonamides are the phosphinic acid amide hydroxamic acid MMP/TACE inhibitors, exemplified by the structure below, which have been disclosed in WIPO international publication WO9808853.

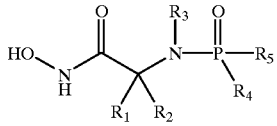

Sulfonamide MMP/TACE inhibitors in which a thiol is the zinc chelating group, as shown below, have been disclosed in WIPO international application 9803166.

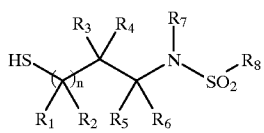

It is an object of this invention to provide aryl sulfonamide hydroxamic acid MMP/TACE inhibitors in which the sulfonyl aryl group is para-substituted with a substituted butynyl moiety or a propargylic ether, amine or sulfide.

DETAILED DESCRIPTION OF THE INVENTION

The invention provides TACE and MMP inhibitors having the formula:

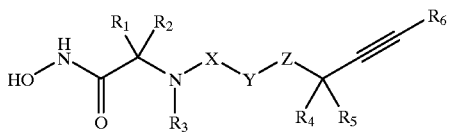

wherein:
X is $SO_2$ or —P(O)—$R_{10}$;
Y is aryl or heteroaryl, with the proviso that X and Z may not be bonded to adjacent atoms of Y;
Z is O, NH, $CH_2$ or S;
$R_1$ is hydrogen, aryl, alkyl of 1–6 carbon atoms, alkenyl of 2–6 carbon atoms, alkynyl of 2–6 carbon atoms;
$R_2$ is hydrogen, aryl, aralkyl, heteroaryl, heteroaralkyl, cycloalkyl of 3–6 carbon atoms, $C_4$–$C_8$ cycloheteroalkyl, alkyl of 1–6 carbon atoms, alkenyl of 2–6 carbon atoms, alkynyl of 2–6 carbon atoms;
or $R_1$ and $R_2$, together with the atom to which they are attached, may form a ring wherein $R_1$ and $R_2$ represent a divalent moiety of the formula:

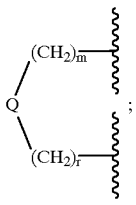

wherein
Q=a carbon-carbon single or double bond, O, S, SO, SO2, —N—$R_{11}$, or —CONR$_{14}$;
m=1–3;
r=1 or 2, with the proviso that when Q is a bond, r is equal to 2;
$R_3$ is hydrogen, alkyl of 1–6 carbon atoms, cycloalkyl of 3–6 carbon atoms, C4–C8 cycloheteroalkyl, aralkyl, or heteroaralkyl;
or $R_1$ and $R_3$, together with the atoms to which they are attached, may form a 5 to 8 membered ring wherein $R_1$ and $R_3$ represent divalent moieties of the formulae:

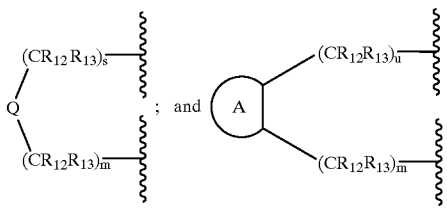

wherein Q and m are as defined above;
A is aryl or heteroaryl;
s is 0–3;
u is 1–4;
$R_4$ and $R_5$ are each, independently, hydrogen or alkyl of 1–6 carbon atoms, —CN, or —CCH;
$R_6$ is hydrogen, aryl, heteroaryl, alkyl of 1–6 carbon atoms, alkenyl of 2–6 carbon atoms, alkynyl of 2–6 carbon atoms, cycloalkyl of 3–6 carbon atoms, or —$C_5$–$C_8$-cycloheteroalkyl;
$R_8$ and $R_9$ are each, independently, hydrogen, alkyl of 1–6 carbon atoms, alkenyl of 2–6 carbon atoms, alkynyl of 2–6 carbon atoms, cycloalkyl of 3–6 carbon atoms, aryl, aralkyl, heteroaryl, heteroaralkyl, or —C4–C8-cycloheteroalkyl;
$R_{10}$ is alkyl of 1–6 carbon atoms, cycloalkyl of 3–6 carbon atoms, aryl or heteroaryl;
$R_{11}$ is hydrogen, alkyl of 1–6 carbon atoms, cycloalkyl of 3–6 carbon atoms, aryl, heteroaryl, —S(O)$_n$R$_8$, —COOR$_8$, —CONR$_8$R$_9$, —SO$_2$NR$_8$R$_9$ or —COR$_8$;
$R_{12}$ and $R_{13}$ are independently selected from H, —OR$_8$, —NR$_8$R$_9$, alkyl of 1–6 carbon atoms, alkenyl of 2–6 carbon atoms, alkynyl of 2–6 carbon atoms, cycloalkyl of 3–6 carbon atoms, aryl, heteroaryl, —COOR$_8$; —CONR$_8$R$_9$; or $R_{12}$ and $R_{13}$ together form a —$C_3$–$C_6$-cycloalkyl of 3–6 carbon atoms or a —$C_5$–$C_8$-cycloheteroalkyl ring; or $R_{12}$ and $R_{13}$ together with the carbon to which they are attached, form a carbonyl group;
with the proviso that $R_{10}$ and $R_{12}$ or $R_{11}$ and $R_{12}$ may form a cycloheteroalkyl ring when they are attached to adjacent atoms;

R₁₄ is hydrogen, aryl, heteroaryl, alkyl of 1–6 carbon atoms or cycloalkyl of 3–6 carbon atoms;

and n is 0–2;

or a pharmaceutically acceptable salt thereof.

Preferred compounds of this invention are those of structure B in which Y is a phenyl ring substituted at the 1- and 4-positions by X and Z, respectively, or a pharmaceutically acceptable salt thereof.

More preferred compounds of this invention are those of structure B in which Y is a phenyl ring substituted at the 1- and 4-positions by X and Z, respectively, X is SO₂, or a pharmaceutically acceptable salt thereof.

More preferred compounds of this invention are those of structure B in which Y is a phenyl ring substituted at the 1- and 4-positions by X and Z, respectively, X is SO₂, Z is oxygen.

More preferred compounds of this invention are those of structure B in which Y is a phenyl ring substituted at the 1- and 4-positions by X and Z, respectively, X is SO₂, Z is oxygen and R₄ and R₅ are hydrogen.

More preferred compounds of this invention are those of structure B in which Y is a phenyl ring substituted at the 1- and 4-positions by X and Z, respectively, X is SO₂, Z is oxygen, R₄ and R₅ are hydrogen, and R₆ is —CH₂OH or methyl.

More preferred compounds of this invention are those of structure B in which R₁ and R₃, together with the atoms to which they are attached, form a piperazine, piperidine, tetrahydroisoquinoline, morpholine, thiomorpholine or diazepine ring.

More preferred compounds of this invention are those of structure B in which R₁ and R₃, together with the atoms to which they are attached, form a piperazine, piperidine, tetrahydroisoquinoline, morpholine, thiomorpholine or diazepine ring, and Y is a phenyl ring substituted at the 1- and 4-positions by X and Z, respectively, X is SO₂, and Z is oxygen, or a pharmaceutically acceptable salt thereof.

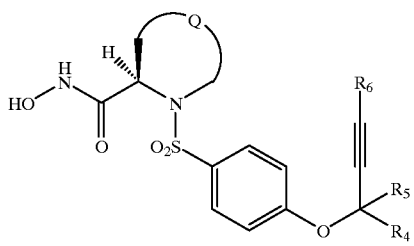

More preferred compounds of this invention are those of structure B in which R₁ and R₃, together with the atoms to which they are attached, form a piperazine, piperidine, tetrahydroisoquinoline, morpholine, thiomorpholine or diazepine ring, Y is a phenyl ring substituted at the 1- and 4-positions by X and Z, respectively, X is SO₂, Z is oxygen, and R₂ is hydrogen, such that structure B has the absolute stereochemistry shown above, or a pharmaceutically acceptable salt thereof.

More preferred compounds of this invention are those of structure B in which R₁ is hydrogen, such that these compounds have the D-configuration, as shown below:

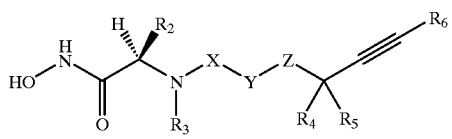

More preferred compounds of this invention are those of structure B in which R₁ is hydrogen, such that these compounds have the D-configuration, as shown above, and R₃ is hydrogen, or a pharmaceutically acceptable salt thereof. Still more preferred compounds of this invention are those of structure B in which R₁ is hydrogen, such that these compounds have the D-configuration, as shown above, R₃ is hydrogen, Y is a phenyl ring substituted at the 1- and 4-positions by X and Z, respectively, X is SO₂, Z is oxygen, or a pharmaceutically acceptable salt thereof.

Most preferred compounds of the present invention are

2-[(4-But-2-ynyloxy-benzenesulfonyl)-methyl-amino]-N-hydroxy-3-methyl-butyramide;

2-[(4-But-2-ynyloxy-benzenesulfonyl)-methyl-amino]-N-hydroxy-acetamide

N-Hydroxy-2-[(4-methoxy-benzenesulfonyl)-methyl-amino]-3-methyl-butyramide;

2-[(4-But-2-ynyloxy-benzenesulfonyl)-pyridin-3-ylmethyl-amino]-N-hydroxy-acetamide hydrochloride;

2-(4-But-2-ynyloxy-benzenesulfonylamino)-N-hydroxy-acetamide;

2-(4-But-2-ynyloxy-benzenesulfonylamino)-N-hydroxy-3-methyl-butyramide;

2-(4-But-2-ynyloxy-benzenesulfonylamino)-N-hydroxy-propionamide;

2-[(4-But-2-ynyloxy-benzenesulfonyl)-pyridin-3-ylmethyl-amino]-N-hydroxy-propionamide hydrochloride;

2-(4-But-2-ynyloxy-benzenesulfonylamino)-N-hydroxy-2-methyl-propionamide;

4-(4-But-2-ynyloxy-benzenesulfonyl)-2,2-dimethyl-thiomorpholine-3-carboxylic acid hydroxyamide;

4-(4-Hept-2-ynyloxy-benzenesulfonyl)-2,2-dimethyl-thiomorpholine-3-carboxylic acid hydroxyamide;

2-(4-But-2-ynyloxy-benzenesulfonyl)-1,2,3,4-tetrahydro-isoquinoline-3-carboxylic acid hydroxyamide;

4-Benzoyl-1-(4-but-2-ynyloxy-benzenesulfonyl)-[1,4]diazepane-2-carboxylic acid hydroxyamide;

1-(4-But-2-ynyloxy-benzenesulfonyl)-4-methyl-piperazine-2-carboxylic acid hydroxyamide hydrochloride;

4-[4-(4-Hydroxy-but-2-ynyloxy)-benzenesulfonyl]-2,2-dimethyl-thiomorpholine-3-carboxylic acid hydroxyamide;

4-(4-But-2-ynyloxy-benzenesulfonyl)-3-hydroxycarbamoyl-piperazine-1-carboxylic acid tert-butyl ester;

2-(4-But-2-ynyloxy-benzenesulfonylamino)-N-hydroxy-2-methylpropionamide;

2-(4-But-2-ynyloxy-benzenesulfonylamino)-5-guanidino-pentanoic acid hydroxyamide;

2-(4-But-2-ynyloxy-benzenesulfonylamino)-5-(4-methylbenzenesulfonyl-guanidino)-pentanoic acid hydroxyamide;

3-(4-But-2-ynyloxy-benzenesulfonylamino)-N-hydroxy-succinamic acid cyclohexyl ester;

2-(4-But-2-ynyloxy-benznesulfonylamino)-3-cyclohexyl-N-hydroxy-propionamide;

2-(4-But-2-ynyloxy-benzenesulfonylamino)-2-cyclohexyl-N-hydroxy-acetamide 3-tert-Butylsulfanyl-2-(4-but-2-ynyloxy-benzenesulfonylamino)-N-hydroxy-propionamide;

2-(4-But-2-ynyloxy-benzenesulfonylamino)-N-hydroxy-3-(4-methoxy-benzylsulfanyl)-propionamide;

2-(4-But-2-ynyloxy-benzenesulfonylamino)-N1-hydroxy-succinamide;

2-(4-But-2-ynyloxy-benzenesulfonylamino)-3-cyclohexyl-N-hydroxy-propionamide;

2-(4-But-2-ynyloxy-benzenesulfonylamino)-2-cyclohexyl-N-hydroxy-acetamide;

2-(4-But-2-ynyloxy-benzenesulfonylamino)-methyl-pentanoic acid hydroxyamide;

2-(4-But-2-ynyloxy-benzenesulfonylamino)-N-hydroxy-4-methylsulfanyl-butyramide;

2-(4-But-2-ynyloxy-benzenesulfonylamino)-N-hydroxy-3-phenyl-propionamide;

1-(4-But-2-ynyloxy-benzenesulfonyl)-pyrrolidine-2-carboxylic acid hydroxyamide;

2-(4-But-2-ynyloxy-benzenesulfonylamino)-N-hydroxy-3-(1H-indol-3-yl)-propionamide;

2-(4-But-2-ynyloxy-benzenesulfonylamino)-N-hydroxy-3-(4-hydroxy-phenyl)-propionamide;

2-(4-But-2-ynyloxy-benzenesulfonylamino)-N-hydroxy-3-methyl-butyramide;

2-(4-But-2-ynyloxy-benzenesulfonylamino)-4-methyl-pentanoic acid hydroxyamide;

2-(4-But-2-ynyloxy-benzenesulfonylamino)-6-(2-chloro-benzylamino)-hexanoic acid hydroxyamide;

2-(4-But-2-ynyloxy-benzenesulfonylamino)-hexanoic acid hydroxyamide;

2-(4-But-2-ynyloxy-benzenesulfonylamino)-N-hydroxy-2-phenyl-acetamide;

3-Benzyloxy-2-(4-but-2-ynyloxy-benzenesulfonylamino)-N-hydroxy-propionamide;

2-(4-But-2-ynyloxy-benzenesulfonylamino)-N-hydroxy-acetamide;

(2R,3S)-2-({[4-(2-Butynyloxy)phenyl]sulfonyl}amino)-N-hydroxy-3-methyl-pentanamide;

(2R)-2-({[4-(2-Butynyloxy)phenyl]sulfonyl}amino)-N-hydroxy-3,3-dimethyl-butanamide;

(2S)-2-[(4-But-2-ynyloxy-benzenesufonyl)-methyl-amino]-N-hydroxy-propionamide;

2-[(4-But-2-ynyloxy-benzenesulfonyl)-ethyl-amino]-N-hydroxy-3-methyl-butyramide;

2-[{[4-(2-Butynyloxy)phenyl]sulfonyl}(2-propynyl)amino]-N-hydroxy-3-methylbutanamide;

2-[(4-But-2-ynyloxy-benzenesulfonyl)-propyl-amino]-N-hydroxy-3-methyl-butyramide;

2-[(4-But-2-ynyloxy-benzenesulfonyl)-(3-phenyl-propyl)-amino]-N-bydroxy-3-methyl-butyramide;

2-[(4-But-2-ynyloxy-benzenesulfonyl)-cyclopropylmethyl-amino]-N-hydroxy-3-methyl-butyramide;

2-[(4-But-2-ynyloxy-benzenesulfonyl)-isobutyl-amino]-N-hydroxy-3-methyl-butyramide;

2-[(4-But-2-ynyloxy-benzenesulfonyl)-pyridin-3-ylmethyl-amino]-N-hydroxy-3-methyl-butyramide;

2-[(4-But-2-ynyloxy-benzenesulfonyl)-methyl-amino]-2-cyclohexyl-N-hydroxy-acetamide;

2-[(4-But-2-ynyloxy-benzenesulfonyl)-pyridin-3-ylmethyl-amino]-2-cyclohexyl-N-hydroxy-acetamide;

2-{(4-But-2-ynyloxy-benzenesulfonyl)-[4-(2-piperidin-1-yl-ethoxy)-benzyl]-amino}-2-cyclohexyl-N-hydroxy-acetamide;

2-{{[4-(2-Butynyloxy)phenyl]sulfonyl}[3-(diethylamino)propyl]amino}-N-hydroxy-3-methylbutanamide;

2-{{[4-(2-Butynyloxy)phenyl]sulfonyl}[3-(4-morpholinyl)propyl]amino}-N-hydroxy-3-methylbutanamide;

2-{{[4-(2-Butynyloxy)phenyl]sulfonyl}[3-(4-methyl-1-piperazinyl)propyl]-amino}-N-hydroxy-3-methylbutanamide hydrochloride;

2-{{[4-(2-Butynyloxy)phenyl]sulfonyl}[4-(diethylamino)butyl]amino}-N-hydroxy-3-methylbutanamide;

2-{{[4-(2-Butynyloxy)phenyl]sulfonyl}[4-(4-methyl-1-piperazinyl)butyl]amino}-N-hydroxy-3-methylbutanamide;

2-[[[4-(2-Butynyloxy)phenyl]sulfonyl][2-(4-morpholinyl)ethyl]amino]-N-hydroxy-3-methylbutanamide;

2-[{[4-(But-2-ynyloxy)phenyl]sulfonyl}(2-morpholin-4-ylethyl)amino]-N-hydroxyacetamide hydrochloride;

2-{{[4-(2-Butynyloxy)phenyl]sulfonyl}[4-(4-methyl-1-piperazinyl)-2-butynyl]amino}-N-hydroxy-3-methylbutanamide;

2-{{[4-(2-Butynyloxy)phenyl]sulfonyl}[4-(diethylamino)-2-butynyl]amino}-N-hydroxy-3-methylbutanamide;

2-{{[4-(2-Butynyloxy)phenyl]sulfonyl}[4-(methylamino)-2-butynyl]amino}-N-hydroxy-3-methylbutanamide;

((2R)-{[4-(2-Butynyloxy)phenyl]sulfonyl}(methyl)amino)[(4-diethylamino)-cyclohexyl]-N-hydroxyethamide;

(2R)-{[4-(2-Butynyloxy)phenyl]sulfonyl}amino-N-hydroxy-2-(4-hydroxycyclo-hexyl)ethanamide;

(2R)-{[4-(2-Butynyloxy)phenyl]sulfonyl}(methyl)amino)-N-hydroxy-2-(4-hydroxycyclohexyl)-ethanamide;

2-[(6-But-2-ynyloxy-pyridine-3-sulfonyl)-methyl-amino]-N-hydroxy-acetamide;

2-[[(4-{[3-(4-Chlorophenyl)-2-propynyl]oxy}phenyl)sulfonyl](methyl)amino]-N-hydroxyacetamide;

N-Hydroxy-2-(methyl{[4-(prop-2-ynylamino)phenyl]sulfonyl}amino)acetamide;

2-[(4-But-2-ynylthiophenylsulfonyl)methylamino]-N-hydroxyacetamide;

2-{{[4-(2-Butynyloxy)phenyl]sulfonyl}[4-(4-methyl-1-piperazinyl)-2-yl][4-(4-methyl-1-piperazinyl)-2-butynyl]amino}-N-hydroxypropanamide;

1-[{[4-(2-Butynyloxy)phenyl]sulfonyl}(methyl)amino]-N-sulfonyl}(methyl)-amino]-N-hydroxycyclohexanecarboxamide;

1-[{[4-(2-Butynyloxy)phenyl]sulfonyl}(3-pyridinylmethyl)amino]N-hydroxy-cyclohexanecarboxamide;

1-({[4-(2-Butynyloxy)phenyl]sulfonyl}amino)-N-hydroxycyclohexane-carboxamide;

1-({[4-(2-Butynyloxy)phenyl]sulfonyl}amino)-N-hydroxycyclopentane-carboxamide;

2-({[4-(2-Butynyloxy)phenyl]sulfonyl)(methyl)amino]-N-hydroxy-3-methyl-3-[(2-(4-morpholinylethyl)sulfanyl]-butanamide hydrochloride;

2-({[4-(2-Butynyloxy)phenyl] sulfonyl)(methyl)amino]-N-hydroxy-3-methyl-3-{[2-(4-methyl-1-ethyl-1-piperazinyl)ethyl]sulfanyl}butanamide;

2-({[4-(2-Butynyloxy)phenyl]sulfonyl)(methyl)amino]-N-hydroxy-3-methyl-3-{[2-(diethylamino)ethyl]sulfanyl}butanamide;

2-({[4-(2-Butynyloxy)phenyl]sulfonyl)(methyl)amino]-N-hydroxy-3-methyl-3-{[2-(1-pyrrolidinyl)ethyl]sulfanyl}butanamide;

2-({[4-(2-Butynyloxy)phenyl]sulfonyl)(methyl)amino]-N-hydroxy-3-methyl-3-{[2-(1H-imidazol-1-yl)ethyl]sulfanyl}butanamide;

Methyl 1-[2-({2-[{[4-(2-butnyloxy)phenyl]sulfonyl}(methyl)]amino]-3-(hydroxyamino)-1,1-dimethyl-3-oxopropyl}sulfanyl)ethyl]-2-pyrrolidine-carboxylate;

2-({[4-(2-Butynyloxy)phenyl]sulfonyl)(methyl)amino]-N-hydroxy-3-methyl-3-[(2(4-morpholinylpropyl)sulfanyl]-butanamide;

2-({[4-(2-Butynyloxy)phenyl]sulfonyl)(methyl)amino]-N-hydroxy-3-methyl-3-{[2(4-methyl-1-ethyl-1-piperazinyl)propyl]sulfanyl}butanamide;

2-({[4-(2-Butynyloxy)phenyl]sulfonyl)(methyl)amino]-N-hydroxy-3-methyl-3-{[2-(diethylamino)propyl]sulfanyl}butanamide;

2-[(4-But-2-ynyloxy-benenesulfonyl)-methyl-amino]-N-hydroxy-3-methyl-3-methylsulfanyl-butyramide;

2-[(4-But-2-ynyloxy-benenesulfonyl)-methyl-amino]-N-hydroxy-3-methyl-3-ethylsulfanyl-butyramide, 2-[(4-But-2-ynyloxy-benenesulfonyl)-methyl-amino]-N-hydroxy-3-methyl-3-propylsulfanyl-butyramide;

2-[(4-But-2-ynyloxy-benenesulfonyl)-methyl-amino]-N-hydroxy-3-methyl-3-(pyridin-3-ylmethylsulfanyl)-butyramide;

2-[(4-But-2-ynyloxy-benenesulfonyl)-methyl-amino]-N-hydroxy-3-methyl-3-benzylsulfanyl-butyramide;

2-[(4-But-2-ynyloxy-benenesulfonyl)-methyl-amino]-N-hydroxy-3-(methylsulfanyl)-butyramide;

2-[(4-But-2-ynyloxy-benenesulfonyl)-methyl-amino]-N-hydroxy-3-(pyridin-3-ylmethylsulfanyl)-butyramide;

3-(Benzylthio)-2-[[[4-(2-butynyloxy)phenyl]sulfonyl]methylamino]-N-hydroxy-propanamide;

3-(Benzylthio)-2-[[[4-(2-butynyloxy)phenyl]sulfonyl]pyridin-3-ylmethylamino]-N-hydroxypropanamide;

2-[[[4-(2-Butynyloxy-phenyl]sulfonyl]amino]-N-hydroxy-3-methyl-(3-methylthio)-butyramide;

2-[(4-But-2-ynyloxy-benenesulfonyl)-amino]-N-hydroxy-3-methyl-3-ethylsulfanyl-butyramide;

2-[(4-But-2-ynyloxy-benenesulfonyl)-amino]-N-hydroxy-3-methyl-3-propylsulfanyl-butyramide;

2-[(4-Butynyloxy-phenylsulfonyl)-amino]-N-hydroxy-3-methyl-[(3-pyridinyl-methyl)thio]butyramide;

2-[(4-Butynyloxy-phenyl)sulfonyl)-amino]-N-hydroxy-3-methyl-(3-benzyl-sulfanyl)butyramide;

2-({[4-(2-Butynyloxy)phenyl]sulfonyl}amino-N-hydroxy-3-{[(-methyl-1H-imidazol-2-yl]methylsulfanyl}butanamide;

2-({[4-(2-butynyloxy)phenyl]sulfonyl}amino-N-hydroxy-3-methyl-3-{[2-(4-morpholinyl)ethyl]sulfanyl}butanamide;

tert-Butyl{[2-({[4-2-butynyloxy)phenyl]sulfonyl}amino)-3-(hydroxyamino)-1,1-dimethyl-3-oxopropyl]sulfanyl}acetate;

tert-Butyl{[2-({[4-2-butynyloxy)phenyl]sulfonyl}amino)-3-(hydroxyamino)-1,1-dimethyl-3-oxopropyl]sulfanyl acetic acid, sodium salt;

2-[(4-Butynyloxy-phenylsulfonyl)-amino]-N-hydroxy-3-(methylthio)-propanamide;

2-[[4-Butynyloxy-phenylsulfonyl]-amino]-N-hydroxy-3-(benzylthio)-propanamide;

2-[[4-Butynyloxy-phenylsulfonyl]-amino]-N-hydroxy-3-(pyridinylthio)-propanamide;

2-({[4-(2-Butynyloxy)phenyl]sulfonyl}amino)-N-hydroxy-3-[(Z)-11-tetradecenylsulfanyl]propanamide;

(2S)-2-({[4-(2-Butynyloxy)phenyl]sulfonyl}amino)-N-hydroxy-3-[(3-hydroxy-propyl)sulfanyl]-3-methylbutanamide;

(2S)-2-({[4-(2-Butynyloxy)phenyl]sulfonyl}amino)-N-hydroxy-3-[(3-hydroxy-propyl)sulfanyl]-3-propanamide;

(3S)-4-({[4-(2-Butynyloxy)phenyl]sulfonyl}-N-hydroxy-2,2-dimethyl-1,4-thiazepane-3-carboxamide;

(3S)-4-({[4-(2-Butynyloxy)phenyl]sulfonyl}-N-hydroxy-1,4-thiazepane-3-carboxamide;

(3S)-4-({[4-(2-Butynyloxy)phenyl]sulfonyl}-N-hydroxy-1,4-thiazepane-3-carboxamide 1,1-dioxide;

2-({[4-(2-Butynyloxy)phenyl]sulfonyl}amino)-N-hydroxy-2-(4-hydroxy-phenyl)acetamide;

2-({[4-(2-Butynyloxy)phenyl]sulfonyl}amino)-N-hydroxy-2-[4-(2-propynyloxy)-phenyl]acetamide;

2-[{[4-(2-Butynyloxy)phenyl]sulfonyl}(methyl)amino]-N-hydroxy-2-(4-methoxyphenyl)acetamide;

2-[{[4-(2-Butynyloxy)phenyl]sulfonyl}(methyl)amino]-N-hydroxy-2-{4-[2-(4-morpholinyl)ethoxy]phenyl}acetamide;

tert-Butyl 2-{4-[1-[{[4-(2-butynyloxy)phenyl]sulfonyl}(methyl)amino]-2-(hydroxyamino)-2-oxoethyl]phenoxy}ethylcarbamate;

2-[4-(2-Aminoethoxy)phenyl]-2-[{[4-(2-butynyloxy)phenyl]sulfonyl}-(methyl)amino]-N-hydroxyacetamide;

2-[{[4-(2-Butynyloxy)phenyl]sulfonyl}(methyl)amino]-2-{4-[2-(dimethylamino)-ethoxy]phenyl}-N-hydroxyacetamide;

2-[{[4-(2-Butynyloxy)phenyl]sulfonyl}(methyl)amino]-N-hydroxy-2-{4-[2-(1-pyrrolidinyl)ethoxy]phenyl}acetamide;

2-[{[4-(2-Butynyloxy)phenyl]sulfonyl}(methyl)amino]-N-hydroxy-2-{4-[2-(2-oxo-1-pyrrolidinyl)ethoxy]phenyl}acetamide;

tert-Butyl 4-(2-{4-[1-[{[4-(2-butynyloxy)phenyl]sulfonyl}(methyl)amino]-2-(hydroxyamino)-2-oxoethyl]phenoxy}ethyl)-1-piperazinecarboxylate;

2-[{[4-(2-Butynyloxy)phenyl]sulfonyl}(methyl)amino]-N-hydroxy-2-{4-[2-(1-piperazinyl)ethoxy]phenyl}acetamide;

tert-Butyl 3-{4-[1-[{[4-(2-butynyloxy)phenyl]sulfonyl}(methyl)amino]-2-(hydroxyamino)-2-oxoethyl]phenoxy}propylcarbamate;

2-[4-(3-Aminopropoxy)phenyl]-2-[{[4-(2-butynyloxy)phenyl]-sulfonyl}(methyl)amino]-N-hydroxyacetamide;

tert-Butyl (3S)-3-{4-[(1R)-1-[{[4-(2-butynyloxy)phenyl]sulfonyl}-(methyl)amino]-2-(hydroxyamino)-2-oxoethyl]phenoxy}-1-pyrrolidine-carboxylate;

(2R)-2-[{[4-(2-Butynyloxy)phenyl]sulfonyl}(methyl)amino]-N-hydroxy-2-{4-[(3S)-pyrrolidinyloxy]phenyl}ethanamide;

tert-Butyl (2-{4-[1-({[4-(2-butynyloxy)phenyl]sulfonyl}(methyl)amino)-2-(hydroxyamino)-2-oxoethyl]phenoxy]ethyl)-(methyl)carbamate;

2-({[4-(2-Butynyloxy)phenyl]sulfonyl}(methyl)amino)-N-hydroxy-2-{4-[2-(methylamino)ethoxy]phenyl}acetamide;

Ethyl 3-{4-[1-[{[4-(2-butynyloxy)phenyl]sulfonyl}(methyl)amino]-2-(hydroxyamino)-2-oxoethyl]phenoxy}propylcarbamate;

2-{4-[3-(Acetylaminopropoxy]phenyl}-2-[{[4-(2-butynyloxy)phenyl]-sulfonyl}(methyl)amino]-N-hydroxyacetamide;

Butyl-3-{4-[1-[{[4-(2-butynyloxy)phenyl]sulfonyl}(methyl)amino]-2-(hydroxyamino)-2-oxoethyl]phenoxy}propylcarbamate;

Benzyl-3-{4-[1-[{[4-(2-butynyloxy)phenyl]sulfonyl}(methyl)amino]-2-(hydroxyamino)-2-oxoethyl]phenoxy}propylcarbamate;

2-[{[4-(2-Butynyloxy)phenyl]sulfonyl}(methyl)amino]-N-hydroxy-2-(4-{3-[(methylsulfonyl)amino]propoxy}phenyl)acetamide;

2-(4-{3-[(Anilinocarbonyl)amino]propoxy}phenyl)-2-[{[4-(2-butynyloxy)-phenyl]sulfonyl}(methyl)amino]-N-hydroxyacetamide;

tert-Butyl 2-{4-[(1R)-1-({[4-(2-butynyloxy)phenyl]sulfonyl}amino)-2-(hydroxyamino)-2-oxoethyl]phenoxy}ethylcarbamate;

(2R)-2-[4-(2-Aminoethoxy)phenyl]-2-({[4-(2-butynyloxy)phenyl]-sulfonyl}-amino)-N-hydroxyethanamide;

(2R)-2-{4-[2-(Acetylamino)ethoxy]phenyl}-2-({[4-(2-butynyloxy)phenyl]-sulfonyl}amino)-N-hydroxyethanamide;

tert-Butyl 4-(2-{4-[1-({[4-(2-butynyloxy)phenyl]sulfonyl}amino)-2-(hydroxyamino)-2-oxoethyl]phenoxy}ethyl)-1-piperazinecarboxylate;

tert-Butyl 4-(2-{4-[1-({[4-(2-butynyloxy)phenyl]sulfonyl}amino)-2-(hydroxyamino)-2-oxoethyl]phenoxy]ethyl)-(methyl)carbamate;

2-{[4-(2-Butynyloxy)phenyl]sulfonyl}amino)-N-hydroxy-2-{4-[2-(methylamino)ethoxy]phenyl})acetamide;

2-({[4-(2-Butynyloxy)phenyl]sulfonyl}amino)-N-hydroxy-2-{4-[2-(1-pyrrolidinyl)ethoxy]phenyl}acetamide;

2-({[4-(2-Butynyloxy)phenyl]sulfonyl}amino)-N-hydroxy-2-{4-[2-(4-morpholinyl)ethoxy]phenyl}acetamide;

2-({[4-(2-Butynyloxy)phenyl]sulfonyl}amino){4-[2-(dimethylamino)ethoxy]-phenyl}-N-hydroxyacetamide;

2-({[4-(2-Butynyloxy)phenyl]sulfonyl}amino)-N-hydroxy-2-{4-[2-(4-methyl-1,3-thiazol-5-yl)ethoxy]phenyl}acetamide;

2-({[4-(2-Butynyloxy)phenyl]sulfonyl}amino)-N-hydroxy-2-(4-{2-[2-(2-thoxyethoxy)ethoxy]ethoxy}phenyl)acetamide;

2-({[4-(2-Butynyloxy)phenyl]sulfonyl}amino)-N-hydroxy-2-{4-[2-(2-methoxy-ethoxy)ethoxy]phenyl}acetamide;

2-{[4-(2-Butynyloxy)phenyl]sulfonyl}(methyl)amino]-N-hydroxy-2-phenyl-acetamide;

2-{[4-(2-Butynyloxy)phenyl]sulfonyl}(methyl)amino]-2-(4-chlorophenyl)-N-hydroxyacetamide;

2-[{[4-(2-Butynyloxy)phenyl]sulfonyl}(methyl)amino]-5-[(4-chlorophenyl)-sulfanyl]-N-hydroxypentanamide;

1-(4-But-2-ynyloxy-benzenesulfonyl)-piperazine-2-carboxylic acid hydroxyamide;

1-(4-But-2-ynyloxy-benzenesulfonyl)-4-(morpholine-4-carbonyl)-piperazine-2-carboxylic acid hydroxyamide;

4-(4-But-2-ynyloxy-benzenesulfonyl)-piperazine-1,3-dicarboxylic acid 1-diethylamide 3-hydroxyamide;

1-(4-But-2-ynyloxy-benzenesulfonyl)-4-(pyrrolidine-1-carbonyl)-piperazine-2-carboxylic acid hydroxyamide;

4-(4-But-2-ynyloxy-benzenesulfonyl)-piperazine-1,3-dicarboxylic acid 1-diisopropylamide 3-hydroxyamide;

Benzyl 4-{[4-(2-butynyloxy)phenyl]sulfonyl}-3-[(hydroxyamino)carbonyl]-1-piperazinecarboxylate;

4-(4-But-2-ynyloxy-benzenesulfonyl)-piperazine-1,3-dicarboxylic acid 3-hydroxyamide 1-(methyl-phenyl-amide);

4-{[4-(2-Butynyloxy)phenyl]sulfonyl}-N-3-hydroxy-N-1-(4-methoxyphenyl)-1,3-piperazinedicarboxamide;

4-{[4-(2-Butynyloxy)phenyl]sulfonyl}-N-1-(4-fluorophenyl)-N-3-hydroxy-1,3-piperazinedicarboxamide;

4-{[4-(2-Butynyloxy)phenyl]sulfonyl}-N-1-(3,5-dichlorophenyl)-N-3-hydroxy-1,3-piperazinedicarboxamide;

4-Acetyl-1-(4-but-2-ynyloxy-benzenesulfonyl)-piperazine-2-carboxylic acid hydroxyamide;

1-(4-But-2-ynyloxy-benzenesulfonyl)-4-propionyl-piperazine-2-carboxylic acid hydroxyamide;

1-(4-But-2-ynyloxy-benzenesulfonyl)-4-(thiophene-2-carbonyl)-piperazine-2-carboxylic acid hydroxyamide;

1-(4-But-2-ynyloxy-benzenesulfonyl)-4-methanesulfonyl-piperazine-2-carboxylic acid hydroxyamide;

4-(4-But-2-ynyloxy-benzenesulfonyl)-3-hydroxycarbamoyl-piperazine-1-carboxylic acid methyl ester;

{2-[4-(4-But-2-ynyloxy-benzenesulfonyl)-3-hydroxycarbamoyl-piperazin-1-yl]-2-oxo-ethyl}-carbamic acid tert-butyl ester;

4-Aminoacetyl-1-(4-but-2-ynyloxy-benzenesulfonyl)-piperazine-2-carboxylic acid hydroxyamide;

1-{[4-(2-Butynyloxy)phenyl]sulfonyl}-N-hydroxy-4-[(2,2,5-trimethyl-1,3-dioxan-5-yl)carbonyl]-2-piperazinecarboxamide;

1-{[4-(2-Butynyloxy)phenyl]sulfonyl)-N-hydroxy-4-[3-hydroxy-2-(hydroxy-methyl)-2-methylpropanoyl-2-piperazinecarboxamide;

4-(4-Bromo-benzyl)-1-(4-but-2-ynyloxy-benzenesulfonyl)-piperazine-2-carboxylic acid hydroxyamide;

1-(4-But-2-ynyloxy-benzenesulfonyl)-4-pyridin-3-ylmethyl-piperazine-2-carboxylic acid hydroxyamide;

(3S)-4-({[4-(2-Butynyloxy)phenyl]sulfonyl)-2,2-dimethyl-thiomorpholine-3-carboxylic acid hydroxyamide;

9-({[4-(2-Butynyloxy)phenyl]sulfonyl}-N-hydroxy-6-thia-9-azaspiro[4,5]-decane-10-carboxamide;

9-({[4-(2-Butynyloxy)phenyl]sulfonyl}-N-hydroxy-1-thia-4-azaspiro[5,5]-undecane-5-carboxamide;

4-({[4-(2-Butynyloxy)phenyl]sulfonyl)-2,2-diethyl-thiomorpholine-3-carboxylic acid hydroxyamide;

4-({[4-(2-Butynyloxy)phenyl]sulfonyl)-N-hydroxy-thiomorpholine-3-carboxamide;

4-([4-(2-Butynyloxy)phenyl]sulfonyl}-N-hydroxy-3-morpholinecarboxamide;

9-Benzyl-4-{[4-(2-butynyloxy)phenyl]sulfonyl}-N-hydroxy-1-thia-4,9-diazaspiro[5.5]undecane-5-carboxamide;

9-Methyl-4-{[4-(2-butynyloxyphenyl]sulfonyl}-N-hydroxy-1-thia-4,9-diazaspiro[5.5]undecane-5-carboxamide;

N-Hydroxy-2,2-dimethyl-4-[(4-{[5-(tetrahydro-2H-pyran-2-yloxy)-2-pentynyl]oxy}phenyl)sulfonyl]-3-thiomorpholine carboxamide;

N-Hydroxy-4-({4-[(5-hydroxy-2-pentynyl)oxy]phenyl}sulfonyl)-2,2-dimethyl-3-thiomorpholine carboxamide, tert-Butyl 5-[4-({3-[(hydroxyamino)carbonyl]-2,2-dimethyl-4-thiomorpholinyl}sulfonyl)phenoxy]-3-pentynylcarbamate;

4-({4-[(5-Amino-2-pentynyl)oxy]phenyl}sulfonyl)-N-hydroxy-2,2-dimethyl-3-thiomorpholine carboxamide;

4-[(4-{[4-(Benloxy)-2-butynyl]oxy}phenyl)sulfonyl]-N-hydroxy-2,2-dimethyl-3-thiomorpholine carboxamide;

N-Hydroxy-2,2-dimethyl-4-[(4-{[6-(tetrahydro-2H-pyran-2-yloxy)-2-hexynyl]-oxy}phenyl)sulfonyl]-3-thiomorpholine carboxamide;

N-Hydroxy-4-({4-[(6hydroxy-2-hexynyl)oxy]phenyl}sulfonyl)-2,2-dimethyl-3-thiomorpholine carboxamide;

tert-Butyl 6-[4-({(3S)-3-[(hydroxyamino)carbonyl]-2,2-dimethyl-thiomorpholinyl}sulfonyl)phenoxy]-4-hexynylcarbamate;

(3S)-4-({4-[(6Amino-2-hexynyl)oxy]phenyl}sulfonyl)-N-hydroxy-2,2-dimethyl-3- thiomorpholine carboxamide;

tert-Butyl 7-[4-({(3S)-3-[(hydroxyamino)carbonyl]-2,2-dimethyl-thiomorpholinyl}sulfonyl)phenoxy]-5-heptynylcarbamate;

(3S)-4-({4-[(7-Amino-2-heptynyl)oxy]phenyl}sulfonyl)-N-hydroxy-2,2-dimethyl-3-thiomorpholine carboxamide;

(3S)-N-Hydroxy-2,2-dimethyl-4-({4-[(3-phenyl-2-propynyl)oxy]-phenyl}sulfonyl)-3-thiomorpholine carboxamide;

(3S)-4-{[4-(2-Butynyloxy)phenyl]sulfonyl}-N-hydroxy-2,2-dimethyl-3-thiomorpholine carboxamide (1S)-oxide;

(3S)-4-{[4-(2-Butynyloxy)phenyl]sulfonyl}-N-hydroxy-2,2-dimethyl-3-thiomorpholine carboxamide (1R)-oxide;

(3S)-4-{[4-(2-Butynyloxy)phenyl]sulfonyl}-N-hydroxy-2,2-dimethyl-3-thiomorpholine carboxamide 1,1-dioxide;

(3S)-N-Hydroxy-2,2-dimethyl-4-{[4-(2-propynyloxy)phenyl]sulfonyl}-3-thiomorpholine carboxamide;

(3S)-N-Hydroxy-2,2-dimethyl-4-{[4-(2-pentynyloxy)phenyl]sulfonyl}-3-thiomorpholine carboxamide;

(3S)-N-Hydroxy-4-({4-[(4-hydroxy-2-butynyl)oxy]phenyl}sulfonyl)-2,2-dimethyl-3-thiomorpholine carboxamide;

4-[4-({(3S)-3-[(Hydroxyamino)carbonyl]-2,2-dimethylthiomoipholinyl-sulfonyl)phenoxy]-2-butynyl acetate;

(3S)-N-Hydroxy-4-({4-[(6-hydroxy-2,4-hexadiynyl)oxy]phenyl}sulfonyl)-2,2-dimethyl-3-thiomorpholine carboxamide;

(3S)-N-Hydroxy-2,2-dimethyl-4-{[4-(2,4-pentadiynyloxy)phenyl]sulfonyl}-3-thiomorpholine carboxamide;

(3S)-4-({4-[(4-Fluoro-2-butynyl)oxy]phenyl}sulfonyl)-N-hydroxy-2,2-dimethyl-3-thiomorpholine carboxamide;

4-({4-[(4-Amino-2-butynyl)oxy]phenyl}sulfonyl)-N-hydroxy-2,2-dimethyl-3-thiomorpholine carboxamide;

tert-Butyl 4-[4-({3-[(hydroxyamino)carbonyl]-2,2-dimethyl-4-thiomorpholinyl}-sulfonyl)phenoxy]-2-butynylcarbamate;

tert-Butyl 4-[4-({3-[(hydroxyamino)carbonyl]-2,2-dimethyl-4-thiomorpholinyl}-sulfonyl)phenoxy]-2-butynyl(methyl)carbamate;

7-[4-({(3S)-3-[(Hydroxyamino)carbonyl]-2,2-dimethylthiomorpholinyl}-sulfonyl)phenoxy]-5-heptynyl acetate;

(3S)-N-Hydroxy-4-({4-[(7-hydroxy-2-heptynyl)oxy]phenyl}sulfonyl)-2,2-dimethyl-3-thiomorpholinecarboxamide;

(3S,5S)-4-{[4-(2-Butynyloxy)phenyl]sulfonyl}-N-hydroxy-2,2,5-trimethyl-3-thiomorpholinecarboxamide;

(3S,5R)-4-{[4-(2-Butynyloxy)phenyl]sulfonyl}-N-hydroxy-2,2,5-trimethyl-3-thiomorpholinecarboxamide, (3S,6S)-4-{[4-(2-Butynyloxy)phenyl]sulfonyl}-N-hydroxy-2,2,6-trimethyl-3-thiomorpholinecarboxamide, tert-Butyl{(2R,5S)-4-{[4-(2-butynyloxy)phenyl]sulfonyl}-5-[(hydroxyamino)-carbonyl]-6,6-dimethylthiomorpholinyl}methylcarbamate;

tert-Butyl{(2S,5S)-4-{[4-(2-butynyloxy)phenyl]sulfonyl}-5-[(hydroxyamino)-carbonyl]-6,6-dimethylthiomorpholinyl}methylcarbamate;

(3S,6R)-Trans-6-(aminomethyl)-4-{[4-(2-butynyloxy)phenyl]sulfonyl}-N-hydroxy-2,2-dimethyl-3-thiomorpholinecarboxamide hydrochloride;

(3S,6S)-Cis-6-(aminomethyl)-4-{[4-(2-butynyloxy)phenyl]sulfonyl}-N-hydroxy-2,2-dimethyl-3-thiomorpholinecarboxamide hydrochloride;

tert-Butyl{(2S,5S)-4-{[4-(2-butynyloxy)phenyl]sulfonyl}-5-[(hydroxyamino)-carbonyl]-6,6-dimethylthiomorpholinyl}acetate;

{(2S,5S)-4-{[4-(2-Butynyloxy)phenyl]sulfonyl}-5-[(hydroxyamino)carbonyl]-6,6-dimethylthiomorpholinyl}acetic acid;

(3S,6S)-4-{[4-(2-Butynyloxy)phenyl]sulfonyl}-N-hydroxy-6-[2-(hydroxyamino)-2-oxoethyl]-2,2-dimethyl-3-thiomorpholinecarboxamide;

(3S,6S)-6-(2-Amino-2-oxoethyl)-4-{[4-2-butynyloxy)phenyl]sulfonyl}-N-hydroxy-2,2-dimethyl-3-thiomorpholinecarboxamide;

(3S,6S)-4-{[4-(2-Butynyloxy)phenyl]sulfonyl}-6-[2-(dimethylamino)-2-oxoethyl]-N-hydroxy-2,2-dimethyl-3-thiomorpholinecarboxamide;

(3S,6S)-4-{[4-(2-Butynyloxy)phenyl]sulfonyl}-N-hydroxy-2,2-dimethyl-6-[2-(4-morpholinyl)-2-oxoethyl]-3-thiomorpholinecarboxamide;

(3S,6S)-4-{[4-(2-Butynyloxy)phenyl]sulfonyl}-N-hydroxy-2,2-dimethyl-6-[2-(4-methyl-1-piperazinyl)-2-oxoethyl]-3-thiomorpholinecarboxamide hydrochloride;

(3S,6S)-4-{[4-(2-Butynyloxy)phenyl]sulfonyl}-6-(2-{[2-(dimethylamino)-ethyl]amino}-2-oxoethyl)-N-hydroxy-2,2-dimethyl-3-thiomorpholinecarboxamide;

Methyl (3S,6S)-6-{[(tert-butoxycarbonyl)amino]methyl}-4-{[4-(2-butynyloxy)phenyl]sulfonyl}-2,2-dimethyl-3-thiomorpholinecarboxylate;

(4S)-3-{[4-(2-Butynyloxy)phenyl]sulfonyl}-N-hydroxy-5,5-dimethyl-1,3-thiazolidine-4-carboxamide;

tert-Butyl 4-({[4-(2-butynyloxy)phenyl]sulfonyl}amino)-4-[(hydroxyamino)-carbonyl]-1-piperidinecarboxylate;

4-({[4-(2-Butynyloxy)phenyl]sulfonyl}amino)-N-hydroxy-4-piperidine-carboxamide;

1-Benzoyl-4-{[4-(2-butynyloxy)phenyl]sulfonyl}-N-hydroxy-1,4-diazepane-5-carboxamide;

1-Benzyl-4-{[4-(2-butynyloxy)phenyl]sulfonyl}-N-hydroxy-1,4-diazepane-5-carboxamide;

tert-Butyl 4-{[4-(2-butynyloxy)phenyl]sulfonyl}-5-[(hydroxyamino)carbonyl]-1,4-diazepane-1-carboxylate;

4-{[4-(2-Butynyloxy)phenyl]sulfonyl}-N-hydroxy-1,4-diazepane-5-carboxamide;

4-{[4-(2-Butynyloxy)phenyl]sulfonyl}-N-hydroxy-1-methyl-1,4-diazepane-5-carboxamide;

4-{[4-(2-Butynyloxy)phenyl]sulfonyl}-N-hydroxy-1,4-thiazepine-5-carboxamide;

(2R)-5-(Acetylamino)-2-({[4-(but-2-ynyloxy)phenyl]sulfonyl}amino)-N-hydroxypentanamide;

N-[(4R)-4-({[4-(But-2-ynyloxy)phenyl]sulfonyl}amino)-5-(hydroxyamino)-5-oxopentyl]thiophene-2-carboxamide;

(2R)-2-({[4-(But-2-ynyloxy)phenyl]sulfonyl}amino)-5-{[(ethylamino)carbonyl]-amino}-N-hydroxypentanamide;

(2R)-5-[(Anilinocarbonyl)amino]-2-({[4-(but-2-ynyloxy)phenyl]sulfonyl}-amino)-N-hydroxypentanamide;

Octyl (4R)-4-({[4-(but-2-ynyloxy)phenyl]sulfonyl}amino)-5-(hydroxyamino)-5-oxopentylcarbamate;

4-Methoxyphenyl (4R)-4-({[4-(but-2-ynyloxy)phenyl]sulfonyl}amino)-5-(hydroxyamino)-5-oxopentylcarbamate;

(2R)-2-({[4-(But-2-ynyloxy)phenyl]sulfonyl}amino)-5-{[(diethylamino)-carbonyl]amino}-N-hydroxypentanamide;

(2R)-2-({[4-(But-2-ynyloxy)phenyl]sulfonyl}amino)-N-hydroxy-5-{[(methylanilino)carbonyl]amino}pentanamide;

(2R)-2-({[4-(But-2-ynyloxy)phenyl]sulfonyl}amino)-N-hydroxy-5-{[(1-methyl-1H-imidazol-4-yl)sulfonyl]amino}pentanamide;

(2R)-2-({[4-(But-2-ynyloxy)phenyl]sulfonyl}amino)-N-hydroxy-5-[(2-morpholin-4-ylacetyl)amino]pentanamide;

(2R)-2-({[4-(But-2-ynyloxy)phenyl]sulfonyl}amino)-N-hydroxy-5-{[2-(4-methylpiperazin-1-yl)acetyl]amino}pentanamide;

(2R)-5-{[2-(Benzylamino)acetyl]amino}-2-({[4-(but-2-ynyloxy)phenyl]-sulfonyl}amino)-N-hydroxypentanamide;

(3S)-4-{[4-(2-Butynyloxy)phenyl]sulfonyl}-N-hydroxy-2,2-dimethyl-3,4-dihydro-2H-1,4-thiazine-3-carboxamide;

(2R)-2-({[4-(2-Butynyloxy)phenyl]sulfonyl}amino)-N-hydroxy-5-[(imino{[(4-{[(4-methoxy-2,3,6-trimethylphenyl)sulfonyl]amino}methyl)amino]pentanamide;

(2R)-2-(4-But-2-ynyloxy-benzenesulfonylamino)-5-guanidino-pentanoic acid hydroxyamide;

(2R)-2-({[4-(2-Butynyloxy)phenyl]sulfonyl}amino)-N-hydroxy-5-[(imino{[(4-methylphenyl)sulfonyl]amino}methyl)amino]pentanamide;

(3R)-3-({[4-(But-2-ynyloxy)phenyl]sulfonyl}amino)-4-(hydroxyamino)-4-oxobutanoic acid;

(2S)-3-(tert-Butylthio)-2-({[4-(but-2-ynyloxy)phenyl]sulfonyl}amino)-N-hydroxypropanamide;

(2S)-3-{[(Acetylamino)methyl]thio}-2-({[4-(but-2-ynyloxy)phenyl]sulfonyl}amino)-N-hydroxypropanamide;

(2S)-2-({[4-(But-2-ynyloxy)phenyl]sulfonyl}amino)-N-hydroxy-3-[(4-methylbenzyl)thio]propanamide;

(2S)-2-({[4-(But-2-ynyloxy)phenyl]sulfonyl}amino)-N-hydroxy-3-[(4-methoxybenyl)thio]propanamide;

(2R)-2-({[4-(But-2-ynyloxy)phenyl]sulfonyl}amino)-N-hydroxypentanediamide;

(4R)-4-({[4-(But-2-ynyloxy)phenyl]sulfonyl}amino)-5-(hydroxyamino)-5-oxopentanoic acid;

(2R)-2-({[4-(But-2-ynyloxy)phenyl]sulfonyl}amino)-N-hydroxy-4-phenyl-butanamide;

(2R)-2-({[4-(But-2-ynyloxy)phenyl]sulfonyl}amino)-N-hydroxy-3-(1H-imidazol-5-yl)propanamide;

(2R,4S)-1-{[4-(But-2-ynyloxy)phenyl]sulfonyl}-N,4-dihydroxypyrrolidine-2-carboxamide;

(2R)-6-Amino-2-({[4-(but-2-ynyloxy)phenyl]sulfonyl}amino)-N-hydroxy-hexanamide;

Benzyl (5R)-5-({[4-(but-2-ynyloxy)phenyl]sulfonyl}amino)-6-(hydroxyamino)-6-oxohexylcarbamate;

(2R)-2-({[4-(But-2-ynyloxy)phenyl]sulfonyl}amino)-N-hydroxy-3-(1-naphthyl)-propanamide;

(2R)-2-({[4-(But-2-ynyloxy)phenyl]sulfonyl}amino)-N-hydroxy-3-(2-naphthyl)-propanamide;

(2R)-2-({[4-(But-2-ynyloxy)phenyl]sulfonyl}amino)-N-hydroxyhexanamide;

(2R)-2-({[4-(But-2-ynyloxy)phenyl]sulfonyl}amino)-N-hydroxypentanamide;

(2R)-5-Amino-2-({[4-(but-2-ynyloxy)phenyl]sulfonyl}amino)-N-hydroxypentanamide;

(2R)-2-({[4-(But-2-ynyloxy)phenyl]sulfonyl}amino)-3-(3,4-difluorophenyl)-N-hydroxypropanamide;

(2R)-2-({[4-(But-2-ynyloxy)phenyl]sulfonyl}amino)-3-(4-fluorophenyl)-N-hydroxypropanamide;

(2R)-2-({[4-(But-2-ynyloxy)phenyl]sulfonyl}amino)-N-hydroxy-3-(4-nitrophenyl)-propanamide;

(2R)-1-{[4-(But-2-ynyloxy)phenyl]sulfonyl}-N-hydroxypiperidine-2-carboxamide;

(2R)-2-({[4-(But-2-ynyloxy)phenyl]sulfonyl}amino)-N,3-dihydroxypropanamide;

(2R)-3-Benzyloxy)-2-({[4-(but-2-ynyloxy)phenyl]sulfonyl}amino)-N-hydroxy-propanamide;

(2R)-2-({[4-(But-2-ynyloxy)phenyl]sulfonyl}amino)-N-hydroxy-3-thien-2-yl-propanamide;

(2R,3S)-2-({[4-(But-2-ynyloxy)phenyl]sulfonyl}amino)-N,3-dihydroxybutanamide;

(2R,3S)-3-(Benzyloxy)-2-({[4-(but-2-ynyloxy)phenyl]sulfonyl}amino)-N-hydroxybutanamide;

(4S)-3-{[4-(But-2-ynyloxy)phenyl]sulfonyl}-N-hydroxy-1,3-thiazolidine-4-carboxamide;
(3R)-2-{[4-(But-2-ynyloxy)phenyl]sulfonyl}-N-hydroxy-1,2,3,4-tetrahydro-isoquinoline-3-carboxamide;
(2R)-3-[4-(Benzyloxy)phenyl]-2-({[4-(but-2-ynyloxy)phenyl]sulfonyl}amino)-N-hydroxypropanamide;
(2R)-2-({[4-(But-2-ynyloxy)phenyl]sulfonyl}amino)-N-hydroxy-2-phenyl-ethanamide;
(2R)-5-(Acetylamino)-2-({[4-(but-2-ynyloxy)phenyl]sulfonyl}amino)-N-hydroxy-pentanamide;
N-[(4R)-4-({[4-(But-2-ynyloxy)phenyl]sulfonyl}amino)-5-(hydroxyamino)-5-oxopentyl]-1H-benzimidazole-5-carboxamide;
N-[(4R)-4-({[4-(But-2-ynyloxy)phenyl]sulfonyl}amino)-5-(hydroxyamino)-5-oxopentyl]benzamide;
4-Bromo-N-[(4R)-4-({[4-(but-2-ynyloxy)phenyl]sulfonyl}amino)-5-(hydroxy-amino)-5-oxopentyl]benzamide;
(2R)-2-({[4-(But-2-ynyloxy)phenyl]sulfonyl}amino)-5-(butyrylamino)-N-hydroxypentanamide;
N-[(4R)-4-({[4-(But-2-ynyloxy)phenyl]sulfonyl}amino)-5-(hydroxyamino)-5-oxopentyl]-3-chlorothiophene-2-carboxamide;
N-[(4R)-4-({[4-(But-2-ynyloxy)phenyl]sulfonyl}amino)-5-(hydroxyamino)-5-oxopentyl]-4-chlorobenzamide;
N-[(4R)-4-({[4-(But-2-ynyloxy)phenyl]sulfonyl}amino)-5-(hydroxyamino)-5-oxopentyl]cyclohexanecarboxamide;
(2R)-2-({[4-(But-2-ynyloxy)phenyl]sulfonyl}amino)-5-{[2-(3,4-dichlorophenyl)-acetyl]amino}-N-hydroxypentanamide;
N-[(4R)-4-({[4-(But-2-ynyloxy)phenyl]sulfonyl}amino)-5-(hydroxyamino)-5-oxopentyl]-2,5-dimethyl-3-furamide;
N-[(4R)-4-({[4-(But-2-ynyloxy)phenyl]sulfonyl}amino)-5-(hydroxyamino)-5-oxopentyl]-3,5-dimethylisoxazole-4-carboxamide;
(2R)-2-({[4-(But-2-ynyloxy)phenyl]sulfonyl}amino)-N-hydroxy-5-[(3-phenyl-propanoyl)amino]pentanamide;
N-[(4R)-4-({[4-(But-2-ynyloxy)phenyl]sulfonyl}amino)-5-(hydroxyamino)-5-oxopentyl]isonicotinamide;
N-[(4R)-4-({[4-(But-2-ynyloxy)phenyl]sulfonyl}amino)-5-(hydroxyamino)-5-oxopentyl]nicotinamide;
N-[(4R)-4-({[4-(But-2-ynyloxy)phenyl]sulfonyl}amino)-5-(hydroxyamino)-5-oxopentyl]-2-methoxybenzamide;
N-[(4R)-4-({[4-(But-2-ynyloxy)phenyl]sulfonyl}amino)-5-(hydroxyamino)-5-oxopentyl]-4-methoxybenzamide;
(2R)-2-({[4-(But-2-ynyloxy)phenyl]sulfonyl}amino)-N-hydroxy-5-{[2-(4-nitrophenyl)acetyl]amino}pentanamide;
(2R)-2-({[4-(But-2-ynyloxy)phenyl]sulfonyl}amino)-N-hydroxy-5-[(2-phenylacetyl)amino]pentanamide;
N-[(4R)-4-({[4-(But-2-ynyloxy)phenyl]sulfonyl}amino)-5-(hydroxyamino)-5-oxopentyl]quinoline-3-carboxamide;
N-[(4R)-4-({[4-(But-2-ynyloxy)phenyl]sulfonyl}amino)-5-(hydroxyamino)-5-oxopentyl]thiophene-3-carboxamide;
(E)-N-[(4R)-4-({[4-(But-2-ynyloxy)phenyl]sulfonyl}amino)-5-(hydroxyamino)-5-oxopentyl]-3-phenylprop-2-enamide;
N-[(5R)-5-({[4-(But-2-ynyloxy)phenyl]sulfonyl}amino)-6-(hydroxyamino)-6-oxohexyl]-1H-benzimidazole-5-carboxamide;
N-[(5R)-5-({[4-(But-2-ynyloxy)phenyl]sulfonyl}amino)-6-(hydroxyamino)-6-oxohexyl]benzamide;
4-Bromo-N-[(5R)-5-({[4-(but-2-ynyloxy)phenyl]sulfonyl}amino)-6-(hydroxyamino)-6-oxohexyl]benzamide;
N-[(5R)-5-({[4-(But-2-ynyloxy)phenyl]sulfonyl}amino)-6-(hydroxyamino)-6-oxohexyl]-3-chlorothiophene-2-carboxamide;
N-[(5R)-5-({[4-(But-2-ynyloxy)phenyl]sulfonyl}amino)-6-(hydroxyamino)-6-oxohexyl]-4-chlorobenzamide;
N-[(5R)-5-({[4-(But-2-ynyloxy)phenyl]sulfonyl}amino)-6-(hydroxyamino)-6-oxohexyl]cyclohexanecarboxamide;
(2R)-2-({[4-(But-2-ynyloxy)phenyl]sulfonyl}amino)-6-{[2-(3,4-dichlorophenyl)-acetyl]amino}-N-hydroxyhexanamide;
N-[(5R)-5-({[4-(But-2-ynyloxy)phenyl]sulfonyl}amino)-6-(hydroxyamino)-6-oxohexyl]-2,5-dimethyl-3-furamide;
N-[(5R)-5-({[4-(But-2-ynyloxy)phenyl]sulfonyl}amino)-6-(hydroxyamino)-6-oxohexyl]-3,5-dimethylisoxazole-4-carboxamide;
(2R)-2-({[4-(But-2-ynyloxy)phenyl]sulfonyl}amino)-N-hydroxy-6-[(3-phenyl-propanoyl)amino]hexanamide;
N-[(5R)-5-({[4-(But-2-ynyloxy)phenyl]sulfonyl}amino)-6-(hydroxyamino)-6-oxohexyl]isonicotinamide;
N-[(5R)-5-({[4-(But-2-ynyloxy)phenyl]sulfonyl}amino)-6-(hydroxyamino)-6-oxohexyl]-2-methoxybenzamide;
N-[(5R)-5-({[4-(But-2-ynyloxy)phenyl]sulfonyl}amino)-6-(hydroxyamino)-6-oxohexyl]-4-methoxybenzamide;
(2R)-2-({[4-(But-2-ynyloxy)phenyl]sulfonyl}amino)-N-hydroxy-6-{[2-(4-nitrophenyl)acetyl]amino}hexanamide;
(2R)-2-({[4-(But-2-ynyloxy)phenyl]sulfonyl}amino)-N-hydroxy-6-[(2-phenylacetyl)amino]hexanamide;
N-[(5R)-5-({[4-(But-2-ynyloxy)phenyl]sulfonyl}amino)-6-(hydroxyamino)-6-oxohexyl]quinoline-3-carboxamide;
N-[(5R)-5-({[4-(But-2-ynyloxy)phenyl]sulfonyl}amino)-6-(hydroxyamino)-6-oxohexyl]thiophene-3-carboxamide;
(E)-N-[(5R)-5-({[4-(But-2-ynyloxy)phenyl]sulfonyl}amino)-6-(hydroxyamino)-6-oxohexyl]-3-phenylprop-2-enamide;
(Z)-N-[(4R)-4-({[4-(But-2-ynyloxy)phenyl]sulfonyl}amino)-5-(hydroxyamino)-5-oxopentyl]octadec-9-enamide;
N-[(4R)-4-({[4-(But-2-ynyloxy)phenyl]sulfonyl}amino)-5-(hydroxyamino)-5-oxopentyl]thiophene-2-carboxamide;
(2R)-2-({[4-(But-2-ynyloxy)phenyl]sulfonyl}amino)-5-{[(ethylamino)carbonyl]-amino}-N-hydroxypentanamide;
(2R)-5-[(Anilinocarbonyl)amino]-2-({[4-(but-2-ynyloxy)phenyl]sulfonyl}amino)-N-hydroxypentanamide,
Octyl (4R)-4-({[4-(but-2-ynyloxy)phenyl]sulfonyl}amino)-5-(hydroxyamino)-5-oxopentylcarbamate;
4-Methoxyphenyl (4R)-4-({[4-(but-2-ynyloxy)phenyl]sulfonyl}amino)-5-(hydroxyamino)-5-oxopentylcarbamate;

(2R)-2-({[4-(But-2-ynyloxy)phenyl]sulfonyl}amino)-5-{[(diethylamino)-carbonyl]amino}-N-hydroxypentanamide;

(2R)-2-({[4-(But-2-ynyloxy)phenyl]sulfonyl}amino)-N-hydroxy-5-{[(methylanilino)carbonyl]amino}pentanamide;

(2R)-2-({[4-(But-2-ynyloxy)phenyl]sulfonyl}amino)-N-hydroxy-5-{[(1-methyl-1H-imidazol-4-yl)sulfonyl]amino}pentanamide;

(2R)-2-({[4-(But-2-ynyloxy)phenyl]sulfonyl}amino)-N-hydroy-5-[(2-morpholin-4-ylacetyl)amino]pentanamide;

(2R)-2-({[4-(But-2-ynyloxy)phenyl]sulonyl}amino)-N-hydroxy-5-{[2-(4-methylpiperazin-1-yl)acetyl]amino}pentanamide; and (2R)-5-{[2-(Benylamino)acetyl]amino}-2-({[4-but-2-ynyloxy)phenyl]sulfonyl}amir hydroxypentanamide;

or a pharmaceutical salt thereof.

Heteroaryl, as used throughout, is a 5–10 membered mono- or bicyclic ring having from 1–3 heteroatoms selected from N, NR14, S and O. Heteroaryl is preferably;

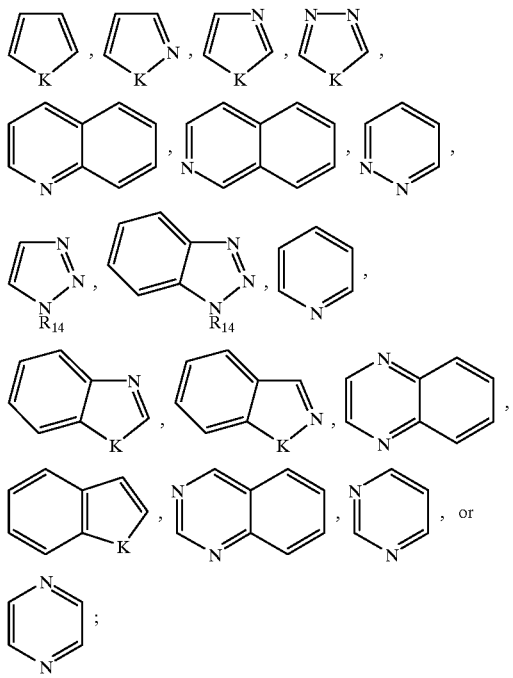

wherein K is O, S or —NR14 and R14 is hydrogen, aryl, heteroaryl, alkyl of 1–6 carbon atoms, or cycloalkyl of 3–6 carbon atoms. Preferred heteroaryl rings include pyrrole, furan, thiophene, pyridine, pyrimidine, pyridazine, pyrazine, triazole, pyrazole, imidazole, isothiazole, thiazole, isoxazole, oxazole, indole, isoindole, benzofuran, benzothiophene, quinoline, isoquinoline, quinoxaline, quinazoline, benzotriazole, indazole, benzimidazole, benzothiazole, benzisoxazole, and benzoxazole. Heteroaryl groups may optionally be mono or di substituted.

C4–C8 cycloheteroalkyl as used herein refers to a 5 to 9 membered saturated or unsaturated mono or bi-cyclic ring having 1 or 2 heteroatoms selected from N, NR14, S or O. Heterocycloalkyl rings of the present invention are preferably selected from;

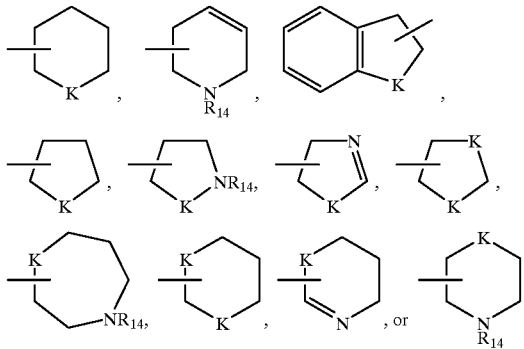

wherein K is NR14, O or S and R14 is a bond, hydrogen, aryl, heteroaryl, alkyl of 1–6 carbon atoms, or cycloalkyl of 3–6 carbon atoms.

Preferred heterocycloalkyl rings include piperidine, piperazine, morpholine, tetrahydropyran, tetrahydrofuran or pyrrolidine.

Cycloheteroalkyl groups of the present invention may optionally be mono- or di- substituted.

Aryl, as used herein refers to a phenyl or napthyl rings which may, optionally be mono-, di- or tri-substituted.

Alkyl, alkenyl, alkynyl, and perfluoroalkyl include both straight chain as well as branched moieties. Alkyl, alkenyl, alkynyl, and cycloalkyl groups may be unsubstituted unsubstituted (carbons bonded to hydrogen, or other carbons in the chain or ring) or may be mono- or poly-substituted. Lower alkyl moieties contain from 1 to 6 carbon atoms.

Aralkyl as used herein refers to a substituted alkyl group, -alkyl-aryl, wherein alkyl is lower alkyl and preferably from 1 to 3 carbon atoms, and aryl is as previously defined.

Heteroaralkyl as used herein refers to a substituted alkyl group, alkyl-heteroaryl wherein alkyl is lower alkyl and preferably from 1 to 3 carbon atoms, and heteroaryl is as previously defined.

Halogen means bromine, chlorine, fluorine, and iodine.

Suitable substituents of aryl, aralkyl, heteroaryl, heteroaralkyl, alkyl, alkenyl, alkynyl, and cycloalkyl include, but are not limited to hydrogen, halogen, alkyl of 1–6 carbon atoms; alkenyl of 2–6 carbon atoms; alkynyl of 2–6 carbon atoms, cycloalkyl of 3–6 carbon atoms, —$OR_8$, —[[O(CH2)p]q]—OCH3, CN, —$COR_8$, perfluoroalkyl of 1–4 carbon atoms, —O-perfluoroalkyl of 1–4 carbon atoms, —$CONR_8R_9$, —$S(O)_nR_8$, —$S(O)_nR_{18}C(O)OR_8$, —$S(O)_nR_{18}OR_9$, —$S(O)_nR_{18}NR_8R_9$, —$S(O)_nR_{18}NR_8R_9COOR_8$, —$S(O)nR_{18}NR_8COR_9$, —$OPO(OR_8)OR_9$, —$PO(OR_8)R_9$, —$OC(O)NR_8R_9$, —$C(O)NR_8OR_9$, —$C(O)R_{18}NR_8R_9$, —$COOR_8$, —$SO_3H$, —$NR_8R_9$, —$N[(CH_2)_2]_2NR_8$, —$NR_8COR_9$, —$NR_8C(O)CH=CHaryl$, —$NR_8C(O)(CH_2)_nNR_8R_9$, —$NR_8C(O)CH_2NHCH_2aryl$, $NR_8C(O)R_{18}$, —$NR_8COOR_9$, —$SO_2NR_8R_9$, —$NO_2$, —$N(R_8)SO_2R_9$, —$NR_8CONR_8R_9$, —$NR_8C(=NR_9)NR_8R_9$, —$NR_8C(=NR_9)N(SO2R_8)R_9$, $NR_8C(=NR_9)N(C=OR_8)R_9$-tetrazol-5-yl, —$SO_2NHCN$, —$SO_2NHCONR_8R_9$, —$(OR18)NR_8S(O)R_9$, —$(OR18)NR_8C(O)R_9$, —$(OR18)NR_8C(O)NR_8R_9$, —$(OR18)NR_8COOR_9$, —$(OR18)NR_8R_9$, phenyl, heteroaryl, or —$C_4$-$C_8$-cycloheteroalkyl;

wherein —$NR_8R_9$ may form a heterocyclic group as previously defined, such as pyrrolidine, piperidine, morpholine, thiomorpholine, oxazolidine, thiazolidine, pyrazolidine, piperazine, and azetidine ring; p is 1 or 2, q is 1 through 3 and $R_{18}$ is alkyl of 1–20 carbon atoms.

In some preferred embodiments of the present invention R8 and R18 may be frrther substituted with halogen, C1–C3 alkyl, C1–C3 alkoxy and OH, and $NO_2$.

When a moiety contains more than substituent with the same designation (i.e., phenyl tri-substituted with $R_1$) each of those substituents ($R_1$ in this case) may be the same or different.

Pharmaceutically acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, naphthalenesulfonic, benzenesulfonic, toluenesulfonic, camphorsulfonic, and similarly known acceptable acids when a compound of this invention contains a basic moiety. Salts may also be formed from organic and inorganic bases, preferably alkali metal salts, for example, sodium, lithium, or potassium, when a compound of this invention contains an acidic moiety.

The compounds of this invention may contain an asymmetric carbon atom and some of the compounds of this invention may contain one or more asymmetric centers and may thus give rise to optical isomers and diastereomers. While shown without respect to stereochemistry, the present invention includes such optical isomers and diastereomers; as well as the racemic and resolved, enantiomerically pure R and S stereoisomers; as well as other mixtures of the R and S stereoisomers and pharmaceutically acceptable salts thereof. It is recognized that one optical isomer, including diastereomer and enantiomer, or stereoisomer may have favorable properties over the other. Thus when disclosing and claiming the invention, when one racemic mixture is disclosed, it is clearly contemplated that both optical isomers, including diastereomers and enantiomers, or stereoisomers substantially free of the other are disclosed and claimed as well.

The compounds of this invention are shown to inhibit the enzymes MMP-1, MMP-9, MMP-13 and TNF-α converting enzyme (TACE) and are therefore useful in the treatment of arthritis, tumor metastasis, tissue ulceration, abnormal wound healing, periodontal disease, graft rejection, insulin resistance, bone disease and HIV infection. In particular, the compounds of the invention provide enhanced levels of inhibition of the activity of TACE in vitro and in cellular assay and/or enhanced selectivity over MMP-1 and are thus particularly useful in the treatment of diseases mediated by TNF.

The invention is further directed to a process for making compounds of structure B involving one or more reactions as follows:

1) alkylating a compound of formula I, or a salt or solvate thereof,

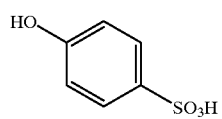

I into a compound of formula II:

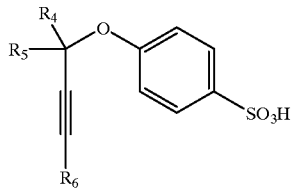

II 2) reacting a compound of formula II above, or a salt or solvate thereof, with a chlorinating agent such as thionyl chloride, chlorosulfonic acid, oxalyl chloride, phosphorus pentachloride, or other halogenating agents such as fluorosulfonic acid or thionyl bromide to a compound of formula III:

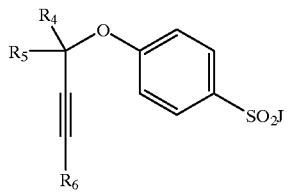

III wherein J is fluorine, bromine, chlorine.

The resultant sulfonyl chloride, fluoride or bromide, may be further converted into triazolide, imidazolide or benzothiazolide derivatives, where J is 1,2,4-triazolyl, benzotriazolyl or imidazol-yl, by reacting the compound with 1,2,4-triazole, imidazole or benzotriazole, respectively. $R_4$, $R_5$ and $R_6$ are as defined above.

The invention is still further directed to a process for making compounds of structure B involving one or more reactions as follows:

1) alkylating phenol, or a salt or solvate thereof, into a compound of formula IV:

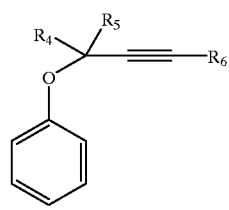

IV 2) reacting a compound of formula IV above, or a salt or solvate thereof with chlorosulfonic acid to prepare a compound of formula II above.

Particularly preferred intermediates are compounds of formulae II and III, with the proviso that R6 is not hydrogen.

Compounds of the present invention are prepared using conventional techniques known to those skilled in the art of organic synthesis. The starting materials used in preparing the compounds of the invention are known, made by known methods or are commercially available.

Compounds of the following general structures (V–XX), and the methods used to prepare them, are known and references are given herein below.

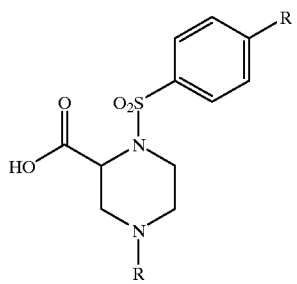
V
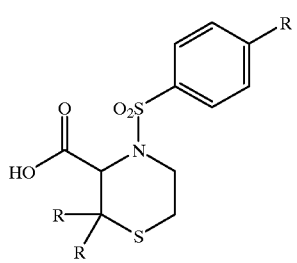
VI
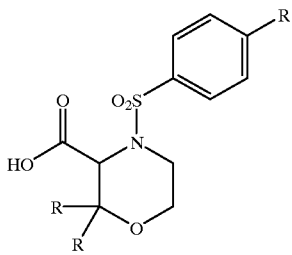
X
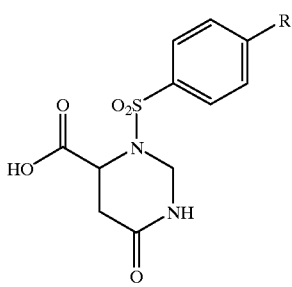
XI
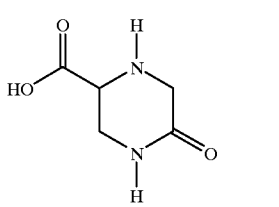
XII
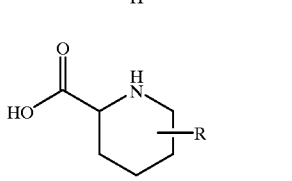
XIII
VII
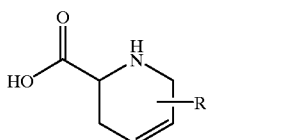
XIV
VIII
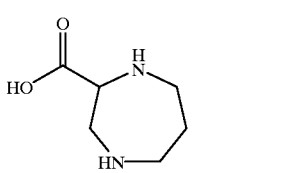
XV
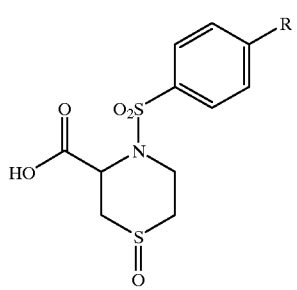
IX
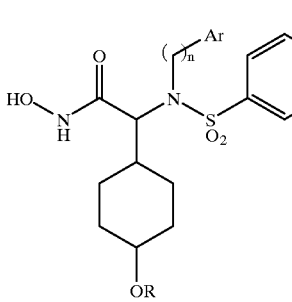
XVI

XVII

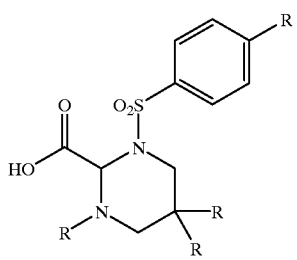

XVIII

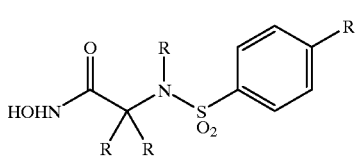

XIX

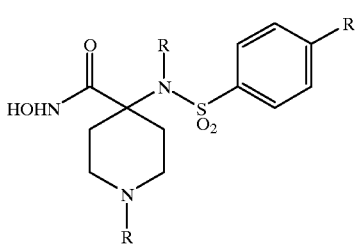

XX

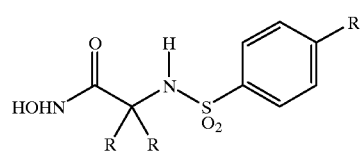

Compounds V–XII:
a) U.S. Pat. No. 5,753,653.
b) Kogami, Yuji; Okawa, Kenji. *Bull. Chem. Soc. Jpn.* 1987, 60(8), 2963.
Compound XII:
Auvin, S.; Cochet, O.; Kucharczyk, N.; Le Goffic, F.; Badet, B. *Bioorganic Chemistry*, 1991, 19, 143.

Compounds XIII–XIV:
a) Angle, S. R.; Breitenbucher, J. G.; Arnaiz, D. O. *J. Org. Chem.* 1992, 57, 5947.
b) Asher, Vikram; Becu, Christian; Anteunis, Marc J. O.; Callens, Roland *Tetrahedron Lett.* 1981, 22(2), 141.

Compounds XV:
Levin, J. I.; DiJoseph, J. F.; Killar, L. M.; Sung, A.; Walter, T.; Sharr, M. A.; Roth, C. E.; Skotnicki, J. S.; Albright, J. D. *Bioorg. & Med. Chem. Lett.* 1988, 8, 2657.

Compounds XVI:
U.S. Pat. No. 5,770,624

Compounds XVII:
Pikul, S.; McDow Dunham, K L.; Almstead, N. G.; De, B.; Natchus, M. G.; Anastasio, M. V.; McPhail, S. J.; Snider, C. E.; Taiwo, Y. O.; Rydel, T.; Dunaway, C. M.; Gu, F.; Mieling, G. E. *J. Med. Chem.* 1998, 41, 3568.

Compounds XVIII:
U.S. Pat. Nos. 5,455,258, 5,506,242, 5,552,419 and 5,770,624
MacPherson, et. al. in *J. Med. Chem,* 1997, 40, 2525.

Compounds XIX:
U.S. Pat. Nos. 5,455,258 and 5,552,419

Compounds XX:
U.S. Pat. No. 5,804,593
Tamura, et. al. in *J. Med. Chem.* 1998, 41, 640.

Those skilled in the art will recognize that certain reactions are best carried out when other potentially reactive functionality on the molecule is masked or protected, thus avoiding undesirable side reactions and/or increasing the yield of the reaction. To this end, those skilled in the art may use protecting groups. Examples of these protecting group moieties may be found in T. W. Greene, P. G. M. Wuts "*Protective Groups in Organic Synthesis*", $2^{nd}$ Edition, 1991, Wiley & Sons, New York. Reactive side chain functionalities on amino acid starting materials are preferably protected. The need and choice of protecting groups for a particular reaction is known to those skilled in the art and depends on the nature of the functional group to be protected (hydroxy, amino, carboxy, etc.), the structure and stability of the molecule of which the substituent is part and the reaction conditions.

When preparing or elaborating compounds of the invention containing heterocyclic rings, those skilled in the art recognize that substituents on that ring may be prepared before, after or concomitant with construction of the ring. For clarity, substituents on such rings have been omitted from the schemes herein below.

Those skilled in the art will recognize that the nature and order of the synthetic steps presented may be varied for the purpose of optimizing the formation of the compounds of the invention.

The hydroxamic acid compounds of the invention, 1, are prepared according to Scheme 1 by converting a carboxylic acid, 2, into the corresponding acid chloride or anhydride, or by reacting it with a suitable peptide coupling reagent, followed by reaction with hydroxylamine to give 1, or with a protected hydroxylamine derivative to give 3. Compounds 3, wherein $R_{30}$ is a t-butyl, benzyl, trialkylsilyl or other suitable masking group may then be deprotected by known methods to provide the hydroxamic acid 1.

Scheme 1

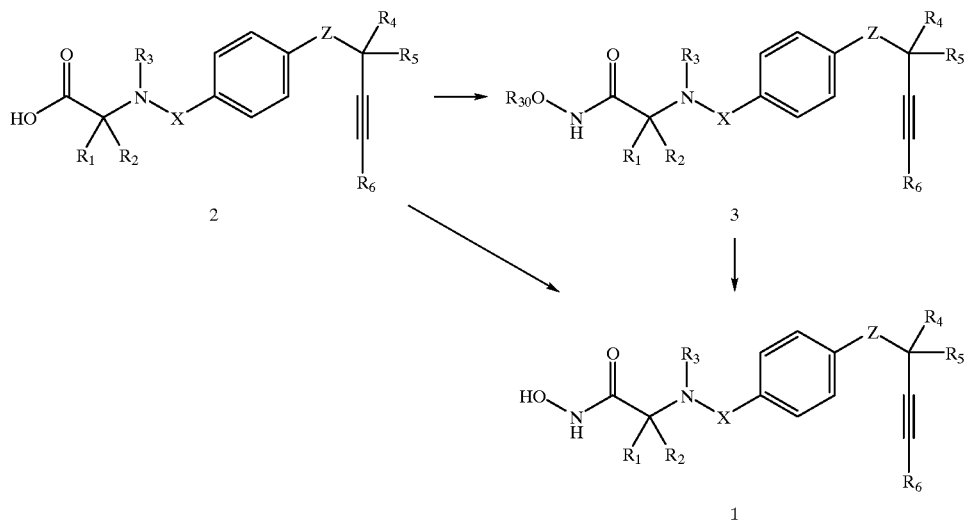

Carboxylic acids 2 may be prepared as shown in Scheme 2. Amino acid derivative 4, in which $R_{40}$ is hydrogen or a suitable carboxylic acid protecting group, may be sulfonylated or phosphorylated by reating with compounds 6, in which J is a suitable leaving group including, but not limited to chlorine. The N—H compound 7 may then be alkylated with $R_3J$ and a base such as potassium carbonate or sodium hydride in a polar aprotic solvent such as acetone, N,N-dimethylformamide (DMF), or tetrahydrofuran (THF) to provide sulfonamide 8. Compound 8 is also available through direct reaction of 6 with an N-substituted amino acid derivative, 5. Conversion of 8 into the carboxylic acid is performed by acid, base hydrolysis, or other method consistent with the choice of protecting group $R_{40}$ and the presence of a carbon—carbon triple bond.

Scheme 2

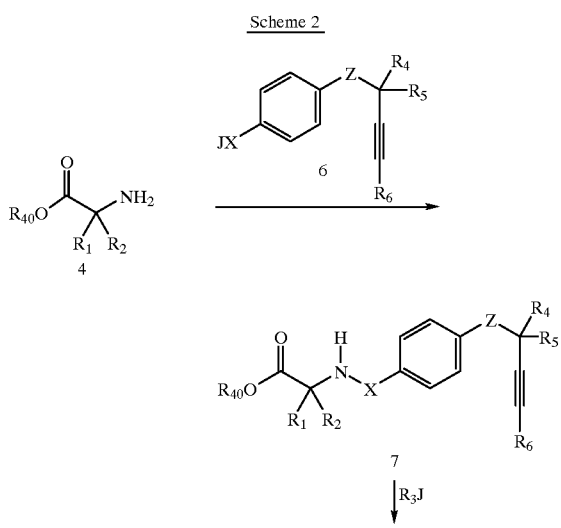

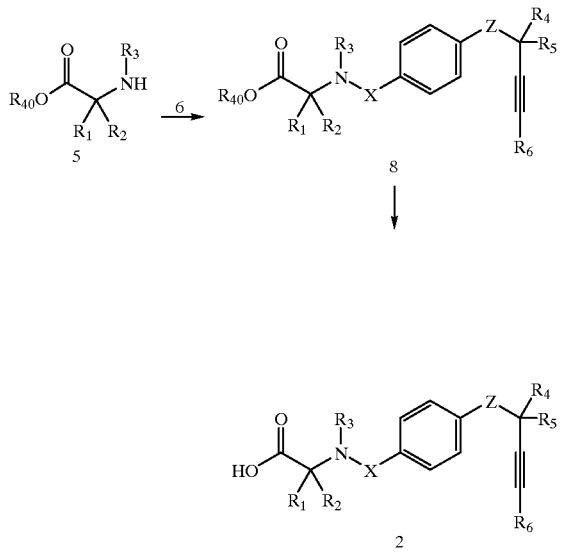

Compounds of formula 2 are also available without starting from an amino acid derivative 4. As shown in Scheme 2A, a compound of formula I is reacted with a compound of formula II (J is bromo or chloro, n is equal to 0 to 3, and R" is phenyl, substituted phenyl or arylthio) in the presence of an acid scavenger such as ethyldiisopropylamine, potassium carbonate, sodium carbonate, sodium diisopropylamide in a solvent such as isopropyl alcohol, acetonitrile, N,N-dimethylformamide in the temperature range 0° to 100° C. to give a compound of formula III, equivalent to compound 8.

Scheme 2A

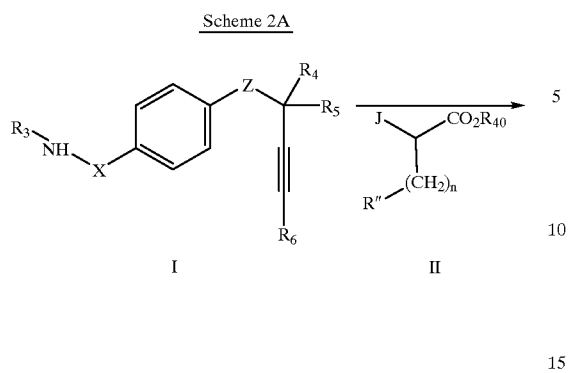

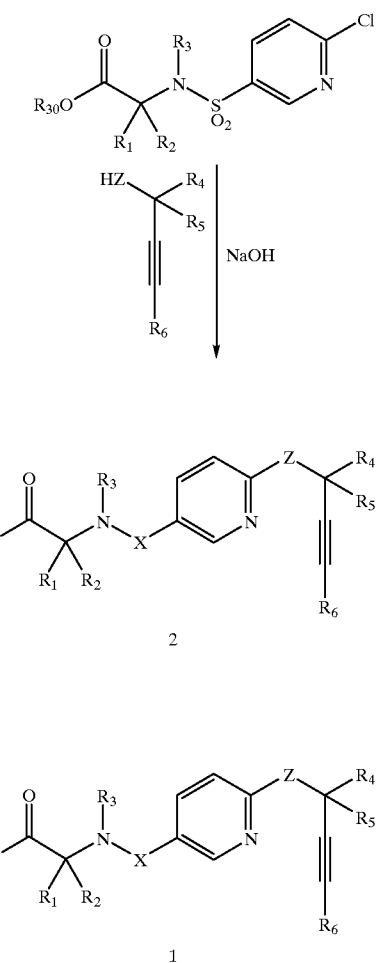

Compounds 1 of the invention containing a heteroaryl sulfonamide may be prepared as shown in Scheme 2B. The 6-chloropyridine 3-sulfonyl chloride is available from the corresponding amino-pyridine. Sulfonylation of the appropriate amino acid with this pyridyl sulfonyl chloride then provides the 6-chloropyridine sulfonamide. Base mediated displacement of the chloro substituent of the 6-chloropyridine sulfonamide with the desired propargylic alcohol, amine or thiol with concomitant ester hydrolysis gives carboxyic acid 2. Conversion of the acid into the corresponding hydroxamic acid as described in Scheme 1 then gives the pyridyl sulfonamide 1.

Scheme 2B

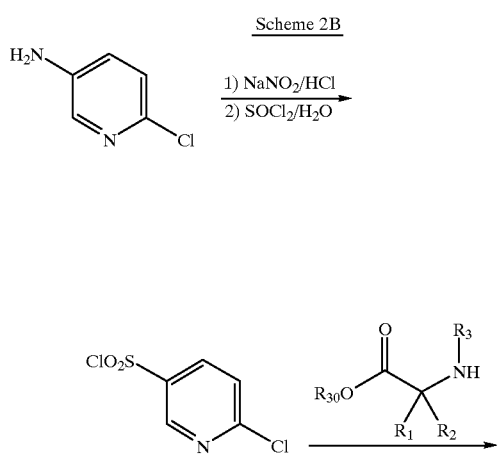

Methods of preparation of sulfonylating agents 6 are shown in Scheme 3. Thus, sulfonic acid salts 9, where $ZR_{50}$ is a hydroxy, thiol or substituted amino moiety may be alkylated with acetylenes 10, where J is a suitable leaving group such as halogen mesylate, tosylate, or triflate to give 11. Acetylenes 10 are commercially available or known compounds, or they may be synthesized by known methods by those skilled in the art. The sulfonic acid salts 11 may be converted into the corresponding sulfonyl chloride or other sulfonylating agent 6 by known methods, such as reaction with oxalyl chloride or other reagent compatible with substituents $R_4$, $R_5$ and $R_6$ and the acetylene. Alternatively, the disulfide 12 may be converted into di-acetylene 13 by reaction with compounds 10, followed by reduction of the disulfide bond to provide the analogous thiols which may be converted into 6 by known methods. Alkylation of the phenol, thiophenol, aniline or protected aniline 14 with 10 to give 15, followed by reaction with chlorosulfonic acid provide sulfonic acids 16 which are readily converted into 6 with oxalyl chloride or similar reagents. Thiophenols 17 are also precursors to 6 via protection of the thiol, alkylation of ZH, where Z is O, N or S, and deprotection of the sulfur followed by oxidation to the sulfonic acid 16.

Scheme 3
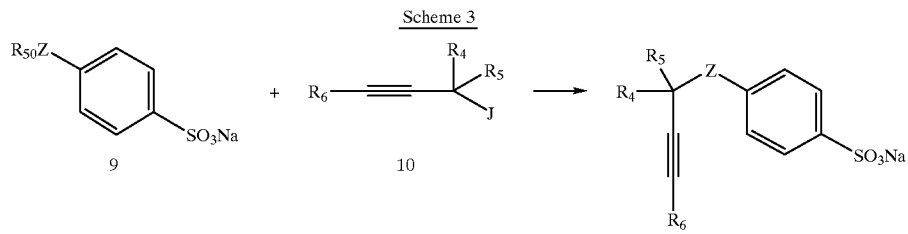
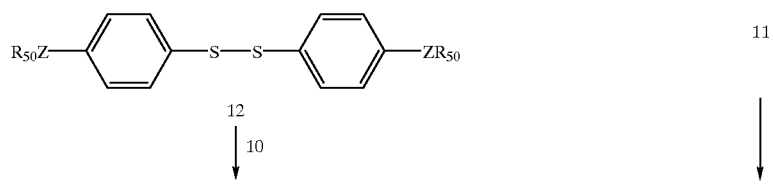
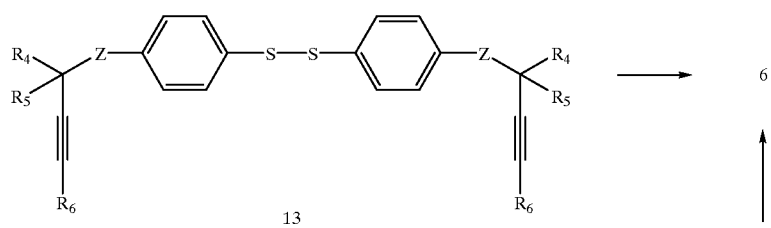
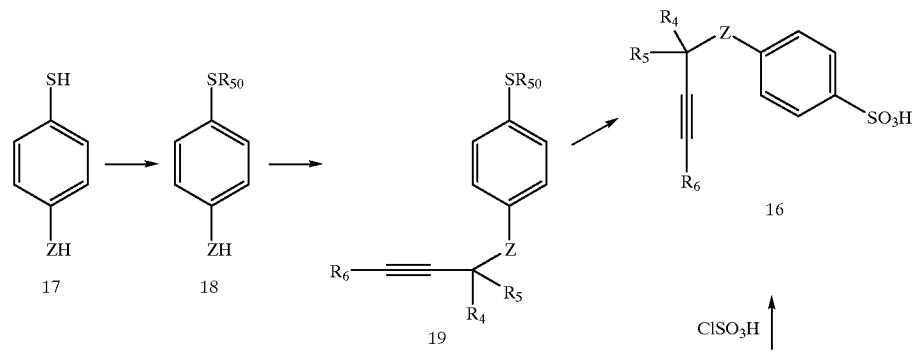
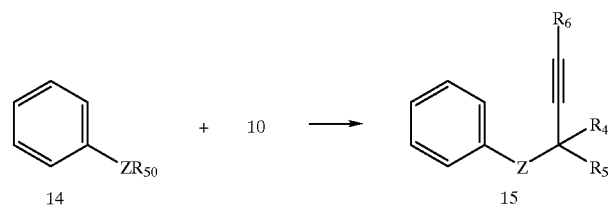
The phosphorus containing analogs of 8 may be prepared using similar methodology, as shown in Scheme 4.

Scheme 4

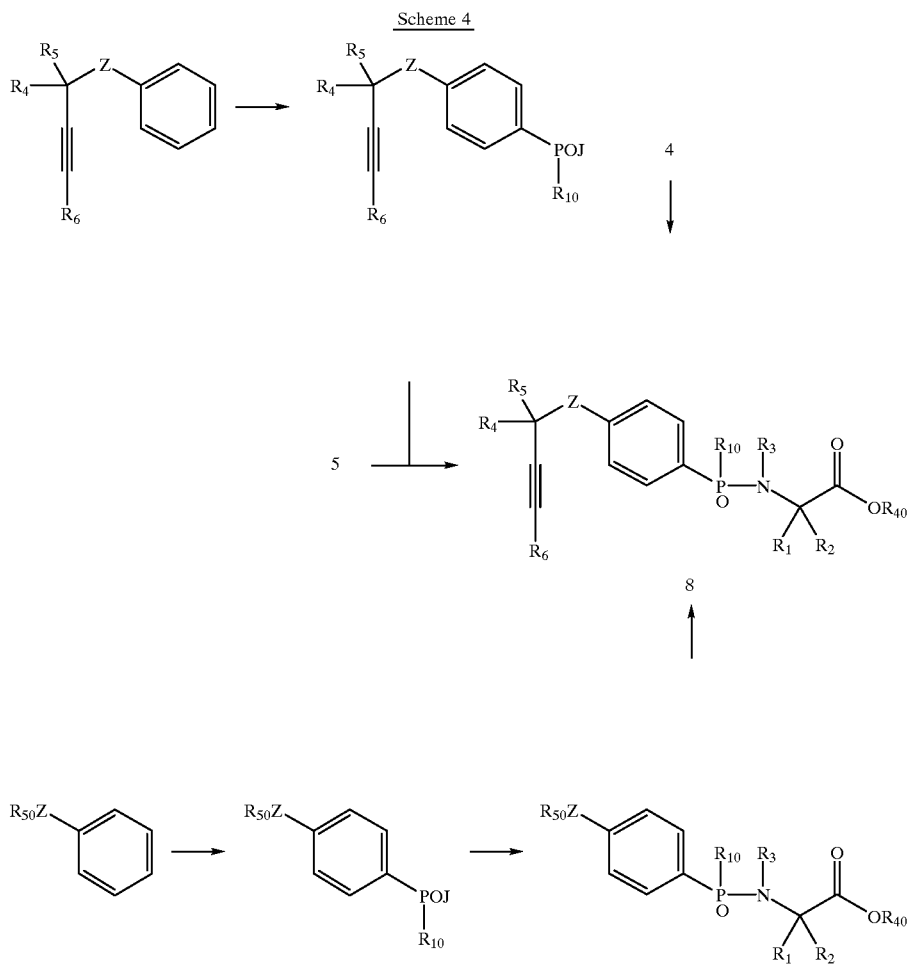

The acetylenic side chain may also be appended after sulfonylation or phosphorylation of the amino acid derivative, as shown in Scheme 5. Thus, the amino acid derivatives 4 and 5 can be sulfonylated or phosphorylated with compounds 20, where $ZR_{50}$ is hydroxy or protected hydroxy, thiol or amine, and, if necessary, alkylated as in Scheme 2, to give 21. Removal of the $R_{50}$ masking group to give 22 and subsequent alkylation of the resulting phenol, thiol or amine with 10 provides 8. In the case where $ZR_{50}$ is equal to OH, no deprotection step is required to give 22.

Scheme 5

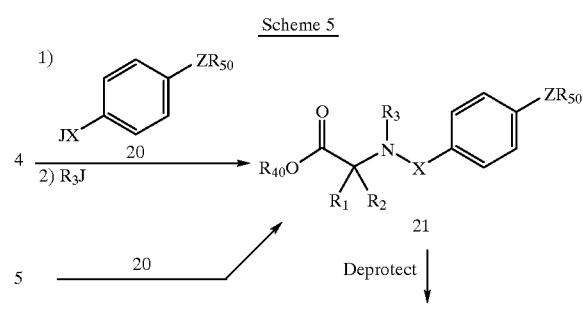

-continued

22

The propargylic amine analogs of 8 can be synthesized as shown in Scheme 6 starting from the amino acid derivatives 4 and/or 5. Sulfonylation or phosphorylation with para-nitro aryl compound 23, for example 4-nitrobenzenesulfonyl chloride, followed by alkylation with $R_3J$ (for 5) using a base such as potassium carbonate or sodium hydride in DMF provides 24. Reduction of the nitro moiety with hydrogen and palladium on carbon, tin chloride or other known method to give aniline 25 and subsequent alkylation with 10 then provides 8. Aniline 25 may be derivatized (26) prior to alkylation with 10 and then deprotected after the alkylation step.

Scheme 6

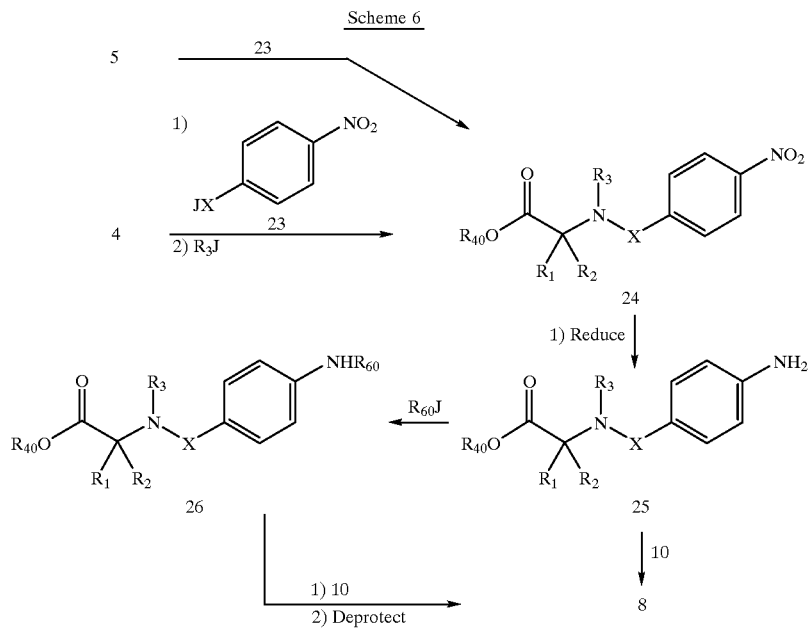

Acetylenic derivatives 8 are also accessible via the fluoro compounds 28, readily prepared from the amino acid derivatives 4 and/or 5 by reaction with fluoroaryl 27, as shown in Scheme 7. Displacement of the fluorine of 28 in the presence of a base such as sodium hydride with a masked hydroxy, thiol, or amino group (HZ$R_{70}$, where $R_{70}$ is a suitable protecting group) in a polar aprotic solvent such as DMF, followed by deprotection gives 29, which can then be alkylated with 10 to provide 8. Conversion of 28 to 29, where Z is sulfur, might also be accomplished with $Na_2S$, $K_2S$, NaSH or KS(C=S)OEt. Disulfide obtained as a result of this displacement followed by oxidation can be reduced to the desired thiol using triphenylphosphine or a similar reducing agent. The fluorine of 28 can also be displaced in a polar aprotic solvent with the propargylic derivative 30, where Z is O, S or NH, in the presence of a base such as sodium hydride, to give 8 directly.

Scheme 7

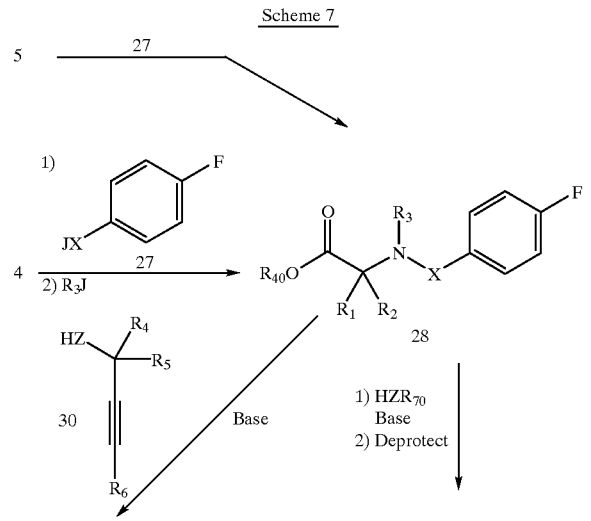

-continued

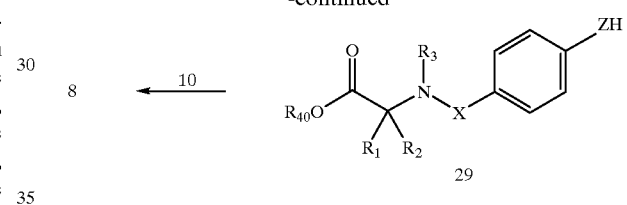

Compound 8, wherein Z is a methylene group, is available via 31, as shown in Scheme 8. Benzylic bromination of 31 with N-bromosuccinimide in a chlorinated hydrocarbon solvent provides bromide 32. This is followed by displacement of the bromide with the appropriate propynyl cuprate to provide sulfonamide 8.

Scheme 8

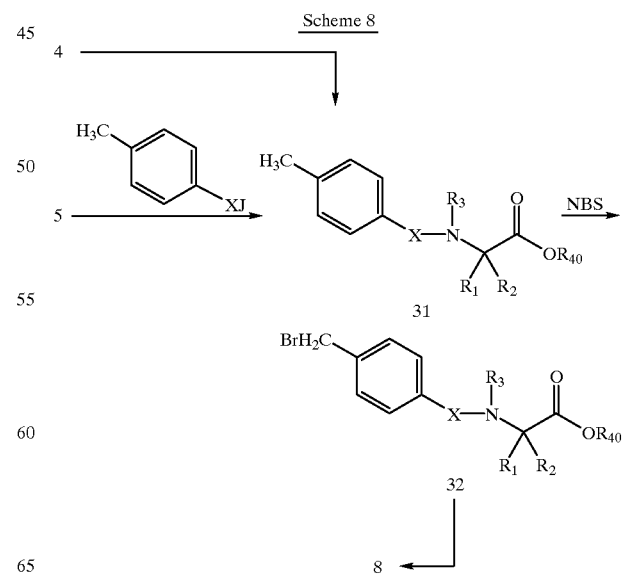

Methods for the solid phase synthesis of the compounds of the invention are shown in Scheme 9 and Scheme 10. In Scheme 9 an Fmoc protected amino acid, or any suitably N-protected amino acid, is bound to a resin using peptide coupling reagent such as 1,3-diisopropylcarbodiimide (DIC) and 1-hydroxybenzotriazole (HOBT) in a polar aprotic solvent such as DMF at room temperature. An amine such as piperidine in an inert solvent such as DMF at room temperature then removes the Fmoc masking moiety and the resulting free amine, 33, can be sulfonylated with compound 6 in the presence of a tertiary amine base or pyridine. The carboxylic acid 2 ($R_3$=H) is then released from the resin with TFA or other strong acid. The resulting carboxylic acids can be converted into the corresponding hydroxamic acids 1 ($R_3$=H) as in Scheme 1.

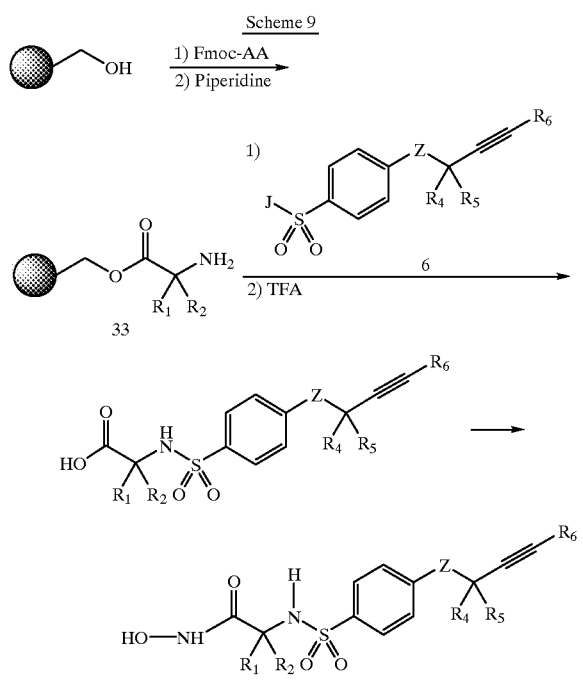

In Scheme 10 a hydroxylamine linked resin is constructed following known methods (Rickter, L. S.; Desai, M. C. *Tetrahedron Lett.* 1997, 38, 321) and a suitably protected amino acid is bound to the resin and deprotected as in Scheme 9 to give 34. Sulfonylation of the free amine may be followed by alkylation of the NH-sulfonamide with $R_3J$ and a base, wherein J is a leaving group such as halide sulfonate or triflate, or via a Mitsonobu protocol. Cleavage of the hydroxamate from the resin is then accomplished using a strong acid such as trifluoroacetic acid to provide 1. Alternatively, the NH-sulfonamide is cleaved from the resin without alkylating to give the NH-sulfonamide hydroxamic acids (1, $R_3$=H).

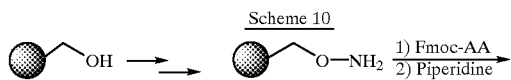

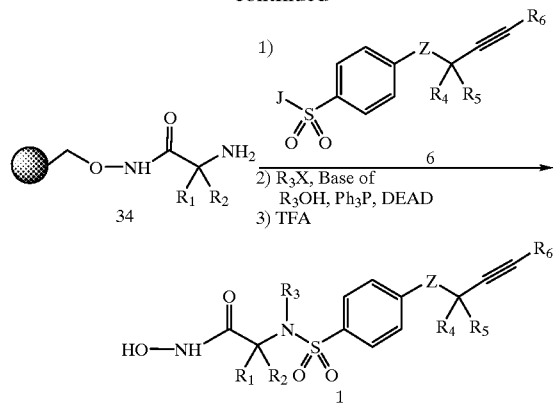

In Scheme 11 commercially available piperazine-2-carboxylic acid (35) or its ester (Demaine, D. A.; Smith, S.; Barraclough, P. *Synthesis* 1992, 1065; Rissi E.; Jucker, E. *Helv. Chim Acta* 1962, 45, 2383.) may be functionalized predominantly at the N-4 position, as described in U.S. Pat. No. 5,753,653 and in *Synthesis* 1992, 1065 and references cited therein, to give 36 or 37. Sulfonylation or phosphorylation at N-1 followed by the requisite functional group manipulations as described in Schemes 2–8, provides compounds of structure 2, wherein $R_1$ and $R_3$ together with the atoms to which they are attached form a piperazine ring. The t-butyl carbamate of compound 36 can be removed after sulfonylation or phosphorylation of N-1, followed by derivatization of N-4 with a variety of functional groups. Conversion to the hydroxamic acids is as shown in Scheme 1.

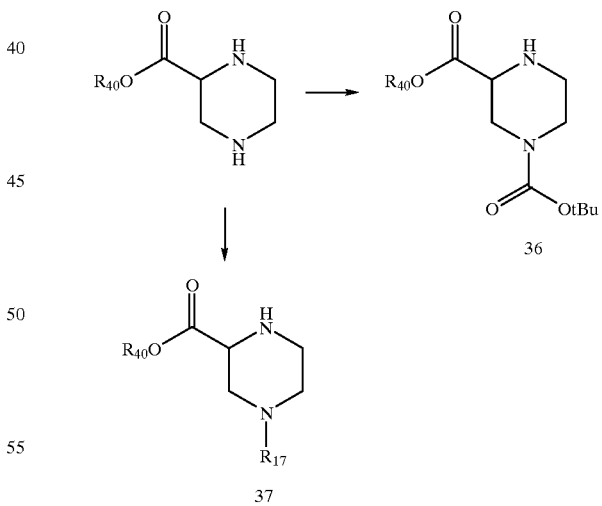

The preparation of intermediates for the synthesis of the diazepine or diazocine analogs of 1 is described in Scheme 12. An ester derivative 38 such as ethyl 1,4-dibromobutyrate, bearing two leaving groups, J, can react with a protected diamine 39, such as N,$N^1$-dibenzylethylenediamine in the presence of a tertiary amine base in a non-polar solvent such as benzene, to provide the 7 or 8-membered ring 40. Deprotection of 40 using hydrogen and a palladium catalyst gives the cyclic diamine 41. Functionalization of 41 predominantly at N-5 provides 42. Compound 42 may then be sulfonylated followed by removal of $R_{17}$, if desired, and subsequent alkylation, acylation or sulfonylation of N-5. Conversion into compound 1 is then accomplished according to Schemes 1–8. Alternatively, N-5 alkyl compounds can be prepared by carrying through the N-5 t-butyl carbamate through to the hydroxamic acid stage, followed by removal of the carbamate and N-5 alkylation with an alkyl halide and tertiary amine base in the presence of the hydroxamic acid.

solvents with a nucleophile, $R_{15}M$, in which M is lithium, magnesium halide or cerium halide to provide the saturated 6-membered ring 45. A variety of protecting groups may be required for functionality in $R_{15}$ prior to metallation. Compounds 45 may then be converted into compounds of structure 1 according to Schemes 1–8.

Scheme 12

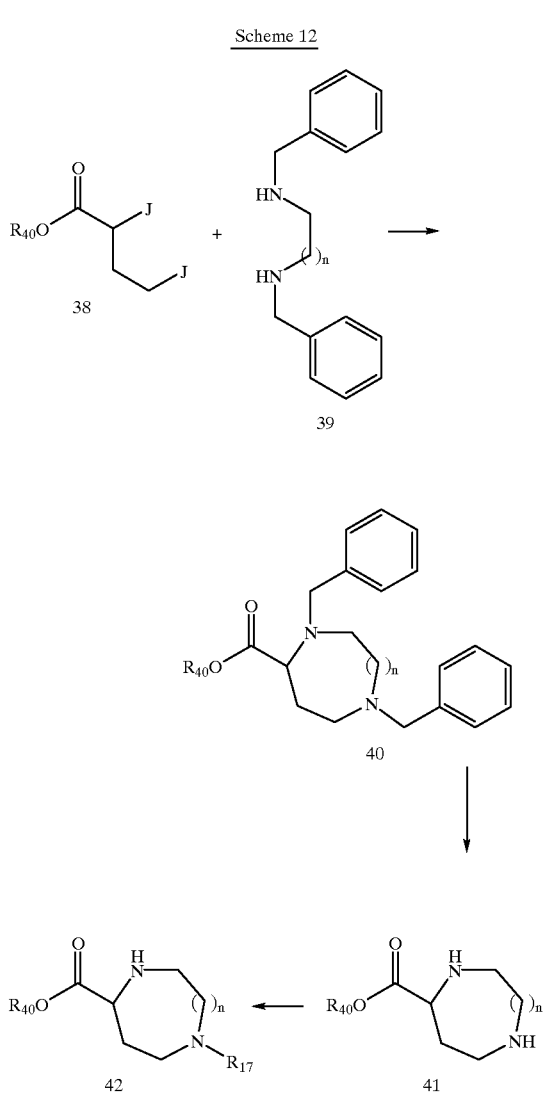

Scheme 13

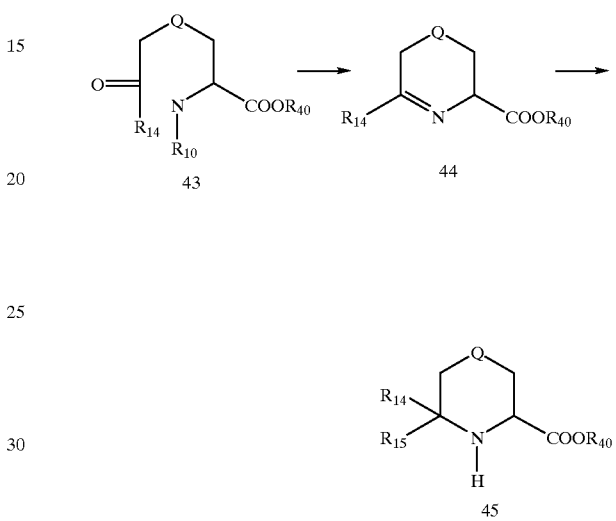

Piperidine, morpholine and piperazine derivatives of compound 1 are available according to Scheme 13. Aminoketone 43, wherein Q is O, S or $NR_{17}$ undergoes removal of protecting group $R_{10}$, wherein $R_{10}$ is a benzyl, t-butoxycarbonyl, benzyloxycarbonyl or other suitable masking group, followed by intramolecular reductive amination to give the cyclic imine 44. Imine 44 reacts in ethereal Thiomorpholines, thiazepines and thiazocines of the invention may be constructed according to Scheme 14. An ester 46 such as 1,3-dibromopropionate, containing two leaving groups, J, can react with an amino-thiol to provide thiazepine 47 which can then be converted into compounds of structure I according to Schemes 1–8. Alternatively, cysteine or homocysteine derivative 48, in the amino acid or amino-ester form, can be alkylated with alkyl halides such as 2-bromoethanol or 3-bromo-1-propanol to give alcohol 49 (R=OH) after sulfonylation or phosphorylation of the free amine group. The moiety $R_{90}$ of compound 49 is consistent with the methods disclosed in Schemes 2–8 for subsequent conversion into compounds 1 of the invention and includes nitro, fluoro, methoxy, hydroxy and —$ZCR_4R_5CCR_6$ where Z is O, $NR_{17}$, or S. Alcohol-sulfonamide 49 can be ring-closed using standard Mitsonobu conditions to afford thiomorpholine or thiazepine 50 which can be converted into compounds of structure 1 according to Schemes 1–8. The acyclic intermediate 49 can also be carried forward to the desired hydroxamic acids 49A and 49B via ester hydrolysis and hydroxamate formation, with or without prior alkylation of the sulfonamide nitrogen. The R moiety of compound 49 can be manipulated prior to conversion into 49B. For example, when R is a hydroxyl group, conversion of the —OH group into a leaving group followed by displacement with amines and subsequent ester hydrolysis and hydroxamate formation gives compounds 49B where R is a secondary amine.

Scheme 14
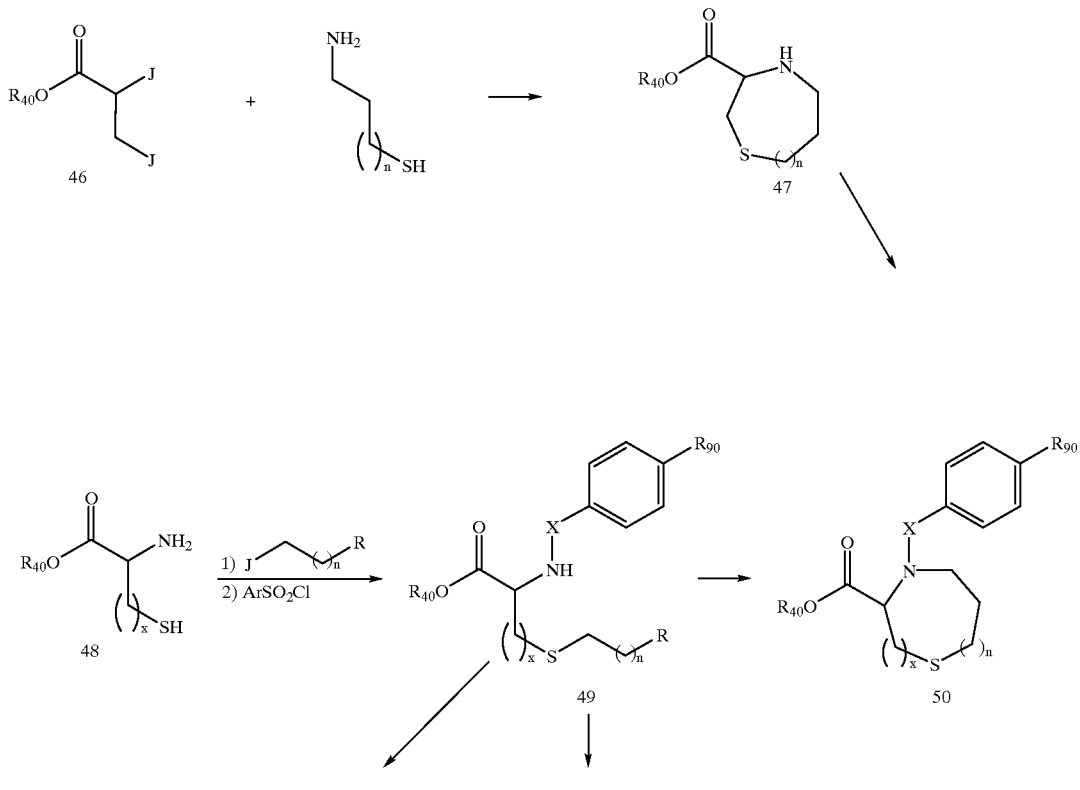
Diazepines or diazocines may be constructed according to Scheme 15, as described in *Bioorg. & Med. Chem. Lett.* 1998, 8, 2657, and modified according to Schemes 1–8 to provide diazepines of structure 1.
Scheme 15
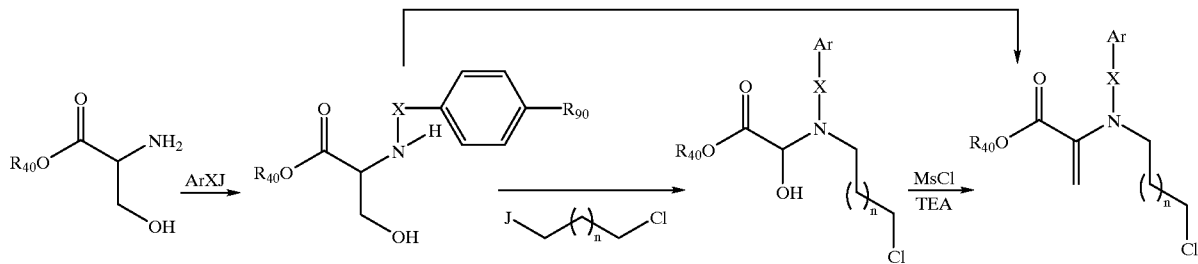

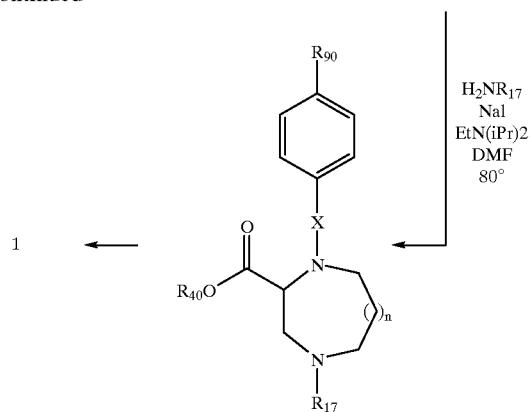

Morpholines, oxazepines and oxazocines of the invention are prepared as shown in Scheme 16. A serine derivative, 51a (x=1), is sulfonylated or phosphorylated to give 51b and then converted into the aziridine 51c. Nucleophilic ring opening of the aziridine with a bifunctional alcohol species, such as 2-bromoethanol, 1,3-propanediol or 3-chloro-1-propanol, then provides 52 (n=0,1) which is ring-closed via intramolecular alkylation or Mitsonobu reaction to form 53.

Compound 53 can be converted into compounds of structure 1 according to Schemes 1–8. The homoserine derivative 51a (x=2) can also be sulfonylated to give 51b, followed by O-alkylation to give 52, with protection of the sulfonamide-NH as required, and subsequent ring closure as before to give 53. Alternatively, the homoserine derivative 51b can be N-alkylated to provide 51d, followed by intramolecular etherification to give 53.

Scheme 16

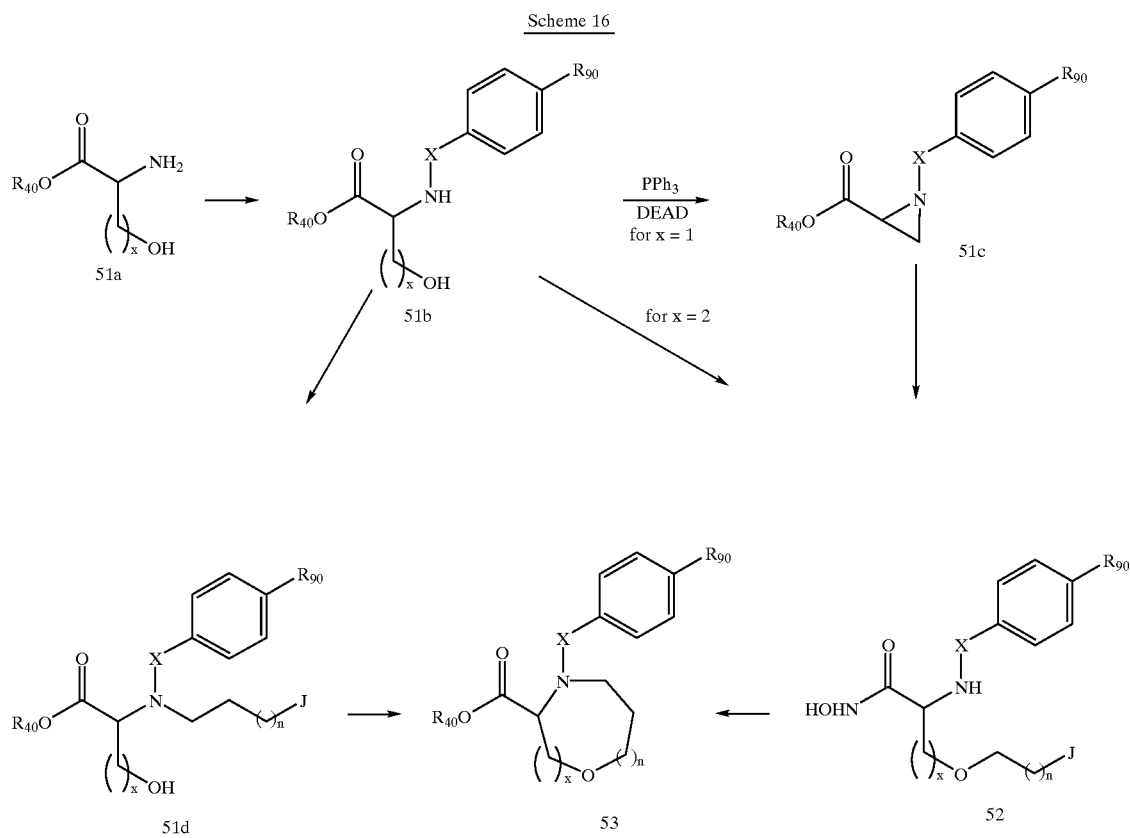

Methodology for preparing additional heterocyclic compounds of the invention are shown in Schemes 17 and 18. Aspartic acid derivatives may be accessed by direct sulfonylation or phosphorylation of aspartic acid to give 54, followed by functional group manipulation as shown in Scheme 17. Alternatively, condensation of isonitrile 55 with alpha-halo ester 56 provides the diester which is selectively deprotected with concomitant conversion of the isonitrile into the amine, 58. Sulfonylation or phosphorylation of 58 then provides 54. Peptide coupling of a primiary amine and compound 54 gives carboxamide 59 which can be cyclized using 1,3,5-trioxane to give heterocycle 60. Seven and eight-membered ring analogs of 60 can be prepared by coupling the appropriate secondary amine, in which one of the amine substituents bears a n alcohol or leaving group, to carboxylic acid 54. Intramolecular alkylation or Mitsonobu reaction then provides the cyclic structure. Compound 60 can be converted into compounds of structure 1 according to Schemes 1–8.

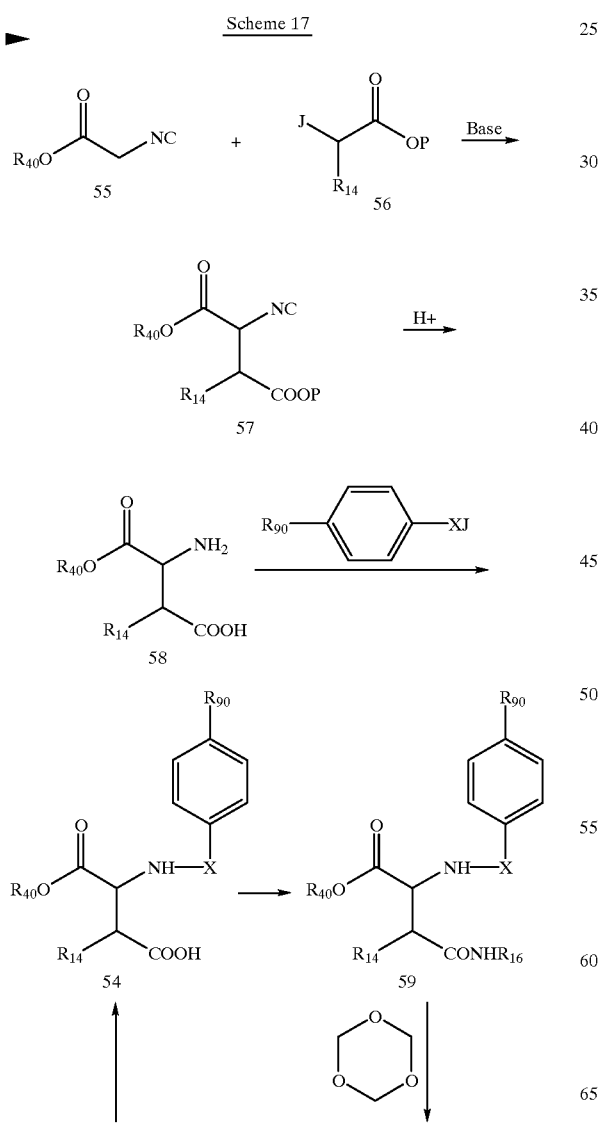

In Scheme 18 the construction of compounds of the invention containing heterocyclic rings with a 1,3-orientation of the sulfonamide or phosphinic acid amide nitrogen and a heteroatom is described. Compound 61, such as a diamine, an amino-alcohol or an amino-thiol, is sulfonylated or phosphorylated to give 62. Addition of a pyruvate or glyoxylate group under standard conditions then forms the heterocycle 63. Compound 63 can be converted into compounds of structure 1 according to Schemes 1–8.

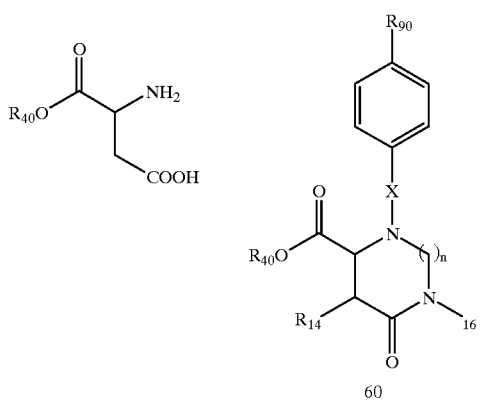

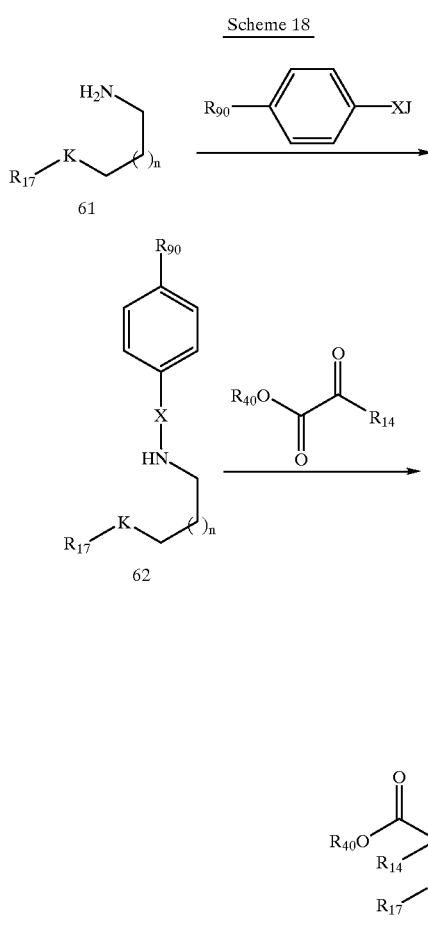

Compounds 1 of the invention derived from the amino acid D-4-hydroxyphenylglycine can be made as shown in Scheme 19. Esterification of the amino acid followed by protection of the amine as the t-butyl or fluorenylmethyl carbamate gives compound 64. Alkylation of the phenol via Mitsunobu reaction with the desired alcohol gives 65. Cleavage of the t-butyl or fluorenylmethyl carbamate using HCl or a secondary amine, respectively, then provides amino-ester 66. Compound 66 can then be sulfonylated to give NH-sulfonamide 67. At this point the NH-sulfonamide can be alkylated, or the amino acid side chain can be manipulated. Hydrolysis of the ester and subsequent conversion into the hydroxamic acid then provides compounds 1.

Scheme 19

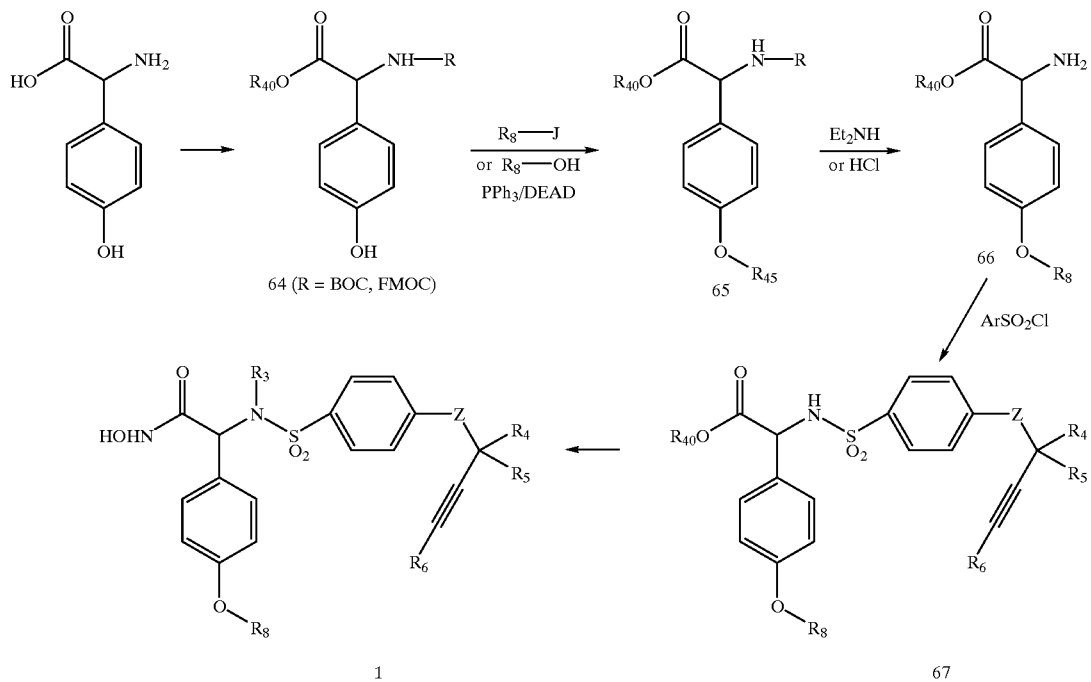

The N-alkyl sulfonamides defived from the amino acid D-4-hydroxyphenylglycine can be made as shown in Scheme 20 via sulfonylation of the ester of D-4-hydroxyphenyl glycine to give 68. $R_8$ is as previously defined, or is a protecting group known to those slilled in the art. Protection of the phenol with a trialkylsilyl, or other suitable protecting group, followed by N-alkylation with an alkyl halide in the presence of sodium hydride or potassium carbonate provides 69. Removal of the silyl protecting group and functionalization of the unmasked phenol via Mitsunobu or base-catalyzed alkylation then provides 70. Conversion of the ester into the desired hydroxamic acid then gives compounds 1 of the invention.

Scheme 20

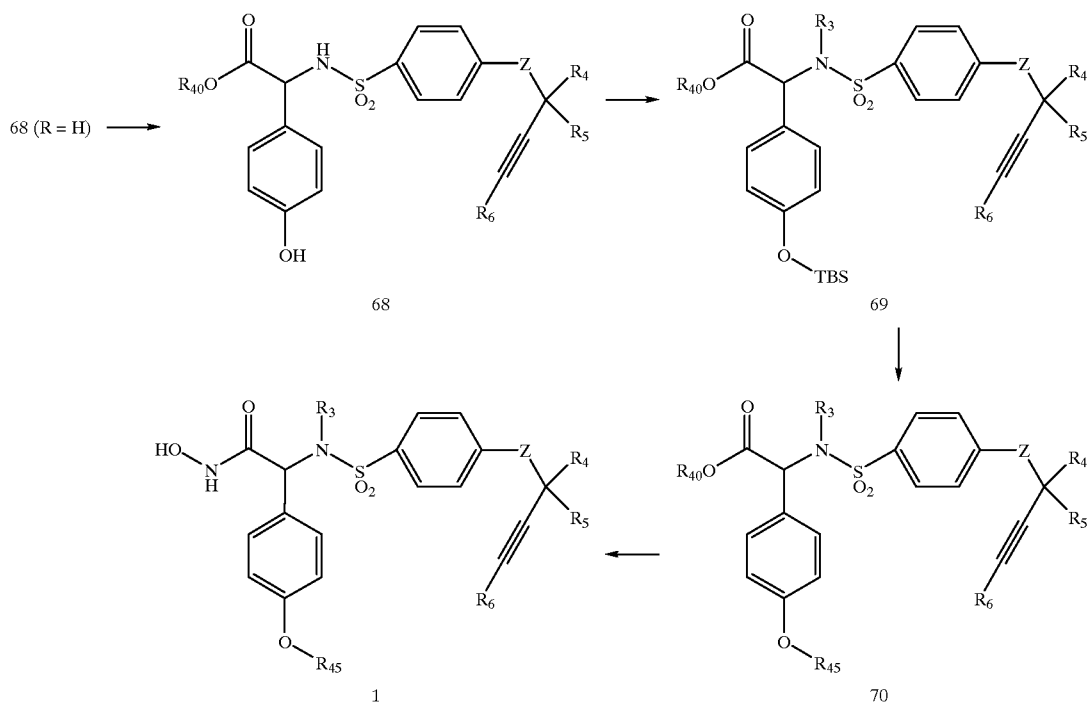

Compounds of the invention in which $R_1$ and $R_3$ together form a thiomorpholine ring can be made according to Scheme 2, in which the thiomorpholine ring is constructed prior to sulfonylation of the amine, or according to Scheme 14. The thiomorpholine ring may be manipulated after sulfonylation as shown in Scheme 21 (Shown for the thiomorpholine derived form D-penicillamine). Thus, sulfonylation of the thiomorpholine 71, gives 72. Oxidation of the thioether with m-chloroperbenzoic acid or other suitable oxidizing agent gives a mixture of diastereomeric sulfoxides 73. Pummerer rearrangement of the sulfoxides in acetic anhydride with subsequent elimination of the resulting acetate gives 74. Ester hydrolysis of 74 followed by hydroxamate formation then gives 75. Alternatively, 72 can be converted into the corresponding hydroxamic acid 76 which can be oxidized to the sulfoxide or sulfone with m-chloroperbenzoic acid or peracetic acid, respectively.

Scheme 21

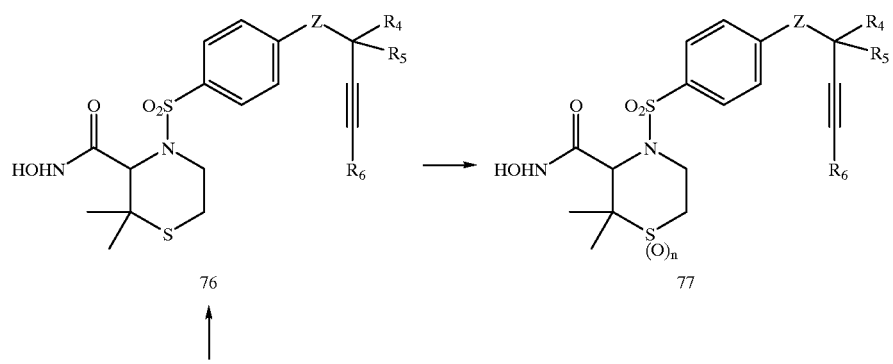

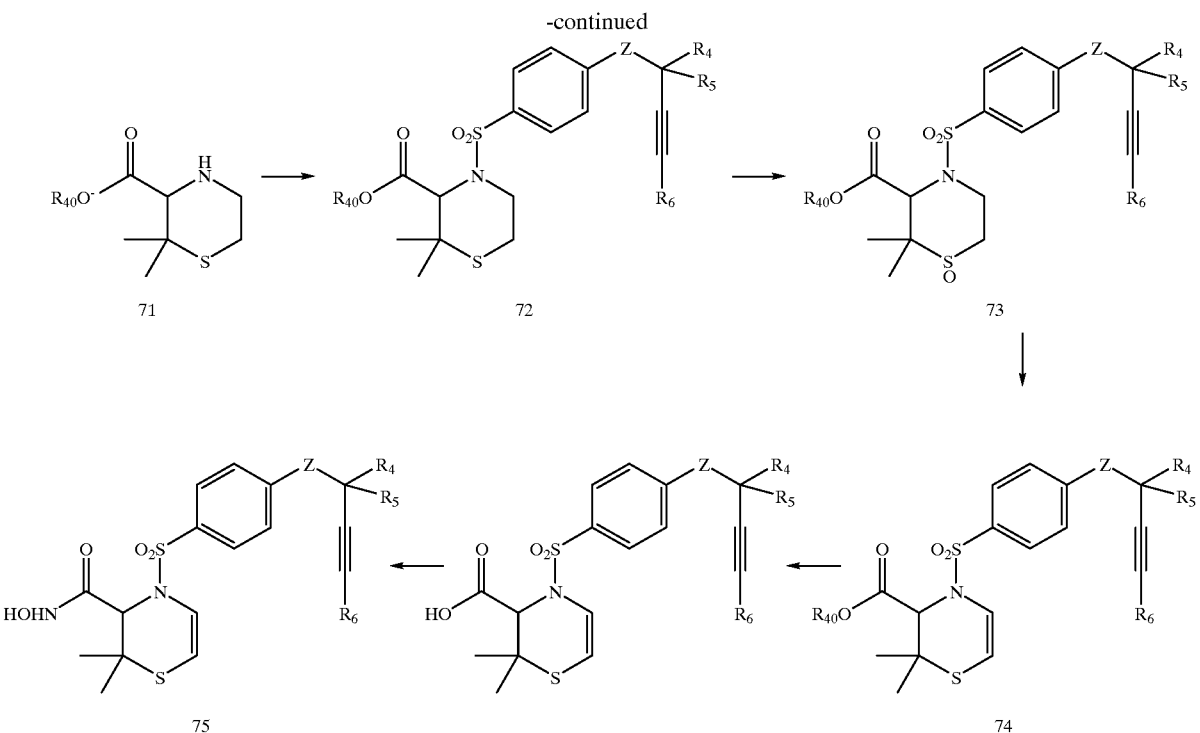

Spiro-fused thiomorpholines are available as shown in Scheme 22. Reaction of a cyclic ketone 78 (X=S, SO, SO2, NR) wih isocyanate 55 (Scheme 17) in the presence of a base such as sodium hydride gives formamide 79 after acid work-up. Use of an acyclic ketone in this reaction provides a route to other geminally disustituted 2-substituted thiomorpholines. Michael addition of 2-mercaptoethanol to 79 provides alcohol 80. Hydrolysis of the formamide then gives amino-ester 81. Sulfonylation of 81 gives hydroxy-sulfonamide 82 which can be cyclized to the thiomorpholine under Mitsunobu conditions to provide 83. Ester hydrolysis and hydroxamate formation then gives 84.

Scheme 22

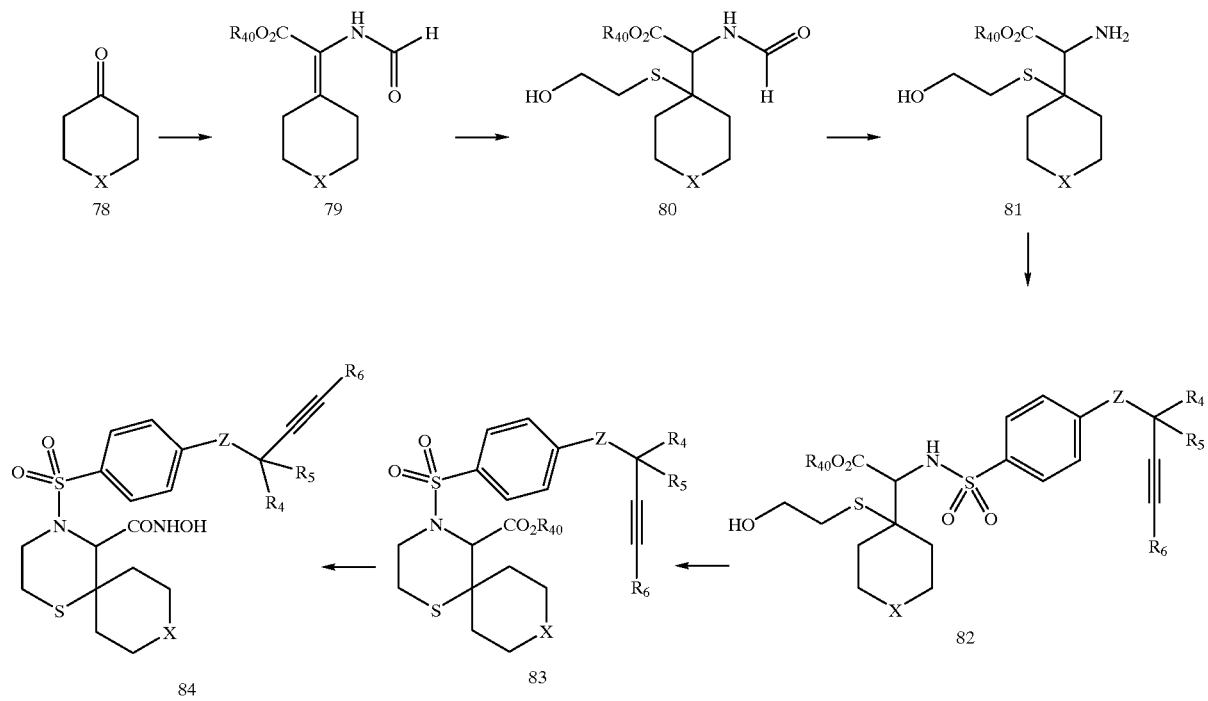

The preparation of 6-substituted thiomorpholines of the invention is shown, starting from D-penicillamine derivatives, in Schemes 23–26. Thus, in Scheme 23 D-penicillamine disulfide or other S-protected penicillamine is esterified and sulfonylated to give 85. Alkylation of the sulfonamide with an allylic bromide gives 86. Deprotection of the thiol using tributylphosphine in the case of the disulfide gives the thiol-olefin 87 which can be cyclized in the presence of benzoyl proxide or other radical initiator to give a mixture of 6-methyl thiomorpholines 88. Base hydrolysis followed by hydroxamate formation gives the cis-6-alkyl thimorpholine 89.

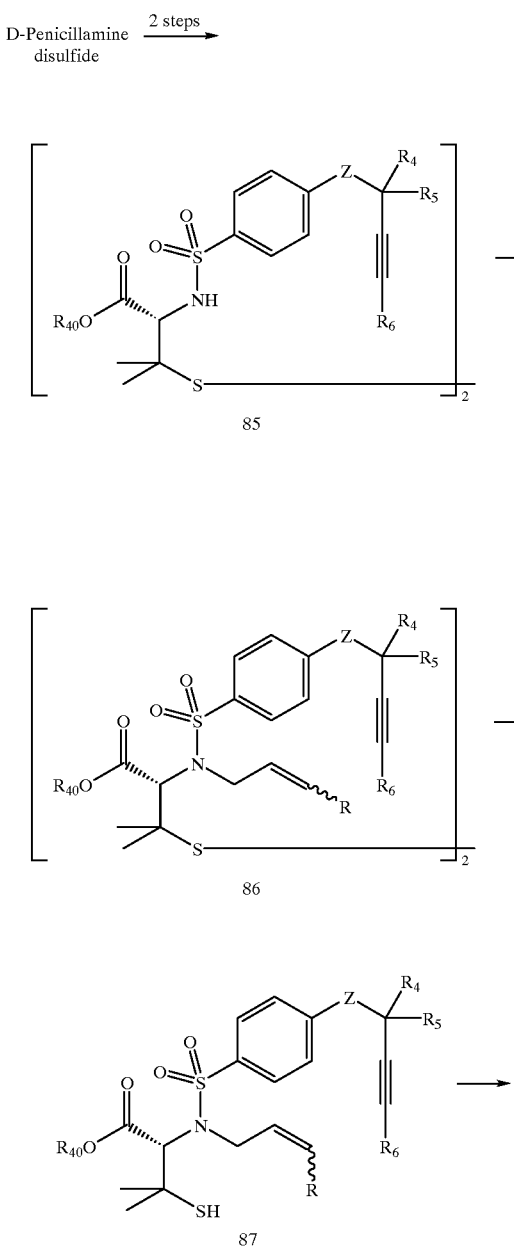

Scheme 23

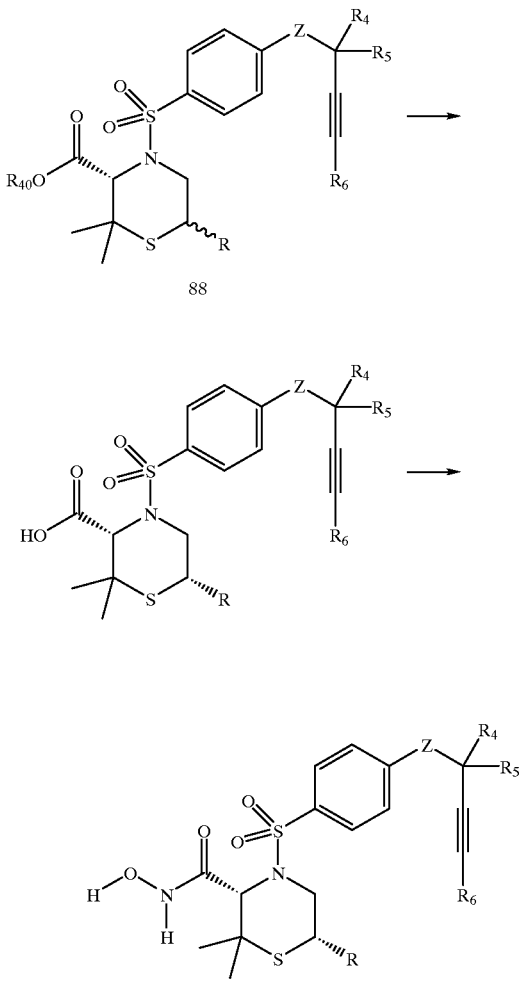

In the case where R of compound 86 is a t-butyl ester deprotection of the thiol occurs with concomitant cyclization via an intramolecular Michael addition to give 88 as the major diastereomer (~10:1) with the 6-substituent cis to the 3-substituent. As shown in Scheme 24, lithium iodide ester cleavage of 88 provides a mixture of mono and diacids, 90 and 91. The diacid, 91, can be directly converted into the dihydroxamic acid 92. Monoacid 90 can be converted into the O-benzyl protected hydroxamic acid 93. Deprotection of the t-butyl ester with TFA or HCl then gives the acid 94. Derivatization of the acid with amines using standard peptide coupling reagents (EDC, HOBT, etc.) to form amides 95, followed by deprotection of the benzyl protecting group with boron tris(trifuoroactetate) and TFA provides compounds 96. Alternatively, the t-butyl ester of compound 88 can be selectively cleaved with TFA or HCl to give a monoacid. This acid can be converted into a variety of amides followed by cleavage of the C-3 ester and its conversion to the corresponding hydroxamic acid, compound 96.

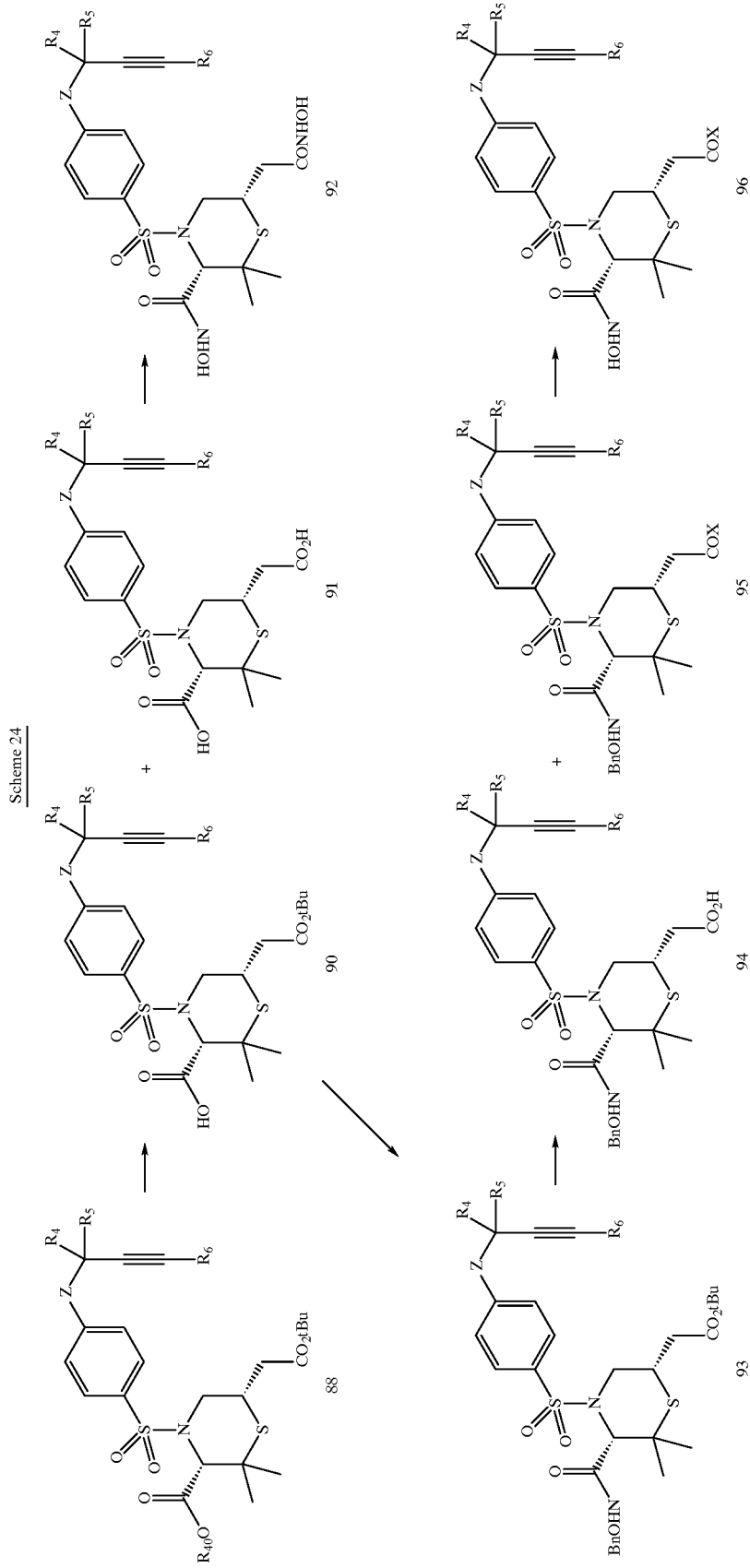

In Scheme 25, compound 87 (R=H) is cyclized in the presence of bromine to give 97 as a mixture of diastereomers. The bromine of 97 may be displaced with a variety of nucleophiles to give 98, followed by ester hydrolysis and hydroxamate formation to give derivatives of structure 99. For the specific example wherein 97 is reacted with sodium azide in DMF to give a mixture of azides 98 (X=$N_3$), the azides can be reduced and carbamoylated to give a separable mixture of t-butyl carbamates, 100a and 100b. Ester cleavage with lithium iodide in ethyl acetate followed by hydroxamate formation gives either diastereomer 101a or 101b (R=BOC). Removal of the BOC protecting group at the hydroxamate stage provides either amine 101a or 101b (R=H). Alternatively, the BOC protecting group of 100 can be removed and the resulting amine acylated, alkylated or sulfonylated prior to hydroxamate formation. In this manner, compounds 101 bearng a variety of functional groups at R may be obtained.

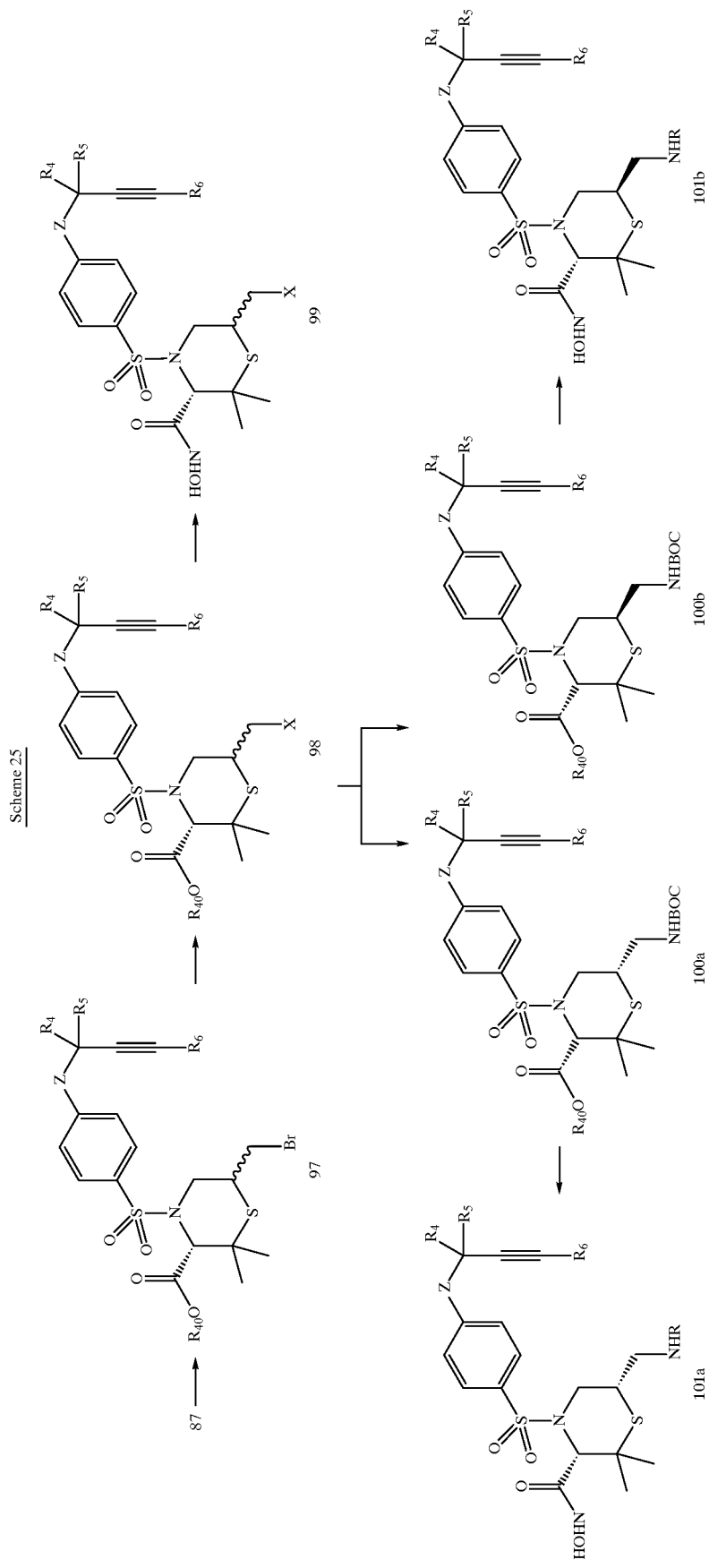

In Scheme 26 an alternative preparation of BOC-carbamate 100a is shown. Thus, selective cleavage of the t-butyl ester of compound 88 with TFA or HCl provides the acid 102. Curtius rearrangement of this acid using diphenylphosphoryl azide triethylamine and t-butanol gives BOC-carbamate 100a as a single diastereomer. Cleavage of the C-3 ester of 100a with lithium iodide (for $R_{40}$=Me) followed by conversion of the resulting acid into the O-benzyl protected hydroxamic acid, using O-benzylhydroxylamine and BOP-Cl gives 103. Deprotection of the t-butyl carbamate of 103 provides primary amine 104 which can be derivatized via alkylation, acylation or sulfonylation, followed by removal of the hydroxamate protecting group to provide analogs of structure 105.

be manipulated by standard methods to form the moieties defined by $R_1$, $R_2$, $R_3$ and $R_6$ of compounds 1. It is recognized by those skilled in the art of organic synthesis that the successful use of these methods is dependent upon the compatibility of substituents on other parts of the molecule. Protecting groups and/or changes in the order of steps described herein may be required.

Scheme 27 describes some of the routes that may be used to append substituents onto the acetylenic side chain. Thus, selectively protected propargylic alcohols 108 are available from the known terminal alkynes 106 via reaction with dihydropyran or other suitable alcohol protecting group to give 107. Metallation of 107 with n-butyllithium and subsequent quenching of the anion with paraformaldehyde then

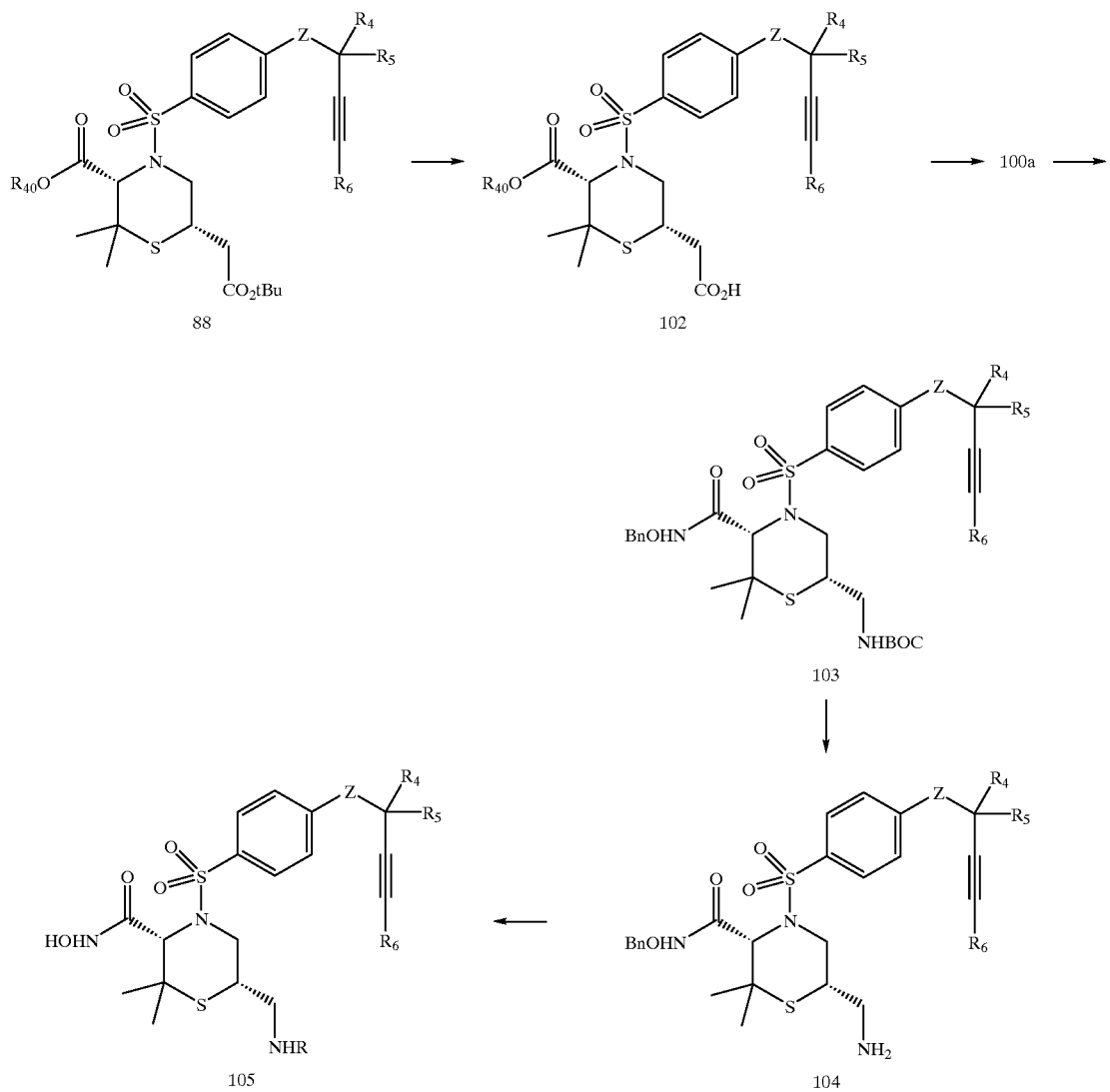

Scheme 26

Compounds of the invention can also be prepared by modifying substituents on the acetylenic side chain at any stage after sulfonylation or phosphorylation of the starting amino acid derivatives 4 or 5. Functional groups such as halogen, hydroxy, amino, aldehyde, ester, ketone, etc. may gives 108. The phenolic coupling partner for alcohols 108 is made by silylating 4-hydroxybenzenesulfonyl chloride in situ with bis(tdimethylsilyl)acetamide and then adding the thiomorpholine and a tertiary amine base. The resulting sulfonamide is desilylated in methanol to give 110. Alkylation of 110 with 108 using Mitsunobu conditions provides propargylic ethers 111. Removal of the THP protecting group of 111 with pyridinium para-toluenesulfonate in methanol gives the corresponding alcohol that is converted into a leaving group by sulfonylation or reaction with carbon tetrabromide and triphenylphosphine. Displacement of the leaving group with sodium azide followed by reduction and acylation, hydrolysis of the C-3 ester and hydroxamate formation gives 113. Alternatively, 111 can be hydrolyzed directly to the carboxylic acid and converted into hydroxamic acid 114. Removal of the THP protecting group at this stage then gives alcohol 115. The alcohol 115, where n is equal to 1, can be made by alkylating 110 directly with 2-butyne-1,4-diol using Mitsunobu conditions to provide 116. Compound 116 can then be converted into 113, where n is equal to 1, in the same manner as for alcohol 112. Compound 116 can be converted into hydroxamic acid 115 via acetylation of 116, followed by selective hydrolysis of the C-3 ester, hydroxamate formation and cleavage of the acetate with an aqueous base such as ammonium hydroxide. In a similar manner, ester derivatives of alcohols 115 and amide, sulfonamide and urea derivatives of 113 can be prepared.

Additional methods available for the derivatization of compounds of structure 116A (equivalent to compound 8 wherein $R_6$ is hydrogen) are shown in Scheme 28. Metallation of the terminal acetylene 116A followed by addition of an aldehyde or alkyl halide, sulfonate or triflate provides derivatives 117 and 118. Reaction of 116A with formaldehyde and an amine provides the Mannich addition product 119. Cyanogen bromide addition to 119 gives the propargylic bromide 120 which may be displaced with a variety of nucleophiles to give, for example, ethers, thioethers and amines, 121. Palladium catalyzed coupling reactions of 116A provide the aryl or heteroaryl acetylenes 122. It is recognized by those skilled in the art of organic synthesis that the successful use of these methods is dependent upon the compatibility of substituents on other parts of the molecule. Protecting groups and/or changes in the order of steps described herein may be required. The variables are described previously. $R_6$, $R_7$ and $R_8$ are as defined previously and may also include suitable protecting groups known to those skilled in the art.

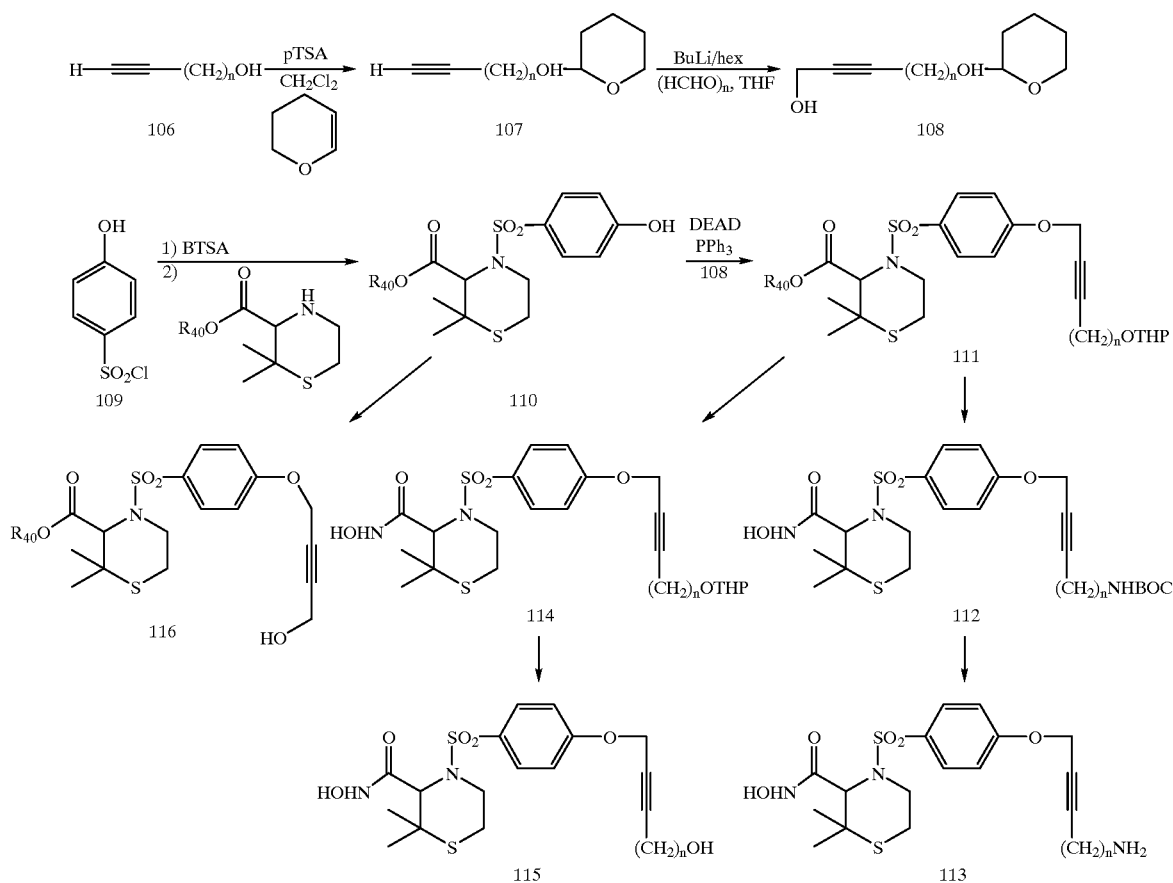

Scheme 28

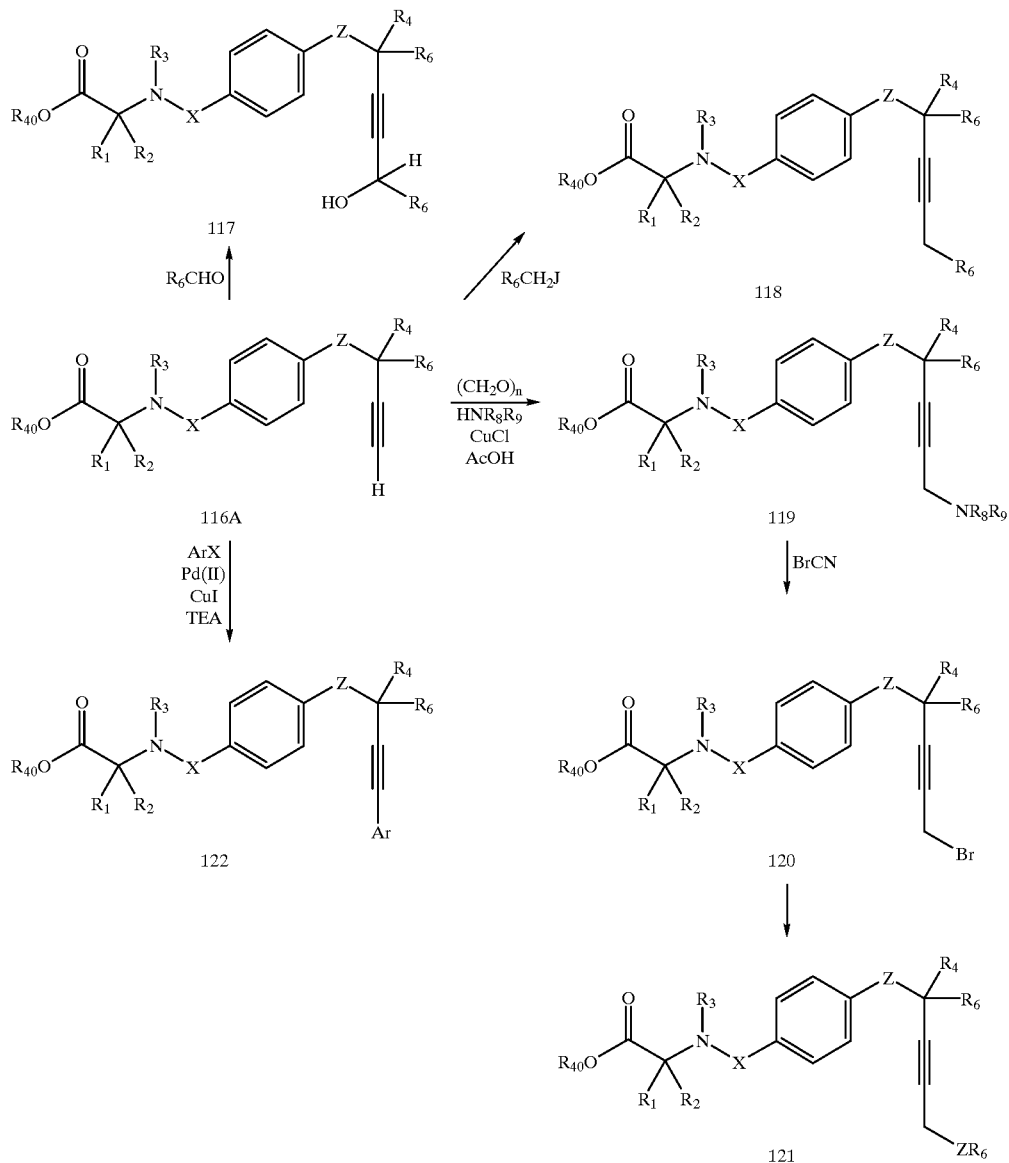

The following specific examples illustrate the preparation of representative compounds of this invention. The starting materials, intermediates, and reagents are either commercially available or can be readily prepared following standard literature procedures by one skilled in the art of organic synthesis.

Example 1

4-But-2ynyloxy-benzenesulfonic add sodium salt

To a solution of 52.35 g (0.225 mol) of 4-hydroxybenzenesulfonate sodium salt in 1 L of isopropanol and 225 mL of a 1.0N solution of sodium hydroxide was added 59.96 g (0.45 mol) of 1-bromo-2-butyne. The resulting mixture was heated to 70° for 15 h and then the isopropanol was removed by evaporation in vacuo. The resulting white precipitate was collected by filtration, washed with isopropanol and ether and dried in vacuo to give 56.0 g (100%) of the butynyl ether as a white solid.

Example 2

4-But-2-ynyloxy-benzenesulfonyl chloride

To a 0° solution of 43.8 mL (0.087 mol) of 2M oxalyl chloride/dichloroethane solution in 29 mL of dichloromethane was dropwise added 6.77 mL (0.087 mol) of DMF followed by 7.24 g (0.029 mol) of the product of Example 1. The reaction mixture was stirred for 10 minutes at 0° then let warm to room temperature and stirred for 2 days. The reaction was then poured into ice and extracted with 150 mL of hexanes. The organics were washed with water and brine, dried over $Na_2SO_4$, filtered and concentrated in vacuo to provide 6.23 g (88%) of the sulfonyl chloride as a yellow solid; m.p. 63–65° C. EI Mass Spec: 243.9 ($M^+$).

Example 3

But-2-ynyloxy-benzene

To a solution of 6.14 g (0.023 mol) of triphenylphosphine dissolved in 100 mL of benzene and 40 mL of THF was added 1.75 mL (0.023 mol) of 2-butyn-1-ol. After five minutes 2.00 (0.023 mol) phenol, dissolved in 10 mL of THF, was added to the reaction followed by 3.69 mL (0.023 mol) of diethyl azodicarboxylate. The resulting reaction mixture was stirred for 18 h at room temperature and then concentrated in vacuo. The residue was chromatographed on silica gel eluting with ethyl acetate/hexanes (1:10) to provide 2.18 g (70%) of the butynyl ether as a clear liquid. EI Mass Spec: 146.0 MH+

Example 4

4-But-2-ynyloxy-benzenesulfonyl chloride

To a solution of 0.146 g (1.0 mmol) of the product of Example 3 in 0.3 mL of dichloromethane in an acetone/ice bath under $N_2$ was dropwise added a solution of 0.073 mL (1.1 mmol) of chlorosulfonic acid in 0.3 mL of dichloromethane. After the addition was complete, the ice bath was removed and the reaction was stirred at room temperature for 2 h. To the reaction was then dropwise added 0.113 mL (1.3 mmol) of oxalyl chloride, followed by 0.015 mL DMF. The reaction was heated to reflux for 2 h and then diluted with hexane and poured into ice water. The organic layer was washed with brine, dried over sodium sulfate, and concentrated in vacuo to provide 0.130 mg (53%) of the desired product as a light brown solid.

Example 5

2-[(4-Methoxy-benzenesulfonyl)-methyl-amino]-3methyl-butyric acid tert-butyl ester To a solution of 1.00 g (2.915 mmol) of N-[(4-methoxyphenyl)sulfonyl]-D-valine tert-butyl ester (*J. Med. Chem.* 1997, 40, 2525) in 10 mL of DMF was added 0.128 g (3.207 mmol) of 60% sodium hydride. After 30 minutes at room temperature 0.45 mL (7.289 mmol) of iodomethane was added and the reaction was stirred for 15 h. The reaction mixture was then diluted with ether and washed with water. The organic layer was dried over $MgSO_4$, filtered and concentrated in vacuo. The residue was chromatographed on silica gel eluting with ethyl acetate/hexanes (1:10) to provide 0.993 g (95%) of the N-methyl sulfonamide as a colorless oil. Electrospray Mass Spec: 357.9 (M+H)+

Example 6

(2R)-2-[(4-Hydroxy-benzenesulfonyl)-methyl-amino]-3-methyl-butyric acid

To a 0° solution of 0.707 g (1.980 mmol) of the product of Example 5 in 50 mL of dichloromethane was added 9.4 mL (9.395 mmol) of a 1.0M solution of boron tribromide in dichloromethane. The resulting mixture was stirred at 0° for 0.5 h and then warmed to room temperature and stirred for an additional 4 h. The reaction mixture was then poured into a saturated sodium bicarbonate solution and extracted with dichloromethane. The aqueous layer was acidified with 5% HCl solution and extracted with dichloromethane. The combined organics were dried over $NaSO_4$, filtered and concentrated in vacuo. The residue was chromatographed on silica gel eluting with ethyl acetate/hexanes (1:1) to provide 0.271 g (48%) of the phenol-carboxylic acid as a colorless oil. Electrospray Mass Spec: 287.9 (M+H)+

Example 7

(2R)-2-[(4-Hydroxy-benzenesulfonyl)-methyl-amino]-3-methyl-butyric acid methyl ester To a solution of 0.240 g (0.836 mmol) of the product of Example 6 in 5.0 mL of DMF was added 0.211 g (2.509 mmol) of sodium bicarbonate followed by 0.104 mL (1.672 mmol) of iodomethane. The resulting mixture was stirred at room temperature for 4 h and then diluted with water and extracted with ether. The combined organics were washed with saturated sodium bicarbonate solution, dried over $MgSO_4$, filtered and concentrated in vacuo to provide 0.210 g (83%) of the methyl ester as a colorless oil. Electrospray Mass Spec: 300.3 (M–H)–

Example 8

2-[(4-But-2-ynyloxy-benzenesulfonyl)-methyl-amino]-3-methyl-butyric acid

To a solution of 0.187 g (0.714 mmol) of triphenylphosphine in 3 mL of benzene was added 0.053 mL (0.714 mmol) of neat 2-butyn-1-ol followed by a solution of 0.172 g (0.571 mmol) of the product of Example 7 dissolved in 1.0 mL of THF. To the resulting reaction mixture was added 0.112 mL (0.714 mmol) of diethyl azodicarboxylate and the reaction was stirred for 15 h at room temperature and then concentrated in vacuo. The residue was chromatographed on silica gel eluting with ethyl acetate/hexanes (1:10) to provide 0.159 g (79%) of the butynyl ether-methyl ester.

To a solution of 0.159 g (0.450 mmol of the butynyl ether-methyl ester dissolved in 6.0 mL of methanol/THF (1:1) was added 0.5 mL of a 5.0N solution of sodium hydroxide. The resulting mixture was stirred at room temperature overnight and then acidified with 10% HCl solution and extracted with dichloromethane. The combined organics were dried over $MgSO_4$, filtered and concentrated in vacuo to provide 0.138 g (90%) of the carboxylic acid as a white solid. Electrospray Mass Spec: 338.0 (M–H)–

Example 9

2-[(4-But-2-ynyloxy-benzenesulfonyl)-methyl-amino]-N-hydroxy-3-methyl-butyramide To a 0° solution of 0.48 mL (0.965 mmol) of a 2.0M solution of oxalyl chloride in dichloromethane, diluted with 4.1 mL of dichloromethane, is added 0.075 mL (0.965 mmol) of DMF and the reaction is stirred for 15 minutes at 0°. A solution of 0.109 g (0.322 mmol) of the carboxylic acid product of Example 8, dissolved in 1 mL of DMF, was added to the reaction and the resulting mixture is stirred for 1 h at room temperature and then poured into a 0° mixture of 1.0 mL of water, 4 mL of THF and 1.0 mL of a 50% aqueous solution of hydroxylamine. The reaction is allowed to warm to room temperature overnight and the organics are then concentrated in vacuo. The residue is diluted with ethyl acetate, washed with 5% HCl solution, water and saturated sodium bicarbonate, dried over $Na_2SO_4$, filtered and concentrated in vacuo to provide 0.102 g (89%) of the hydroxamic acid as a white solid. Electrospray Mass Spec 354.9 (M+H)+

Example 10

2-[(4-Fluoro-benzenesulfonyl)-methyl-amino]-3-methyl-butyric acid methyl ester

To a solution of 6.00 g (0.051 mol) of D, L-valine in 380 mL of THF/water (1:1) was added 10.9 mL (0.077 mol) of triethylamine followed by 9.94 g (0.051 mol) of 4-fluorobenzenesulfonyl chloride and the resulting mixture was stirred for 15 h at room temperature. The THF was then removed in vacuo and the resulting solution was extracted with ethyl acetate. The combined organics were washed with 10% HCl solution and water, dried over $MgSO_4$, filtered and concentrated in vacuo to provide 4.8 g of the sulfonamide as a white solid.

To a solution of 4.8 g (0.017 mol) of the sulfonamide in 30 mL of DMF was added 14.5 g (0.105 mol) of potassium carbonate followed by 4.35 mL (0.070 mol) of iodomethane. The reaction was stirred at room temperature for 5 h and then diluted with water and extracted with ether. The combined organics were washed water, dried over $MgSO_4$, filtered and concentrated in vacuo. The residue was chromatographed on silica gel eluting with ethyl acetate/hexanes (1:10) to provide 2.8 g (53%) of the methyl ester as a colorless oil. Electrospray Mass Spec 303.9 (M+H)+

Example 11

2-[(4-Fluoro-benzenesulfonyl)-methyl-amino]-3-methyl-butyric acid

To a solution of 2.7 g (8.910 mmol) of the product of Example 10 in 90 mL of THF/methanol (1:1) was added 45 mL of a 1.0N sodium hydroxide solution and the reaction was stirred at room temperature for 24 h. The reaction mixture was then acidified with 10% HCl solution and extracted with ethyl acetate. The combined organics were dried over $MgSO_4$, filtered and concentrated in vacuo to provide 2.5 g (97%) of the carboxylic acid as a white waxy solid. Electrospray Mass Spec 287.9 (M–H)–

Example 12

2-[(4But-2ynyloxy-benzenesulfonyl)-methyl-amino]-3-methyl-butyric acid

To a solution of 3.17 mL (0.042 mol) of 2-butyn-1-ol in 60 ml of DMF at room temperature was added 1.70 g (0.040 mol) 60% sodium hydride. The resulting mixture was stirred for 0.5 h and then a solution of 2.45 g (8.478 mmol) the product of Example 11 dissolved in 20 mL of DMF was added to the reaction. The reaction mixture was then heated to reflux for 24 h, cooled to room temperature and then acidified to pH 2 with 10% HCl solution. After stirring for 1 h the resulting mixture was diluted with water and extracted with ethyl acetate. The combined organics were then dried over $MgSO_4$, filtered and concentrated in vacuo. The residue was chromatographed on silica gel eluting with ethyl acetate/hexanes (1:2) to provide 1.67 g (58%) of the desired carboxylic acid product as a white solid identical to the product of Example 8.

Example 13

(4-Fluoro-benzenesulfonylamino)acetic add ethyl ester

To a solution of 4.00 g (0.029 mol) of glycine ethyl ester hydrochloride in 40 mL of chloroform and 7.0 mL of pyridine was added 5.58 g (0.029 mol) of 4-fluorobenzenesulfonyl chloride and the reaction was stirred at room temperature for 15 h. The reaction mixture was then washed with water and 5% HCl solution and the organics were dried over $MgSO_4$, filtered and concentrated in vacuo. The resulting white solid was washed with ether/hexanes (1:1) and dried in vacuo to provide 4.72 g (63%) of the sulfonamide as a white solid. Electrospray Mass Spec 261.8 (M+H)+

Example 14

[(4-Fluoro-benzenesulfonyl)-methyl-amino]-acetic acid ethyl ester

To a solution of 3.00 g (0.011 mol) of the product of Example 13 in 30 mL of DMF was added 4.76 g (0.034 mol) of potassium carbonate followed by 1.43 mL (0.023 mol) of iodomethane. The reaction was stirred at room temperature for 5 h and then diluted with water and extracted with ether. The combined organics were washed water, dried over $MgSO_4$, filtered and concentrated in vacuo. The residue was chromatographed on silica gel eluting with ethyl acetate/hexanes (1:3) to provide 3.0 g (95%) of the N-methyl sulfonamide as a colorless oil. Electrospray Mass Spec 275.9 (M+H)+

Example 15

[(4-Fluoro-benzenesulfonyl)-methyl-amino]-acetic add

According to the procedure of Example 11, 3.0 g (0.011 mol) of the product of Example 14 provided 2.32 g (86%) of the carboxylic acid as a white solid. Electrospray Mass Spec 245.9 (M–H)–

Example 16

[(4-But-2-ynyloxy-benzenesulfonyl)-methyl-amino]-acetic acid

According to the procedure of Example 12, 0.350 g (1.417 mmol) of the product of Example 15 provided 0.164 g (39%) of the butynyl ether-carboxylic acid as a white solid. Electrospray Mass Spec 297.9 (M+H)+

Example 17

2-[(4-But-2-ynyloxy-benzenesulfonyl)-methyl-amino]-N-hydroxy-acetamide

According to the procedure of Example 9, 0.139 g (0.468 mmol) of the product of Example 16 provided 0.118 g (81%) of the hydroxamic acid as a white solid. Electrospray Mass Spec 312.9 (M+H)+

Example 18

2-[(4-Methoxy-benzenesulfonyl)-methyl-amino]-3-methyl-butyric acid

To a solution of 0.250 g (0.700 mmol) of the product of Example 5 in 1.0 mL of dichloromethane was added 0.5 mL of trifluoroacetic acid and the resulting mixture was stirred for 2 h at room temperature and then concentrated in vacuo. The residue was chromatographed on silica gel eluting with a gradient of ethyl acetate/hexanes (1:3) to (1:1) to provide 0.211 g (100%) of the carboxylic acid as a colorless oil. Electrospray Mass Spec 300.0 (M–H)–

Example 19

N-Hydroxy-2-[(4-methoxy-benzenesulfonyl)-methyl-amino]-3-methyl-butyramide

According to the procedure of Example 9, 0.179 g (0.595 mmol) of the product of Example 18 provided 0.156 g (83%) of the hydroxamic acid as a colorless oil. Electrospray Mass Spec 316.9 (M+H)+

Example 20

(4-But-2-ynyloxy-benzenesulfonylamino)-acetic acid ethyl ester

To a solution of 1.00 g (7.163 mmol) of glycine ethyl ester in 10 mL of chloroform and 2.0 mL of pyridine was added 1.75 g (7.163 mmol) of 4-but-2-ynyloxy-benzenesulfonyl chloride and the reaction was stirred at room temperature for 15 h. The reaction mixture was then diluted with ether and the organics were washed with 5% HCl solution and water, dried over MgSO4, filtered and concentrated in vacuo. The resulting brown solid was washed with ether to provide 0.96 g (43%) of the sulfonamide as a white solid. Electrospray Mass Spec 311.8 (M+H)+

Example 21

[(4-But-2-ynyloxy-benzenesulfonyl)-pyridin-3-ylmethyl-amino]-acetic acid ethyl ester To a solution of 0.300 g (0.965 mmol) of the product of Example 20 in 5.0 mL of DMF was added 0.419 g (3.038 mmol) of potassium carbonate followed by 0.166 g (1.013 mmol) of 3-picolyl chloride hydrochloride. The resulting mixture was stirred at room temperature for 15 h and then diluted with ether and water. The organics were washed with water, dried over $Na_2SO_4$, filtered and concentrated in vacuo to give a pale yellow solid. The solid was washed with ether/hexanes (1:1) and dried in vacuo to provide 0.334 g (86%) of the N-picolyl sulfonamide as a tan solid. Electrospray Mass Spec 402.9 (M+H)+

Example 22

[(4-But-2ynyloxy-benzenesulfonyl)-pyridin-3-ylmethyl-amino]-acetic acid

To a solution of 0.282 g (0.701 mmol) of the product of Example 21 in 7.0 mL of THF/methanol (1:1) was added 3.5 mL of a 1.0N solution of sodium hydroxide and the reaction was stirred overnight at room temperature. The reaction was then neutralized with 5% HCl solution and extracted with dichloromethane. The combined organics were dried over $Na_2SO_4$, filtered and concentrated in vacuo to provide 0.216 g (82%) of the carboxylic acid as a pale yellow solid. Electrospray Mass Spec 375.0 (M+H)+

Example 23

2-[(4-But-2-ynyloxy-benzenesulfonyl)-pyridin-3-ylmethyl-amino]-N-hydroxy-acetamide hydrochloride To a 0° solution of 0.71 mL (1.412 mmol) of a 2.0M solution of oxalyl chloride in dichloromethane, diluted with 6.2 mL of dichloromethane, is added 0.109 mL (1.412 mmol) of DMF and the reaction is stirred for 15 minutes at 0°. A solution of 0.176 g (0.471 mmol) of the carboxylic acid product of Example 22, dissolved in 1 mL of DMF, was added to the reaction and the resulting mixture is stirred for 1 h at room temperature and then poured into a 0° mixture of 1.4 mL of water, 7.0 mL of THF and 1.4 mL of a 50% aqueous solution of hydroxylamine. The reaction is allowed to warm to room temperature overnight and the organics are then concentrated in vacuo. The residue is diluted with ethyl acetate, washed with water and saturated sodium bicarbonate, dried over $Na_2SO_4$, filtered and concentrated in vacuo to provide 0.123 g (67%) of the hydroxamic acid as a white solid.

To a solution of 0.119 g (0.306 mmol) of the amino-hydroxamic acid dissolved in 5.0 mL of dichloromethane and 5.0 mL of methanol was added 0.61 mL (0.61 mmol) of a 1.0M solution of HCl in ether. The resulting mixture was stirred for 1 h at room temperature and then concentrated in vacuo. The residue was dissolved in 1.0 mL of dichloromethane and 10 mL of ether was added. The resulting precipitate was filtered, washed with ether and dried in vacuo to provide 0.096 g (74%) of the hydrochloride salt of the amino-hydroxamic acid as a brown solid. Electrospray Mass Spec 389.9 (M+H)+

Example 24

(4-But-2-ynyloxy-benzenesulfonylamino)-acetic acid

To a solution of 0.30 g (0.965 mmol) of the product of Example 20 in 10 mL of THF/methanol (1:1) was added 4.8 mL of a 1.0N sodium hydroxide solution and the reaction was stirred overnight at room temperature and then acidified to pH 2 with 10% HCl solution. The resulting mixture was extracted with dichloromethane and the combined organics were dried over MgSO4, filtered and concentrated in vacuo to provide 0.238 g (83%) of the sulfonamide as a white solid. Electrospray Mass Spec 281.9 (M–H)–

Example 25

2-(4-But-2-ynyloxy-benzenesulfonylamino)-N-hydroxy-acetamide

To a solution of 0.150 g (0.505 mmol) of the product of Example 24 dissolved in 2.7 mL of DMF was added 0.082 g (0.606 mmol) of 1-hydroxybenzotriazole hydrate (HOBT) followed by 0.129 g (0.672 mmol) of 1-(3-dimethylaminopropyl)-3-ethylcarbodiimide hydrochloride (EDC). The resulting mixture was stirred at room temperature for 1 h and then 0.15 mL of a 50% aqueous hydroxylamine solution was added. The reaction was then stirred overnight and then diluted with ethyl acetate. The organics were washed with 5% HCl solution, water and saturated sodium bicarbonate solution and then dried over MgSO4, filtered and concentrated in vacuo to provide 0.086 g (54%) of the hydroxamic acid as a white solid. Electrospray Mass Spec 298.9 (M+H)+

Example 26

2-(4-But-2-ynyloxy-benzenesulfonylamino)-3-methyl-butyric acid

To a solution of 0.500 g (4.255 mmol) D,L-valine in 40 mL of THF/water (1:1) was added 5.0 mL of triethylamine followed by 1.144 g (4.681 mmol) of 4-but-2-ynyloxy-benzenesulfonyl chloride and the reaction was stirred overnight at room temperature. The reaction mixture was then diluted with ethyl acetate and the organic layer was washed with water and 5% HCl solution, dried over $MgSO_4$, filtered and concentrated in vacuo. The solid residue was washed with ether/hexanes (1:1) to provide 0.383 g (28%) of the sulfonamide as a white solid. Electrospray Mass Spec 323.9 (M–H)–

Example 27

2-(4-But-2-ynyloxy-benzenesulfonylamino)-N-hydroxy-3-methyl-butyramide

According to the procedure of Example 25, 0.189 g (0.583 mmol) of the product of Example 26 provides 0.110 g (56%) of the desired hydroxamic acid as a white solid. Electrospray Mass Spec 341.0 (M+H)+

Example 28

2-(4-But-2-ynyloxy-benzenesulfonylamino)-propionic acid ethyl ester

According to the procedure of Example 20, 1.00 g (6.51 mmol) of D,L-alanine ethyl ester hydrochloride reacted with 1.75 g (7.16 mmol) of 4-but-2-ynyloxy-benzenesulfonyl chloride to provide 1.22 g (58%) of the sulfonamide as a white solid. Electrospray Mass Spec: 325.9 (M+H)+

Example 29

2-(4-But-2-ynyloxy-benzenesulfonylamino)-propionic acid

According to the procedure of Example 24, 0.500 g (1.538 mmol) of the product of Example 28 provided 0.457 g (100%) of the carboxylic acid as a tan solid. Electrospray Mass Spec: 295.9 (M–H)–

Example 30

2-(4-But-2-ynyloxy-benzenesulfonylamino)-N-hydroxy-propionamide

According to the procedure of Example 25, 0.410 g (1.38 mmol) of the product of Example 29 provided 0.287 g (67%) of the hydroxamic acid as a white solid. Electrospray Mass Spec: 313.4 (M+H)+

Example 31

2-[(4-But-2-ynyloxy-benzenesulfonyl)-pyridin-3-ylmethyl-amino]-propionic acid ethyl ester According to the procedure of Example 21, 0.500 g (1.538 mmol) of the product of Example 28 provided 0.461 g (72%) of the N-3-picolyl sulfonamide as a pale yellow oil. Electrospray Mass Spec: 416.9 (M+H)+

Example 32

2-[(4-But-2-ynyloxy-benzenesulfonyl)-pyridin-3-ylmethyl-amino]-propionic acid

According to the procedure of Example 22, 0.419 g (1.007 mmol) of the product of Example 31 provided 0.39 g (1005) of the carboxylic acid as a white foam. Electrospray Mass Spec: 388.9 (M+H)+

Example 33

2-[(4-But-2-ynyloxy-benzenesulfonyl)-pyridin-3-ylmethyl-amino]-N-hydroxy-propionamide hydrochloride According to the procedure of Example 23, 0.364 g (0.938 mmol) of the product of Example 32 provided 0.149 g of the hydroxamic acid N-3-picolyl hydrochloride salt as a light brown solid. Electrospray Mass Spec: 403.9 (M+H)+

Example 34

4-Amino-2,6dimethyl-pyrimidine-5-carboxylic acid ethyl ester

To a solution of 0.65 g (6.31 mmol) of 2-aminoisobutyric acid, 0.077 g of 4-dimethylaminopyridine and 7.4 mL of triethylamine in 20 mL of THF and 20 mL of water was added 1.68 g (6.87 mmol) of 4-but-2-ynyloxy-benzenesulfonyl chloride and the resulting mixture was stirred overnight at room temperature. The mixture was then diluted with ethyl acetate and washed with 5% HCl solution and water, dried over $Na_2SO_4$, filtered and concentrated in vacuo. The residue was chromatographed on silica gel eluting with ethyl acetate/hexanes (1:1) to provide 0.396 g (20%) of the sulfonamide as a white solid. Electrospray Mass Spec: 309.9 (M–H)–

Example 35

2-(4-But-2-ynyloxy-benzenesulfonylamino)-N-hydroxy-2-methyl-propionamide

According to the procedure of Example 25, 0.359 g (1.154 mmol) of the product of Example 34 provided 0.193 g (51%) of the hydroxamic acid as a clear glass. Electrospray Mass Spec: 327.3 (M+H)+

Example 36

(3S)-4-(4-Fluoro-benzenesulfonyl)-2,2-dimethyl-thiomorpholine-3-carboxylic acid

To a 0° solution of 1.00 g (3.155 mmol) of 3-(S)-dimethylthexylsilyl-2,2-dimethyl-tetrahydro-2H-1,4thiazine-3-carboxylate (prepared as described in PCT patent application WO9720824) in 20 mL of dichloromethane was added 0.693 mL (6.85 mmol) of 4-methylmorpholine followed by 0.606 g (3.114 mmol) of 4-fluorobenzenesulfonyl chloride. The reaction was allowed to warm to room temperature and then stirred oveniight The reaction mixture was then poured into water and the organic layer was washed with water, dried over $Na_2SO_4$, filtered and concentrated in vacuo. The residue was dissolved in 20 mL of methanol and the solution was heated to reflux for 1 h and then concentrated in vacuo. The residue was then chromatographed on silica gel eluting with ethyl acetate/hexanes (1:3) to provide 0.385 g (40%) of the sulfonamide as a white foam. Electrospray Mass Spec 331.8 (M–H)–

Example 37

4-(4-But-2-ynyloxy-benzenesulfonyl)-2,2-dimethyl-thiomorpholine-3-carboxylic acid 4-(4-Hydroxy-benzenesulfonyl)-2,2-dimethyl-thiomorpholine-3-carboxylic acid To a solution of 3.07 mL (0.041 mol) of 2-butyn-1-ol in 75 ml of DMF at room temperature was added 1.64 g (0.041 mol) 60% sodium hydride. The resulting mixture was stirred for 0.5 h and then a solution of 2.50 g (8.197 mmol) the product of Example 36 dissolved in 10 mL of DMF was added to the reaction. The reaction mixture was stirred overnight at room temperature and then acidified to pH 2 with 10% HCl solution and extracted with ether. The combined organics were then dried over $MgSO_4$, filtered and concentrated in vacuo. The residue was chromatographed on silica gel eluting with ethyl acetate/hexanes (1:3) to provide 1.2 g (42%) of the butynyl ether-carboxylic acid product as a tan solid (Electrospray Mass Spec 383.9 (M+H)+) and 0.947 g of the phenol-carboxylic acid as a pale yellow oil (Electrospray Mass Spec 329.9 (M–H)–)

Alternatively, 4-(4-But-2-ynyloxy-benzenesulfonyl)-2,2-dimethyl-thiomorpholine-3-carboxylic acid may be prepared in 31% yield according to the procedure of Example 36 using 4-but-2-ynyloxy-benzenesulfonyl chloride as the sulfonylating agent.

Example 38

4-(4-But-2-ynyloxy-benzenesulfonyl)-2,2-dimethyl-thiomorpholine-3-carboxylic acid hydroxyamide To a 0° solution of 0.75 mL (1.504 mmol) of a 2.0M solution of oxalyl chloride in dichloromethane, diluted with 6.4 mL of dichloromethane, is added 0.116 mL (1.504 mmol) of DMF and the reaction is stirred for 15 minutes at 0°. A solution of 0.176 g (0.501 mmol) of the butynyl ether-carboxylic acid product of Example 37, dissolved in 1 mL of DMF, was added to the reaction and the resulting mixture is stirred for 1 h at room temperature and then poured into a 0° mixture of 1.5 mL of water, 7.4 mL of THF and 1.5 mL of a 50% aqueous solution of hydroxylamine. The reaction is allowed to warm to room temperature overnight and the organics are then concentrated in vacuo. The residue is diluted with ethyl acetate, washed with 5% HCl solution, water and saturated sodium bicarbonate, dried over $Na_2SO_4$, filtered and concentrated in vacuo to provide 0.168 g (91%) of the hydroxamic acid as a tan solid. Electrospray Mass Spec 398.9 (M+H)+

Example 39

4-(4-Hept-2-ynyloxy-benzenesulfonyl)-2,2-dimethyl-thiomorpholine-3-carboxylic acid According to the procedure of Example 37, 0.350 g (1.051 mmol) of the product of Example 36 and 0.730 mL (5.738 mmol) of 2-heptyn-1-ol provides 0.306 g (63%) of the heptynyl ether-carboxylic acid as a white solid. Electrospray Mass Spec 424.0 (M–H)–

Example 40

4-(4-Hept-2-ynyloxy-benzenesulfonyl)-2,2-dimethyl-thiomorpholine-3-carboxylic acid hydroxyamide According to the procedure of Example 38, 0.257 g (0.605 mmol) of the product of Example 39 provides 0.214 g (80%) of the hydroxamic acid as a white solid. Electrospray Mass Spec 440.9 (M+H)+

Example 41

2-(4-But-2-ynyloxy-benzenesulfonyl)-1,2,3,4-tetrahydro-isoquinoline-3-carboxylic acid hydroxyamide To a solution of 2.00 g (9.359 mmol) of 1,2,3,4-tetrahyro-3-isoquinolinecarboxylic acid hydrochloride in 70 mL of THF/water (1:1) was added 10.0 mL of triethylamine followed by 2.30 g (9.407 mmol) of 4-but-2-ynyloxy-benzenesulfonyl chloride and the reaction was stirred overnight at room temperature. The reaction mixture was then diluted with ethyl acetate and the organic layer was washed with water and 5% HCl solution, dried over MgSO4, filtered and concentrated in vacuo. The solid residue was washed with ether/hexanes (1:1) to provide 2.73 g (76%) of the sulfonamide as a pale yellow solid. Electrospray Mass Spec 385.9 (M+H)+

According to the procedure of Example 38, 0.736 g (1.912 mmol) of the sulfonamide provides 0.503 g (66%) of the hydroxamic acid as a white solid. Electrospray Mass Spec 400.9 (M+H)+

Example 42

Methyl 3-Hydroxy-2-(4-methoxybenzenesulfonylamino)propionate

Reference Example 13 in Case# 33,315:

3-Hydroxy-2-(4-methoxy-benzenesulfonylamino)-propionic acid methyl ester

To a mixture of 5.0 g (32.14 mmol) of D, L-serine methyl ester and 15.7 mL (0.012 mol) of triethylamine in 100 mL of dichloromethane, cooled to 0° C., was added 6.64 g (32.14 mmol) of 4-methoxybenzenesulfonyl chloride. The mixture was then stirred under argon at room temperature for two days. The mixture was diluted with 100 mL of dichloromethane and then washed with 60 mL each of water, 2N citric acid and brine and than dried over $Na_2SO_4$. The solvent was removed under vacuum to give a solid which was recrystallized from ethyl acetate to give 5.0 g (54%) of the product as white crystals, m.p. 92–94° C.

Anal for $C_{11}H_{15}NO_6S$:

Calc'd: C,45.7; H, 5.2; N, 4.8; S, 11.1;

Found: C,45.6; H, 5.2; N, 4.8; S, 11.1;

Example 43

2-[(3-Chloro-propyl)-(4-methoxy-benzenesulfonyl)-amino]-3-hydroxy-propionic acid methyl ester and 2-[(3-Chloro-propyl)-(4-methoxy-benzenesulfonyl)-amino]-acrylic acid methyl ester To a solution of 0.25 g (0.865 mmol) of the sulfonamide of Example 42 in 4.5 mL of DMF was added 0.042 g (1.038 mmol) of 60% sodium hydride. The resulting mixture was stirred for 30 min at room temperature and then 0.26 mL (2.595 mmol) of 1,3-dibromopropane was added and the reaction was stirred overnight at room temperature.

The reaction mixture was diluted with water and extracted with ether. The combined organics were washed with water and brine, dried over $MgSO_4$, filtered and concentrated in vacuo. The residue was chromatographed on silica gel eluting with ethyl acetate/hexanes (1:1) to give 0.148 g (47%) of the chloro-alcohol and 0.049 g (16%) of the acrylic acid methyl ester. Electrospray Mass Spec: 382.9 (M+$NH_4^+$) chloro-alcohol; 348.1 (M+H)$^+$ acrylic acid methyl ester.

Example 44

2-[(3-Chloro-propyl)-(4-methoxy-benzenesulfonyl)-amino]-acrylic acid methyl ester To a solution of 1.213 g (3.319 mmol) of the chloro-alcohol product of Example 43 in 60 mL of dichloromethane was added 2.31 mL (16.59 mmol) of triethylamine followed by 0.31 mL (3.982 mmol) of methanesulfonyl chloride. The resulting mixture was stirred at room temperature for 1 h and an additional 0.31 mL (3.982 mmol) of methanesulfonyl chloride was then added and the reaction was stirred overnight.

The reaction was then diluted with ether, washed with 2N citric acid solution, water and brine, dried over MgSO$_4$, filtered and concentrated in vacuo. The residue was chromatographed on silica gel eluting with ethyl acetate/hexanes (1:3) to give 0.989 g (86%) of the chloro-olefin. Electrospray Mass Spec: 348.1 (M+H)$^+$ Example 45

4-Benzyl-1-(4-methoxy-benzenesulfonyl)-[1,4] diazepane-2-carboxylic acid methyl ester To a solution of 0.910 g (0.2.619 mmol) of the product of Example 44 in 30 mL of DMF was added 0.432 g (0.2.881 mmol) of sodium iodide. The reaction was stirred for 30 min at room temperature and then 0.590 mL (5.499 mmol) of benzylamine and 0.96 mL (5.499 mmol) of diisopropylethylamine was added and the resulting mixture was heated at 80 degrees for 3 h and then cooled to room temperature.

The reaction was diluted with ether, washed with water and then extracted with 10% HCl solution. The combined acid extracts were then basified with 1N NaOH solution and extracted with ether. The ether layer was dried over Na$_2$SO$_4$, filtered and concentrated in vacuo. The residue was chromatographed on silica gel eluting with ethyl acetate/hexanes (1:3) to give 0.835 g (76%) of the diazepane. Electrospray Mass Spec: 418.9 (M+H)$^+$ Example 46

1-(4-methoxy-benzenesulfonyl)-[1,4]diazepane-2-carboxylic acid methyl ester

To a solution of 11.0 g (0.026 mol) of the product of Example 45 in 50 mL of ethanol was added 4.40 g of 20% palladium hydroxide on carbon (Pearlman's catalyst) and the resulting suspension was shaken at room temperature in a Parr reactor under 44 psi of hydrogen for 4 h. The reaction mixture was then filtered through Celite and the filter cake was washed with 100 mL of methanol. The filtrate was concentrated in vacuo and the residue was diluted with ethyl acetate. The solution was washed with water, dried over Na$_2$SO$_4$, filtered and concentrated in vacuo. The resulting oil was pure enough for use in the next step. Electrospray Mass Spec: 328.9 (M+H)$^+$ Example 47

4-Benzoyl-1-(4-hydroxy-benzenesulfonyl)-[1,4] diazepane-2-carboxylic acid methyl ester To a solution of 2.576 g (7.854 mmol) of the product of Example 46 in 60 mL of dichloromethane was added 3.28 ml (0.024 mol) of triethylamine followed by 2.74 mL (0.024 mol) of benzoyl chloride and the resulting mixture was stirred at room temperature for 18 h. The reaction mixture was then diluted with ether and washed with 5% citric acid solution, water and saturated sodium bicarbonate solution. The organics were dried over MgSO$_4$, filtered and concentrated in vacuo. The residue was chromatographed on silica gel eluting with ethyl acetate/hexanes (2:1) to provide 2.35 g (69%) of the carboxamide-ester as a colorless oil.

To a 0° solution of 1.88 g (4.352 mnol) of the carboxamide-ester in 100 mL of dichloromethane was added 17.4 mL (17.4 mmol) of a 1.0M solution of boron tribromide in dichloromethane. The reaction was stirred at room temperature for 2 h and then poured into an ice cold solution of saturated sodium bicarbonate. The resulting mixture was extracted with dichloromethane and the combined organics were dried over MgSO$_4$, filtered and concentrated in vacuo to provide 0.645 g (35%) of the phenol as a white foam. Electrospray Mass Spec: 419.0 (M+H)$^+$ Example 48

4-Benzoyl-1-(4-but-2-ynyloxy-benzenesulfonyl)-[1, 4]diazepane-2-carboxylic acid

To a solution of 0.096 g (0.368 mmol) of triphenylphosphine in 3 mL of benzene was added 0.028 mL (0.368 mmol) of neat 2-butyn-1-ol followed by a solution of 0.123 g (0.294 mmol) of the phenol product of Example 47 dissolved in 1.0 mL of THF. To the resulting reaction mixture was added 0.058 mL (0.368 mmol) of diethylazodicarboxylate and the reaction was stirred for 15 h at room temperature and then concentrated in vacuo. The residue was chromatographed on silica gel eluting with ethyl acetate/hexanes (1:1) to provide the butynyl ether-methyl ester.

The methyl ester was then dissolved in 6.0 mL of THF/methanol (1:1) and 1.5 mL of 1N sodium hydroxide solution was added. The reaction was stirred overnight at room temperature and then the THF/methanol was removed in vacuo. The residue was diluted with 1N sodium hydroxide solution and washed with ether, ethyl acetate and dichloromethane. The aqueous layer was acidified with 10% HCl solution and extracted with dichloromethane and these extracts were dried over MgSO4, filtered and concentrated in vacuo to provide 0.093 g (70%) of the butynyl ether-carboxylic acid as a colorless oil. Electrospray Mass Spec: 457.0 (M+H)+

Example 49

4-Benzoyl-1-(4-but-2-ynyloxy-benzenesulfonyl)-[1, 4]diazepane-2-carboxylic acid hydroxyamide According to the procedure of Example 38, 0.108 g (0.238 mmol) of the product of Example 48 provides 0.067 g (60%) of the hydroxamic acid as a white foam. Electrospray Mass Spec: 472.0 (M+H)$^+$ Example 50

Piperzine-1,3-dicarboxylic acid 1-tert-butyl ester 3-ethyl ester

To a solution of 1.00 g (6.329 mmol) of ethyl piperazine-2-carboxylate [Rissi, E.; Jucker, E. *Helv. Chim. Acta* 1962, 45, 2383.]in 25 mL of chloroform was added 1.66 g (7.595 mmol) of di-t-butyl dicarbonate followed by 0.168 g of 4-dimethylaminopyridine. The reaction was stirred at room temperature for 15 h and then concentrated in vacuo. The

Example 51

4-(4-Fluoro-benzenesulfonyl)-piperazine-1,3-dicarboxylic acid 1-tert-butyl ester 3-ethyl ester To a solution of 1.35 g (5.233 mmol) of the product of Example 50 dissolved in 20 mL of chloroform and 1.5 mL of pyridine was added 1.02 g (5.233 mmol) of 4-fluorobenzenesulfonyl chloride and the resulting mixture was stirred overnight at room temperature. The chloroform was removed in vacuo and the residue was diluted with ether and washed with water, 5% HCl solution and saturated sodium bicarbonate solution and then dried over MgSO4, filtered and concentrated in vacuo. The residue was triturated with ether/hexanes (1:1) and the solid was collected by filtration and dried in vacuo to provide 1.50 g (69%) of the sulfonamide as a white solid. Electrospray Mass Spec: 416.9 (M+H)$^+$

Example 52

1-(4-Fluoro-benzenesulfonyl)-piperazine-2-carboxylic acid ethyl ester

To a solution of 0.75 g (1.803 mmol) of the product of Example 51 in 5 mL of dichloromethane was added was added 2.0 mL of trifluoroacetic acid and the resulting mixture was stirred for 2 h at room temperature. The reaction mixture was then concentrated in vacuo and the residue was diluted with ether. The organics were washed with saturated sodium bicarbonate solution, dried over $Na_2SO_4$, filtered and concentrated in vacuo to provide 0.515 g (90%) of the amine as a colorless oil pure enough for use in the next step. Electrospray Mass Spec: 316.9 (M+H)$^+$

Example 53

1-(4-Fluoro-benzenesulfonyl)-4-methyl-piperazine-2-carboxylic acid ethyl ester To a solution of 0.469 g (1.484 mmol) of the product of Example 52 dissolved in 10 mL of DMF was added 0.614 g (4.452 mmol) of potassium carbonate followed by 0.092 mL (1.484 mmol) of iodomethane and the resulting mixture was stirred at room temperature for 3 h. The reaction mixture was then diluted with ether and washed with water. The organics were dried over $Na_2SO_4$, filtered and concentrated in vacuo to provide 0.446 g (91%) of the N-methyl amine as a colorless oil. Electrospray Mass Spec: 330.9 (M+H)$^+$

Example 54

1-(4-Fluoro-benzenesulfonyl-4-methyl-piperazine-2-carboxylic acid

To a solution of 0.390 (1.182 mmol) of the product of Example 53 dissolved in 12 mL of methanol/THF (1:1) was added 5.9 mmol of 1.0N sodium hydroxide solution and the resulting mixture was stirred for 15 h at room temperature. The reaction was then brought to pH 6 with 5% HCl and extracted with dichloromethane. The organics were dried over $Na_2SO_4$, filtered and concentrated in vacuo to provide 0.265 g (74%) of the carboxylic acid as a pale yellow solid. Electrospray Mass Spec: 302.9 (M+H)$^+$

Example 55

1-(4-But-2-ynyloxy-benzenesulfonyl)-4-methyl-piperazine-2carboxylic acid

To a solution of 0.302 mL (4.04 mmol) of 2-butyn-1-ol in 5.5 mL of DMF at room temperature was added 0.162 g (4.04 mmol) of 60% sodium hydride. The resulting mixture was stirred for 0.5 h and then a solution of 0.244 g (0.808 mmol) of the product of Example 54 dissolved in 2.0 mL of DMF was added to the reaction. The reaction mixture was then stirred at room temperature for 3 h and then neutralized with 5% HCl and extracted with dichloromethane. The combined organics were then dried over $NA_2SO_4$, filtered and concentrated in vacuo. The residue was chromatographed on silica gel eluting with ethyl acetate to provide 0.118 g (42%) of the desired butynyl ether-carboxylic acid product as a tan solid. Electrospray Mass Spec: 352.9 (M+H)+

Example 56

1-(4-But-2-ynyloxy-benzenesulfonyl)-4-methyl-piperazine-2-carboxylic acid hydroxyamide hydrochloride According to the procedure of Example 38, 0.095 g (0.270 mmol) of the product of Example 55 provides 0.080 g (81%) of the amino-hydroxamic acid.

To a solution of 0.070 g (0.191 mmol) of the amino-hydroxamic acid dissolved in 2.0 mL of dichloromethane was added 0.38 mL (0.38 mmol) of a 1.0M solution of HCl in ether. The resulting mixture was stirred for 1 h at room temperature and then diluted with ether. The precipitate was filtered, washed with ether and dried in vacuo to provide 0.064 g (83%) of the hydrochloride salt of the amino-hydroxamic acid as a tan solid. Electrospray Mass Spec 367.9 (M+H)+

Example 57

4-(4-But-2-ynyloxy-benzenesulfonyl)-piperazine-1,3-dicarboxylic acid 1-tert-butyl ester 3-ethyl ester According to the procedure of Example 51, 1.55 g (5.99 mmol) of the product of Example 50 and 1.61 g (6.59 mmol) of 4-but-2-ynyloxy-benzenesulfonyl chloride provided 1.96 g (72%) of the sulfonamide as a white solid. Electrospray Mass Spec 467.0 (M+H)+

Example 58

4-(4-But-2-ynyloxy-benzenesulfonyl)-3-hydroxycarbamoyl-piperazine-1-carboxylic acid tert-butyl ester According to the procedure of Example 54, 0.400 g (0.858 mmol) of the product of Example 57 provided 0.376 g (100%) of the carboxylic acid as a clear glass.

According to the procedure of Example 25, 0.472 g (1.078 mmol) of the carboxylic acid provided 0.342 g (70%) of the hydroxamic acid as a white foam. Electrospray Mass Spec 454.0 (M+H)+

Example 59

4-(4-Hydroxy-benzenesulfonyl)-2,2-dimethyl-thiomorpholine-3-carboxylic acid methyl ester To a solution of 0.919 g (2.776 mmol) of 4-(4hydroxy-benzenesulfonyl)-2,2-dimethyl-thiomorpholine-3-carboxylic acid in 20 mL of DMF was added 0.764 g (9.099 mmol) of sodium bicarbonate and 0.19 mL (3.03 mmol) of iodomethane. The resulting mixture was stirred for 5 h at room temperature and then diluted with ether, washed with water, dried over $Na_2SO_4$, filtered and concentrated in vacuo to provide 0.743 g (78%) of the methyl ester as a pale yellow solid. Electrospray Mass Spec 345.8 (M+H)+

Example 60

2,2-Dimethyl-4-{4-[4-(tetrahydro-pyran-2-yloxy)-but-2-ynyloxy]-benzenesulfonyl}-thiomorpholine-3-carboxylic acid methyl ester To a solution of 0.633 g (2.415 mmol) of triphenylphosphine in 10 mL of benzene/THF (3:1) was added 0.410 g (2.415 mmol) of 4-tetrahydropyran-2-butyn-1,4-diol followed by 0.38 mL (2.415 mmol) of diethyl azodicarboxylate and 0.696 g (2.017 mmol) of the product of Example 59. The resulting mixture was stirred at room temperature for 24 h and then concentrated in vacuo. The residue was chromatographed on silica gel eluting with ethyl acetate/hexanes (1:10) to provide 0.56 g (56%) of the butynyl ether as a colorless oil. Electrospray Mass Spec 497.9 (M+H)+

Example 61

4-[4-(4-Hydroxy-but-2-ynyloxy)-benzenesulfonyl]-2,2-dimethyl-thiomorpholine-3-carboxylic acid hydroxyamide To a solution of 0.413 g (0.831 mmol) of the product of Example 60 in 10 mL of methanol/THF (1:1) was added 4.2 mL (4.20 mmol) of a 1.0N sodium hydroxide solution and the resulting mixture was heated to reflux for 5 h and concentrated in vacuo. The residue was diluted with water and neutralized with 5% HCl solution. The mixture was extracted with ethyl acetate and washed with water, dried over MgSO4, filtered and concentrated in vacuo to provide 0.335 g (84%) of the carboxylic acid as a colorless oil.

To a solution of 0.270 g (0.559 mmol) of the carboxylic acid dissolved in 3.0 mL of DMF was added 0.091 g (0.671 mmol) of 1-hydroxybenzotriazole hydrate (HOBT) followed by 0.143 g (0.743 mmol) of 1-(3-dimethylaminopropyl)-3-ethylcarbodiimide hydrochloride (EDC). The resulting mixture was stirred at room temperature for 1 h and then 0.17 mL of a 50% aqueous hydroxylamine solution was added. The reaction was then stirred overnight and then diluted with ethyl acetate. The organics were washed with 5% HCl solution, water and saturated sodium bicarbonate solution and then dried over MgSO4, filtered and concentrated in vacuo.

The residue was dissolved in 10 mL of methanol and 20 mg of pyridinium p-toluenesulfonate was added and the mixture was heated to reflux for 18 h. After cooling to room temperature, the reaction mixture was diluted with ethyl acetate and the organics were washed with 5% HCl solution, water, and saturated sodium bicarbonate solution. The organics were then dried over $Na_2SO_4$, filtered and concentrated in vacuo. The residue was chromatographed on silica gel eluting with ethyl acetate/hexanes (4:1) to provide 0.073 g (32%) of the hydroxamic acid alcohol as a pale yellow solid. Electrospray Mass Spec 414.9 (M+H)+

Example 62A

[(4-Hydroxy-benzenesulfonyl)-methyl-amino]-acetic acid ethyl ester

To a solution of 1.00 g (6.51 mmol) of sarcosine ethyl ester hydrochloride in 10 mL of chloroform was added 2.0 mL of pyridine followed by 1.25 g (6.51 mmol) of 4-hydroxybenzenesulfonyl chloride. The reaction was stirred at room temperature for 15 h and then concentrated in vacuo. The residue was diluted with ethyl acetate and washed with 5% HCl solution and water, dried over $MgSO_4$, filtered and concentrated in vacuo to provide 1.47 g (83%) of the sulfonamide-phenol as a white solid. Electrospray Mass Spec 273.8 (M+H)+

Example 62B

L-2-(4-But-2-ynyloxy-benzenesulfonylamino)-N-hydroxy-propionamide

Step A:

Coupling of N-(9-Fluorenylmethoxycarbonyl)-L-alanine to hydroxylamine resin.

4-O-Methylhydroxylamine-phenoxymethyl-copoly (strene-1%-divinylbenzene)-resin[1] (0.9 g, 1.1 meq/g) was placed in an empty SPE cohlmn (Jones Chromatography USA, Inc. Part # 120-1024-H) and suspended in DMF (4 mL). N-9-Fluorenylmethoxycarbonyl)-L-alanine (560 mg, 2.0 eq.) HOBt (730 mg 6.0 eq.) and DIC (454 uL, 4.0 eq.) were added. The reaction was shaken on an orbital shaker at oom temperature for 2–16 hours. The reaction was filtered and washed with DMF (3×20 mL). A sample of resin was removed and subjected to the Kaiser test. If the test showed the presence of free amine (resin turned blue) the coupling desctibed above was repeated, otherwise the resin was washed with DCM (3×20 mL), MeOH (2×20 mL), and DCM (2×20 mL). (A wash consisted of addition of the solvent and agitation either by nitrogen bubbling or shaking on the orbital shaker for 1–5 minutes, then filtration under vacuum). The resin was dried in vacuo at room temperature.

Step B:

Removal of the N-(9-Fluorenylmethoxycarbonyl) protecting group. The N-(9-fluorenylmethoxycarbonyl) amino hydroxamate resin prepared in Step A (0.9 g) was suspended in 20% piperidine in DMF (4 mL). The reaction was shaken at room temperature for 15 minutes, then the resin was filtered and washed with DMF (1×4 mL) and the deprotection repeated for 30 minutes. The reaction was filtered and washed with DMF (2×2 mL), MeOH (2×2 mL), and DCM (2×2 mL). The resin was dried in vacuo at room temperature.

Step C:

Sulfonamide formation.

The amino hydroxamate resin prepared in Step B (0.9 g) was suspended in DCM (3.0 mL) and pyridine (142 □L, 2.0 eq.) and 4-but-2-ynyloxy-benzenesulfonyl chloride (220 mg, 1.1 eq.) were added. The reaction mixture was shaken on an orbital shaker at room temperature for 12–24 hours. The reaction was filtered and washed with DCM (2×2 mL), DMF (2×2 mL), MeOH (2×2 mL), and DCM (2×2 mL). The resin was dried in vacuo at room temperature.

Step D:

Cleavage of the 4-but-2-ynyloxybenzenesulfonyl amino hydroxamate from resin.

The 4-but-2-ynyloxybenzenesulfonyl amino hydroxamate resin prepared in Step C (300 mg) was suspended in DCM (1.0 mL) and TFA (1.0 mL) was added. The reaction was shaken for 1 hour at room temperature. The reaction was filtered and the resin washed with DCM (2×1 mL). The filtrate and the washing were combined and concentrated to dryness on a Savant SpeedVac Plus. MeOH (1 mL) was added and the mixture concentrated.

The crude product was purified by reverse phase HPLC under the following conditions:

Column: ODS-AM, 20 mm×50 mm, 5 μm particle size (YMC, Inc. Wilmington, N.C.)

Solvent Gradient: 5–95% acetonitrile (0.05% TFA) in water (0.05% TFA) over 16 minutes.

Flow Rate: 22.5 mL/minute.

L-2-(4-But-2-ynyloxy-benzenesulfonylamino)-N-hydroxy-propionamide (22.5 mg, 24%) had HPLC retention time[2] 3.59 min. and MS[3] 313 (M+H).

The hydroxamic acids compounds shown in Table I are synthesized according to the procedures of Example 62B using the following Fmoc protected amino acids as starting materials: Fmoc-α-Me-Ala, Fmoc-Abu, Fmoc-Ala, Fmoc-Arg, Fmoc-Arg(Ts), Fmoc-Asn, Fmoc-Asp(All), Fmoc-Asp (Chx), Fmoc-β-Ala, α-Fmoc-γ-Boc-Diaminobutyric acid, Fmoc-Cha, Fmoc-Chg, Fmoc-Cys(Bu-t), Fmoc-Cys(Mob), Fmoc-D-Asn, Fmoc-D-Orn(Boc), Fmoc-D-Cha, Fmoc-D-Chg, Fmoc-D-Leu, Fmoc-D-Met, Fmoc-D-Phe, Fmoc-D-Pro, Fmoc-D-Trp, Fmoc-D-Tyr(Bu-t), Fmoc-D-Val, Fmoc-Glu(Bu-t), Fmoc-His(Boc), Fmoc-Hyp(Bn), Fmoc-Ile, Fmoc-Leu, Fmoc-Lys(2-Cl-Bn), Fmoc-Lys(Boc), Fmoc-Nle, Fmoc-Phe, Fmoc-Cys(Acm), Fmoc-Ser(Ac), Fmoc-Ser (Bn), Fmoc-Ser(Bu-t), Fmoc-Thr(Bn), Fmoc-Thr(Bu-t), Fmoc-Trp(Boc), Fmoc-Tyr(Bu-t), Fmoc-Tyr(Bn), Fmoc-Val, Fmoc-Phg, Fmoc-Gly, Fmoc-D-Arg(Mtr), Fmoc-D-Arg (Pbf), Fmoc-D-Arg(Mtr), Fmoc-D-Asp, Fmoc-D-Cys(t-Bu), Fmoc-D-Cys(Acm), Fmoc-D-Cys(Mbzl), Fmoc-D-Cys (Mob), Fmoc-D-Gln, Fmoc-D-Glu, Fmoc-D-Hfe, Fmoc-D-His, Fmoc-D-Hyp, Fmoc-D-Lys, Fmoc-D-Lys(Cbz), Fmoc-D-1-Nal, Fmoc-D-2-Nal, Fmoc-D-Nle, Fmoc-D-Nve, Fmoc-D-Orn, Fmoc-D-3,4-diF-Phe, Fmoc-D-4-F-Phe, Fmoc-D-4-nitro-Phe, Fmoc-D-Pip, Fmoc-D-Ser, Fmoc-D-Ser(Bn), Fmoc-D-2-Thi, Fmoc-D-Thr, Fmoc-D-Thr(Bn), Fmoc-D-Thz, Fmoc-D-Tic, Fmoc-D-Tyr(Bn), Fmoc-D-Phg.

TABLE 1

| Example | Amino acid[4] | HPLC retention time[2] (min.) | MS[3] (M + H) |
| --- | --- | --- | --- |
| 62B | L-Ala | 3.59 | 313 |
| 63 | L-Abu | 3.73 | 327 |
| 64 | L-Arg | 3.21 | 398 |
| 65 | L-Arg(Ts) | 4.30 | 552 |
| 66 | L-Asn | 4.00 | 356 |
| 67 | L-Asp | 4.00 | 357 |
| 68 | L-Asp(Chx) | 4.73 | 439 |
| 69 | β-Ala | 3.63 | 313 |
| 70 | L-A$_2$bu | 3.12 | 342 |
| 71 | L-Cha | 4.75 | 395 |
| 72 | L-Chg | 4.41 | 381 |
| 73 | L-Cys(t-Bu) | 4.49 | 401 |
| 74 | L-Cys(Mob) | 4.76 | 465 |
| 75 | D-Asn | 3.99 | 356 |
| 76 | D-Orn | 3.10 | 356 |
| 77 | D-Cha | 4.70 | 395 |
| 78 | D-Chg | 4.43 | 381 |
| 79 | D-Leu | 4.20 | 355 |
| 80 | D-Met | 4.00 | 373 |
| 81 | D-Phe | 4.36 | 389 |
| 82 | D-Pro | 3.90 | 339 |
| 83 | D-Trp | 4.64 | 428 |
| 84 | D-Tyr | 3.83 | 405 |
| 85 | D-Val | 3.89 | 341 |
| 86 | L-Glu | 3.92 | 371 |
| 87 | L-His | 3.06 | 379 |
| 88 | L-Hyp(Bn) | 4.67 | 445 |
| 89 | L-Ile | 4.13 | 355 |
| 90 | L-Leu | 4.21 | 355 |
| 91 | L-Lys(2-Cl—Bn) | 4.91 | 495 |
| 92 | L-Lys | 4.22 | 370 |
| 93 | L-Nle | 4.25 | 355 |
| 94 | L-Phe | 4.37 | 389 |
| 95 | L-Phg | 4.24 | 375 |
| 96 | L-Cys(Acm) | 3.56 | 416 |
| 97 | L-Ser(Bn) | 4.57 | 419 |
| 98 | L-Ser | 3.38 | 329 |
| 99 | L-Thr(Bn) | 4.69 | 433 |
| 100 | L-Thr | 3.45 | 343 |
| 101 | L-Trp | 4.33 | 428 |
| 102 | L-Tyr | 3.80 | 405 |
| 103 | L-Tyr(Bn) | 5.14 | 495 |
| 104 | L-Val | 3.87 | 341 |
| 295 | D-Arg(Mtr) | 4.72 | 610 |
| 296 | D-Arg | 3.24 | 398 |
| 297 | D-Arg(Ts) | 4.34 | 552 |
| 298 | D-Asp | 4.02 | 357 |
| 299 | D-Cys(t-Bu) | 4.54 | 401 |
| 300 | D-Cys(Acm) | 3.61 | 416 |
| 301 | D-Cys(Mbzl) | 5 | 449 |
| 302 | D-Cys(Mob) | 4.76 | 465 |
| 303 | D-Gln | 3.94 | 370 |
| 304 | D-Glu | 3.94 | 371 |
| 305 | D-Hfe | 4.63 | 403 |
| 306 | D-His | 3.11 | 379 |
| 307 | D-Hyp | 3.43 | 355 |
| 308 | D-Lys | 3.18 | 370 |
| 309 | D-Lys(Cbz) | 4.75 | 504 |
| 310 | D-1-Nal | 4.78 | 439 |
| 311 | D-2-Nal | 4.83 | 439 |
| 312 | D-Nle | 4.3 | 355 |
| 313 | D-Nva | 4.05 | 341 |
| 314 | D-Orn | 3.15 | 356 |
| 315 | D-3,4-diF-Phe | 4.58 | 425 |
| 316 | D-4-F-Phe | 4.48 | 407 |
| 317 | D-4-NO2-Phe | 4.44 | 434 |
| 318 | D-Pip | 4.26 | 353 |
| 319 | D-Ser | 3.42 | 329 |
| 320 | D-Ser-(Bn) | 4.62 | 419 |
| 321 | D-Thi | 4.33 | 395 |
| 322 | D-Thr | 3.5 | 343 |
| 323 | D-Thr(Bn) | 4.75 | 433 |

TABLE 1-continued

| Example | Amino acid[4] | HPLC retention time[2] (min.) | MS[3] (M + H) |
|---|---|---|---|
| 324 | D-Thz | 4.17 | 357 |
| 325 | D-Tic | 4.63 | 401 |
| 326 | D-Tyr(Bn) | 5.19 | 495 |
| 327 | D-Phg | 4.29 | 375 |

[2]LC conditions: Hewlett Packard 1100; YMC ODS-A 4.6 mm × 50 mm 5 u column at 23° C.; 10 uL injection, Solvent A: 0.05% TFA/water; Solvent B: 0.05% TFA/acetonitrile; Gradient: Time 0.98% A; 1 min: 98% A; 7 min: 10% A, 8 min: 10% A; 8.9 min: 98% A; Post time 1 min. Flow rate 2.5 mL/min; Detection: 220 and 254 mn DAD.
[3]MS conditions: API-electrospray
[4]Amino acid refers to the amino acid portion of the molecule, for example in Example 62B the amino acid is D-Ala.

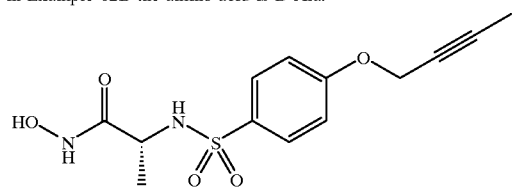

Example 62B

| | Abbreviations: |
|---|---|
| Cha | cyclohexylalanine |
| Chg | cyclohexylglycine |
| Mob | 4-methoxybenzyl |
| Hyp | hydroxyproline |
| 2-Cl—Bn | 2-chlorobenzyl |
| Phg | phenylglycine |
| Mtr | 4-methoxy-2,3,4-trimethylbenzenesulfonyl |
| Pbf | 2,2,4,6,7-pentamethyldihydrobenzofuran-5-sulfonyl |
| Mbzl | 4-methylbenzyl |
| Hfe | homophenylalanine |
| Cbz | benzyloxycarbonyl |
| Nal | naphthylalanine |
| Nve | norvaline |
| 3,4-diF—Phe | 3,4-difluorophenylalanine |
| 4-F—Phe | 4-fluorophenylalanine |
| 4-nitro-Phe | 4-nitrophenylalanine |
| Pip | pipecolic acid |
| Thi | thienylalanine |
| Thz | thiazolidine-4-carboxylic acid |
| Tic | tetrahydroisoquinoline-3-carboxylic acid |
| Abu | -Diaminobutyric acid |
| Acm | Acetamidomethyl |
| Ts | p-toluenesulfonyl |
| All | allyl |
| Bn | Benzyl |
| Chx | Cyclohexyl |
| TFA | trifluoroacetic acid |
| DCM | dichloromethane |
| Fmoc | N-(9-Fluorenylmethoxycarbonyl) |
| HOBt | 1-hydroxybenzotriazole hydrate |
| DIC | 1,3-diisopropylcarbodiimide |
| EDC | 1-ethyl-3(3'-dimethylaminopropyl)carbodiimide hydrochloride |

Example 105

(2R,3S)-2-({[4(2-Butynyloxy)Phenyl]Sulfonyl}Amino)-N-Hydroxy-3-Methylpentanamide According to the procedure of Example 26, 0.5 g (3.811 mmol) of D-isoleucine and 1.025 g (4.192 mmol) of 4but-2-ynyloxy-benzenesulfonyl chloride provided 0.378 g of the NH-sulfonamide carboxylic acid as a white solid. Electrospray Mass Spec 338.2 (M−H)[−]

According to the procedure of Example 25, 0.345 g (1.018 mmol) of the carboxylic acid provided 0.191 g of the hydroxamic acid, (2R,3S)-2-({[4-(2-butynyloxy)phenyl]sulfonyl}amino)-N-hydroxy-3-methylpentanamide, as a white solid. Electrospray Mass Spec 355.2 (M+H)[+]

Example 106

(2R)-2-({[4-(2-Butynyloxy)Phenyl]Sulfonyl}Amino)-N-Hydroxy-3,3-Dimethylbutanamide According to the procedure of Example 26, 0.422 g (3.216 mmol) of D-tert-leucine and 0.865 g (3.538 mmol) of 4-but-2-ynyloxy-benzenesulfonyl chloride provided 0.532 g of the NH-sulfonamide carboxylic acid as a white solid. Electrospray Mass Spec 338.3 (M−H)[−]

According to the procedure of Example 25, 0.472 g (1.392 mmol) of the carboxylic acid provided 0.131 g of the hydroxamic acid, (2R)-2-({[4(2-butynyloxy)phenyl]sulfonyl}amino)-N-hydroxy-3,3-dimethylbutanamide, as a white solid. Electrospray Mass Spec 355.2 (M+H)[+]

Example 107

(2S)-2-[(4-But-2-Ynyloxy-Benzenesulfonyl)-Methyl-Amino]-N-Hydroxy-Propionamide

According to the procedure of Example 20, 0.500 g (3.58 mmol) of D-alanine methyl ester hydrochloride and 0.877 g (3.58 mmol) of 4but-2-ynyloxybenzenesulfonyl chloride provided 0.532 g of the NH-sulfonamide ester, (2R)-2-(4-but-2-ynyloxy-benzenesulfonylamino)-propionic acid methyl ester, as a white solid. Electrospray Mass Spec 312.1 (M+H)[+]

According to the procedure of Example 21, 0.30 g (0.971 mmol) of (2R)2-(4-but-2-ynyloxy-benzenesulfonylamino)-propionic acid methyl ester provided 0.31 g of (2R)-2-[(4-but-2-ynyloxy-benzenesulfonyl)-methyl-amino]-propionic acid methyl ester as a colorless oil. Electrospray Mass Spec 326.2 (M+H)[+]

To a solution of 0.273 g (0.840 mmol) of (2R)-2-[(4-but-2-ynyloxy-benzenesulfonyl)-methyl-amino]-propionic acid methyl ester in 6 mL of THF/methanol (1/1) was added 0.123 g (2.94 mmol) of lithium hydroxide monohydrate and the resulting solution was stirred at room temperature for 3 h. The reaction was then acidified with 5% HCl solution and extracted with chloroform. The combined organics were dried over MgSO4, filtered and concentrated in vacuo to give 0.256 g of 2-[(4-but-2-ynyloxy-benzenesulfonyl)-methyl-amino]-propionic acid as a white solid. Electrospray Mass Spec 310.2 (M−H)[−]

According to the procedure of Example 25, 0.220 g (0.707 mmol) of of 2-[(4-but-2-ynyloxy-benzenesulfonyl)methyl-amino]-propionic acid provided 0.172 g of (2S)-2-[(4but-2-ynyloxy-benzenesulfonyl)-methyl-amino]-N-hydroxy-propionamide as a white solid. Electrospray Mass Spec 327.2 (M+H)[+]

Example 108

2-[(4-But-2-Ynyloxy-Benzenesulfonyl)-Ethyl-Amino]-N-Hydroxy-3-Methyl-Butyramide

According to the procedure of Example 20, 1.500 g (8.95 mmol) of D,L-valine methyl ester hydrochloride and 2.19 g (8.95 mmol) of 4-but-2-ynyloxybenzenesulfonyl chloride provided 2.15 g of the NH-sulfonamide ester, 2-(4-but-2-ynyloxy-benzenesulfonylamino)-3-methyl-butyric acid methyl ester, as a white solid.

According to the procedure of Example 5, 0.350 g (1.032 mmol) of 2-(4-but-2-ynyloxy-benzenesulfonylamino)3-methyl-butyric acid methyl ester and 0.25 mL (3.097 mmol) of iodoethane provided 0.334 g of 2-[(4-but-2-ynyloxy-benzenesulfonyl)ethyl-amino]-3-methyl-butyric acid methyl ester as a white solid. Electrospray Mass Spec 368.4 (M+H)$^+$ According to the procedure of Example 11, 0.304 g (0.828 mmol) of 2-[(4-but-2-ynyloxy-benzenesulfonyl)-ethyl-amino]-3-methyl-butyric acid methyl ester provided 0.273 g of 2-[(4-but-2-ynyloxy-benzenesulfonyl)-ethyl-amino]-3-methylbutyric acid as a white solid. Electrospray Mass Spec 352.2 (M–H)$^-$ According to the procedure of Example 9, 0.232 g (0.657 mmol) of 2-[(4but-2-ynyloxy-benzenesulfonyl)-ethyl-amino]-3-methyl-butyric acid provided 0.235 g of 2-[(4but-2-ynyloxy-benzenesulfonyl)-ethyl-amino]-N-hydroxy-3-methyl-butyramide as an off-white solid. Electrospray Mass Spec 369.3 (M+H)$^+$

Example 109

2-[{[4-(2-Butynyloxy)Phenyl]Sulfonyl}(2-Propynyl)Amino]-N-Hydroxy-3-Methylbutanamide According to the procedure of Example 108, starting from D, L-valine methyl ester hydrochloride and propargyl bromide, 2-[{[4-(2-butynyloxy)phenyl]sulfonyl}(2-propynyl)amino]-N-hydroxy-3-methylbutanamide was obtained as a white foam. Electrospray Mass Spec 379.4 (M+H)$^+$ propynyl)amino]-N-hydroxy-3-methylbutanamide was obtained as a white foam Electrospray Mass Spec 379.4 (M+H)$^+$

Example 110

2-[(4-But-2-Ynyloxy-Benzenesulfonyl)-Propyl-Amino]-N-Hydroxy-3-Methyl-Butyramide According to the procedure of Example 108, starting from D, L-valine methyl ester hydrochloride and propyl iodide, 2-[(4-but-2-ynyloxy-benzenesulfonyl)-propyl-amino]-N-hydroxy-3-methyl-butyramide was obtained as a white solid. Electrospray Mass Spec 383.2 (M+H)$^+$

Example 111

2-[(4-But-2-Ynyloxy-Benzenesulfonyl)-(3-Phenyl-Propyl)-Amino]-N-hydroxy-3-Methyl-Butyramide According to the procedure of Example 108, starting from D, L-valine methyl ester hydrochloride and 1-bromo-3-phenylpropane, 2-[(4-but-2-ynyloxy-benzeneulfonyl)-(3-phenyl-propyl)-amino]-N-hydroxy-3-methyl-butyramide was obtained as a white solid. Electrospray Mass Spec 459.2 (M+H)$^+$

Example 112

2-[(4-But-2-Ynyloxy-Benzenesulfonyl)-Cyclopropylmethyl-Amino]-N-Hydroxy-3-Methyl-Butyramide According to the procedure of Example 108, starting from D, L-valine methyl ester hydrochloride and (bromomethyl) cyclopropane, 2-[(4-but-2-ynyloxy-benzenesulfonyl)cyclopropylmethyl-amino]-N-hydroxy-3-methyl-butyramide was obtained as a white solid. Electrospray Mass Spec 395.3 (M+H)$^+$

Example 113

2-[(4-But-2-Ynyloxy-Benzenesulfonyl)-Isobutyl-Amino]-N-Hydroxy-3-Methyl-Butyramide According to the procedure of Example 108, starting from D, L-valine methyl ester hydrochloride and 2-methyl-1-iodopropane, 2-[(4-but-2-ynyloxy-benzenesulfonyl)-isobutyl-amino]-N-hydroxy-3-methyl-butyramide was obtained as a white solid. Electrospray Mass Spec 397.2 (M+H)$^+$

Example 114

2-[(4-But-2-Ynyloxy-Benzenesulfonyl)-Pyridin-3-Ylmethyl-Amino]-N-Hydroxy-3-Methyl-Butyramide According to the procedure of Example 108, starting from D, L-valine methyl ester hydrochloride and 3-picolyl chloride hydrochloride, 2-[(4-but-2-ynyloxy-benzenesulfonyl)-pyridin-3-ylmethyl-amino]-N-hydroxy-3-methyl-butyramide was obtained as a white solid. Electrospray Mass Spec 432.2 (M+H)$^+$

Example 115

2-[(4-But-2-Ynyloxy-Benzenesulfonyl)-Methyl-Amino]-2-Cyclohexyl-N-Hydroxy-Acetamide According to the procedure of Example 107, starting from D-cyclohexylglycine methyl ester hydrochloride and iodomethane, 2-[(4but-2-ynyloxy-benzenesulfonyl)-methyl-amino]-2-cyclohexyl-N-hydroxy-acetamide was obtained as a white solid. Electrospray Mass Spec 395.2 (M+H)$^+$

Example 116

2-[(4-But-2-Ynyloxy-Benzenesulfonyl)-Pyridin-3-Ylmethyl-Amino]-2-Cyclohexyl-N-Hydroxy-Acetamide According to the procedure of Example 107, starting from D-cyclohexylglycine methyl ester hydrochloride and 3-picolyl chloride hydrochloride, 2-[(4-but-2-ynyloxy-benzenesulfonyl)-pyridin-3-ylmethyl-amino]-2cyclohexyl-N-hydroxy-acetamide was obtained as a tan solid. Electrospray Mass Spec 472.3 (M+H)$^+$

Example 117

2-{{(4-But-2-Ynyloxy-Benzenesulfonyl)-[4-(2-Piperidin-1-yl-Ethoxy)-Benzyl]-Amino}-2-Cyclohexyl-N-Hydroxy-Acetamide According to the procedure of Example 107, starting from D-cyclohexylglycine methyl ester hydrochloride and 4-(2-piperidin-1-yl-ethoxy)-benzyl chloride (U.S. Pat. No. 5,929, 097), 2-{(4but-2-ynyloxy-benzenesulfonyl)-[4-(2-piperidin-1-yl-ethoxy)-benzyl]-amino}-2-cyclohexyl-N-hydroxy-acetamide was obtained as a white solid. Electrospray Mass Spec 598.3 (M+H)$^+$

Example 118

2-{{[4-(2-Butynyloxy)Phenyl]Sulfonyl}[3-(Diethylamino)Propyl]Amino}-N-Hydroxy-3-Methylbutanamide According to the procedure of Example 5, 1.00 g (2.95 mmol) 2-(4but-2-ynyloxy-benzenesulfonylamino)-3- methyl-butyric acid methyl ester and 0.88 mL (8.849 mmol) of 1-bromo-3-chloropropane provided 0.92 g of methyl2-[{[4-(2-butynyloxy)penyl]sulfonyl}(3-chloropropyl)amino]-3-methylbutanoate as a white solid. Electrospray Mass Spec 416.2 (M+H)+

To a solution of 0.45 g (1.08 mmol) of methyl 2-[{[4-(2-butynyloxy)-phenyl]-sulfonyl}(3-chloropropyl)amino]-3-methylbutanoate in 5.0 mL of DMF was added 0.163 g (1.08 mmol) of sodium iodide and 0.34 mL (3.24 mmol) of diethylamine. The reaction was heated to 80° C. for 3 h and then cooled to room temperature. The mixture was then diluted with water and extracted with ethyl acetate. The combined organics were washed with water and brine, dried over $Na_2SO_4$, filtered and concentrated in vacuo to provide 0.441 g of methyl 2-{{[4-(2-butynyloxy)-phenyl]sulfonyl}[3-(diethylamino)propyl]amino}-3-methylbutanoate as a brown oil. Electrospray Mass Spec 453.5 (M+H)+

According to the procedure of Example 11, 0.412 g (0.912 mmol) of methyl 2-{{[4-(2-butynyloxy)phenyl]sulfonyl}[3-(diethylamino)propyl]amino}-3-methyl-butanoate provided 0.368 g of N-{[4-(2-butynyloxy)phenyl]sulfonyl}-N-[3-(diethylamino)propyl]valine as a tan foam. Electrospray Mass Spec 439.4 (M+H)+

According to the procedure of Example 9, 0.338 g (0.772 mmol) of of N-{[4-(2-butynyloxy)phenyl]sulfonyl}-N-[3-(diethylamino)propyl]valine provided 0.223 g of 2-{{[4-(2-butynyloxy)phenyl]sulfonyl}3-(diethylamino)propyl]amino}-N-hydroxy-3-methylbutanamide as a brown foam. Electrospray Mass Spec 369.3 (M+H)+

Example 119

2-{{[4-(2-Butynyloxy)Phenyl]Sulfonyl}3-(4-Morpholinyl)Propyl]Amino}-N-Hydroxy-3-Methylbutanamide According to the procedure of Example 118, using morpholine instead of diethylamine, 2-[{[4-(2-butynyloxy)phenyl]sulfonyl}(3-chloropropyl)amino]-3-methylbutanoate was converted into 2-{{[4-(2-butynyloxy)phenyl]sulfonyl}[3-(4-morpholinyl)propyl]amino}-N-hydroxy-3-methylbutanamide, obtained as a white foam. Electrospray Mass Spec 468.4 (M+H)+

Example 120

2-{{[4-(2-Butynyloxy)Phenyl]Sulfonyl}[3-(4-Methyl-1-Piperazinyl)Propyl]Amino}-N-Hydroxy-3-Methylbutanamide Hydrochloride According to the procedure of Example 118, using 1-methylpiperazine instead of diethylamine, 2-[{[4-(2-butynyloxy)phenyl]sulfonyl}(3-chloropropyl)-amino-3-3-methylbutanoate was converted into 2-{{[4-(2-butynyloxy)phenyl]sulfonyl}-[3-(4-methyl-1-piperazinyl)propyl]amino}-N-hydroxy-3-methylbutanamide, which was converted into the corresponding hydrochloride salt with ethereal HCl solution to provide an off-white solid. Electrospray Mass Spec 481.4 (M+H)+

Example 121

2-{{4-(2-Butynyloxy)Phenyl]Sulfonyl}[4-(Diethylamino)Butyl]Amino}-N-Hydroxy-3-Methylbutanamide According to the procedure of Example 118, using 1-bromo-4-chlorobutane instead of 1-bromo-3-chlorobutane, 2-(4-but-2-ynyloxy-benzenesulfonylamino)-3-methyl-butyric acid methyl ester was converted into 2-{{[4-(2-butynyloxy)phenyl]-sulfonyl}[4-(diethylamino)butyl]amino}-N-hydroxy-3-methylbutanamide, which was converted into the corresponding hydrochloride salt with ethereal HCl solution to provide a brown solid. Electrospray Mass Spec 468.2 (M+H)+

Example 122

2-{{[4-(2-Butynyloxy)Phenyl]Sulfonyl}[4-(4-Methyl-1-Piperazinyl)Butyl]Amino}-N-Hydroxy-3-Methylbutanamide According to the procedure of Example 118, using 1-bromo-4chlorobutane instead of 1-bromo-3-chlorobutane and 1-methylpiperazine instead of diethylamine, 2-(4but-2-ynyloxy-benzenesulfonylamino)-3-methyl-butyric acid methyl ester was converted into 2-{{[4-(2-butynyloxy)phenyl]sulfonyl}[4-(4-methyl-1-piperazinyl)-butyl]amino}-N-hydroxy-3-methylbutanamide, which was converted into the corresponding hydrochloride salt with ethereal HCl solution to provide a brown solid. Electrospray Mass Spec 495.2 (M+H)+

Example 123

2-[[[4-(2-Butynyloxy)Phenyl]Sulfonyl][2-(4-Morpholinyl)Ethyl]Amino]-N-Hydroxy-3-Methylbutanamide According to the procedure of Example 21, 0.419 g (1.236 mmol) of 2-(4but-2-ynyloxy-benzenesulfonylamino)-3-methyl-butyric acid methyl ester and 0.408 g (2.20 mmol) of 4-(2-chloroethyl)morpholine hydrochloride provided 0.506 g of 2-[(4-but- 2-ynyloxy-benzenesulfonyl)-(2-morpholin-4-yl-ethyl)-amino]-3-methyl-butyric acid methyl ester as a colorless oil. Electrospray Mass Spec 453.0 (M+H)+

According to the procedure of Example 11, 0.469 g (1.04 mmol) of 2-[(4-but-2-ynyloxy-benzenesulfonyl)-(2-morpholin4-yl-ethyl)-amino]-3-methyl-butyric acid methyl ester provided 0.245 g of 2-[(4-but-2-ynyloxy-benzenesulfonyl)-(2-morpholin-4-yl-ethyl)- amino]-3-methyl-butyric acid as a white solid. Electrospray Mass Spec 438.9 (M+H)+

According to the procedure of Example 9, 0.243 g (0.554 mmol) of 2-[(4-but-2-ynyloxy-benzenesulfonyl)-(2-morpholin-4-yl-ethyl)- amino]-3-methyl-butyric acid provided 0.05 g of 2-[[[4-(2-butynyloxy)phenyl]sulfonyl][2-(4-morpholinyl)ethyl]amino]-N-hydroxy-3-methylbutanamide, which was converted into the corresponding hydrochloride salt with etheral HCl solution to give 0.105 g of 2-[[[4-(2-butynyloxy)phenyl]sulfonyl][2-(4-morpholinyl)ethyl]amino]-N-hydroxy-3-methylbutanamide hydrochloride as a white solid. Electrospray Mass Spec 454.0 (M+H)+

Example 124

2-[{[4-(But-2-Ynyloxy)Phenyl]Sulfonyl}(2-Morpholin-4-Ylethyl)Amino]-N-Hydroxyacetamide Hydrochloride According to the procedure of Example 123, (4-but-2-ynyloxy-benzenesulfonylamino)-acetic acid ethyl ester provided 2-[{[4-(but-2-ynyloxy)phenyl]sulfonyl}(2-morpholin-4-ylethyl)amino]-N-hydroxyacetamide hydrochloride as an off-white solid. Electrospray Mass Spec 412.3 (M+H)$^+$

Example 125

2-{{[4-(2-Butynyloxy)Phenyl]Sulfonyl}[4-(4-Methyl-1-Piperazinyl)-2-Butynyl]Amino}-N-Hydroxy-3-Methylbutanamide According to the procedure of Example 5, 0.800 g (2.36 mmol) of 2-(4-but-2-ynyloxy-benzenesulfonylamino)-3-methyl-butyric acid methyl ester and 0.53 g (4.72 mmol) of 80% propargyl bromide gave 0.89 g of methyl 2-[{[4-(2-butynyloxy)phenyl]sulfonyl}(2-propynyl)amino]-3-methylbutanoate as a colorless oil. Electrospray Mass Spec 378.2 (M+H)$^+$ To a solution of 0.500 g (1.326 mmol) of methyl 2-[{[4-(2-butynyloxy)phenyl]sulfonyl}(2-propynyl)amino]-3-methylbutanoate in 4.0 mL of dioxane was added 0.099 g (3.316 mmol) of paraformaldehyde, 5mg of cuprous chloride, 0.5 mL of acetic acid and 0.294 ml (2.652 mmol) of 1-methylpiperazine. The resulting mixture was stirred at room temperature for 15 minutes after which the reaction had turned green. The reaction was then heated to reflux for 2 h, after which the reaction had turned brown. The reaction mixture was cooled to room temperature and extracted with ether. The combined organics were washed with saturated sodium bicarbonate solution, dried over Na$_2$SO$_4$, filtered and concentrated in vacuo to give 0.649 g of methyl 2-{{[4-(2-butynyloxy)phenyl]sulfonyl)}-4-(4-methyl-1-piperazinyl)-2-butynyl]amino}-3-methylbutanoate as a brown oil. Electrospray Mass Spec 490.3 (M+H)$^+$ According to the procedures of Examples 11 and 9 methyl2-{{[4-(2-butynyloxy)phenyl]sulfonyl}-4-(4-methyl-1-piperazinyl)-2-butynyl]amino}-3-methylbutanoate provided the hydroxamic acid 2-{{[4-(2-butynyloxy)phenyl]sulfonyl}[4-(4-methyl-1-piperazinyl)-2-butynyl]amino}-N-hydroxy-3-methylbutanamide as a white solid. This was converted into 2-{{[4-(2-butynyloxyphenyl]sulfonyl}[4-(4-methyl-1-piperazinyl)-2-butynyl]amino}-N-hydroxy- 3-methylbutanamide hydrochloride with ethereal HCl solution to give the product as a brown powder. Electrospray Mass Spec 491.3 (M+H)$^+$

Example 126

2-{{[4-(2-Butynyloxy)Phenyl]Sulfonyl}[4-(Diethylamino)-2-Butynyl]Amino}-N-Hydroxy-3-Methylbutanamide To a solution of 1.00 g (2.653 mmol) of methyl 2-[{[4-(2-butynyloxy)phenyl]sulfonyl}(2-propynyl)amino]-3-methylbutanoate in 8.0 mL of dioxane was added 0.198 g (6.632 mmol) of paraformaldehyde, 10 mg of cuprous chloride, 1.0 mL of acetic acid and 0.55 ml (5.305 mmol) diethylamine. The resulting mixture was stirred at room temperature for 15 minutes after which the reaction had turned green. The reaction was then heated to reflux for 2 h, after which the reaction had turned brown- The reaction mixture was cooled to room temperature and extracted with ether. The combined organics were washed with saturated sodium bicarbonate solution, dried over Na$_2$SO$_4$, filtered and concentrated in vacuo to give 1.23 g of methyl 2-{{[4-(2-butynyloxy)phenyl]sulfonyl}[4-(diethylamino)-2-butynyl]amino}-3-methylbutanoate as a brown oil.

Methyl 2-{{[4-(2-butynyloxy)phenyl]sulfonyl}[4-(diethylamino)-2-butynyl]amino}-3-methylbutanoate was converted into 2-{{[4-(2-butynyloxy)phenyl]sulfonyl}[4-(diethylamino)2-butynyl]amino}-N-hydroxy-3-methylbutanamide hydrochloride, isolated as a brown foam, according to the procedures of Examples 11 and 9. Electrospray Mass Spec 464.5 (M+H)$^+$

Example 127

2-{{[4-(2-Butynyloxy)Phenyl]Sulfonyl}[4-(Methylamino)-2-Butynyl]Amino}-N-Hydroxy-3-Methylbutanamide To a 0° solution of 0.689 g (1.491 mmol) of methyl 2-{{[4(2-butynyloxy)phenyl]sulfonyl}[4-(diethylamino)-2-butynyl]amino}-3-methylbutanoate in 12 mL of diethyl ether was added 0.60 mL of a 3.0M solution of cyanogen bromide in dichloromethane. The reaction was allowed to warm to room temperature and stirred overnight. The resulting mixture was diluted with ether, washed with 5% HCl and brine, dried over Na2SO4, filtered and concentrated in vacuo to provide the crude propargylic bromide.

The bromide was dissolved in 7.0 mL of THF and 7.0 mL of a 2.0 M solution of methylamine in THF was added. The resulting mixture was stirred at room temperature overnight and then diluted with ethyl acetate and saturated sodium bicarbonate solution. The organics were dried over Na2SO4, filtered and concentrated in vacuo. The residue was then dissolved in 10.0 mL of DMF and 0.39 g of di-t-butyldicarbonate and 0.039 g of 4-dimethylaminopyridine was added. The reaction was again stirred overnight at room temperature and then diluted with water and extracted with ether. The combined organics were washed with water, dried over Na2SO4, filtered and concentrated in vacuo to provide methyl 2-{{[4-(2-butynyloxy)phenyl]sulfonyl}[4-(methylamino)-2-butynyl]amino}-3-methylbutanoate.

The carbamate was dissolved in 3.2 mL of THF/MeOH (1:1) and 1.6 mL of a 1.0N NaOH solution was added. The reaction was heated to reflux for 15 h and then cooled, neutralized with 5% HCl solution and extracted with dichloromethane. The organics were dried over Na2SO4, filtered and concentrated in vacuo to provide 0.157 g of 2-{{[4-(2-butynyloxy)phenyl]sulfonyl}[4-(methylamino)-2-butynyl]amino}-3-methylbutanoic acid.

According to the procedure of Example 25, 0.143 g (0.283 mmol) of 2-{{[4-(2-butynyloxy)phenyl]sulfonyl}[4-methylamino)-2-butynyl]amino}-3-methylbutanoic acid was converted into 0.079 g of the hydroxamic acid, 2-{{[4-(2-butynyloxy)phenyl]sulfonyl}[4-methylamino)-2-butynyl]amino}-N-hydroxy-3-methylbutanamide, obtained as a brown solid. Electrospray Mass Spec 422.3 (M+H)$^+$

Example 128

((2R)-{[4-(2-Butynyloxy)Phenyl]Sulfonyl}(Methyl) Amino)[(4-Diethylamino)Cyclohexyl]-N-Hydroxyethamide To a solution of D-4-hydroxy phenylglycine dissolved in 3N NaOH was added Raney nickel (6.75 g) and water (45 mL )and the mixture was then hydrogenated on a Parr hydrogenator at 50–80° C. for 24 h at 40 psi of hydrogen. The reaction mixture was filtered through Celite, washed with dioxane, filtered and concentrated to 20 mL. An additional 20 mL of dioxane was added and the reaction was cooled to 0° C. and triethylamine (2.72 mL, 19.4 mmol) was added, followed by 4(2-butynyloxy)-benzenesulfonyl chloride (3.21 g, 13.2 mmol). The mixture was stirred at room temperature overnight and then concentrated in vacuo. The residue was dissolved in water and neutralized with 1N HCl to pH 2–3. The precipitated white solid was filtered to provide 2.8 g of (2R)-{[4-(2-butynyloxy)phenyl]sulfonyl{amino)(4-hydroxycyclohexyl)ethanoic acid. mp 90–100° C. Electrospray Mass Spec 382.1 (M+H)$^+$ To a solution of (2R)-{[4-2-butynyloxy)phenyl]sulfonyl}amino)(4-hydroxycyclohexyl)ethanoic acid (0.39 g, 1.0 mmol) in 3 mL of DMF was added iodomethane (0.14 mL, 2.2 mmol) and potassium carbonate (0.69 g, 5 mmol) and the resulting mixture was stirred at room temperature overnight. The reaction was thendiluted with ethyl acetate and theorganic layer was washed with water and brine, dried over sodium sulfate, filtered, and concentrated. Chromatography on silica gel eluting with hexane:ethyl acetate (3:7) provided 0.05 g of the cis -isomer as an oil, Electrospray Mass Spec410.2 (M+H )$^+$; and 0.28 g of the trans-isomer as a white solid. mp 94–96° C. Electrospray Mass Spec 410.3 (M+H )$^+$.

To a solution of a 1:5 mixture of (cis)- and (trans)-methyl (2R)-){[4-(2-butynyloxy)phenyl]sulfonyl}(methyl)amino)(4-hydroxycyclohexyl)ethanoate (0.65 g, 0.159 mmol) in dichloromethane (2 mL) was added Dess-Martin periodinane (0.75 g, 1.77 mmol ) and the reaction was stirred at room temperature for 1 h. The mixture was diluted with 50 mL of ether and poured into 1N NaOH (20 mL) and stirred until the solid disappeared. The ether was washed with 20 mL of 1N NaOH, water and brine, dried over sodium sulfate, filtered, and concentrated to obtain 0.61 g of methyl (2R)-{[4-(2-butynyloxy)phenyl]sulfonyl}(methyl)amino)(4-oxocyclohexyl)ethanoate. Electrospray Mass Spec 408.2 (M+H)$^+$.

To a solution of methyl (2R)-{4-(2-butynyloxy)phenyl]sulfonyl}(methyl)amino)(4-oxocyclohexyl)ethanoate (0.54 g, 1.32 mmol) dissolved in 4 mL of 1,2 dichloroethane was added diethylamine (0.097 mL, 0.93 mmol) and the reaction was stirred at room temperature overnight. Sodium triacetoxyborohydride (0.49 g, 2.32 mmol) was then added, followed by acetic acid (0.078 g, 1.32 mmol). The mixture was stirred at room temperature overnight. The reaction was then concentrated in vacuo and the residue was diluted with ethyl acetate and washed with saturated NaHCO$_3$. The ethyl acetate was washed with 1N HCL and the aqueous layer was neutralized with 5N NaOH to pH~8–9, and then extracted with CH$_2$Cl$_2$. The organic layer was washed with water and brine, dried over sodium sulfate, filtered, and concentrated to provide 0.18 g of methyl ((2R)-{[4-(2-butynyloxy)phenyl]sulfonyl}(methyl)amino)[(4-diethylamino)cyclohexyl]ethanoate. Electrospray Mass Spec 465.5 (M+H )$^+$.

To a solution of methyl ((2R)-{[4-(2-butynyloxy)phenyl]sulfonyl}(methyl)amino)[(4-diethylamino)cyclohexyl]ethanoate (0.15 g, 0.32 mmol) in 2.0 mL of THF was added 1N NaOH (0.40 mL) and 2 mL of methanol and the mixture was heated to ~55° C. overnight. The reaction was concentrated in vacuo to give 0.17 g of ((2R)-{[4-(2-butynyloxy)phenyl]sulfonyl}(methyl)amino)[(4diethylamono)cyclohexyl]ethanoicacid, sodium salt. Electrospray Mass Spec 451.4 (M+H )$^+$.

According to the procedure of Example 9, ((2R){[4-(2-butynyloxy)phenyl]sulfonyl}(methyl)-amino)[(4-diethylamono)cyclohexyl]ethanoicacid, sodium salt was converted into the hydroxamic acid, ((2R}{[4-(2-butynyloxy)phenyl]sulfonyl}(methyl)amino)[(4-diethylamono)cyclohexyl]-N-hydroxy-ethamide. Electrospray Mass Spec 466.4 (M+H)$^+$.

Example 129

(2R)-{[4-(2-Butynyloxy)Phenyl]Sulfonyl}Amino-N-Hydroxy-2-(4-Hydroxycyclohexyl)Ethanamide To a mixture of (cis)- and (trans)-(2R)-{[4-(2-butynyloxy)phenyl]-sulfonyl}amino)(4-hydroxycyclohexyl)ethanoic acid from Example 128 (0.57 g, 1.5 mmol) was added t-butyldimethylsilyl chloride (0.56 g, 3.6 mmol), imidazole (0.5 g 7.5 mmol) and DMF (4 mL) and the mixture was stirred at room temperature overnight. After removing the solvent, the resulting oil was extracted with ether and water. The ether layer was washed with water and brine, dried over sodium sulfate, filtered and concentrated to provide 0.78 g of tert-butyl(dimethyl)silyl(2R)-{[4-(2-butynyloxy)phenyl]sulfonyl}amino)(4-{[tert-butyl(dimethyl)silyl]oxy}cyclohexyl)ethanoate. Yield 85.2%. Electrospray Mass Spec 610.2 (M+H )$^+$.

To a solution of tert-butyl(dimethyl)silyl(2R)-){[4-(2-butynyloxy)phenyl]sulfonyl}amino)(4-{[tert-butyl(dimethyl)silyl]oxy}cyclohexyl)ethanoate (0.76 g ,1.24 mmol) in 8 mL of THF/methanol (1:1) was added 1 N NaOH (1.25 mL, 1.25 mmol) and the reaction was stirred at room temperature overnight. Reducing the solvent to one quarter volume, then adding brine, the aqueous layer was neutralized with 1M KHSO4 to pH~4 and then extracted with ethyl acetate. The combined organics were washed with water and brine, dried over sodium sulfate, filtered, and concentrated to obtain 0.68 g of (2R)-{[4-(2-butynyloxy)phenyl]sulfonyl}amino)(4-{[tert-butyl(dimethyl)silyl]oxy}cyclohexyl) ethanoic acid. Electrospray Mass Spec 494.2 (M–H)$^-$.

To a solution of (2R)-{[4-(2-butynyloxy)phenyl]sulfonyl}amino)(4-{[tert-butyl(dimethyl)silyl]oxy}cyclohexy) ethanoic acid (0.62 g 1.25 mmol) and 1-(3-dimethyl aminopropyl) 3- ethyl carbodimide (0.39 g, 1.67 mmol) in DMF (7 mL), was added 1-hydroxybenzotriazole (0.23 g, 1.50 mmol) and the reaction was stirred at room temperature for 2 h. Hydroxylamine (0.54 mL of 50% in water, 8.75 mmol) was added and the reaction was stirred overnight. The solvent was removed in vacuo and the residue was diluted with ethyl acetate and water. The organic layer was washed with saturated NaHCO$_3$ and water, dried over Na$_2$SO$_4$ and concentrated. The residue was purified by using preparative TLC to obtain 0.3 g of (2R)-){[4-(2-butynyloxy)phenyl]sulfonyl}amino)(4-{[tert-butyl(dimethyl)silyl]oxy}cyclohexyl)-N-hydroxyethanamide as an off-white solid. mp 125° C. (d). Electrospray Mass Spec 511.2 (M+H)$^+$.

To a solution of (2R)-{[4-(2-butynyloxy)phenyl] sulfonyl}amino)(4-{[tert-butyl(dimethyl)silyl] oxy}cyclohexyl)-N-hydroxyethanamide (0.11 g, 0.21 mmol) in 2.5 mL of acetonitrile, cooled in an ice bath, was added 1 mL of 8% HF in acetonitrile. After a couple of minutes, a solid precipitated. The reaction was diluted with dichloromethane and water and filtered to give a white solid 0.06 g. The dichloromethane layer was washed with water and brine, dried over sodium sulfate, filtered, and concentrated to provide an additional 0.02 g of (2R)-{[4-(2-butynyloxy)phenyl]sulfonyl}amino-N-hydroxy-2-(4-hydroxycyclohexyl)ethanamide. mp 180–182° C. Electrospray Mass Spec 397.2 (M+H)$^+$.

Example 130

(2R)-{[4-(2-Butynyloxy)Phenyl]Sulfonyl}(Methyl) Amino)-N-Hydroxy-2-(4Hydroxycyclohexyl)-Ethanamide According to the procedure in Example 129, (trans)-methyl (2R)-{[4-2-butynyloxy)phenyl]sulfonyl}(methyl) amino)(4-hydroxycyclohexyl)ethanoate (from Example 128) was converted into (2R){-[(2-butynyloxy)phenyl] sulfonyl}(methyl)amino)-N-hydroxy-2-(4hydroxycyclohexyl)ethanamide. Mp 195–197° C. Electrospray Mass Spec 411.2 (M+H)$^+$.

Example 131

2-[(6-But-2-Ynyloxy-Pyridine-3-Sulfonyl)-Methyl-Amino]-N-Hydroxy-Acetamide

In a 250 mL three neck round bottom flask equipped with an overhead stirrer was charged 27 mL water, and cooled to −3° C. (ice/NaCl). Thionyl chloride (4.52 mL, 61.96 mmol, 4.5 eq) was added slowly so the temperature did not exceed 7° C. The ice bath was removed, allowed to warm to room temperature, then 0.07 g (0.69 mmol, 0.05 eq) of copper (I) chloride was added. The mixture was then recooled to −5° C.

5-Amino-2-chloropyridine (1.77 g, 13.67 mmol) was dissolved in 14 mL of concentrated HCl and cooled to −5° C. to which a solution of 1.04 g (15.14 mmol, 1.1 eq) NaNO2 in 12 mL of water was added slowly so the temperature was maintained between −5 and 0° C. This mixture was then added to the thionyl chloride/water/CuCl mixture. A frothing precipitate resulted and was allowed to stir for another 30 min. The product was filtered and air dried. Solids were taken up in ethyl acetate, washed with brine, dried over MgSO4 and concentrated in vacuo to afford 1.7 g (62%) of 6-chloro-pyridine-3-sulfonyl chloride as a light tan solid. Electrospray Mass Spec 210.9 (M+H)$^+$ To a solution of 6-chloro-pyridine-3-sulfonylchloride (5.15 g, 24.3 mmol) in 50 mL of anhydrous chloroform, 7.4 mL of pyridine and 8.82 g (48.6 mmol, 2 eq) of sarcosine hydrochloride were added and the reaction proceeded overnight at room temperature. The solvent was removed in vacuo, diluted with water, neutralized with sodium bicarbonate and extracted with ethyl acetate which was then washed with brine, dried over MgSO4, directly preadsorbed onto silica gel and purified via flash chromatography using 5:1 Hex:EtOAc to afford 3.97 g (51%) of [(6-chloro-pyridine-3-sulfonyl)-methyl-amino]-acetic acid tert-butyl ester. Electrospray Mass Spec 321.1 (M+H)$^+$ To a solution of 0.77 mL (19.3 mmol) of 2- butynl-ol and 0.18 g (4.37 mmol) of sodium hydroxide were heated at 100° C. for one hour. [(6-chloro-pyridine-3-sulfonyl)methyl-amino]-acetic acid tert-butyl ester (1.0 g, 3.12 mmol) was added to this solution. Additional butynol was added to facilitate stirring, and the reaction was stirred at 100° C. overnight. The reaction was cooled, diluted with water, and washed with ethyl acetate. The aqueous layer was acidified with 2N HCl, and extracted with ethyl acetate (2×). The combined organics were washed with brine, dried over MgSO4, concentrated to solids which were slurried in 1:1:1 dichloromethane: hexane:ethyl acetate to afford 0.4 g (45%) of [(6-but-2-ynyloxy-pyridine-3-sulfonyl)-methyl-amino]-acetic acid as an off-white solid. Electrospray Mass Spec 299.0 (M+H)$^+$ In an oven dried 50 mL round bottom flask was combined 0.228 g (0.579 mmol)) [(6-but-2-ynyloxy-pyridine-3-sulfonyl)-methyl-amino]-acetic acid in 5 mL of anhydrous dichloromethane and 0.22 mL DMF and the mixture was cooled to 0° C. Oxalyl chloride (1.45 mL, 2.9 mmol, 3.5 eq) was slowly added to the cold solution, the ice bath was removed and the reaction let warm to room temperature for 45 min. The solvent was then removed in vacuo and the residue was dissolved in 5 mL of dichloromethane and dropwise added to a solution of 0.46 g hydroxylamine hydrochloride, 1.2 mL DMF, 1.2 mL triethylamine, 8 mL dichloromethane and 8 mL acetonitrile. After stirring overnight at room temperature, the solvent was removed in vacuo, diluted with water and neutralized. The solids in the mixture were filtered and dried in vacuo. Reverse phase HPLC afforded 0.084 g (39%) of 2-[(6-but-2-ynyloxy-pyridine-3-sulfonyl)-methyl-amino]-N-hydroxy-acetamide. Electrospray Mass Spec 314.3 (M+H)$^+$ Example 132

2-[[(4-{[3-(4Chlorophenyl)-2-Propynyl] Oxy}Phenyl)Sulfonyl](Methyl)amino]-N-Hydroxyacetamide To a solution of 4-3-bromo-prop-1-ynyl)-phenol (5.0 g, 30.12 mmol) dissolved in dichloromethane, 8.3 g (31.63 mmol, 1.05 eq) of triphenylphosphine was added and the solution was cooled to 0° C. Bromine (1.55 mL, 30.12 mmol, 1.0 eq) was added dropwise and the reaction was warmed to room temperature. The reaction was then diluted with dichloromethane, washed with sodium hydrosulfite pentahydrate, washed with brine, dried over MgSO4 and concentrated. The residue was purified via flash chromatography using 4:1 hexane:ethyl acetate to afford 5.56 g (80%) of 1-(3-bromo-prop-1-ynyl)-4-chloro-benzene as an amber oil. Electrospray Mass Spec 280.4 (M+H)+

To a solution of 4-hydroxybenzenesulfonic acid sodium salt (2.81 g, 12.11 mmol) in 50 mL of isopropyl alcohol, 11.8 mL 2N NaOH and 5.56 g (24.2 mmol, 2 eq) of 1-(3-bromo-prop-1-ynyl)-4-chloro-benzene was added. The solution was heated to 70° C. overnight. The reaction was cooled, concentrated in vacuo, filtered and air dried to afford 2.8 g (67%) of 4-[3-(4-chloro-phenyl)-prop-2-ynyloxy]-benzenesulfonic acid, sodium salt. Electrospray Mass Spec 321.3 (M−H)−

To a solution of the crude 4-[3-(4-chloro-phenyl)-prop-2-ynyloxy]-benzenesulfonic acid sodium salt (2.81 g, 8.7 mmol) was added 2.8 g of phosphorous pentachloride and 50 mL of dichloromethane. The reaction warmed to 40° followed by dissolution of the reagents. The reaction was then quenched with ice, extracted with dichloromethane, washed with water, brine, dried over magnesium sulfate, filtered and concentrated in vacuo. The resulting oil was purified via flash chromatography using 20:1 Hex:EtOAc to afford 0.5 g (17%) of 4-[3-(4-chloro-phenyl)-prop-2-ynyloxy]-benzenesulfonyl chloride.

A solution of 0.57 g (1.67 mmol) of 4-[3-(4-chloro-phenyl)-prop-2-ynyloxy]-benzenesulfonyl chloride and 0.61 g (3.34 mmol, 2 eq) of sarcosine t-butyl ester hydrochloride in 0.51 mL of pyridine and 15 mL of chloroform was allowed to react overnight at room temperature. The reaction was concentrated in vacuo, diluted with water/ethyl acetate, neutralized with NaHCO3 and extracted with EtOAc (2×). The combined organics were washed with brine, dried over MgSO4, filtered and concentrated to afford a yellow oil which was purified via flash chormatography using 6:1 hexane: ethyl acetate to afford 0.396 g (53%) of tert-butyl [[(4-{[3-(4-chlorophenyl)-2-propynyl]oxy}phenyl) sulfonyl](methyl)amino]acetate as a white solid. Electrospray Mass Spec 450.4 (M+H)+

To a solution of tert-butyl [[(4-{[3-(4-chlorophenyl)-2-propynyl]oxy}phenyl)sulfonyl](methyl)amino]acetate (0.331 g, 0.736 mmol in methanol/THF was added 1.23 mL (3.5 eq) of a 1.0 N solution of LiOH and the reaction was stirred at room temp overnight. The solvent was removed in vacuo and the residue was suspended in water, adjusted to pH to 3 with 2N HCl. The resulting solid was rinsed with ether and dried in vacuo to afford 0.27 g (89%) of [[(4-{[3-(4-chlorophenyl)-2-propynyl]oxy}phenyl)sulfonyl](methyl) amino]acetic acid. Electrospray Mass Spec 392.1 (M+H)+

A solution of [[(4-{[3-(4-chlorophenyl)-2-propynyl] oxy}phenyl)sulfonyl](methyl)amino]acetic acid (0.231 g, 0.586 mmol) was converted to the desired hydroxamic acid as described in Example 131, to give 2-[[(4-{[3-(4-chlorophenyl)-2-propynyl]oxy}phenyl)sulfonyl](methyl) amino]-N-hydroxyacetamide after reverse phase HPLC (0.097 g 42%) as a white solid. Electrospray Mass Spec 407.3 (M+H)+

Example 133

N-Hydroxy-2-Methyl{[4-(Prop-2-Ynylamino) Phenyl]Sulfonyl}Amino)Acetamide

To a solution of 5.0 g (0.028 mol) of t-butyl sarcosine hydrochloride in 40 mL of chloroform and 7.0 mL of pyridine was added 5.35 g (0.028 mol) of 4-fluorobenzenesulfonyl chloride. The reaction was stirred at room temperature for 48 h and then concentrated in vacuo. The residue was diluted with ether, washed with water and dried over magnesium sulfate, filtered and concentrated in vacuo. The resulting pale yellow solid was washed with ether/hexanes (1:1) to give 5.7 g of [(4-fluorobenzenesulfonyl)methyl-amino]-acetic acid tert-butylester as a white solid. Electrospray Mass Spec 304.3 (M+H)+

To a solution of 1.820 g (6.00 mmol) of of [(4-fluoro-benzenesulfonyl)-methyl-amino]-acetic acid tert-butylester in 25 mL of dimethylformamide was added 5.0 mL (4.0 g, 72.89 mmol) of propargylamine. The mixture was heated to 80° C. and stirred for 48 h. The mixture was partitioned between 400 mL of dichloromethane and 200 mL of 20% aqueous NH4Cl solution. The organic layer was separated, washed with 200 mL of water, dried over anhydrous MgSO4, filtered, and concentrated in vacuo. Silica gel column chromatography of the residue, eluting with 1% MeOH/CH2Cl2, provides 1.067 g (53%) of 2-(methyl{[4-(prop-2-ynylamino)phenyl]sulfonyl}amino)acetic acid, tert-butyl ester as a light brown oil. Electrospray Mass Spec 339.3 (M+H)+

To a solution of 0.160 g (0.047 mmol) of 2-(methyl{[4-(prop2-ynylamino)phenyl]sulfonyl}amino)acetic acid, tert-butyl ester in 1 mL of dichloromethane was added 1 mL of trifluoroacetic acid and the reaction was stirred at room temperature for 19 h. Concentration of the mixture in vacuo provides 0.115 g (86%) of 2-methyl{[4-(prop-2-ynylamino) phenyl]sulfonyl}amino)acetic acid as a brown glass. Electrospray Mass Spec 281.1 (M–H)–

According to the procedure of Example 25, 0.115 g (0.29 mmol) of 2-(methyl{[4-(prop-2-ynylamino)phenyl] sulfonyl}amino)acetic acid provides 0.070 g (58%) of N-hydroxy-2-(methyl{[4-(prop-2-ynylamino)phenyl] sulfonyl}amino)acetamide as an orange foam. Electrospray Mass Spec 298.2 (M+H)+

Example 134

2-[(4-But-2-Ynylthiophenylsulfonyl)Methylamino]-N-Hydroxyacetamide

To a solution of 1.820 g (6.00 mmol) of the product of [(4-fluoro-benzenesulfonyl)-methyl-amino]-acetic acid tert-butylester in 25 mL of dimethylsulfoxide was added 4.809 g (30.00 mmol) of potassium ethyl xanthate. The mixture was heated to 100° C. and stirred for 24 h. It was then partitioned between 400 mL of dichloromethane and 400 mL of dilute HCl solution. The organic layer was separated, dried over anhydrous MgSO4, filtered, and concentrated in vacuo. Silica gel column chromatography of the residue, eluting with 1% MeOH/CH2Cl2 provided 1.242 g (65%) of bis-(4[{N-(2-acetic acid)-N-methyl}sulfonamido]phenyl) disulfide, bis-tert-butyl ester as a colorless powder. Electrospray Mass Spec 633.2 (M+H)+

To a solution of 0.633 g (1.00 mmol) of bis-(4-[{N-(2-acetic acid)-N-methyl}sulfonamido]phenyl)disulfide, bis-tert-butyl ester in a mixture of 3 mL of dioxane and 0.75 mL of water was added a drop of 2N HCl solution and 0.289 g (1.10 mmol) of triphenylphosphine. The mixture was stirred 3 h at room temperature and the solvents were then removed in vacuo, heating the flask to ensure thorough drying of the residue. It was then dissolved in 4 mL of dimethylformamide and 0.088 g (2.20 mmol) of a 60% dispersion of NaH in mineral oil was added. The mixture was stirred 30 min at room temperature and 0.25 mL (0.380 g, 2.86 mmol) of 1-bromo-2-butyne was added. The mixture was stirred an additional 30 min at room temperature then partitioned between 200 mL of diethyl ether and 200 mL of dilute HCl solution. The organic layer was separated, dried over anhydrous MgSO4, filtered, and concentrated in vacuo. Silica gel column chromatography of the residue provides 0.588 g (80%) of the thioether, 2-[(4-but-2-ynylthiophenylsulfonyl)

methylamino]acetic acid tert-butyl ester, as a colorless oil. Electrospray Mass Spec 370.3 (M+H)+

To a solution of 0.313 g (1.00 mmol) of 2-[(4but-2-ynylthiophenylsulfonyl)methylamino]acetic acid tert-butyl ester in 2 mL of dichloromethane was added 2 mL of trifluoroacetic acid. The mixture was stirred at room temperature for 2 h and then concentrated in vacuo. Trituration of the residue with diethyl ether provides 0.262 g (90%) of the carboxylic acid, 2-[(4-but-2-ynylthiophenylsulfonyl) methylamino]acetic acid, as an off-white solid. Electrospray Mass Spec 312.3 (M–H)–

According to the procedure of Example 25, 0.200 g (0.638 mmol) of 2-[(4-but-2-ynylthiophenylsulfonyl)methylamino] acetic acid provides 0.147 g (70%) of the hydroxamic acid, 2-[(4-but-2-ynylthiophenylsulfonyl)methylamino]-N-hydroxyacetamide, as a colorless solid. Electrospray Mass Spec 329.2 (M+H)+

Example 135

2-{{[4-(2-Butynyloxy)Phenyl]Sulfonyl}[4-(4-Methyl-1-Piperazinyl)-2-yl]}-2-Butynyl]Amino}-N-Hydroxypropanamide According to the procedure for Example 125, starting with (2R)-2-(4-but-2-ynyloxy-benzenesulfonylamino)-propionic acid methyl ester (from Example 107), the desired 2-{{[4-(2-butynyloxy)phenyl]sulfonyl}[4-(4-methyl-1-piperazinyl)-2-yl-2-butynyl]amino}-N-hydroxypropanamide was obtained. Electrospray Mass Spec 463.4 (M+H)+

Example 136

1-[{[4-(2-Butnyloxy)Phenyl]Sulfonyl}(Methyl) Amino]-N-Hydroxycyclohexanecarboxamide To a stirred suspension of methyl-1-amino-1-cyclohexane carboxylate hydrochloride (10 g, 51.7 mmol) and N,N-diisopropylethylamine in methylene chloride (200 mL) and acetonitrile (50 mL), 4-but-2-ynyloxy-benzenesulfonyl chloride (14.0 g, 56.8 mmol) was slowly added at room temperature. The reaction mixture was stirred for 16 hrs and evaporated to dryness. It was extracted with chloroform, washed well with water and dried over anhydrous $MgSO_4$. The chloroform layer was filtered and concentrated. The product was crystallized from a mixture acetone:hexane 1:10 to give methyl 1-({[4-(2-butynyloxy)phenyl] sulfonyl}amino)cyclohexanecarboxylate as white crystals, 12.5 g.(66%), mp 118-2° C. Electrospray Mass Spec 366 (M+H)+.

A mixture of methyl 1-({[4-(2-butynyloxy)phenyl] sulfonyl}amino)cyclohexanecarboxylate (4.5 g.,12.3 mmol), anhydrous potassium carbonate (20.0 g, excess) and methyl iodide (2 g, 14.08 mmol) was refluxed in acetone for sixteen hours. The reaction mixture was then cooled to room temperature and filtered. The acetone layer was concentrated and extracted with chloroform. The chloroform layer was washed well with water, dried over anhydrous $MgSO_4$, filtered and concentrated to provide methyl1-[{[4-(2-butynyloxy)phenyl]sulfonyl}(methyl)amino] cyclohexanecarboxylate as a yellow oil. Yield: 4.6 g(quantitative) Electrospray Mass Spec 380 (M+H)+.

To a stirred solution of methyl1-[{[4-(2- butynyloxy) phenyl]sulfonyl}(methyl)amino]cyclohexanecarboxylate (4.6 g, 12.1 mmol) in methanol:THF (4:1, 100 ml), 10 N sodium hydroxide (15 ml) was added at room temperature. The reaction was stirred for 16 h and evaporated to dryness in vacuo and the residue was dissolved in 100 mL water. The pH was adjusted to 1 with 5N hydrochloric acid solution and the mixture was extracted with chloroform, washed with water, dried and concentrated to give 1-[{[4-(2-butynyloxy) phenyl]sulfonyl}(methyl)amino] cyclohexanecarboxylic acid as a yellow solid. Yield: 4 g(88%); mp 124–6° C. Electrospray Mass Spec 364(M–H)–.

To a stirred suspension of 1-[{[4-(2-butynyloxy)phenyl] sulfonyl}(methyl)amino] cyclohexanecarboxylic acid (4.0 gm, 10.9 mmol) in methylene chloride (200 ml)/DMF (5 ml), oxalyl chloride (8.0 gm, 63 mmol) in methylene chloride (10 ml) was added slowly at 0° C. After the addition, the reaction mixture was stirred at room temperature for 1 h. In a separate flask, hydroxylamine hydrochloride (6.9 gm, 100 mmol) was dissolved in DMF/acetonitrile (1:1, 100 ml) and triethylamine (20 gm, 200 mmol) was added. It was stirred at room temperature for 1 h and diluted with methylene chloride (50 ml). The acid chloride formed was concentrated to dryness and redissolved in methylene chloride. Hydroxylamine was cooled to 0° C., and the acid chloride was added to the hydroxylamine. The reaction mixture was stirred at room temperature for 6 h and concentrated to dryness. It was extracted with chloroform, washed well with water and dried over anhydrous $MgSO_4$. It was filtered and concentrated. Product was purified by silica-gel column chromatography by eluting it with ethyl acetate: hexane (3:1) to give as a white spongy solid; Yield 3.6 g (88%); mp 89–92° C.; Electrospray Mass Spec 381 (M+H)+; $H^1$ NMR ($CDCl_3$) □: 1.35–1.41 (m, 2H) 1.55–1.72 (m, 6H), 1.80 (s, 3H), 2.23–2.26 (m, 2H), 3.41 (s, 3H), 4.81 (s,2H), 7.22 (dd,2H), 7.89 (dd, 2H), 9.66 (bs, 1H).

Example 137

1-[{[4-(2-Butynyloxy)Phenyl]Sulfonyl}(3-Pyridinylmethyl)Amino] N-Hydroxycyclohexanecarboxamide According to the procedure of Example 136, but using 3-picolyl chloride hydrochloride to alkylate the sulfonamide instead of iodomethane, methyl 1-({[4-(2-butynyloxy) phenyl]sulfonyl}amino)cyclohexanecarboxylate was converted into 1-[{[4-(2-butynyloxy)phenyl]sulfonyl}(3-pyridinylmethyl)amino]-N-hydroxycyclohexanecarboxamide, obtained as a white solid. mp 179–81° C.; Electrospray Mass Spec: 458 (M+H)+; $H^1$ NMR (DMSO) □: 1.21–1.24 (m, 2H), 1.61–1.72 (m, 6H), 1.81 (s, 3H), 2.48 (m, 2H), 4.59 (s, 2H), 4.72 (s,2H), 6.91 (m,1H), 7.20 (dd,2H), 7.62 (m, 2H), 7.79 (dd, 2H), 7.84 (m, 1H), 12.42–12.58 (bs, 1H).

Example 138

1-({[4-(2-Butynyloxy)Phenyl]Sulfonyl}Amino)-N-Hydroxycyclohexanecarboxamide

To a stirred solution of methyl 1-({[4-(2-butynyloxy) phenyl]sulfonyl}amino) cyclohexane carboxylate (4.3 g, 11.8 mmol) in methanol: THF (4:1, 100 ml) 10 N sodium hydroxide (15 ml) was added at room temperature. It was stirred for 16 hrs and evaporated to dryness in vacuo. The residue was dissolved in 100 mL water, pH adjusted to 7 with 5N hydrochloric acid solution. It was extracted with chloroform/methanol (3:1), washed with water, dried and concentrated to give 1-({[4-(2-butynyloxy)phenyl]sulfonyl}amino) cyclohexane carboxylic acid. Yield 4.0 g (98%); White solid, mp. 112–4° C. Electrospray Mass Spec 349 (M–H)⁻.

To a stirred suspension of 1-({[4-(2-butynyloxy)phenyl]sulfonyl}amino) cyclohexane carboxylic acid (4.0 gm, 11.4 mmol) in methylene chloride (200 ml)/DMF (5 ml) oxalyl chloride (8.0 gm, 63 mmol) in methylene chloride (10 ml) was added slowly at 0° C. After addition, reaction mixture was stirred at room temperature for 1 hr. In a separate flask, hydroxylamine hydrochloride (6.9 gm, 100 mmol) was dissolved in DMF/acetonitrile (1:1, 100 ml) and triethylamine (20 gm, 200 mmol) was added. It was stirred at room temperature for 1 hr and diluted with methylene chloride (50 ml). The acid chloride formed was concentrated to dryness and redissolved in methylene chloride. Hydroxylamine was cooled to 0° C., and the acid chloride was added to the bydroxylamine. Reaction mixture was stirred at room temperature for 6 hrs and concentrated to dryness. It was extracted with chloroform, washed well with water and dried over anhydrous $MgSO_4$. It was filtered and concentrated. Product was purified by silica-gel column chromatography by eluting it with ethyl acetate: hexane (3:1) to give 1-({[4-(2-butynyloxy)phenyl]sulfonyl}amino)-N-hydroxy cyclohexanecarboxamide. White solid; Yield 3.2 g (78%); M.Pt. 82–84° C.; Electrospray Mass Spec: 367 (M+H)⁺; $H^1$ NMR ($CDCl_3$) ☐: 1.35–1.41 (m, 2H), 1.55–1.72 (m, 6H), 1.80 (s, 3H), 2.23–2.26 (m, 2H), 4.81 (s,2H), 5.27 (s,1H) 7.22 (dd,2H), 7.89 (dd, 2H), 9.66 (bs, 1H).

Example 139

1-({[4-(2-Butynyloxy)Phenyl]Sulfonyl}Amino)-N-Hydroxycyclopentanecarboxamide

To a stirred suspension of methyl-1-amino-1-cyclopentane carboxylate hydrochloride (15 g, 84.0 mmol) and N,N-diisopropylethylamine in methylene chloride (200 mL) and acetonitrile (50 mL), 4-butynyloxyphenylsulfonylchloride (24.7 g, 100 mmol) was slowly added at room temperature. Reaction mixture was stirred for 16 hrs and evaporated to dryness. It was extracted with chloroform, washed well with water and dried over anhydrous $MgSO_4$. Chloroform layer was filtered and concentrated. The product was crystallized from a mixture acetone:hexane (1:1) to give methyl 1-({[4-2-butynyloxy) phenyl]sulfonyl}amino)cyclopentane carboxylate as white crystals, 26.8 g (91%), mp 81–3° C. Electrospray Mass Spec352 (M+H)⁺.

To a stirred solution of methyl 1-({[4-(2- butynyloxy) phenyl]sulfonyl}amino) cyclopentane carboxylate (5.5 g, 15.6 mmol) in methanol:THF (4:1, 100 ml) 10 N sodium hydroxide (15 ml) was added at room temperature. It was stirred for 16 h and evaporated to dryness in vacuo, the residue was dissolved in 100 mL water, pH adjusted to 7 with 5N hydrochloric acid solution. It was extracted with chloroform;methanol (3:1) washed with water, dried and concentrated to give 1-({[4-(2- butynyloxyphenyl]sulfonyl}amino) cyclopentane carboxylic acid. Yield 4.5 g (86%); White solid, mp. 108–110° C. Electrospray Mass Spec 336 (M–H)⁻.

To a stirred suspension of 1-({[4-(2-butynyloxy)phenyl]sulfonyl}amino) cyclopentane carboxylic acid. (1.2 g, 3.56 mmol) in methylene chloride (200 ml)/DMF (5 ml) oxalyl chloride (8.0 g, 63 mmol) in methylene chloride (10 ml) was added slowly at 0° C. After addition, reaction mixture was stirred at room temperature for 1 hr. In a separate flask, hydroxylamine hydrochloride (6.9 g, 100 mmol) was dissolved in DMF/acetonitrile (1:1, 100 ml) and triethylamine (20 g, 200 mmol) was added. It was stirred at room temperature for 1 hr and diluted with methylen chloride (50 ml). The acid chloride formed was concentrated to dryness and redissolved in methylene chloride. Hydroxylamine was cooled to 0° C., and the acid chloride was added to the hydroxylamine. Reaction mixture was stirred at room temperature for 6 hrs and concentrated to dryness. It was extracted with chloroform, washed well with water and dried over anhydrous $MgSO_4$. It was filtered and concentrated. Product was purified by silica-gel column chromatography by eluting it with ethyl acetate: hexane (3:1) to give 1-({[4-(2-butynyloxy)phenyl]sulfonyl}amino)-N-hydroxy cyclopentanecarboxamide. White solid; Yield 1.1 g (88%); mp 66–68° C.; Electrospray Mass Spec: 353 (M+H)⁺; $H^1$ NMR ($CDCl_3$) ☐: 1.32–1.40 (m, 2H), 1.58–1.80 (m, 4H), 1.83 (s, 3H), 1.91–1.94 (m, 1H), 2.03–2.12 (m,1H), 4.70 (s,2H), 5.25 (s,1H), 7.20 (dd,2H), 7.85 (dd, 2H), 9.58 (bs, 1H).

Example 140

2-({[4-(2-Butynyloxy)Phenyl]Sulfonyl}(Methyl) Amino]-N-Hydroxy-3 Methyl-3-[(2 (4-Morpholinylethyl)Sulfanyl]-Butanamide Hydrochloride Step 1

A solution of D-penicillamine (0.5 g, 3.35 mmol) in methanol (5 mL) was cooled to 0° C. and crushed sodium hydroxide (0.28 g, 6.87 mmol) was added to give a clear solution. 2-Bromoethanol (0.26 mL, 3.71 mmol) was added and stirred at 0° C. for 1 h and at room temperature for an additional 1.5 h. The reaction was concentrated, and the oily residue was dissolved in 3 mL water and 6 mL DMF and stirred with sodium carbonate (0.82 g 7.2 mmol) and 4butynyloxy-benzenesufonyl chloride (0.78 g, 3.18 mmol) at room temperature overnight. The reaction was concentrated and the residue was extracted with ethyl acetate and water. The aqueous layer was acidified to pH ~3 with concentrated HCl and extracted with ethyl acetate. The second ethyl acetate extract was washed with water and brine, dried over sodium sulfate, filtered and concentrated to obtain 1.2 g of N-{[4-(2 butynyloxy)phenyl]sulfonyl}-3-[(2-hydroxyethyl)sulfanyl]valine as an oil. Yield 89.6%. Electrospray Mass Spec 400.1 (M–H)⁻.

Step 2

To a solution of N-{[4-2-butynyloxy)phenyl]sulfonyl}-3-[(2-hydroxyethyl)-sulfanyl]valine (1.2 g, 2.99 mmol) in dimethylacetamide (8 mL) was added potassium carbonate (33 g, 23.9 mmol), benzyltriethylammonium chloride (0.20 g, 0.90 mmol) and 2-bromo-2methyl-propane (5.5 mL, 47.9 mmol) and the mixture was heated at 50° C. overnight. The mixture was then diluted with ethyl acetate and washed with water and brine, dried over sodium sulfate, filtered and evaporated to obtain 1.10 g of tert-butyl 2-({[4-(2-butynyloxy)phenyl]sulfonyl}amino-3-[(2hydroxyethyl) sulfanyl]-3-methylbutanoate as an oil. Yield ~80.9%. Electrospray Mass Spec 458.2 (M+H)+.

Step 3

To a solution of tert-butyl 2-({[4-(2-butynyloxy)phenyl] sulfonyl}amino-3-[(2-sulfonyl}amino)-3-[(2-hydroxyethyl) sulfanyl]-3-methylbutanoate (1.1 g, 2.41 mmol) in DMF (8 mL) was added iodomethane (0.18 mL, 2.89 mmol) and potassium carbonate (0.99 g, 7.22 mmol) and the resulting mixture was stirred at room temperature overnight. After evaporating the solvent, the residue was extracted with ethyl acetate and water. The organic layer was washed with water and brine, dried over sodium sulfate, filtered, and evaporated to obtain 0.96 g of tert-butyl 2-({[4-(2-butynyloxy)phenyl] sulfonyl](methyl)}amino)-3-[(2-hydroxyethyl)sulfanyl]-3-methylbutanoate. Yield ~85%. Electrospray Mass Spec 472.2 (M+H)+.

Step 4

To a 0° dichloromethane solution (4 mL) of tert-butyl 2-({[4-(2-butynyloxy) phenyl]sulfonyl)(methyl)]-amino)-3-[(2-hydroxyethyl)sulfanyl]-3-methylbutanoate (0.96 g, 2.04 mmol), carbon tetrabromide (0.68 g, 2.04 mmol), was added a dichloromethane solution (2 mL) of triphenylphosphine and the reaction mixture was stirred at 0° C. for 10 minutes and at room temperature overnight. After evaporating the solvent, the oily mixture was purified by column chromatography, eluting with hexane:ethyl acetate (4:1) to give 0.71 g of tert-butyl 2-{[4-(2-butynyloxy)phenyl] sulfonyl)(methyl)]amino)-3-[(2-bromoethyl) sulfanyl]-3-methylbutanoate.

Yield: 66.4% . FAB Mass Spec 556 (M+Na)+.

Step 5

To a solution of tert-butyl 2-({[4-(2-butynyloxy)phenyl] sulfonyl)(methyl)]-amino)-3-[(2-bromoethyl)sulfanyl]-3-methylbutanoate (0.65 g, 1.24 mmol) and morpholine (0.27 mL, 3.1 mmol) in DMF (6 mL) was added potassium carbonate (0.4 g, 2.93 mmol). The mixture was stirred at room temperature overnight. After evaporating the solvent, the mixture was extracted with dichloromethane and water. The organic layer was washed with water and brine, dried over sodium sulfate, filtered and concentrated to obtain 0.65 g of tert-butyl 2-{[4-(2-butynyloxy)phenyl]sulfonyl) (methyl)]amino)-3-methyl-3-[(2(4-morpholinylethyl) sulfanyl]-butanoate as an oil. Yield: 96%. Electrospray Mass Spec 541.2 (M+H)+.

Step 6

A solution of tert-butyl 2-{[4-(2-butynyloxy)phenyl] sulfonyl)(methyl)]amino)-3-methyl-3-[(2(4-morpholinylethyl)sulfanyl]-butanoate (0.59 g, 1.1 mmol) and trifluoroacetic acid (5 mL) in dichloromethane (10 mL) was stirred at room temperature overnight. Evaporating the solvent provide 0.71 g of the trifluoroacetic acid salt of N-{[4-2-butynyloxy)phenyl]sulfonyl}-3-{[2-4-morpholinyl)ethyl]-sulfanyl}valine. Electrospray Mass Spec 485.2 (M+H)+.

Step 7

A solution of N-{[4-2-butynyloxy)phenyl]sulfonyl}-3-{[2-4-morpholinyl)ethyl]sulfanyl}valine (0.69 g, 1.42 mmol) in dichloromethane (6 mL) and DMF (0.22 mL, 2.85 mmol) was cooled in an ice bath and oxalyl chloride (0.71 mL of 2M in CH$_2$Cl$_2$, 2.85 mmol) was dropped in. The reaction mixture was stirred at 0° C. for 10 minutes and at room temperature for 2 h. The reaction was recooled to 0°, and a THF (4.5 mL) solution of triethylamine (0.80 mL, 5.70 mmol) and hydroxylamine (0.52 mL of 50% hydroxyamine in water, 8.55 mmol) was added in one portion. The reaction was warmed to room temperature and stirred overnight. After evaporating the solvent, the oily residue was extracted with ethyl acetate and water. The organic layer was washed with water and brine, dried over sodium sulfate, filtered, and evaporated to obtain 0.5 g of 2-({[4-(2-butynyloxy)phenyl] sulfonyl)(methyl)amino]-N-hydroxy-3 methyl-3-[(2(4-morpholinylethyl)sulfanyl]butanamide as a light yellow solid. Yield ~86.2%. mp 45–50° C. Electrospray Mass Spec 500.2 (M+H)+.

The above compound (0.39 g, 0.78 mmol) was dissolved in dichloromethane (3 mL) and cooled in an ice bath. Then a 1M hydrogen chloride solution in ethyl ether (0.86 mL, 0.86 mmol) was dropped in. The mixture was stirred at 0° C. for 10 minutes and at room temperature for 1.5 h. The residue was diluted with ethyl ether and filtered to give 0.37 g of 2-({[4-(2-butynyloxy)phenyl]sulfonyl)(methyl)amino]-N-hydroxy-3 methyl-3-[(2(4-morpholinylethyl)sulfanyl]-butanamide hydrochloride as a white solid. Mp 50° C. (d). Electrospray Mass Spec 500.2 (M+H)+.

Example 141

2-({[4-(2-Butynyloxy)Phenyl]Sulfonyl)(Methyl) Amino]-N-Hydroxy-3-Methyl-3-{[2(4-Methyl-1-Ethyl-1-Piperazinyl)Ethyl]Sulfanyl}Butanamide According to the procedure of Example 140, using 1-methylpiperazine in Step 5, 2-({[4-(2-butynyloxy)phenyl] sulfonyl)(methyl)amino]-N-hydroxy--3-methyl-3-{[2(4-methyl-1-ethyl-1-piperazinyl)ethyl]sulfanyl}butanamide was obtained. mp 110–115° C. Electrospray Mass Spec 513.3 (M+H)+. Hydrochloride salt mp 90–95° C. Electrospray Mass Spec 513.3 (M+H)+.

Example 142

2-({[4-(2-Butynyloxy)Phenyl]Sulfonyl)(Methyl) Amino]-N-Hydroxy-3-Methyl-3-{[2-(Diethylamino) Ethyl]Sulfanyl}Butanamide According to the procedure of Example 140, using diethylamine in Step 5, 2-({[4-(2-butynyloxy)phenyl]sulfonyl) (methyl)amino]-N-hydroxy-3 methyl-3-{[2-(diethylamino) ethyl]sulfanyl}butanamide was obtained. mp 55–57° C. Electrospray Mass Spec 486.4 (M+H)+. Hydrochloride salt mp 87–90° C. Electrospray Mass Spec 486.5 (M+H)+.

Example 143

2-({[4-(2-Butynyloxy)Phenyl]Sulfonyl)(Methyl) Amino]-N-Hydroxy- –3 Methyl-3-{[2(1-Pyrrolidinyl)Ethyl]Sulfanyl}Butanamide According to the procedure of Example 140, using pyrrolidine in Step 5, 2-({[4-(2-butynyloxy)phenyl]sulfonyl)

(methyl)amino]-N-hydroxy-3 methyl-3-{[2(1-pyrrolidinyl) ethyl]sulfanyl}butanamide was obtained mp 55–57° C. Electrospray Mass Spec 484.4(M+H)+. Hydrochloride salt mp 58–60° C. Electrospray Mass Spec 484.4 (M+H)+.

Example 144

2-({[4-(2-Butynyloxy)Phenyl]Sulfonyl)(Methyl) Amino]-N-Hydroxy- –3 Methyl-3-{[2-(1H-Imidazol-1-yl)Ethyl]Sulfanyl}Butanamide According to the procedure of Example 140, using imidazole in Step 5, 2-({[4-(2-butynyloxy)phenyl]sulfonyl) (methyl)amino]-N-hydroxy-3-methyl-3-{[2-(1H-imidazol-1-yl)ethyl]sulfanyl}butanamide was obtained. mp 97–100° C. Electrospray Mass Spec 481.4 (M+H)+. Hydrochloride salt mp 67–70° C. Electrospray Mass Spec 481.4 (M+H)+.

Example 145

Methyl 1-[2-({2-[{[4-(2-Butynyloxy)Phenyl] Sulfonyl}(Methyl)]Amino]-3-(Hydroxyamino-1,1-Dimethyl-3-Oxopropyl}Sulfanyl)Ethyl]-2-Pyrrolidinecarboxylate According to the procedure of Example 140, using proline ethyl ester in Step 5, methyl 1-[2-({2-[{[4-(2-butynyloxy) phenyl]sulfonyl}(methyl)]amino]-3-(hydroxyamino)-1,1-dimethyl-3-oxopropyl)sulfanyl)ethyl]-2-pyrrolidine-carboxylate was obtained. mp 57–60° C. Electrospray Mass Spec 542.4 (M+H)+. Hydrochloride salt mp 85–90° C. Electrospray Mass Spec 542.5 (M+)+.

Example 146

2-({[4-(2-Butynyloxy)Phenyl]Sulfonyl)(Methyl) Amino]-N-Hydroxy-–3 Methyl-3-[(2(4-Morpholinylpropyl)Sulfanyl]-Butanamide According to the procedure of Example 140, using 1-bromo-3-propanol in Step 1, 2-({[4-(2-butynyloxy) phenyl]sulfonyl)(methyl)amino]-N-hydroxy-–3 methyl-3-[(2(4-morpholinylpropyl)sulfanyl]-butanamide was obtained. mp 48–52° C. Electrospray Mass Spec 514.4 (M+H)+. Hydrochloride salt mp 94–96° C. Electrospray Mass Spec 514.4(M+H)+.

Example 147

2-({[4-(2-Butynyloxy)Phenyl]Sulfonyl)(Methyl) Amino]-N-Hydroxy-–3 Methyl-3-{[2(4-Methyl-1-Ethyl-1-Piperazinyl)Propyl]Sulfanyl}Butanamide According to the procedure of Example 140, using 1-bromo-3-propanol in Step 1 and 1-methylpiperazine in Step 5, 2-({[4-(2-butynyloxy)phenyl]sulfonyl)(methyl) amino]-N-hydroxy-–3 methyl-3-{[2(4-methyl-1-ethyl-1-piperazinyl)propyl]sulfanyl}butanamide was obtained. mp 58–62° C. Electrospray Mass Spec 527.6 (M+H)+. Hydrochloride salt mp 74–80° C. Electrospray Mass Spec 527.4 (M+H)+.

Example 148

2-({[4-(2-Butynyloxy)Phenyl]Sulfonyl)(Methyl) Amino]-N-Hydroxy-–3 Methyl-3-{[2-(Diethylamino)Propyl]Sulfanyl}Butanamide According to the procedure of Example 140, using 1-bromo-3-propanol in Step 1 and diethylamine in Step 5, 2-({[4-(2-butynyloxy)phenyl]sulfonyl)(methyl) amino]-N-hydroxy-–3 methyl-3-}[2-(diethylamino)propyl] sulfanyl}butanamide was obtained. mp65–68° C. Electrospray Mass Spec 500.4 (M+H)+. Hydrochloride salt mp 58–60° C. Electrospray Mass Spec 500.4 (M+H)+.

Example 149

2-[(4-But-2-Ynyloxy-Benenesulfonyl)-Methyl-Amino]-N-Hydroxy-3-Methyl-3-Methylsulfanyl-Butyramide Step 1

A solution of D-penicillamine (0.5 g, 3.35 mmol) in methanol was cooled to 0° C. and crushed sodium hydroxide (0.28 g, 7.04 mmol) was added to give a clear solution. Iodomethane (0.23 mL, 3.69 mmol) was added and the reaction was stirred at 0° C. for 10 minutes and at room temperature for an additional 1.5 h. After evaporating the solvent, the residue was dissolved in 2 mL of water and acidified with 6N HCl to pH ~3. After evaporating the solvent again, the oily residue was dissolved in 3 mL of water and 6 mL of DMF and stirred with sodium carbonate (1.17 g, 11.0 mmol) and 4-but-2-ynyloxy-benzenesufonyl chloride (0.9 g, 3.69 mmol) at room temperature overnight. The solvent was evaporated and the residue was diluted with ethyl acetate and water. The aqueous layer was acidified to pH ~3 with concentrated HCl and extracted with ethyl acetate. The second ethyl acetate extract was washed with water and brine, dried over sodium sulfate, filtered and concentrated to provide 0.94 g of 2-(4-but-2-ynyloxy-benenesulfonylamino)-3-methyl-3- methylsulfanyl-butyric acid as a white solid. Yield 75.8%. mp 108–110° C. Electrospray Mass Spec 369.9 (M–H)−.

Step 2

To a solution of 2-(4-but-2-ynyloxy-benenesulfonylamino)-3-methyl-3-methylsulfanyl-butyric acid (0.37 g, 1 mmol) dissolved in dimethylacetamide (3 mL) was added potassium carbonate (1.12 g, 8.1 mmol), benzyltriethylammonium chloride (0.073 g, 0.32 mmol) and 2-bromo-2methyl-propane (1.9 mL, 16.4 mmol). The mixture was heated to 50° C. overnight and then diluted with ethyl acetate and washed with water and brine, dried over sodium sulfate, filtered and evaporated to provide 0.43 g of 2-(4-but-2-ynyloxy-benenesulfonylamino)-3-methyl-3-methylsulfanyl-butyric acid tert-butyl ester as an oil. Yield ~100%. Electrospray Mass Spec 427.9 (M+H)+.

Step 3

A solution of 2-(4-but-2-ynyloxy-benenesulfonylamino)-3-methyl-3-methyl-sulfanyl-butyric acid tert-butyl ester (0.4 g, 0.94 mmol) in DMF (5 mL) was treated with iodomethane (0.07 mL, 1.13 mmol) and 0.39 g of potassium carbonate at room temperature overnight. After evaporating the solvent, the residue was extracted with ethyl acetate and water. The organic layer was washed with water and brine, dried over sodium sulfate, filtered and evaporated to provide 0.33 g of 2-[(4-but-2-ynyloxy-benenesulfonyl)- 3-methyl-amino]-3-methyl-3-methylsulfanyl-butyric acid tert-butyl ester. Yield ~80.4%. Electrospray Mass Spec 442 (M+H)+.

Step 4

To a solution of 2-[(4but-2-ynyloxy-benenesulfonyl)-3-methyl-amino]-3-methyl-3-methylsulfanyl-butyric acid tert-butyl ester (0.31 g, 0.7 mmol) in dichloromethane (6 mL) was added trifluoroacetic acid (3 mL) and the reaction was stirred at room temperature for 1 h. The dichloromethane and TFA were evaporated to give the 0.29 g of 2-[(4-but-2-ynyloxy-benenesulfonyl)-3-methyl-amino]-3-methyl-3-methylsulfanyl-butyric acid, which was used for next step without further purification. Yield ~100%. Electrospray Mass Spec 383.9(M−H)⁻.

Step 5

A solution of 2-[(4but-2-ynyloxy-benenesulfonyl)-3-methyl-amino]-3-methyl-3-methylsulfanyl-butyric acid (0.24 g, 0.62 mmol) in dichloromethane (2 mL) was cooled in an ice bath and DMF (0.96 mL, 1.25 mmol) was added and followed by oxalyl chloride (0.62 mL of a 2M solution in $CH_2C_2$, 1.25 mmol). The reaction mixture was stirred at 0° C. for 10 minutes and at room temperature for 2 h. The reaction was recooled to 0° and a THF (1.5 mL) solution of triethylamine (0.35 mL 2.49 mmol) and hydroxylamine (0.23 mL of 50% hydroxylamine in water, 3.74 mmol) was added in one portion. The reaction was warmed to room temperature and stirred overnight. After removing solvent, the oily residue was diluted with ethyl acetate and water. The organic layer was washed with water and brine, dried over sodium sulfate, filtered and evaporated to provide 2-[(4-but-2-ynyloxy-benenesulfonyl)-methyl-amino]-N-hydroxy-3-methyl-3-methylsulfanyl-butyramide as a white solid which was triturated with ethyl ether to give 0.23 g. Yield ~92%. mp 132–135° C. Electrospray Mass Spec 401 (M+H)⁺.

Example 150

2-[(4-But-2-Ynyloxy-Benenesulfonyl)-Methyl-Amino]-N-Hydroxy-3-Methyl-3-Ethylsulfanyl-Butyramide According to the procedure of Example 149, using iodoethane in Step 1 instead of iodomethane, 2-[(4but-2-ynyloxy-benenesulfonyl)-methyl-amino]-N-hydroxy-3-methyl-3-ethylsulfanyl-butyramide was obtained. mp 130–131° C. Electrospray Mass Spec 425.2 (M+H)⁺.

Example 151

2-[(4-But-2-Ynyloxy-Benenesulfonyl)-Methyl-Amino]-N-Hydroxy-3-Methyl-3-Propylsulfanyl-Butyramide According to the procedure of Example 149, using iodopropane in Step 1 instead of iodomethane, 2-[(4but-2-ynyloxy-benenesulfonyl)-methyl-amino]-N-hydroxy-3-methyl-3-propylsulfanyl-butyramide was obtained. mp 132–135° C. Electrospray Mass Spec 429.2 (M+H)⁺.

Example 152

2-[(4-But-2-Ynyloxy-Benenesulfonyl)-Methyl-Amino]-N-Hydroxy-3-Methyl-3-(Pyridin-3-Ylmethylsulfanyl)-Butyramide According to the procedure of Example 149, using 3-picolyl chloride hydrochloride in Step 1 instead of iodomethane, 2-[(4-but-2-ynyloxy-benenesulfonyl)-methyl-amino]-N-hydroxy-3-methyl-3-(pyridin-3-ylmethylsulfanyl)-butyramide was obtained. mp 85–88° C. Electrospray Mass Spec 478.1 (M+H)⁺.

Example 153

2-[(4-But-2-Ynyloxy-Benenesulfonyl)-Methyl-Amino]-N-Hydroxy-3-Methyl-3-Benzylsulfanyl-Butyramide According to the procedure of Example 149, using benzyl bromide in Step 1 instead of iodomethane, 2-[(4but-2-ynyloxy-benenesulfonyl)-methyl-amino]-N-hydroxy-3-methyl-3-benzylsulfanyl-butyramide was obtained. mp 156–158° C. Electrospray Mass Spec 477.2 (M+H)⁺.

Example 154

2-[(4-But-2-Ynyloxy-Benenesulfonyl)-Methyl-Amino]-N-Hydroxy-3-(Methylsulfanyl)-Butyramide According to the procedure of Example 149, using D-cysteine in Step 1 instead of D-penicillamine, 2-[(4-but-2-ynyloxy-benenesulfonyl)-methyl-amino]-N-hydroxy-3-(methylsulfanyl)-butyramide was obtained. Electrospray Mass Spec 373.2 (M+H)⁺.

Example 155

2-[(4-But-2-Ynyloxy-Benenesulfonyl)-Methyl-Amino]-N-Hydroxy-3-(Pyridin-3-Ylmethylsulfanyl)-Butyramide According to the procedure of Example 149, using D-cysteine in Step 1 instead of D-penicillamine and 3-picolyl chloride hydrochloride instead of iodomethane, 2-[(4-but-2-ynyloxy-benenesulfonyl)-methyl-amino]-N-hydroxy-3-(pyridin-3-ylmethylsulfanyl)-butyramide was obtained. mp 90–95° C. Electrospray Mass Spec 450.2 (M+H)⁺.

Example 156

3-(Benzylthio)-2-[[[4-(2-Butynyloxy)Phenyl]Sulfonyl]Methylamino]-N-Hydroxypropanamide According to the procedure of Example 149, using D-cysteine in Step 1 instead of D-penicillamine and benzyl bromide instead of iodomethane, 2-[(4-but-2-ynyloxy-benenesulfonyl)-methyl-amino]-N-hydroxy-3-(pyridin-3-ylmethylsulfanyl)-butyramide was obtained. Electrospray Mass Spec 449.2 (M+H)⁺.

Example 157

3-(Benzylthio)-2-[[[4-(2-Butynyloxy)Phenyl]Sulfonyl]Pyridin-3-Ylmethylamino]-N-Hydroxypropanamide According to the procedure of Example 149, using D-cysteine in Step 1 instead of D-penicillamine and benzyl bromide instead of iodomethane, and using 3-picolyl chloride hydrochloride instead of iodomethane in Step 3, 3-(benzylthio)-2-[[[4-(2-butynyloxy)phenyl]sulfonyl]pyridin-3-ylmethylamino]-N-hydroxy-propanamide was obtained. mp 74–78° C. Electrospray Mass Spec 526.2 (M+H)⁺.

Example 158

2-[[[4-(2-Butynyloxy-Phenyl]Sulfonyl]Amino]-N-Hydroxy-3-Methyl-(3-Methylthio)-Butyramide Step 1

A solution of D-penicillamine (0.5 g, 3.35 mmol) in methanol was cooled to 0° C. and crushed sodium hydroxide (0.28 g, 7.04 mmol) was added to give a clear solution. Iodomethane (0.23 mL, 3.69 mmol) was added and the reaction was stirred at 0° C. for 10 minutes and at room temperature for an additional 1.5 h. After evaporating the solvent, the residue was dissolved in 2 mL of water and acidified with 6N HCl to pH ~3. After evaporating the solvent again, the oily residue was dissolved in 3 mL of water and 6 mL of DMF and stirred with sodium carbonate (1.17 g, 11.0 mmol) and 4-but-2-ynyloxy-benzenesulfonyl chloride (0.9 g, 3.69 mmol) at room temperature overnight. The solvent was evaporated and the residue was diluted with ethyl acetate and water. The aqueous layer was acidified to pH ~3 with concentrated HCl and extracted with ethyl acetate. The second ethyl acetate extract was washed with water and brine, dried over sodium sulfate, filtered and concentrated to provide 0.94 g of 2-(4-but-2-ynyloxy-benenesulfonylamino)-3-methyl-3- methylsulfanyl-butyric acid as a white solid. Yield 75.8%. mp 108–110° C. Electrospray Mass Spec 369.9 (M–H)$^-$.

Step 2

According to the procedure of Step 5, Example 149, 2-(4-but-2-ynyloxy-benenesulfonylamino)3-methyl-3-methylsulfanyl-butyric acid was converted into the corresponding hydroxamic acid, 2-[[[4-(2-butynyloxy-phenyl]sulfonyl]amino]-N-hydroxy-3-methyl-(3-methylthio)-butyramide. mp 128–132° C. Electrospray Mass Spec 386.9 (M+H)$^+$.

Example 159

2-[(4-But-2-Ynyloxy-Benenesulfonyl)Amino]-N-Hydroxy-3-Methyl-3-Ethylsulfanyl-Butyramide According to the procedure of Example 158, using iodoethane instead of iodomethane in Step 1, 2-[(4-but-2-ynyloxy-benenesulfonyl)amino]-N-hydroxy-3-methyl-3-ethylsulfanyl-butyramide was obtained. mp 46–50° C. Electrospray Mass Spec 401.3 (M+H)$^+$.

Example 160

2-[(4-But-2-Ynyloxy-Benenesulfonyl)-Amino]-N-Hydroxy-3-Methyl-3-Propylsulfanyl-Butyramide According to the procedure of Example 158, using iodopropane instead of iodomethane in Step 1, 2-[(4-but-2-ynyloxy-benenesulfonyl)-amino]-N-hydroxy-3-methyl-3-propylsulfanyl-butyramide was obtained. mp 152–155° C. Electrospray Mass Spec 415.2 (M+H)$^+$.

Example 161

2-[(4-Butynyloxy-Phenylsulfonyl)-Amino]-N-Hydroxy-3-Methyl-[(3-Pyridinylmethyl)Thio]Butyramide According to the procedure of Example 158, using 3-picolyl chloride hydrochloride instead of iodomethane in Step 1, 2-[(4-butynyloxy-phenylsulfonyl)-amino]-N-hydroxy-3-methyl-[(3-pyridinylmethyl)thio]butyramide was obtained. mp 95–100° C. Electrospray Mass Spec 464.0 (M+H)$^+$.

Example 162

2-[(4-Butynyloxy-Phenyl)Sulfonyl)-Amino]-N-Hydroxy-3-Methyl-(3-Benzylsulfanyl)Butyramide According to the procedure of Example 158, using benzyl bromide instead of iodomethane in Step 1, 2-[(4-butynyloxy-phenyl)sulfonyl)amino]-N-hydroxy-3-methyl-(3-benzylsulfanyl)butyramide was obtained. mp 92–95° C. Electrospray Mass Spec 463.1 (M+H)$^+$.

Example 163

2-({[4-(2-Butynyloxy)Phenyl]Sulfonyl}Amino-N-Hydroxy-3-{[(1-Methyl-1H-Imidazol-2-yl]Methyl Sulfanyl}Butanamide According to the procedure of Example 158, using 1-methylchloromethylimidazole instead of iodomethane in Step 1, 2-({[4-(2-butynyloxy) phenyl]sulfonyl}amino-N-hydroxy-3-{[(1-methyl-1H-imidazol-2-yl]methyl sulfanyl}-butanamide was obtained. mp 112–115° C. Electrospray Mass Spec 467.1(M+H)$^+$.

Example 164

2-({[4-(2-Butynyloxy)Phenyl]Sulfonyl}Amino-N-Hydroxy-3-Methyl-3-{[2-(4-Morpholinyl)Ethyl]Sulfanyl}Butanamide According to the procedure of Example 158, using 4-(2-chloroethyl)morpholine hydrochloride instead of iodomethane in Step 1, 2-({[4-(2-butynyloxy)phenyl]sulfonyl}amino-N-hydroxy-3-methyl-3-{[2-(4-morpholinyl)ethyl]sulfanyl}butanamide was obtained. mp 72° C. Electrospray Mass Spec 486.2 (M+H)$^+$.

Example 165

Tert-Butyl{[2-({[4-2-Butynyloxy)Phenyl]Sulfonyl}Amino)-3-(Hydroxyamino)-1,1-Dimethyl-3-Oxopropyl]Sulfanyl}Acetate According to the procedure of Example 158, using tert-butyl bromoacetate instead of iodomethane in Step 1, tert-butyl {[2-({[4-2-butynyloxy)phenyl]sulfonyl}amino)-3-(hydroxyamino)-1,1-dimethyl-3-oxopropyl]sulfanyl}acetate was obtained. mp 47–52° C. Electrospray Mass Spec 487 (M+H)$^+$.

Example 166

Tert-Butyl{[2-({[4-2-Butynyloxy)Phenyl]Sulfonyl}Amino)-3-(Hydroxyamino)-1,1-Dimethyl-3-Oxopropyl]Sulfanyl Acetic Acid, Sodium Salt The product of Example 165 (0.6 g, 1.23 mM) was dissolved in trifluoroacetic acid (5 mL) and dichloromethane (10 mL) and stirred at room temperature overnight. After evaporating the solvent, the residue was purified by preparative TLC, eluting with dichloromethane:methanol (92:8) to obtain 0.23 g of tert-butyl {[2-({[4-2-butynyloxy)phenyl]

sulfonyl)amino)-3-(hydroxyamino)-1,1-dimethyl-3-oxopropyl]sulfanyl acetic acid. mp 162–164° C. (d). Electrospray Mass Spec 429.3 (M–H)⁻. To this acid (0.22 g, 0.51 mmol) in methanol (12 mL), was added 1N NaOH (0.52 mL, 0.52 mM) and the reaction was stirred at room temperature for 1 h, and then concentrated to provide 0.24 g of tert-butyl {[2-({[4-2-butynyloxy)phenyl]sulfonyl}amino)-3-(hydroxyamino)-1,1-dimethyl-3-oxopropyl]sulfanyl acetic acid, sodium salt as a yellow-orange solid. m.p. 75° C.(d). Electrospray Mass Spec 429 (M–H)⁻.

Example 167

2-[(4-Butynyloxy-Phenylsulfonyl)-Amino]-N-Hydroxy-3-(Methylthio)Propanamide

According to the procedure of Example 158, using D-cysteine instead of D-penecillamine in Step 1, 2-[(4-butynyloxy-phenylsulfonyl)-amino]-N-hydroxy-3-(methylthio) propanamide was obtained. mp 128–130° C. Electrospray Mass Spec 359.2 (M+H)⁺.

Example 168

2-[[4-Butynyloxy-Phenylsulfonyl]-Amino]-N-Hydroxy-3-(Benzylthio) Propanamide

According to the procedure of Example 158, using D-cysteine instead of D-penecillamine and benzyl bromide instead of iodomethane in Step 1, 2-[[4-butynyloxy-phenylsulfonyl]-amino]-N-hydroxy-3-(benzylthio) propanamide was obtained. mp 137–138° C. Electrospray Mass Spec 435.1 (M+H)⁺.

Example 169

2-[[4-Butynyloxy-Phenylsulfonyl]-Amino]-N-Hydroxy-3-(Pyridinylthio) Propanamide

According to the procedure of Example 158, using D-cysteine instead of D-penecillamine and 3-picolyl chloride hydrochloride instead of iodomethane in Step 1, 2-[[4-butynyloxy-phenylsulfonyl]-amino]-N-hydroxy-3-(pyridinylthio) propanamide was obtained. mp 115–120° C. Electrospray Mass Spec 436.1 (M+H)⁺.

Example 170

2-({[4-(2-Butynyloxy)Phenyl]Sulfonyl}Amino)-N-Hydroxy-3-[(Z)-11-Tetradecenylsulfanyl] Propanamide Cis-11-tetradecen-1-ol (1 g, 4.72 mmol) and carbon tetrabromide (1.56 g 4.72 mmol) were dissolved in dichloromethane (3 ml) and the solution was cooled in ice bath. A solution of triphenylphosphine (1.24 g, 4.72 mmol) in 2 mL of dichloromethane was added dropwise. After siring at 0° C. for 15 minutes and at room temperature for 3 h the solvent was evaporated and the residue was diluted with ether. The ether solution was filtered and concentrated and purified using column chromatography on silica gel eluting with hexane:ethyl acetate (3:1) to give 0.23 g of (Z)-14-bromo-3-tetradecene.

According to the procedure of Example 158, using D-cysteine instead of D-penecillamine and (Z)-14-bromo-3-tetradecene instead of iodomethane in Step 1, 2-({[4-(2-butynyloxy)phenyl]sulfonyl}amino)-N-hydroxy-3-[(Z)-11-tetradecenylsulfanyl]propanamide was obtained. Electrospray Mass Spec 539.5 (M+H)⁺.

Example 171

(2S)-2-({[4-(2-Butynyloxy)Phenyl] Sulfonyl}Amino)-N-Hydroxy-3[(3-Hydroxypropyl) Sulfanyl]-3-Methylbutanamide Step 1

A solution of 2N sodium hydroxide (11.3 mL, 22.7 mmol) was added to D-(−)-penicillamine (2.5 g, 16.8 mmol) at 0° C. Once all the solid was dissolved, a solution of 3-bromopropanol (3.03 g, 21.8 mmol) in ethanol (17 mL) was slowly added at 0° C. and the resulting mixture was stirred for 15 h at room temperature. The mixture was treated with 1N hydrochloric acid until pH is ~6 and the solvents were removed to obtain (2S)-2-amino-3-[(3-hydroxypropyl) sulfanyl]-3-methylbutanoic acid as a white solid. This solid was used for the next step without further purification; Electrospray Mass Spec 208.1 (M+H)+

Step 2

The (2S)-2-amino-3-[(3-hydroxypropyl)sulfanyl]-3-methylbutanoic acid was dissolved in dioxane:water (1:1) (40 mL). Triethylamine (5.1 mL, 50.4 mmol) was added to the solution followed by 2-butynyloxybenzenesulfonyl chloride (4.1 g, 16.8 mmol). The resulting mixture was stirred for 15 h at room temperature. The mixture was acidified to pH ~2 with 1N hydrochloric acid and partitioned between ethyl acetate and water. The organic layer was dried over anhydrous sodium sulfate. Removal of the solvent gave 5.78 g (83%) of (2S)-2-({[4-(2-butynyloxy)phenyl]sulfonyl}amino)-3-[(3-hydroxypropyl)sulfanyl]-3-methylbutanoic acid as a solid; ¹H NMR (300 MHz, acetone-d₆) δ 1.34 (s, 3H), 1.39 (s, 3H), 1.66 (m, 2H), 2.06 (m, 3H), 2.54–2.68 (m, 2H), 3.89 (m, 1H), 4.82 (m, 2H), 6.56 (d, 1H, J=9.0 Hz), 7.12(d, 2H, J=8.7 Hz), 7.81(d, 2H, J=8.7 Hz). HRMS (C₁₈H₂₅NOS₂)(M+H);

calcd. 416.1196, found 416.1199.

Step 3

To a solution of (2S)-2-({[4-(2-butynyloxy)phenyl]sulfonyl}amino)-3-[(3-hydroxypropyl)sulfanyl]-3-methylbutanoic acid (500 mg, 1.2 mmol) in dimethylformamide (10 mL) was added N-hydroxybenzotriazole (194 mg, 1.44 mmol), 1-(3-dimethylaminopropyl)-3-ethylcarbodiimide (322 mg, 1.68 mmol) followed by N-methylmorpholine (0.198 mL, 1.8 mmol) and the resulting mixture was stirred for 1 h at room temperature. A 50% aqueous solution of hydroxylamine (0.367 mL, 6 mmol) was added and the mixture was stirred for 15 h at room temperature. The solvent was removed and the product was partitioned between ethyl acetate and water. The organic layer was washed with 1N hydrochloric acid, saturated aqueous sodium bicarbonate solution, brine, and dried over anhydrous sodium sulfate. Removal of the solvent gave (2S)-2-({[4-(2-butynyloxy)phenyl]sulfonyl}amino)-N-hydroxy-3-[(3-hydroxypropyl)sulfanyl]-3-methylbutanamide, which was triturated with hexanes to obtain 130 mg (25%) of the pure product; HRMS (C₁₈H₂₆N₂O₆S₂)(M+H);

calcd. 431.1305, found 431.1313.

Example 172

(2S)-2-({[4-(2-Butynyloxy)Phenyl]
Sulfonyl}Amino)-N-Hydroxy-3-[(3-Hydroxypropyl)
Sulfanyl]-3-Propanamide According to the procedure of Example 171, starting with D-cysteine instead of D-penicillamine, (2S)-2-({[4-(2-butynyloxy)phenyl]sulfonyl}amino)-N-hydroxy-3-[(3-hydroxypropyl)sulfanyl]-3-propanamide was obtained. HRMS ($C_{16}H_{22}N_2O_6S_2$)(M+H);

calcd. 403.0992, found 403.0991.

Example 173

(3S)-4-({[4-(2-Butynyloxy)Phenyl]Sulfonyl}-N-
Hydroxy-2,2-Dimethyl-1,4-Thiazepane-3-
Carboxamide Step 1

To a solution of (2S)-2-({[4-(2-butynyloxy)phenyl]sulfonyl}amino)-3-[(3-hydroxypropyl)sulfanyl]-3-methylbutanoic acid from Example 171, (1 g, 2.41 mmol) in dimethylacetamide (6 mL) was added t-butyl bromide (4.16 mL, 36.2 mmol), potassium carbonate (2.66 g, 19.28 mmol), and benzyltriethylammonium chloride (82 mg, 0.36 mmol) and the resulting mixture was heated at 55° C. for 15 h. The solvent was removed and the residue was partitioned with ethylacetate and water. The organic layer was separated, washed with brine and dried over anhydrous sodium sulfate. The solvent was removed to obtain 600 mg (56%) of tert-butyl (2S)-2-({[4-(2-butynyloxy)phenyl]sulfonyl}amino)-3-[(3-hydroxypropyl)sulfanyl]-3-methylbutanoate; $^1$H NMR (300 MHz, CDCl$_3$) □ 1.22 (s, 9H), 1.35 (s, 3H), 1.39 (s, 3H), 1.76 (m, 2H), 1.80 (m, 3H), 2.41 (m, 1H), 2.68 (m, 2H, 3.71 (m, 3H), 4.69 (m, 2H), 5.74 (d, 1H, J=9.9 Hz), 7.03 (d, 2H, J=7.2 Hz), 7.79 (d, 2H, J=7.2 Hz); HRMS($C_{22}H_{33}NO_6S_2$)(M+Na);

cald. 494.1641, found 494.1644.

Step 2

To a solution of tert-butyl (2S)-2-({[4-(2-butynyloxyphenyl]sulfonyl}amino)-3-[(3-hydroxypropyl)sulfanyl]-3-methylbutanoate (380 mg, 0.81 mmol) in tetrahydrofuran (5 mL) was added triphenylphospine (255 mg, 0.97 mmol) followed by diethylazodicarboxylate (0.14 mL, 0.89 mmol) and the resulting mixture was stirred for 2 h at room temperature. The solvent was removed and the crude product was flash chromatographed to obtain 280 mg (62%) of tert-butyl (3S)-4-({[4-(2-butynyloxy)phenyl]sulfonyl}-2,2-dimethyl-1,4-thiazepane-3-carboxylate; $^1$H NMR (300 MHz, CDCl$_3$) 1.29 (S, 9H), 1.37 (s, 3H), 1.61 (s, 3H), 1.85 (m, 3H), 1.91 (m, 1H), 2.26 (m, 1H), 2.72 (m, 1H), 2.86 (m, 1H), 3.52 (m, 1H), 4.12 (m, 1H), 4.44 (s, 1H), 4.68 (m, 2H), 7.02 (d, 2H, J=9.0 Hz), 7.76 (d, 2H, J=9.0 Hz); HRMS ($C_{22}H_{31}NO_5S_2$)(M+);

cald. 453.1644, found 452.9784.

Step 3

A solution of tert-butyl (3S)4-({[4-(2-butynyloxy)phenyl]sulfonyl}-2,2-dimethyl-1,4-thiazepane-3-carboxylate (220 mg, 0.49 mmol) in methylene chloride (4 mL) was added trifluoroacetic acid (1.5 mL) and the mixture was stirred for 2 h at room temperature. The solvent was removed in vacuo.

Traces of trifluoroacetic acid was removed by adding toluene (1 mL) and removing the solvent to obtain 170 mg (88%) of (3S)-4-({[4-(2-butynyloxy)phenyl]sulfonyl}-2,2-dimethyl-1,4-thiazepane-3-carboxylic acid; $^1$H NMR (300 MHz, CDCl$_3$) δ 1.42 (s, 3H), 1.60 (s, 3H), 1.85 (m, 3H), 1.91 (m, 1H), 2.17 (m, 1H), 2.67 (m, 1H), 2.82 (m, 1H), 3.54 (m, 1H), 3.82 (m, 1H), 4.59 (s, 1H), 4.68 (m, 2H), 7.0 (d, 2H, J=8.7 Hz), 7.75 (d, 2H, J=8.7 Hz); HRMS ($C_{18}H_{23}NO_5S_2$) (M+);

cald. 397.1018, found 397.0998.

Step 4

Following the procedure of Step 3, Example 171, (3S)-4-({[4-(2-butynyloxy)phenyl]sulfonyl}-2,2-dimethyl-1,4-thiazepane-3-carboxylic acid (140 mg, 0.35 mmol), N-hydroxybenzotriazole (57 mg, 0.42 mmol), 1-(3-dimethylaminopropyl)-3-ethylcarbodimide (94 mg, 0.49 mmol), N-methylmorpholine (0.058 mL, 0.53 mmol), and aqueous hydroxylamine (0.107 mL, 1.75 mmol) in dimethylformamide (3 mL) provided 80 mg (56%) of (3S)-4({[4-(2-butynyloxy)phenyl]sulfonyl}-N-hydroxy-2,2-dimethyl-1,4-thiazepane-3-carboxamide; $^1$H NMR(300 MHz, DMSO-d$_6$) δ 1.26 (s, 3H), 1.56 (s, 3H), 1.87 (m, 1H), 1.91 (m, 3H), 2.06 (m, 1H), 2.73 (m, 2H), 3.20 (m, 1H), 4.21 (s, 1H), 4.80 (m, 1H), 4.90 (m, 2H), 7.16 (d, 2H, J=9.0 Hz), 7.79 (d, 2H, J=9.0 Hz); HRMS ($C_{18}H_{24}N_2O_5S_2$)(M+Na);

cald. 413.1199, found 413.1205.

Example 174

(3S)-4-({[4-(2-Butynyloxy)Phenyl]Sulfonyl}-N-
Hydroxy-1,4-Thiazepane-3-Carboxamide Starting with D-cysteine, following the procedure of Steps 1 and 2 of Example 171, (2S)-2-({[4-(2-butynyloxy)phenyl]sulfonyl}amino)-3-[(3-hydroxypropyl)-sulfanyl]-3-propanoic acid was obtained.

According to the procedure of Step 1 of Example 173, the acid (2 g, 5.17 mmol) was converted into the corresponding t-butyl ester using t-butylbromide (8.9 mL, 77.5 mmol), potassium carbonate (5.7 g, 41.4 mmol), and benzyltriethylammonium chloride (177 mg, 0.77 mmol) in dimethylacetamide (12 mL) to obtain 1.5 g (66%) of tert-butyl (2S)-2-({[4-(2-butynyloxy)phenyl]sulfonyl}amino)-3-[(3-hydroxypropyl)sulfanyl]-3-propanoate; $^1$H NMR (300 MHz, CDCl$_3$) δ 6 1.32 (s, 9H), 1.82 (m, 1H), 1.85 (m, 3H), 1.93 (br s, 1H), 2.71 (t, 2H, J=6.9 Hz), 2.85 9 m, 2H), 3.74 (m, 2H), 4.02 (m, 1H), 4.72 (m, 2H), 5.58 (d, 1H, J=8.4 Hz), 7.04 (d, 2H, J=8.7 Hz), 7.81 (d, 2H, J=8.7 Hz); Electrospray Mass Spec 444.1 (M+H)$^+$;

Following the procedure for Step 2 of Example 173, tert-butyl (2S)-2-({[4-(2-butynyloxy)phenyl]sulfonyl}amino)-3-[(3-hydroxypropyl)sulfanyl]-3-propanoate (1.4 g, 3.16 mmol), triphenylphospine (993 mg, 3.79 mmol), and diethylazodicarboxylate (0.547 mL, 3.48 mmol) in tetrahydrofuran (20 mL) provided 1.1 g (82%) of tert-butyl (3S)-4-({[4-(2-butynyloxy)phenyl]sulfonyl}-1,4-thiazepane-3-carboxylate; $^1$H NMR(300 MHz, CDCl$_3$) 1.31 (s, 9H), 1.85 (m, 3H), 1.93 (m, 1H), 2.04 (m, 1H), 2.65 (m, 1H), 2.76 (m, 1H), 2.88 (m, 1H), 3.15 (m, 1H), 3.31 (m, 1H), 3.80 (m, 1H), 4.70 (m, 3H), 7.03 (d, 2H, J=8.7 Hz), 7.77 (d, 2H, J=8.7 Hz); HRMS ($C_{20}H_{27}NO_5S_2$)(M+H);

calcd. 426.1403, found 426.1404.

Following the procedure of Step 3 of Example 173, tert-butyl (3S)-4-({[4-(2-butynyloxy)phenyl]sulfonyl}-1,4-thiazepane-3-carboxylate (800 mg, 1.88 mmol), trifluoroacetic acid (6 mL) in methylene chloride (15 mL) provide 650 mg (94%) of (3S)-4-({[4-(2-butynyloxy)phenyl]sulfonyl}-1,4-thiazepane-3-carboxylic acid; $^1$H NMR (300 MHz, acetone-d$_6$): δ 1.74 (m, 3H), 1.90 (m, 2H), 2.59 (m, 2H), 2.90 (m, 1H), 3.18 (m, 1H), 3.26 (m, 1H), 3.70 (m, 1H), 4.70 (m, 3H), 7.03 (d, 2H, J=8.7 Hz), 7.77 (d, 2H, J=8.7 Hz); HRMS (C$_{16}$H$_{19}$NO$_5$S$_2$)(M+H);

calcd. 370.0777, found 370.0765.

Following the procedure Step 3 of Example 171, (3S)-4-({[4-(2-butynyloxy)phenyl]sulfonyl}-1,4-thiazepane-3-carboxylic acid (400 mg, 1.08 mmol), N-hydroxybenzotriazole (175 mg, 1.29 mmol), 1-(3-dimethylaminopropyl)-3-ethylcarbodimide hydrochloride (290 mg, 1.51 mmol), N-methylmorpholine (200 □L, 1.62 mmol), and 50% aqueous hydroxylamine (331 mL, 5.4 mmol) provided 200 mg (48%) of (3S)-4-({[4-(2-butynyloxy)phenyl]sulfonyl}-N-hydroxy-1,4-thiazepane-3-carboxamide; HRMS (C$_{16}$H$_{20}$N$_2$O$_5$S$_2$)(M+H);

calcd. 385.0886, found 385.0886.

Example 175

(3 S)-4-({[4-(2- Butynyloxy)Phenyl]Sulfonyl}-N-Hydroxy-1,4-Thiazepane-3-Carboxamide 1,1-Dioxide To a cooled (0° C.) solution of (3S)-4-({[4-(2-butynyloxy)phenyl]sulfonyl}-N-hydroxy-1,4-thiazepane-3-carboxamide (80 mg, 0.21 mmol) in chloroform (2 mL) was added 32% peracetic acid (0.132 mL, 0.63 mmol) and the reaction mixture was stirred overnight at room temperature. The solvent was removed and the residue was dissolved in ethyl acetate and dried over anhydrous sodium sulfate. Removal of the solvent gave 60 mg (69%) of (3S)-4-({[4-(2-butynyloxy)phenyl]sulfonyl}-N-hydroxy-1,4-thiazepane-3-carboxamide 1,1-dioxide; $^1$H NMR(300 MHz, DMSO-d$_6$) δ 1.80 (br s, 2H), 1.84 (m, 3H), 3.07–3.80 (m, 5H), 4.00 (m, 1H), 4.53 (m, 1H), 4.84 (m, 2H), 7.03 (d, 2H, J=8.7 Hz), 7.77 (d, 2H, J=8.7 Hz), 9.05 (s, 1H), 10.32 (s, 1H); MS (ES)(M+H)); 416.9.

Example 176

2-({[4-(2-Butynyloxy)Phenyl]Sulfonyl}Amino)-N-Hydroxy-2-(4-Hydroxyphenyl)Acetamide To a solution of 167.2 mg (1.00 mmol) of D-4-hydroxyphenyl glycine in 3.7 ml of CH$_3$CN was added 0.56 ml (2.09 mmol) of bis(trimethylsilyl)trifloroacetamide, and the reaction mixture was gently refluxed for 2h. The resulting clear solution was cooled to 40° C., and 0.096 ml (1.2 mmol) pyridine and 269.2 mg (1.099 mmol) of 4-but-2-ynyloxy-benzenesulfonyl chloride were added. The reaction mixture was heated at 70° C. for 3 h and stirred at room temperature for 14 h. The solvent was evaporated and the resulting oily residue was treated with 15% NaHSO$_4$ and stirred for 1 h. The mixture was extracted with ethyl acetate. The combined organics were then dried over MgSO$_4$, filtered and concentrated in vacuo. The crude material was triturated in hexane to get 319 mg (85%) of ({[4-(2-butynyloxy)phenyl]-sulfonyl}amino)(4-hydroxyphenyl) acetic acid as a pale yellow solid. Electrospray Mass Spec 374.3 (M−H)$^-$ To a solution of 12.18 g (32.48 mmol) of product of ({[4-(2-butynyloxy)phenyl]sulfonyl}amino)(4hydroxyphenyl)acetic acid in 5 ml of DMF at room temperature was added 165.65 g (1.95 mol) of NaHCO$_3$, 17.4 g (90.9 mmol) of EDC, 10.53 g (77.95 mmol) of HOBT and 61.2 g (487.2 mmol) of O-t-butylhydroxylamine hydrochloride. The reaction was stirred at 50° C. for 6 h, then at room temperature overnight. DMF was removed. The resulting light brown solid was diluted with ethyl acetate/water, extracted with ethyl acetate, washed with brine, dried over MgSO$_4$, filtered, and concentrated in vacuo. The crude material was washed with 3–5 ml dichloromethane, The product, 'N-(tert-butoxy)-2-({[4-(2-butynyloxy)phenyl]-sulfonyl}amino)-2-(4hydroxyphenyl)acetamide, (12 g, 83%) was obtained as a light yellow solid. Electrospray Mass Spec 447.4 (M+H)$^+$ A 450 mg (1.007 mmol) portion of 'N-(tert-butoxy)-2-({[4-2-butynyloxy)phenyl]sulfonyl}amino)-2-(4-hydroxyphenyl)acetamide was stirred in neat TFA at room temperature for 72 h. TFA was removed in vacuo. The residue was chromatographed on preparative TLC, eluting with 1% HOAc and 10% MeOH in dichloromethane to provide 33.8 mg (9%) of 2-{[4-(2-butynyloxy)phenyl]-sulfonyl}amino)-N-hydroxy-2-(4-hydroxyphenyl) acetamide as a white solid. Electrospray Mass Spec 391.4 (M+H)$^+$ Example 177

2-({[4-(2-Butynyloxy)Phenyl]Sulfonyl}Amino)-N-Hydroxy-2-[4-(2-Propynyloxy)Phenyl]Acetamide To a solution of 321.6 mg (0.72 mmol) of 'N-(tert-butoxy)-2-({[4-2-butynyloxy)phenyl]sulfonyl}amino)-2-(4-hydroxyphenyl)acetamide from Example 176 in 3 ml DMF at 0° C. was added 199 mg (1.44 mmol) of K$_2$CO$_3$. The reaction mixture was stirred for 15 min, 94.4 mg (0.79 mmol) of propargyl bromide was added, and reaction mixture was stirred at room temperature overnight. DMF was removed in vacuo. The residue was diluted with ethyl acetate, washed with 1N HCl solution, water and brine. The organic layer was dried over MgSO$_4$, filtered, and concentrated in vacuo. The crude material was chromatographed on silica gel, eluting with hexane/ethyl acetate (5:1, 4:1 then 3:1) to provide 75 mg (17%) of 'N-(tert-butoxy)-2-({[4-(2-butynyloxy)phenyl]sulfonyl}amino)-2-[4-(2-propynyloxy) phenyl]acetamide as a white solid. Electrospray Mass Spec 485.4 (M+H)$^+$ The 75 mg (0.154 mmol) sample of 'N-(tert-butoxy)-2-({[4-(2-butynyloxy)phenyl]sulfonyl}amino)-2-[4-(2-propynyloxy)phenyl]acetamide was stirred in neat TFA at room temperature for 72 h TFA was removed in vacuo. The residue was chromatographed on prep. TLC eluting with 1% HOAc in 10% MeOH/CH$_2$Cl$_2$ to provide 11.1 mg (17%) of 2-({[4-(2-butynyloxy)phenyl]sulfonyl}amino)-N-hydroxy-2-[4-(2-propynyloxy)phenyl]acetamide as a white solid was obtained. High Resolution Mass Spec 429.11155 (M+H)$^+$;

Calc'd for C$_{21}$H$_{21}$N$_2$O$_6$S 429.11149.

Example 178

2-[{[4-(2-Butynyloxy)Phenyl]Sulfonyl}(Methyl) Amino]-N-Hydroxy -2-(4-Methoxyphenyl) Acetamide To 50 mL of methanol cooled to 0° C. was dropwise added 3.75 mL of thionyl chloride foolowed by 5.0 g (0.030 mmol) of D-4-hydroxyphenylglycine. The reaction was heated to reflux for 5 h then stirred overnight at room temperature. The resulting mixture was concentrated in vacuo and the residue was diluted with ether. The resulting solid was collected by filtration and dried in vacuo to provide 5.9 g of amino-(4-hydroxy-phenyl)-acetic acid methyl ester as a white solid. Electrospray Mass Spec 182.2 (M+H)+

To a solution of 5.0 g (0.023 mmol) of amino-(4-hydroxyphenyl)-acetic acid methyl ester dissolved in 30 mL of chloroform was added 30 mL of pyridine followed by 5.85 g (0.023 mmol) of 4-but-2-ynyloxy-benzenesulfonyl chloride. The reaction was stirred overnight at room temperature and then diluted with ethyl acetate. The organics were washed with 5% HCl solution and water, dried over magnesium sulfate, filtered and concentrated in vacuo. The residue was chromatographed on silica gel eluting with ethyl acetate/hexanes (1:3) to provide [{[4-(2-butynyloxy)phenyl]sulfonyl}amino](4-hydroxyphenyl)acetate as pale yellow crystals.

To a solution of 0.350 g (0.900 mmol) of [{[4-(2-butynyloxy)phenyl]sulfonyl}amino](4-hydroxyphenyl) acetate dissolved in 3 mL of DMF was added 0.079 g (1.979 mmol) of a 60% oil dispersion of sodium hydride. The reaction was stirred for 30 min at room temperature and then 0.224 mL of iodomethane was added. After 5 h the reaction was diluted with water and extracted with ether. The combined organics were washed with water, dried over magnesium sulfate, filtered and concentrated in vacuo. The residue was chromatographed on silica gel eluting with ethyl acetate/hexanes (1:3) to provide [([4-(2-butynyloxy)phenyl] sulfonyl](methylamino](4-methoxyphenyl)acetate as a white waxy solid. Electrospray Mass Spec 418.1 (M+H)+

According to the procedures of Examples 11 and 9 [{[4-(2-butynyloxy)phenyl]sulfonyl}(methyl)amino](4-methoxyphenyl)acetate was hydrolyzed to the carboxylic acid and then converted into the hydroxamic acid, 2-[{[4-(2-butynyloxy)phenyl]sulfonyl}(methyl)amino]-N-hydroxy-2-(4-methoxyphenyl)acetamide. Electrospray Mass Spec 419.3 (M+H)+

Example 179

2-[{[4-(2-Butynyloxy)Phenyl]Sulfonyl}(Methyl) Amino]-N-Hydroxy-2-{4-[2-(4-Morpholinyl) Ethoxy]Phenyl}Acetamide To a solution of 6.62 g (0.017 mmol) of []{4-(2-butynyloxy)phenyl]sulfonyl}amino](4-hydroxyphenyl) acetate from Example 178 in 50 mL of DMF was added 3.08 g (0.020 mmol) of tert-butyldimethylsilyl chloride followed by 2.89 g (0.043 mmol) of imidazole. The reaction was stirred at room temperature for 5 h and then diluted with ether. The resulting mixture was washed with water, dried over magnesium sulfate, filtered and concentrated in vacuo to give 7.06 g of [4-(tert-butyl-dimethyl-silanyloxy)-phenyl]-(4-but-2-ynyloxy-benzenesulfonylamino)-acetic acid methyl ester as a white solid. Electrospray Mass Spec 504.4 (M+H)+

To a solution of 7.06 g (0.014 mmol) of [(tert-butyl-dimethylsilanyloxy)-phenyl]-(4-but-2-ynyloxy-benzenesulfonylamino)-acetic acid methyl ester dissolved in 50 mL of DMF was added 0.618 g (0.015 mmol) of a 60% oil dispersion of sodium hydride. The reaction was stirred for 30 min at room temperature and then 2.62 mL of iodomethane was added. After 5 h the reaction was diluted with water and extracted with ether. The combined organics were washed with water, dried over magnesium sulfate, filtered and concentrated in vacuo. The residue was chromatographed on silica gel eluting with ethyl acetate/hexanes (1:3) to provide [4-tert-butyl-dimethyl-silanyloxy)-phenyl]-[(4-but-2-ynyloxy-benzenesulfonyl)-methyl-amino]-acetic acid methyl ester as a white waxy solid. Electrospray Mass Spec 518.4 (M+H)+

To a solution of 6.0 g (0.012 mmol) of [4-(tert-butyl-dimethyl-silanyloxy)-phenyl]-[(4-but-2-ynyloxy-benzenesulfonyl)-methyl-amino]-acetic acid methyl ester in 100 mL of THF was added 11.6 mL of a 1.0M solution of tetrabutylammonium fluoride in THF. The reaction was stirred for 1 h at room temperature and then acidified with 5% HCl solution and extracted with ethyl acetate. The organics were dried over magnesium sulfate, filtered and concentrated in vacuo. The residue was chromatographed on silica gel eluting with ethyl acetate/hexanes (1:1) to give 2.7 g of methyl [{[4-(2-butynyloxy)phenyl]sulfonyl}(methyl) amino](4-hydroxyphenyl)acetate as a white solid. . Electrospray Mass Spec 404.2 (M+H)+

To a solution of 0.25 g (0.620 mmol) of methyl [{[4-(2-butynyloxy)phenyl]sulfonyl}(methyl)amino](4-hydroxyphenyl)acetatein 10 mL of acetone was added 0.342 g of potassium carbonate, 0.231 g (1.241 mmol) of 4-(2-chloroethyl)morpholine hydrochloride and 1 equivalent of sodium iodide. The reaction was heated to reflux for 5 h, diluted with water and extracted with chloroform. The organics were dried over sodium sulfate, filtered and concentrated in vacuo. The residue was chromatographed on silica gel eluting with chloroform/methanol (9:1) to provide 0.156 g of methyl 2-[{[4-(2-butynyloxy)phenyl]sulfonyl} (methyl)amino]-2-{4-[2-(4-morpholinyl)ethoxy] phenyl}acetate.

According to the procedures of Examples 11 and 9 methyl 2-[{[4-(2-butynyloxy)phenyl]sulfonyl}(methyl)amino]-2-{4-[2-(4-morpholinyl)ethoxy]phenyl}acetate was hydrolyzed to the carboxylic acid and then converted into the hydroxamic acid, 2-[{[4-(2-butynyloxy)phenyl]-sulfonyl} (methyl)amino]-N-hydroxy-2-{4-[2-(4-morpholinyl) ethoxy]phenyl}-acetamide. Electrospray Mass Spec 518.3 (M+H)+

Example 180

Tert-Butyl 2-{4-[1-[{[4-(2-Butynyloxy)Phenyl] Sulfonyl}(Methyl)Amino]-2-(Hydroxyamino)-2-Oxoethyl]Phenoxy}Ethylcarbamate To a solution of 0.488 g (1.861 mmol) of triphenylphosphine in 10 mL of THF was added 0.287 g (1.861 mmol) of tert-butyl N-(2-hydroxyethyl)-carbamate followed by 0.500 g (1.241 mmol) of methyl [{[4-(2-butynyloxy)phenyl] sulfonyl}(methyl)amino](4-hydroxyphenyl)acetate (from Example 179) and 0.293 mL (1.861 mmol) of diethyl azodicarboxylate. The reaction was stirred overnight at room temperature and then concentrated m vacuo. The residue was chromatographed on silica gel eluting with ethyl acetate/hexanes (1:3) to give 0.677 g of methyl (4-{2-[(tert-butoxycarbonyl)amino]ethoxy}phenyl)[{[4-(2-butynloxy) phenyl]sulfonyl(methyl)amino]acetate as a white solid. Electrospray Mass Spec 547.4 (M+H)+

According to the procedures of Examples 11 and 25 methyl (4-{2-[(tert-butoxycarbonyl)amino]ethoxy}phenyl) [{[4-(2-butynyloxy)phenyl]sulfonyl}(methyl)amino]acetate was hydrolyzed to the carboxylic acid and then converted into the hydroxamic acid, tert-butyl 2-{4-[1-[{[4-(2-butynyloxy)phenyl]sulfonyl}(methyl)amino]-2-(hydroxyamino)-2-oxoethyl]phenoxy}ethylcarbamate. Electrospray Mass Spec 548.5 (M+H)+

Example 181

2-[4-(2-Aminoethoxy)Phenyl]-2-[{[4-(2-Butynyloxy)Phenyl]Sulfonyl}(Methyl)Amino]-N-Hydroxyacetamide To a solution of 0.156 g(0.285 mmol) of tert-butyl 2-{4-[1-[{[4-(2-butynyloxy)phenyl]sulfonyl}(methyl)amino]-2-(hydroxyamino)-2-oxoethyl]phenoxyethylcarbamate from Example 180 dissolved in 2 mL of dichloromethane was added 3.0 mL of a 1.0 M solution of HCl in ether. The reaction was stirred at room temperature for 3 h and then diluted with ether. The resulting solid was collected by filtration and dried in vacuo to give 0.099 g of the hydrochloride salt of 2-[4-(2-aminoethoxy)phenyl]- 2-[{[4-(2-butynyloxy)phenyl]sulfonyl}(methyl)amino]-N-hydroxyacetamide as a tan solid. Electrospray Mass Spec 448.3 (M+H)+

Example 182

2-[{[4-(2-Butynyloxy)Phenyl]Sulfonyl}(Methyl) Amino]-2-{4-[2-(Dimethylamino)Ethoxy]Phenyl}-N-Hydroxyacetamide To a solution of 0.390 g (1.489 mmol) of triphenylphosphine in 8 mL of THF was added 0.150 mL (1.489 mmol) of N,N-dimethylethanolamine followed by 0.400 g (0.993 mmol) of methyl [{[4-(2-butynyloxy)phenyl]sulfonyl} (methyl)amino](4-hydroxyphenyl)acetate (from Example 179) and 0.234 mL (1.489 mmol) of diethyl azodicarboxylate. The reaction was stirred overnight at room temperature and then concentrated in vacuo. The residue was chromatographed on silica gel eluting with ethyl acetate/hexanes (1:3) to give 0.246 g of methyl[{[4-(2-butynyloxy)phenyl] sulfonyl}(methyl)amino]{4-[2-(dimethylamino)ethoxy] phenyl}acetate as a white solid. Electrospray Mass Spec 475.2 (M+H)+

According to the procedures of Examples 11 and 9 methyl[{[4-(2-butynyloxy)phenyl]sulfonyl}(methyl)amino] {4-[2-dimethylamino)ethoxy]phenyl}acetate was hydrolyzed to the carboxylic acid and then converted into the hydroxamic acid, 2-[{[4-(2-butynyloxy)phenyl]sulfonyl} (methyl)amino]-2-{4-[2-(dimethylamino)ethoxy]phenyl}-N-hydroxyacetamide. Electrospray Mass Spec 476.4 (M+H)+

Example 183

2-[}[4-(2-Butynyloxy)Phenyl]Sulfonyl}(Methyl) Amino]-N-Hydroxy-2-{4-[2-(1-Pyrrolidinyl)Ethoxy] Phenyl}Acetamide According to the procedure of Example 182, using 1-(2-hydroxyethyl)pyrrolidine instead of N,N-diethylethanolamine, 2-[{[4-(2-butynloxy)phenyl]sulfonyl) (methyl)amino]-N-hydroxy-2-{4-[2-(1-pyrrolidinyl)ethoxy] phenyl}acetamide was obtained as a tan solid. Electrospray Mass Spec 502.2 (M+H)+

Example 184

2-[{[4-(2-Butynyloxy)Phenyl]Sulfonyl}(Methyl) Amino]-N-Hydroxy-2-{4-[2-(2-Oxo-1-Pyrrolidinyl) Ethoxy]Phenyl}Acetamide According to the procedure of Example 180, using 1-(2-hydroxyethyl)-2-pyrrolidinone instead of tert-butyl N-(2-hydroxyethyl)-carbamate, 2-[{[4-(2-butynyloxy)phenyl] sulfonyl}(methyl)amino]-N-hydroxy-2-{4-[2-(2-oxo-1-pyrrolidinyl)ethoxy]phenyl}acetamide was obtained as a white foam. Electrospray Mass Spec 516.2 (M+H)+

Example 185

Tert-Butyl 4-(2-{4-[1-[{[4-(2-Butynyloxy)Phenyl] Sulfonyl}(Methyl)Amino]-2-(Hydroxyamino)-2-Oxoethyl]Phenoxy}Ethyl)-1-Piperazinecarboxylate According to the procedure of Example 180, using tert-butyl N-(2-hydroxyethyl)piperazine carbamate instead of tert-butyl N-2-hydroxyethyl)-carbamate, tert-butyl 4-(2-{4-[1-[{[4-(2-butynyloxy)phenyl]sulfonyl}(methyl)amino]-2-(hydroxyamino)-2-oxoethyl]phenoxy}ethyl)-1-piperazinecarboxylate was obtained as a white solid. Electrospray Mass Spec 617.4 (M+H)+

Example 186

2-[{[4-(2-Butynyloxy)Phenyl]Sulfonyl}(Methyl) Amino]-N-Hydroxy-2-{4-[2-(1-Piperazinyl)Ethoxy] Phenyl}Acetamide To a solution of 0.300 g (0.487 mmol) of tert-butyl 4-(2-{4-[1-[{[4-(2-butynyloxy)phenyl]sulfonyl}(methyl) amino]-2-(hydroxyamino)-2-oxoethyl]phenoxy}ethyl)-1-piperazinecarboxylate (from Example 185) in 1 mL of dichloromethane was added 1 mL of trifluoroacetic acid. The reaction was stirred at room temperature for 3 h and then concentrated in vacuo. The residue was diluted with chloroform/methanol(9:1) and washed with saturated sodium bicarbonate solution. The organics were dried over sodium sulfate, filtered and concentrated in vacuo. The residue was diluted with 2 mL of dichloromethane and 0.25 mL of methanol and 1 mL of a 1.0 M solution of HCl in ether was added. After 30 minutes the mixture was concentrated in vacuo to provide 0.189 g of the hydrochloride salt of 2-[{[4-(2-butynyloxy)phenyl]sulfonyl}(methyl)amino]-N-hydroxy-2-{4-[2-(1-piperazinyl)ethoxy]phenyl}acetamide as a tan solid. Electrospray Mass Spec 517.3 (M+H)+

Example 187

Tert-Butyl 3-{4-[1-[{[4-(2-Butynyloxy)Phenyl]
Sulfonyl}(Methyl)Amino]-2-(Hydroxyamino)-2-
Oxoethyl]Phenoxy}Propylcarbamate According to the procedure of Example 180, Mitsunobu reaction of tert-butyl N-(3-hydroxypropyl)carbamate and methyl [{[4-(2-butynyloxy)phenyl]sulfonyl-(methyl)amino] (4-hydroxyphenyl)acetate provides methyl (4-{3-[(tert-butoxycarbonyl)amino]propoxy}phenyl)[{[4-(2-butynyloxy)phenyl]sulfonyl}(methyl)amino]acetate.

According to the procedures of Examples 11 and 25 this methyl ester was converted into the hydroxamic acid tert-butyl 3-{4-[1-[{[4-(2-butynyloxy)phenyl]sulfonyl}(methyl) amino]-2-(hydroxyamino)-2-oxoethyl]phenoxy}-propylcarbamate, obtained as a white foam. Electrospray Mass Spec 560.2 (M–H)⁻

Example 188

2-[4-(3-Aminopropoxy)phenyl]-2-[{[4-(2-Butynyloxy)Phenyl]Sulfonyl}(Methyl)Amino]-N-Hydroxyacetamide Hydrogen chloride gas was bubbled through a solution of 0.371 g (0.661 mmol) of tert-butyl 3-{4-[1-[{[4-(2-butynyloxy)phenyl]sulfonyl}(methyl)amino]-2-(hydroxyamino)-2-oxoethyl]phenoxy}propylcarbamate (from Example 187) dissolved in 5 mL of dichloromethane for 5 minutes. The reaction was stopped at let sit at room temperature for 1 h and then the solvent was evaporated. The residue was triturated with ether, filtered and dried in vacuo to give 0.314 g of 2-[4-(3-aminopropoxy)phenyl]- 2-[{[4-(2-butynyloxy)phenyl]sulfonyl}(methyl)amino]-N-hydroxyacetamide as a white solid. Electrospray Mass Spec 462.2 (M+H)⁺

Example 189

Tert-Butyl (3S)-3-{4-[(1R)-1-[{[4-(2-Butynyloxy)
Phenyl]Sulfonyl}(Methyl)Amino]-2-
(Hydroxyamino)-2-Oxoethyl]Phenoxy}-1-
Pyrrolidinecarboxylate According to the procedure of Example 180, using tert-butyl N-(3-pyrrolidinol)carbamate instead of tert-butyl N-(2-hydroxyethyl)-carbamate, tert-butyl (3S)-3-{4-[(1R)-1-[{[4-(2-butynyloxy)phenyl]sulfonyl}(methyl)amino]-2-(hydroxy amino)-2-oxoethyl]phenoxy}-1-pyrrolidinecarboxylate was obtained as a white solid. Electrospray Mass Spec 574.1 (M+H)⁺

Example 190

(2R)-2-[{[4-(2-Butynyloxy)Phenyl]Sulfonyl}
(Methyl)Amino]-N-Hydroxy-2-{4-[(3S)-
Pyrrolidinyloxy]Phenyl}Ethanamide According to the procedure of Example 188, 0.20 g (0.349 mmol) of tert-butyl (3S)-3-{4-[(1R)-1-[{[4-(2-butynyloxy) phenyl]sulfonyl}(methyl)amino]-2-(hydroxy amino)-2-oxoethyl]phenoxy}-1-pyrrolidinecarboxylate (the product of Example 189) was converted into 0.157 g of (2R)-2-[{ [4-(2-butynyloxy)phenyl]-sulfonyl}(methyl)amino]-N-hydroxy-2-{4-[(3S)-pyrrolidinyloxy]phenyl}ethanamide hydrochloride, obtained as a tan glass. Electrospray Mass Spec 474.1 (M+H)⁺

Example 191

Tert-Butyl (2-{4-[1-({[4-(2-Butynyloxy)Phenyl]
Sulfonyl}(Methyl) Amino)-2-(Hydroxyamino)-2-
Oxoethyl) Phenoxyl Ethyl)-(Methyl) Carbamate According to the procedure of Example 182, starting with the t-butyl carbamate of 2-(methylamino)ethanol, tert-butyl (2-{4-[1-({[4-(2-butynyloxy) phenyl] sulfonyl} (methyl) amino)-2-(hydroxyamino)-2-oxoethyl) phenoxy]ethyl)-(methyl) carbamate was obtained. mp 62° C. (d). Electrospray Mass Spec 562.3 (M+H)⁺

Example 192

2-({[4-(2-Butynyloxy) Phenyl] Sulfonyl} (Methyl)
Amino)-N-Hydroxy-2-{4-[2-(Methylamino) Ethoxy]
Phenyl} Acetamide According to the procedure of Example 181, tert-butyl (2-{4-[1-({[4-(2-butynyloxy) phenyl] sulfonyl} (methyl) amino)-2-(hydroxyamino)-2-oxoethyl) phenoxy] ethyl)-(methyl) carbamate from Example 191 was converted into the hydrochloride salt of 2-{[4-(2-butynyloxy) phenyl] sulfonyl} (methyl) amino)-N-hydroxy-2- {4-[2-(methylamino) ethoxy] phenyl} acetamide. mp 165° C.(d). Electrospray Mass Spec 462.4 (M+H)⁺.

Example 193

Ethyl 3-}4-[1-[}[4-(2-Butynyloxy)Phenyl]Sulfonyl}
(Methyl)Amino]-2-(Hydroxyamino)-2-Oxoethyl]
Phenoxy}Propylcarbamate Step 1

Through a solution of 7.0 g (12.8 mmol) of methyl (4-{3-[(tert-butoxycarbonyl)amino]propoxy}phenyl)[{[4-(2-butynyloxy)phenyl]sulfonyl}(methyl)amino]acetate (from Example 187) dissolved in dichloromethane was bubbled hydrogen chloride gas for 1.5 h. The reaction was stopped and let sit at room temperature for 30 minutes. The reaction was then poured into water, neutralized with 1N sodium hydroxide solution to pH~8 and extracted with dichloromethane. The organics were washed with water and brine, dried over sodium sulfate, filtered and concentrated to give 5.41 g of methyl [4-3-(3-aminopropoxy)phenyl][{[4-(2-butynyloxy)phenyl]sulfonyl}methyl)amino]acetate. Electrospray Mass Spec 461.1 (M+H)⁺.

Step 2

To a solution of methyl [4-3-(3-aminopropoxy)phenyl][{ [4-(2-butynyloxy)phenyl]sulfonyl}methyl)amino]acetate (0.5 g, 1.1 mmol) and N,N-diisopropylethyl amine (0.95 mL, 5.4 mmol) in dichloromethane, cooled in an ice bath was dropwise added a dichloromethane (1 ml) solution of ethyl chlorofornate (0.178 ml, 1.1 mmol). The reaction was stirred at 0° C. for 10 minutes and at room temperature for 2 h. The reaction was diluted with dichloromethane, washed with water and brine, dried over sodium sulfate, filtered, and concentrated. The residue was separated using column chromatogaphy on silica gel eluting with dichloromethane:methanol (100:2) to give 0.5 g of methyl [{[4-

(2-butynyloxy)phenyl]sulfonyl}(methyl)amino}(4-{3-[(ethoxycarbonyl)amino]propoxy] phenyl) acetate. Yield 76.3%. Electrospray Mass Spec 533.1 (M+H)$^+$.

Step 3

A mixture of methyl [{[4-(2-butynyloxy)phenyl]sulfonyl}(methyl)amino}(4-{3-[(ethoxycarbonyl)amino]propoxy]phenyl)acetate (0.45 g, 0.85 mmol) and 1N NaOH (4.2 ml, 4.23 mmol) in THF (5 ml) and methanol (5 ml) was stirred at room temperature for 2 h. After removing the solvent, the residue was dissolved in water, neutralized with HCl to pH~5–6 and extracted with dichloromethane. The organic layer was washed with water and brine, dried over sodium sulfate, filtered and concentrated to provide 0.36 g of [{[4-(2-butynyloxy)phenyl]-sulfonyl}(methyl)amino}(4-{3-[(ethoxycarbonyl) amino]propoxy]phenyl)acetic acid as a solid . Yield 81.8%. Electrospray Mass Spec 519.1 (M+H)$^+$.

Step 4

To [{[4- (2-butynyloxy) phenyl] sulfonyl} (methyl) amino} (4-{3-[(ethoxycarbonyl) amino] propoxy] phenyl) acetic acid (0.35 g, 0.67 mmol) and 1-(3-dimethyl aminopropyl) 3-ethyl carbodiimide (0.2 g, 1.01 mmol) in DMF (8 ml), 1-hydroxybenzotriazole (0.13 g, 0.95 mmol) was added and the reaction was stirred at room temperature for 2 h. Hydroxylamine (0.23 ml.of 50% in water, 3.71 mmol) was added and the reaction was stirred overnight. After evaporating the solvent, the residue was extracted with ethyl acetate and water, the organic layer was washed with saturated NaHCO$_3$, water and brine, dried over Na$_2$SO$_4$, and concentrated. The residue was purified with preparative TLC plates (eluting with ethyl acetate:methanol (85:15) to provide 0.1 g of ethyl 3-{4-[1-[{[4-(2-butynyloxy)phenyl]sulfonyl}(methyl)amino]-2-(hydroxyamino)-2-oxoethyl] phenoxy}propylcarbamate as a yellow solid. mp 60–62° C. Electrospray Mass Spec 532 (M+H)$^+$.

Example 194

2-{4-}3-(Acetylamino)Propoxy]Phenyl}-2-[{[4-(2-Butynyloxy)Phenyl]Sulfonyl}(Methyl)Amino]-N-Hydroxyacetamide According to the procedure of Example 193, using acetyl chloride instead of ethyl chloroformate in Step 2, 2-{4-[3-(acetylamino)propoxy]phenyl}-2-[{[4-(2-butynyloxy)phenyl]sulfonyl}(methyl)amino]-N-hydroxyacetamide was obtained. mp 88° C. (d). Electrospray Mass Spec 504 (M+H)$^+$.

Example 195

Butyl 3-{4-[1-[{[4-(2-Butynyloxy)Phenyl]Sulfonyl} (Methyl)Amino]-2-(Hydroxyamino)-2-Oxoethyl] Phenoxy}Propylcarbamate According to the procedure of Example 193, using n-butyl chloroformate instead of ethyl chloroformate in Step 2, butyl 3-{4-[1-[{[4-(2-butynyloxy)phenyl]-sulfonyl}(methyl)amino]-2-(hydroxyamino)-2-oxoethyl]phenoxy}-propylcarbamate was obtained. mp 50–55° C. Electrospray Mass Spec 562 (M+H)$^+$.

Example 196

Benzyl3-{4-[1-[{[4-(2-Butynyloxy)Phenyl]Sulfonyl}(Methyl)Amino]-2-(Hydroxyamino)-2-Oxoethyl]Phenoxy}Propylcarbamate According to the procedure of Example 193, using benzyl chloroformate instead of ethyl chloroformate in Step 2, benzyl 3-{4-[1-[{[4-(2-butynyloxy)phenyl]sulfonyl} (methyl)amino]-2-(hydroxyamino)-2-oxoethyl] phenoxy}propylcarbamate was obtained. mp 48–50° C. Electrospray Mass Spec 596.4 (M+H)$^+$.

Example 197

2-[{[4-(2-Butynyloxy)Phenyl]Sulfonyl}(Methyl) Amino]-N-hydroxy-2-(4-{3-[(Methylsulfonyl) Amino]Propoxy}Phenyl)Acetamide According to the procedure of Example 193, using methanesulfonyl chloride instead of ethyl chloroformate in Step 2, 2-[{[4-(2-butynyloxy)phenyl]sulfonyl}(methyl)amino]-N-hydroxy-2-(4-{3-[(methylsulfonyl)amino]propoxy}phenyl)acetamide was obtained. mp 65–70° C. Electrospray Mass Spec 540.4 (M+H)$^+$.

Example 198

2-(4-{-3-[(Anilinocarbonyl)Amino] Propoxy}Phenyl)-2-[{[4-(2-Butynyloxy)Phenyl] Sulfonyl}(Methyl)Amino]-N-Hydroxyacetamide According to the procedure of Example 193, using phenyl isocyanate instead of ethyl chloroformate in Step 2, 2-(4-{3-[(anilinocarbonyl)amino]propoxy}phenyl)-2-[{[4-(2-butynyloxy)phenyl]sulfonyl}(methyl)amino]-N-hydroxyacetamide was obtained. mp 135° C. (d). Electrospray Mass Spec 581 (M+H)$^+$.

Example 199

Tert-Butyl 2-{4-[(1R)-1-({[4-(2-Butynyloxy)Phenyl] Sulfonyl}Amino)-2-(Hydroxyamino)-2-Oxoethyl] Phenoxy}Ethylcarbamate Step 1

To a 0° solution of 2.50 g (11.48 mmol) of amino-(4-hydroxy-phenyl)-acetic acid methyl ester (from Example 178) in 125 mL of dichloromethane was added 10 mL of N,N-diisopropylethylamine followed by 2.97 g (11.48 mmol) of 9-fluorenylmethyl chlorformate and the resulting mixture was stirred at 0° for 2 h and room temperature for 2 h. The reaction mixture was then concentrated and the residue was diluted with ethyl acetate and water. The organics were washed with water, dried over magnesium sulfate, filtered and concentrated in vacuo. The residue was chromatographed on silica gel eluting with ethyl acetate/hexanes (1:3) to provide methyl(2R)-{[(9H-fluoren-9-ylmethoxy) carbonyl]amino}(4-hydroxyphenyl)ethanoate as a white solid. Electrospray Mass Spec 404.1 (M+H)$^+$.

Step 2

To a solution of 0.465 g (1.77 mmol) of triphenylphosphine in 10 mL of THF was added 0.286 g (1.77 mmol) of tert-butyl N-(2-hydroxyethyl)-carbamate followed by 0.476 g (1.18 mmol) of methyl (2R)-{[(9H-fluoren-9-ylmethoxy) carbonyl]amino}(4-hydroxyphenyl)ethanoate and 0.279 mL (1.77 mmol) of diethyl azodicarboxylate. The reaction was stirred overnight at room temperature and then concentrated in vacuo. The residue was chromatographed on silica gel eluting with ethyl acetate/hexanes (1:3) to give 0.383 g of methyl (2R)-(4-{2-[(tert-butoxycarbonyl)amino] ethoxy}phenyl){[(9H-fluoren-9-ylmethoxy)carbonyl] amino}ethanoate as a white solid. Electrospray Mass Spec 547.2 (M+)$^+$

125

Step 3

A solution of 1.695 g (3.10 mmol) of methyl (2R)-(4-{2-[(tert-butoxycarbonyl)amino]ethoxy}phenyl){[(9H-fluoren-9-ylmethoxy)carbonyl]amino}ethanoate in 10 mL of diethylamine was stirred at room temperature for 2 h and then concentrated in vacuo. The residue was chromatographed on silica gel eluting with a gradient starting with ethyl acetate/hexanes (1:2) and ending with chloroform/methanol (9:1) to provide 0.717 g of methyl (2R)-amino(4-{2-[(tert-butoxycarbonyl)amino]ethoxy}phenyl)ethanoate as a colorless oil. Electrospray Mass Spec 325.2 (M+H)$^+$

Step 4

To a solution of 0.682 g (2.10 mmol) of methyl (2R)-amino(4-{2-[(tert-butoxycarbonyl)amino]ethoxy}phenyl)ethanoate dissolved in 10 mL of chloroform and 2.2 mL of pyridine was added 0.566 g (2.315 mmol) of 4-but-2-ynyloxy-benzenesulfonyl chloride. The reaction was stirred at room temperature for 15 h and then diluted with ether. The organics were washed with water, 5% HCl solution and brine, dried over magnesium sulfate, filtered and concentrated in vacuo to provide 0.691 g of methyl (2R)-(4-{2-[(tert-butoxycarbonyl)amino]ethoxy}phenyl)({[4-(2-butynyloxy)phenyl]sulfonyl}amino)ethanoate as a white foam Electrospray Mass Spec 533.1 (M+H)$^+$

Step 5

According to the procedure of Example 11, 0.388 g (0.729 mmol) of methyl(2R)-(4-{2-[(tert-butoxycarbonyl)amino]ethoxy}phenyl)({[4-(2-butynyloxy)phenyl]sulfonyl}amino)ethanoate provided 0.378 g of (2R)-(4-{2-[(tert-butoxycarbonyl)amino]ethoxy}phenyl)({[4-(2-butynyloxy)phenyl]sulfonyl}amino)ethanoic acid as a white foam. Electrospray Mass Spec 519.4 (M+H)$^+$

Step 6

According to the procedure of Example 25, 0.159 g of (2R)(4-{2-[(tert-butoxycarbonyl)amino]ethoxy}phenyl)({[4-(2-butynyloxy)phenyl]sulfonyl}amino)ethanoic acid provided 0.127 g of tert-butyl 2-{4-[(1R)-1-({[4-(2-butynyloxy)phenyl]sulfonyl}amino)-2-(hydroxyamino)-2-oxoethyl]phenoxy}ethylcarbamate as a pale yellow glass. Electrospray Mass Spec 534.3 (M+H)$^+$

Example 200

(2R)-2-[4-(2-Aminoethoxy)Phenyl]-2-({[4-(2-Butynyloxy)Phenyl]Sulfonyl}Amino)-N-Hydroxyethanamide Through a solution of 0.354 g (0.664 mmol) of the product of Example 199, tert-butyl 2-{4-[(1R)-1-({[4-(2-butynyloxy)phenyl]sulfonyl}amino)-2-(hydroxyamino)-2-oxoethyl]phenoxy}ethylcarbamate, in 10 mL of dichloromethane was bubbled hydrogen chloride gas for 10 minutes. The reaction was stopped and let sit at room temperature for 30 minutes. The reaction was then diluted with 15 mL of ether and the resulting white precipitate was collected by filtration and dried in vacuo to give 0.283 g of (2R)-2-[4-(2-Aminoethoxy)phenyl]-2-({[4-(2-butynyloxy)phenyl]sulfonyl}amino)-N-hydroxyethanamide as a white solid. Electrospray Mass Spec 434.3 (M+H)$^+$

126

Example 201

(2R)-2-{4-[2-(Acetylamino)Ethoxy]Phenyl}-2-({[4-(2-Butynyloxy)Phenyl]Sulfonyl}Amino)-N-Hydroxyethanamide

Step 1

To a solution of 0.300 g (0.564 mmol) of methyl (2R)-(4-{2-[(tert-butoxycarbonyl)amino]ethoxy}phenyl)({[4-(2-butynyloxy)phenyl]sulfonyl}amino)ethanoate (from Example 199) in 1.5 mL of dichloromethane was added 1.5 mL of trifluoroacetic acid and the resulting mixture was stirred for 2 h at room temperature and then concentrated in vacuo. The residue was diluted with ethyl acetate and the organics were washed with saturated sodium bicarbonate solution, dried over sodium sulfate, filtered and concentrated to provide 0.244 g of methyl(2R)-[4-(2-aminoethoxy)phenyl]({[$^4$-(2-butynyloxy)phenyl]sulfonyl}amino)ethanoate pure enough for use in the next step. Electrospray Mass Spec 433.3 (M+H)$^+$

Step 2

A solution of 0.219 g (0.507 mmol) of methyl(2R)-[4-(2-aminoethoxy)phenyl]({[4(2-butynyloxy)phenyl]sulfonyl}amino)ethanoate in 2.5 mL of acetic anhydride and 0.25 mL of pyridine was stirred at room temperature for 15 h and then concentrated in vacuo. The residue was chromatographed on silica gel eluting with ethyl acetate/hexanes (1:1) to provide 0.213 g of methyl (2R)-{4-[2-(acetylamino)ethoxy]phenyl}({[4-(2-butynyloxy)phenyl]sulfonyl}amino)-ethanoate as a white foam. Electrospray Mass Spec 475.3 (M+H)$^+$

Step 3

According to the procedure of Example 11, 0.192 g (0.405 mmol) of methyl (2R)-{4-[2-(acetylamino)ethoxy]phenyl}({[4-(2-butynyloxy)phenyl]sulfonyl}amino)ethanoate provided 0.165 g of (2R)-{4-[2-acetylamino)ethoxy]phenyl}({[4-(2-butynyloxy)phenyl]sulfonyl}amino)ethanoic acid as a white solid. Electrospray Mass Spec 461.3 (M+H)$^+$

Step 4

According to the procedure of Example 25, 0.142 g of (2R)-(4-{2-[(tert-butoxycarbonyl)amino]ethoxy}phenyl)({[4-2-butynyloxy)phenyl]sulfonyl}amino)ethanoic acid provided 0.099 g of (2R)-2-{4-[2-(Acetylamino)ethoxy]phenyl}-2-({[4-(2-butynyloxy)phenyl]sulfonyl}amino)-N-hydroxyethanamide as a white solid. Electrospray Mass Spec 498.4 (M+Na)$^+$

Example 202

Tert-Butyl 4-(2-{4-[1-({[4-(2-Butynyloxy)Phenyl]Sulfonyl}Amino)-2-(Hydroxyamino)-2-Oxoethyl)Phenoxy]Ethyl)-1-Piperazinecarboxylate According to the procedure of Example 199, using tert-butyl N-(2-hydroxyethyl)piperazine carbamate as the alcohol in Step 2, tert-butyl 4-(2-{4-[1-({[4-(2-butynyloxy)phenyl]sulfonyl}amino)-2-(hydroxyamino)-2-oxoethyl)phenoxy]ethyl)-1-piperazinecarboxylate was obtained as a yellow solid mp 92–95° C. Electrospray Mass Spec 603.1 (M+H)$^+$.

Example 203

Tert-Butyl 4-(2-{4-[1-({[4-(2-Butynyloxy)Phenyl]Sulfonyl}Amino)-2-(Hydroxyamino)-2-Oxoethyl)Phenoxy]Ethyl)-(Methyl)Carbamate According to the procedure of Example 199, using the t-butyl carbamate of 2-(methylamino)ethanol as the alcohol in Step 2, tert-butyl 4-(2-{4-[1-({[4-(2-butynyloxy)phenyl]sulfonyl}amino)-2-(hydroxyamino)-2-oxoethyl]phenoxy]ethyl)-(methyl)carbamate was obtained. mp 90–92° C. Electrospray Mass Spec 548.5 (M+H)+.

Example 204

2-{[4-(2-Butynyloxy)Phenyl]Sulfonyl}Amino)-N-Hydroxy-2-{4-[2-(Methylamino)Ethoxy]Phenyl}) Acetamide According to the procedure of Example 181, the product of Example 203 provided 2- {[4-(2-butnyloxy)phenyl]sulfonyl}amino)-N-hydroxy-2-(4-[2-(methylamino)ethoxy]phenyl})acetamide. mp 105–108° C. Electrospray Mass Spec 448.3 (M+H)+.

Example 205

2-({[4-(2-Butynyloxy)Phenyl]Sulfonyl}Amino)-N-Hydroxy-2-{4-2-(1-Pyrrolidinyl)Ethoxy] Phenyl}Acetamide Step 1

To a 0° solution of 16.58 g (0.076 mol) dissolved in 100 mL of dichloromethane was added 22.11 g (0.101 mol) of di-tert-butyl dicarbonate followed by 25 mL (0.179 mol) of triethylamine. The reaction was stirred at 0° for 1.5 h and then at room temperature for 2 h. The reaction was then washed with water and brine, dried over sodium sulfate, filtered and concentrated. The residue was chromatographed on silica gel eluting with hexanes/ethyl acetate (1:1) to provide methyl [(tert-butoxycarbonyl)amino]4hydroxyphenyl}acetate as a white solid.

Step 2

According to the procedure of Step 2 in Example 199, Mitsunobu reaction of 2.25 g (8.0 mmol) of methyl [(tert-butoxycarbonyl)amino]4-hydroxyphenyl}acetate and 1.41 mL (12.0 mmol) of 1-(2-hydroxyethyl)pyrrolidine provided methyl [(tert-butoxycarbonyl)amino]{4-[2-(1-pyrrolidinyl)ethoxy]phenyl}acetate after column chromatography on silica gel Yield 65.2 Electrospray Mass Spec 379.2 (M+H)+.

Step 3

To a solution of methyl [(tert-butoxycarbonyl)amino]{4-[2-(1-pyrrolidinyl)ethoxy]phenyl}acetate was dissolved in dichloromethane, hydrogen chloride gas was bubbled in for 5 minutes. The reaction was then stirred at room temperature for 0.5 h. The solvent was removed to provide 1.80 g of methyl amino{4-[2-(1-pyrrolidinyl)ethoxy]phenyl}acetate dihydrochloride as a light pink solid Yield ~100%. mp 80° C. (d). Electrospray Mass Spec 279.2 (M+H)+.

Step 4

To a 0° solution of methyl amino{4-[2-(1-pyrrolidinyl)ethoxy]phenyl}acetate dihydrochloride (1.67 g; 4.55 mmol) in dichloromethane (10 mL) was added 4but-2-ynyloxybenzenesufonyl chloride followed by triethyl amine was dropped in. The mixture was stirred at room temperature overnight and then diluted with dichloromethane. The organic layer was washed with water and brine, dried over sodium sulfate, filtered and concentrated. The residue was purified using column chromatography on silica gel eluting with ethyl acetate to obtain 2.52 g of methyl ({[4-(2-butynyloxy)phenyl]sulfonyl}amino){4-[2-(1-pyrrolidinyl) ethoxy]phenyl}acetate as an oil. Yield 92.6%. Electrospray Mass Spec 487.1 (M+H)+.

Step 5

A mixture of methyl ({[4-(2-butynyloxy)phenyl]sulfonyl}amino){4-[2-(1-pyrrolidinyl)ethoxy]phenyl}acetate (2.52 g, 5.19 mmol) and 5N NaOH (5.18 mL) in THF (32 mL) and methanol (32 mL) was stirred at room temperature for 2 h. After removing the solvent, the residue was dissolved in water and neutralized with HCl to pH~6. The precipitated solid was filtered to provide 1.61 g of ({[4-(2-butynyloxy)phenyl]sulfonyl}amino){4-[2-(1-pyrrolidinyl)ethoxy]phenyl}acetic acid as a white solid. Yield 66%. mp 245–247° C. Electrospray Mass Spec 473.2 (M+H)+.

Step 6

To a 0° solution of ({[4-(2-butynyloxy)phenyl]sulfonyl}amino){(4-[2-(1-pyrrolidinyl)ethoxy]phenyl}acetic acid (1.58 g, 3.35 mmol) and DMF (0.52 ml, 6.69 mmol) in dichloromethane (29 ml) was added oxalyl chloride (3.35 ml of 2M in $CH_2Cl_2$; 6.69 mmol). The reaction mixture was stirred at 0° C. for 10 minutes and at room temperature for 2 h, then cooled again. A THF (2 ml) solution of triethylamine (1.87 ml 13.38 mmol) and hydroxylamine (2.05 mL of 50% hydroxylamine in water, 33.5 mmol) was added in one portion. The reaction was stirred at room temperature overnight. After removing the solvent, the oily residue was extracted with ethyl acetate and water. The organic layer was washed with water and brine, dried over sodium sulfate, filtered and evaporated. Preparative TLC chromatography eluting with dichloromethane:methanol (8:2) provided 0.33 g of 2-({[4-(2-butynyloxy)phenyl]sulfonyl}amino)-N-hydroxy-2-{4-[2-(1-pyrrolidinyl)ethoxy]phenyl}acetamide. mp 70° C. This compound (0.28 g, 0.57 mmol) was dissolved in dichloromethane (3 ml) and methanol (2 ml) cooled in ice bath. Then 1M hydrogen chloride in ethyl ether (0.86 ml, 0.86 mmol) was dropped in. The mixture was stirred at 0° C. for 10 minutes and at room temperature for 1.5 h, and then concentrated to obtain 0.27 g of the hydrochloride salt. mp 68–70° C. Electrospray Mass Spec 488.1 (M+H)+.

Example 206

2-({[4-(2-Butynyloxy)Phenyl]Sulfonyl}Amino)-N-Hydroxy-2-{4-[2-(4-Morpholinyl)Ethoxy] Phenyl}Acetamide According to the procedure of Example 205, using 4-(2-hydroxyethyl)morpholine as the alcohol in Step 2, provided 2-({[4-(2-butynyloxy)phenyl]sulfonyl}amino)-N-hydroxy-2-{4-[2-(4-morpholinyl)ethoxy]phenyl}acetamide. mp 80–86° C. Electrospray Mass Spec 504.1(M+H)+. Hydrochloride salt mp 72° C. (d). Electrospray Mass Spec 504.1 (M+H)+.

Example 207

2-({[4-(2-Butynyloxy)Phenyl]Sulfonyl}Amino){4-[2-(Dimethylamino)Ethoxy]Phenyl}-N-Hydroxyacetamide According to the procedure of Example 205, using N,N-dimethylethanloamine as the alcohol in Step 2, provided 2-({[4-(2-butynyloxy)phenyl]sulfonyl}amino){4-[2--(dimethylamino)ethoxy]phenyl}-N-hydroxyacetamide hydrochloride. Electrospray Mass Spec 462.4 (M+H)+.

Example 208

2-({[4-(2-Butynyloxy)Phenyl]Sulfonyl}Amino)-N-Hydroxy-2-{4-[2-(4-methyl-1,3-Thiazol-5-yl)Ethoxy]Phenyl}Acetamide According to the procedure of Example 205, using 4-methyl-5-thiazoleethanol as the alcohol in Step 2, provided 2-({[4-(2-butynyloxy)phenyl]sulfonyl}amino)-N-hydroxy-2-{4-[2-(4-methyl-1,3-thiazol-5-yl)ethoxy]phenyl}acetamide as a white solid. High Resolution Mass Spec: m/z 516.12504 (M+H)+, calcd for $C_{24}H_{26}N_3O_6S_2$ 516.12576.

Example 209

2-({[4-(2-Butynyloxy)Phenyl]Sulfonyl}Amino)-N-Hydroxy-2-(4-{2-[2-(2-Methoxyethoxy)Ethoxy]Ethoxy}Phenyl)Acetamide According to the procedure of Example 205, using tri(ethylene glycol)monomethylether as the alcohol in Step 2, provided 2-({[4-(2-butynyloxy)phenyl]sulfonyl}amino)-N-hydroxy-2-(4-{2-[2-(2-thoxyethoxy)methoxy]ethoxy}-phenyl)acetamide as a yellow oil. High Resolution Mass Spec: m/z 537.1903 (M+H)+, calcd for $C_{25}H_{33}N_2O_9S$ 537.19013.

Example 210

2-({[4-(2-Butynyloxy)Phenyl]Sulfonyl}Amino)-N-Hydroxy-2-{4-[2-(2-Methoxyethoxy)Ethoxy]Phenyl}Acetamide According to the procedure of Example 205, using di(ethylene glycol)monomethylether as the alcohol in Step 2, provided 2-({[4-(2-butynyloxy)phenyl]sulfonyl}amino)-N-hydroxy-2-{4-[2-(2-methoxyethoxy)ethoxy]phenyl}acetamide as a yellow oil. High Resolution Mass Spec: m/z 491.15081 (M−H)−, calcd for $C_{23}H_{27}N_2O_8S$ 491.14936.

Example 211

2-[{[4-(2-Butynyloxy)Phenyl]Sulfonyl}(Methyl)Amino]-N-Hydroxy-2-Phenylacetamide

Step 1

Solid 4-(2-butynyloxy)phenyl]sulfonyl chloride was added to excess 40% aqueous methylamine, and the resultant solution was stirred at room temperature for two hours. Evaporation under reduced pressure, followed by recrystallization from methanol gave N-methyl-[4-(2-butynyloxy)phenyl]sulfonamide] as colorless crystals, mp 78–80° C.

Step 2

A mixture of 2.39 g. (10 mmol)of the above sulfonamide, 2.29 g (10 mmol) of methyl alpha-bromophenylacetate, and 2.0 g of powdered potassium carbonate in 10 ml of DMF was stirred at room temperature for 18 hours. The mixture was combined with 100 ml of water, and the resultant crystals were collected by filtration to give methyl 2-[{4-(2-butynyloxy)phenyl]sulfonyl}(methyl)amino]-2-phenylacetate as colorless crystals: NMR (CDCl₃) δ 1.869 (t, 3H), 2.744 (s,3H), 3.605 (s, 3H), 4.696–4.736 (m,2H), 5.862 (s, 1H), 7.062 (d,2H), 7.199–7.378 (m, 5H), 7.781 (d,2H).

Step 3

A solution of 1.50 g of methyl 2-[{[4-(2-butynyloxy)phenyl]-sulfonyl}(methyl)amino]-2-phenylacetate and 1.50 g of KOH in a methanol/water/THF mixture was stirred at room temperature for 18 hours. The solution was then evaporated, the residue was dissolved in water and then acidified with 2N hydrochloric acid, and the precipitate was collected and dried to give 1.07 g of 2-[{[4-(2-butynyloxy)-phenyl]sulfonyl}(methyl)amino]-2-phenylacetic acid as colorless crystals, Calc'd for $C_{19}H_{19}NO_5S$: C, 61.11; H, 5.13; N, 3.75. Found: C, 60.66; H, 5.16; N, 3.53.

Step 4

The above acid (500 mg, 1.3 mmol) was dissolved in 5 ml dichloromethane and 1 ml DMF, and this was cooled to 0° C. and a solution of 3 ml of oxalyl chloride in 5 ml dichloromethane was added slowly, and this was stirred for 45 min. at 0° C.-room temperature. This mixture was evaporated under reduced pressure and the residue was dissolved in 5 ml of dichloromethane, and this solution was added at room temperature to a solution prepared at 0° C. from 3.0 g of hydroxylamine hydrochloride in 10 ml of DMF, 15 ml of triethylamine, and 10 ml of acetonitrile. This mixture was stirred at room temperature for 18 hours, solvent was evaporated, and the residue was combined with water. Extraction of this mixture with dichloromethane, drying over sodium sulfate, and evaporation of the solvent gave 2-[{[4-(2-butynyloxy)phenyl]sulfonyl}(methyl)amino]-N-hydroxy-2-phenylacetamide as colorless crystals, Electrospray Mass Spec 389.3 (M+H)+

Example 212

2-[{[4-(2-Butynyloxy)Phenyl]Sulfonyl}(Methyl)Amino]-2-(4Chlorophenyl)-N-Hydroxyacetamide In a similar manner as described in Example 211,a mixture of 2.39 g N-methyl-[4-(2-butynyloxy)phenyl]sulfonamide], methyl alpha-bromo(4-chlorophenyl)acetate, and powdered potassium carbonate in DMF was stirred at room temperature for 18 hours. The mixture was combined with water and the precipitate was collected and purified by chromatography on silica gel using hexane-ethyl acetate, 4:1 to give methyl 2-[{[4-(2-butynyloxy)phenyl]sulfonyl}(methyl)amino]-2-(4-chlorophenyl)acetate as a yellow oil which was then used in the subsequent step without further purification.

This ester was reacted with excess methanolic lithium hydroxide at room temperature, followed by evaporation of the methanol. The residue was dissolved in water and acidified with 2N hydrochloric acid to give 2-[{[4-(2-butynyloxy)phenyl]sulfonyl}(methyl)amino]-2-(4-chlorophenyl)acetic acid as colorless crystals, mp 170–172° C., Electrospray Mass Spec 406.4 (M−H)−

Reaction of this acid in a procedure similar to that of Example 211, gave 2-[{[4-(2-butynyloxy)- phenyl]sulfonyl}

(methyl)amino]-2-(4-chlorophenyl)-N-hydroxyacetamide as colorless crystals, Electrospray Mass Spec 423.1 (M+H)+

Example 213

2-[{[4-(2-Butynyloxy)Phenyl]Sulfonyl}(Methyl) Amino]-5-[(4-Chlorophenyl)Sulfanyl]-N-Hydroxypentanamide Step 1

A solution of 7.17 g (30 mmol) N-methyl-[4-(2-butynyloxy)-phenyl]sulfonamide] in 25 ml of DMF was cooled to 0° C. and 30 ml of 1M sodium hexamethyldisilazide (30 mmol) was slowly added and this mixture was stirred for 15 min and then added to a solution of 6.89 g (30 mmol) of methyl 2-bromo-5-chloropentanoate in 25 ml of DMF and was stirred at room temperature for 18 hours. The mixture was combined with water and the precipitate was collected and purified by chromatography on silica gel using hexane-ethyl acetate, 4:1 to give methyl 2-[{[4-(2-butynyloxy)phenyl]sulfonyl}(methyl)amino]-5-chloropentanoate Electrospray Mass Spec 410.2 (M+Na)+

Step 2

A solution of 4.80 g of methyl 2-[{[4-(2-butynyloxy) phenyl]-sulfonyl}(methyl)amino]-5-chloropentanoate of Step 1 and 15 g of sodium iodide in 25 ml of acetone was stirred at room temperature for 3 days. Solvent was removed under reduced pressure, and the residue was washed with water. The product was dried to give methyl 2-[{[4-(2-butynyloxy)phenyl]-sulfonyl}(methyl)amino]-5-iodopentanoate as a pale yellow solid, Electrospray Mass Spec 480.2 (M+H)+

Step 3

A solution of 0.958 g (2.0 mmol) of methyl 2-[{[4-(2-butynyloxy)phenyl]sulfonyl}(methyl)amino]-5-iodopentanoate, 0.35 g (2.4 mmol) of 4-chlorobenzenethiol, and 0.323 g of diisopropylethylamine in 50 ml of isopropyl alcohol was stirred at room temperature for 18 hours. Evaporation of solvent gave 0.8 g of methyl 2-[{[4-(2-butynyloxy)-phenyl]sulfonyl}-(methyl)amino]-5-[(4-chlorophenyl)sulfanyl]-pentanoate as colorless crystals, mp 88–89° C., Electrospray Mass Spec 496.1 (M+H)+

Step 4

This ester (0.496 g)was hydrolyzed with methanolic LiOH, followed by acidification to give 2-[{[4-(2-butynyloxy)-phenyl]sulfonyl}-(methyl)amino]-5-[(4-chlorophenyl)sulfanyl]-N-methylnorvaline (0.421 g) as a colorless powder, mp 143–145° C., ESI MS m/z 480.0 (M–H) calcd. for $C_{22}H_{24}ClNO_5S_2$ 482.02. From 0.362 g of this acid, and using the procedure of Example 211 there was obtained 0.30 g of 2-[{[4-(2-butynyloxy)phenyl]sulfonyl} (methyl)amino]-5-[(4-chlorophenyl)sulfanyl]-N-hydroxypentanamide as colorless crystals, mp 144–145.5° C., Electrospray Mass Spec 497.1 (M+H)+

Example 214

1-(4-But-2-Ynyloxy-Benzenesulfonyl)-Piperazine-2-Carboxylic Acidhydroxyamide

To a solution of 0.147 g (0.325 mmol) of the product of Example 58, 4-(4-but-2-ynyloxy-benzenesulfonyl)-3-hydroxycarbamoyl-piperazine-1-carboxylic acid tert-butyl ester, in 3.0 mL of dichloromethane was added 0.3 mL of trifluoroacetic acid and the reaction was stirred at room temperature for 1 h. The reaction was then concentrated in vacuo and the residue was diluted with dichloromethane. The organics were washed with saturated sodium bicarbonate solution, dried over sodium sulfate, filtered and concentrated in vacuo to provide 0.053 g of 1-(4-but-2-ynyloxy-benzenesulfonyl)-piperazine-2-carboxylic acid hydroxyamide as a tan solid. Electrospray Mass Spec 354.2 (M+H)+

Example 215

1-(4-But-2-Ynyloxy-Benzenesulfonyl)-4-(Morpholine-4-Carbonyl)-Piperazine-2-Carboxylic Acid Hydroxyamide Step 1

To a solution of ethyl 2-piperazinecarboxylate (0.71 g, 4.5 mmol) in toluene (8.4 mL) was added triethylamine (0.67 mL, 4.82 mmol). To this was added dropwise a solution of 4-morpholine carbonyl chloride (0.67 g, 4.51 mmol) in toluene (8.4 mL). The reaction was heated at reflux overnight and then cooled to 0° C. and filtered. The filtrate was concentrated in vacuo and purified via column chromatography on silica gel eluting with chloroform/methanol (15/1) to provide 478 mg (39%) of the acylated product, ethyl 4-(4-morpholinylcarbonyl)-2-piperazinecarboxylate, as a gold oil. Electrospray Mass Spec: 272.3 (M+H)+.

Step 2

The ethyl 4-(4-morpholinylcarbonyl)-2-piperazinecarboxylate (0.41 g, 1.55 mmol) was dissolved in pyridine (1.44 mL). To this solution was added a solution of 4-but-2-ynyloxy-benzenesulfonyl chloride (0.38 g, 1.55 mmol) in pyridine (1 mL). The reaction was stirred overnight and then poured into water. The mixture was extracted three times with chloroform. The organics were combined, washed with 10% HCl, twice with water, then brine and dried over $Na_2SO_4$. The solution was filtered and concentrated in vacuo to provide 0.6 g (81%) of 1-(4but-2-ynyloxy-benzenesulfonyl)-4-(morpholine4-carbonyl)- piperazine-2-carboxylic acid ethyl ester as a gold oil. Electrospray Mass Spec 480.2 (M+H)+.

Step 3

The 1-(4-but-2-ynyloxy-benzenesulfonyl)-4-(morpholine-4-carbonyl)-piperazine-2-carboxylic acid ethyl ester (0.56 g, 1.18 mmol) was dissolved in THF/MeOH/H2O (3 mL each) and treated with lithium hydroxide monohydrate (0.099 g, 2.3 mmol). The reaction was heated at reflux overnight and then concentrated and acidified to pH 4 with acetic acid. The solution was extracted with methylene chloride and then washed with water, brine, dried over $Na_2SO_4$, filtered and concentrated in vacuo to provide 0.298 g (53%) of 1-(4-but-2-ynyloxy-benzenesulfonyl)-4-(morpholine-4-carbonyl)- piperazine-2-carboxylic acid as a yellow powder. Electrospray Mass Spec 452.2 (M+H)+.

Step 4

To a solution of 2M oxalyl chloride in $CH_2Cl_2$ (0.55 mL, 1.1 mmol) at 0° C. was added DMF (0.085 mL, 1.1 mmol) and the mixture was stirred at 0° C. for 15 min, then let warm to room temperature and stirred for an additional 1 h. A solution of the 1-(4-but-2-ynyloxy-benzenesulfonyl)-4-(morpholine-4-carbonyl)-piperazine-2-carboxylic acid, (0.25 g, 0.554 mmol) in 2.54 mL of DMF, was then added to the reaction mixture and the reaction was stirred for 2 h at room temperature.

In a separate flask, triethylamine (1.16 mL, 8.31 mmol) was added to a 0° C. mixture of hydroxylamine hydrochloride (0.38 g, 5.54 mmol) 5.23 mL of THF and 1.5 mL of water. After this mixture had stirred for 15 min at 0° C., the acid chloride solution was added to it in one portion and the resulting solution was allowed to warm to room temperature with stirring overnight. The reaction mixture next was diluted with $CH_2Cl_2$ and washed with water and saturated sodium bicarbonate solution. The organic layer was dried over $Na_2SO_4$, filtered and concentrated in vacuo. The crude residue was triturated with ether to provide 0.161 g (62%) of the 1-(4-but-2-ynyloxy-benzenesulfonyl)-4-(morpholine-carbonyl)-piperazine-2-carboxylic acid hydroxyamide as a beige powder. Electrospray Mass Spec 466.9 $(M+H)^+$.

Example 216

4-(4-But-2-Ynyloxy-Benzenesulfonyl)-Piperazine-1, 3-Dicarboxylic Acid 1-Diethylamide 3-Hydroxyamide In the same manner as described in Example 215, using diethylcarbamoyl chloride in Step 1, the desired hydroxamic acid, 4-(4-but-2-ynyloxy-benzenesulfonyl)-piperazine-1,3-dicarboxylic acid 1-diethylamide 3-hydroxyamide, was obtained as a gold oil. Electrospray Mass Spec 453.3 $(M+H)^+$.

Example 217

1-(4-But-2-Ynyloxy-Benzenesulfonyl)-4-(Pyrrolidine-1-Carbonyl)-Piperazine-2-Carboxylic Acid Hydroxyamide In the same manner as described in Example 215, using 1-pyrrolidinecarbonyl chloride in Step 1, the desired hydroxamic acid, 1-4-but-2-ynyloxy-benzenesulfonyl)-4-(pyrrolidine-1-carbonyl)-piperazine-2-carboxylic acid hydroxyamide, was obtained as a white powder. Electrospray Mass Spec 451.4 $(M+H)^+$.

Example 218

4-(4-But-2-Ynyloxy-Benzenesulfonyl)-Piperazine-1, 3-Dicarboxylic Acid 1-Diisopropylamide 3-Hydroxyamide In the same manner as described in Example 215, using diisopropylcarbamoyl chloride in Step 1, the desired hydroxamic acid, 4-(4-but-2-ynyloxy-benzenesulfonyl)-piperazine-1,3-dicarboxylic acid 1-diisopropylamide 3-hydroxyamide, was obtained as a white powder. Electrospray Mass Spec 481.5 $(M+H)^+$.

Example 219

Benzyl 4-{[4-(2-Butynyloxy)Phenyl]Sulfonyl}-3-[(Hydroxyamino)Carbonyl]-1-Piperazinecarboxylate In the same manner as described in Example 215, using benzyl chloroformate in Step 1, the desired hydroxamic acid, benzyl 4-{[4-(2-butynyloxy)phenyl]sulfonyl}-3-[(hydroxyamino)carbonyl]-1-nyloxy)phenyl]sulfonyl}-3-[(hydroxyamino)carbonyl]-1-piperazinecarboxylate, was obtained as a white powder. Electrospray Mass Spec 488.2 $(M+H)^+$.

Example 220

4-(4-But-2-Ynyloxy-Benzenesulfonyl)-Piperazine-1, 3-Dicarboxylic Acid 3-Hydroxyamide 1-(Methyl-Phenyl-Amide)

Step 1

The product of Example 57, 4-(4-but-2-ynyloxy-benzenesulfonyl)-piperazine-1,3-dicarboxylic acid 1-tert-butyl ester 3-ethyl ester (3.8 g, 8.1 mmol), was dissolved in dichloromethane (3 mL). To this solution was added trifluoroacetic acid (3 mL) and the reaction was allowed to stir overnight. The reaction was then concentrated in vacuo and the residue triturated with dichloromethane to provide 2.64 g (88%) of 1-(4-but-2-ynyloxy-benzenesulfonyl)-piperazine-2-carboxylic acid ethyl ester. Electrospray Mass Spec 367.3$(M+H)^+$.

Step 2

In the same manner as described in Step 1 of Example 215, the 1-(4but-2-ynyloxy-benzenesulfonyl)-piperazine-2-carboxylic acid ethyl ester (1.0 g, 2.7 mmol) was treated with N-methyl-N-phenylcarbamoyl chloride to provide 1.33 g (98%) of ethyl 1-{[4-(2-butynyloxy)phenyl]sulfonyl}-4-[(methylanilino)carbonyl]-2-piperazine-carboxylate as a brown oil. Electrospray Mass Spec 500.2 $(M+H)^+$.

Step 3

In the same manner as described in Step 3 of Example 215, the ethyl 1-{[4-(2-butynyloxy)phenyl]sulfonyl}-4-[(methylanilino)carbonyl]-2-piperazinecarboxylate (1.28 g, 2.57 mmol) provided 0.84 g (69%) of the 1-{[4-(2-butynyloxy)phenyl]sulfonyl}-4-[(methylanilino)carbonyl]-2-yl]-2-piperazinecarboxylic acid as a beige powder. Electrospray Mass Spec 472.2 $(M+H)^+$.

Step 4

In the same manner as described in Step 4 of Example 215, the 1-{[4-(2-butynyloxy)phenyl]sulfonyl}-4-[(methylanilino)carbonyl]-2-yl]-2-piperazinecarboxylic acid (0.74 g, 1.57 mmol) provided 0.45 g (59%) of 4-(4-but-2-ynyloxy-benzenesulfonyl)-piperazine-1,3-dicarboxylic acid 3-hydroxyamide 1-(methyl-phenyl-amide) as a beige powder. Electrospray Mass Spec 487.1 $(M+H)^+$.

Example 221

4-{[4-(2-Butynyloxy)Phenyl]Sulfonyl}-N-3-Hydroxy-N-1-(4-Methoxyphenyl)-1,3-Piperazinedicarboxamide Step 1

To a solution of p-anisidine (0.5 g, 4.06 mmol) in dichloromethane (21 mL) was added pyridine (0.36 mL, 4.46 mmol) followed by 4-nitrophenylchloroformate (0.9 g, 4.46 mmol). The reaction was stirred for 72 hours and then diluted with dichloromethane, washed with water, brine, dried over $MgSO_4$ to provide 1.2 g (100%) of the desired carbamate as a solid.

To a solution of the carbamate (0.5 g, 1.75 mmol) in chloroform (41 mL) was added triethylamine (0.32 mL, 2.2 mmol) followed by trimethylsilyl chloride (0.24 mL, 1.9 mmol). The reaction was stirred for five hours at which time 1-(4-but-2-ynyloxy-benzenesulfonyl)-piperazine-2-carboxylic acid ethyl ester from Step 1, Example 220, (0.6 g, 1.6 mmol) was added. The reaction was stirred overnight and then diluted with chloroform, washed with water, brine, dried over $Na_2SO_4$, filtered, concentrated in vacuo and purified via column chromatography on silica gel eluting with dichloromethane:methanol (90:10) to provide 0.44 g (48%) of ethyl 1-{[4-(2-butynyloxy)phenyl]sulfonyl}-4-[(4-methoxyanilino)carbonyl]-2- piperazinecarboxylate as a gold sap. Electrospray Mass Spec516.2 $(M+H)^+$.

Step 2

In the same manner as described in Step 3 of Example 215, the ethyl 1-{[4-(2-butynyloxy)phenyl]sulfonyl}-4-[(4-methoxyanilino)carbonyl]-2-piperazine-carboxylate (0.40 g, 0.78 mmol) provided 0.066 g (17%) of the 1-{[4-(2-butynyloxy)phenyl]sulfonyl}-4-[(4-methoxyanilino)carbonyl]-2-piperazinecarboxylic acid. Electrospray Mass Spec 488.1 $(M+H)^+$.

Step 3

In the same manner as described in Step 4 of Example 215, the 1-{[4-(2-butynyloxy)phenyl]sulfonyl}-4-[(4-methoxyanilino)carbonyl]-2-piperazinecarboxylic acid (0.067 g, 0.14 mmol) provided 0.033 g (50%) of the 4-{[4-(2-butynyloxy)phenyl]sulfonyl}-N-3-hydroxy-N-1-(4-methoxyphenyl)-1,3-piperazine-dicarboxamide as a brown powder. Electrospray Mass Spec 503.6 $(M+H)^+$.

Example 222

4-{[4-2-Butynyloxy)Phenyl]Sulfonyl}-N-1-(4-Fluorophenyl)-N-3-Hydroxy-1,3-Piperazinedicarboxamide Step 1

In the same manner as described in Step 1 of Example 221, 4-fluoroaniline (0.60 g, 5.4 mmol) and 4-nitrophenylchloroformate provided 1.29 g (87%) of the desired carbamate as a yellow powder. Electrospray Mass Spec 276.1 $(M-H)^-$.

The carbamate (1.15 g, 4.16 mmol) was reacted with ethyl 2-piperazinecarboxylate, also as in Step 1 of Example 221, to provide 0.451 g (37%) of the desired urea, ethyl 4-[(4-fluoroanilino)carbonyl]-2-piperazinecarboxylate, as a gold oil. Electrospray Mass Spec 296.3 $(M+H)^+$.

Step 2

In the same manner as described in Step 2 of Example 215, ethyl 4-[(4-fluoroanilino)carbonyl]-2-piperazinecarboxylate (0.41 g, 1.4 mmol) and 4-but-2-ynyloxy-benzenesulfonyl chloride provided 0.49 g (70%) of ethyl 1-{[4-(2-butynyloxy)phenyl]sulfonyl}-4-[(4fluoroanilino)carbonyl]-2-piperazinecarboxylate as a white powder. Electrospray Mass Spec 504.4 $(M+H)^+$.

Step 3

In the same manner as described in Step 3 of Example 215, ethyl 1-{[4-(2-butynyloxy)phenyl]sulfonyl}-4-[(4-fluoroanilino)carbonyl]-2-piperazinecarboxylate (0.45 g, 0.91 mmol) provided 0.026 g (61%) of 1-{[4-(2-butynyloxy) phenyl]sulfonyl}-4-[(4-fluoroanilino)carbonyl]-2-piperazinecarboxylic acid. Electrospray Mass Spec 476.4 $(M+H)^+$.

Step 4

In the same manner as described in Step 4 of Example 215, 1-{[4-(2-butynyloxy)phenyl]sulfonyl}-4-[(4-fluoroanilino)carbonyl]-2-piperazinecarboxylic acid (0.24 g, 0.50 mmol) provided 0.080 g (32%) of 4-{[4-(2-butynyloxy)phenyl]sulfonyl}-N-1-(4-fluorophenyl)-N-3-hydroxy-1,3-piperazinedicarboxamide as a yellow powder. Electrospray Mass Spec 491.4 $(M+H)^+$.

Example 223

4-{[4-(2-Butynyloxy)Phenyl]Sulfonyl}-N-1-(3,5-Dichlorophenyl)-N-3-Hydroxyl-1,3-Piperazinedicarboxamide Step 1

To a solution of ethyl 2-piperazinecarboxylate (0.9 g, 5.7 mmol) in chloroform (11 mL) was added 3,5-dichlorophenyl isocyanate (1.05 g, 5.7 mmol). The reaction was stirred overnight after which time a precipitate had formed. The reaction was concentrated and the solid was chromatographed on silica gel using ethyl acetate as eluant to provide 0.53 g (27%) of ethyl 4-[(3,5-dichloroanilino)carbonyl]-2-piperazinecarboxylate as an off white powder. Electrospray Mass Spec 346.1 $(M+H)^+$.

Step 2

In the same manner as described in Step 2 of Example 215, ethyl 4-[(3,5-dichloroanilino)carbonyl]-2-piperazinecarboxylate (0.49 g, 1.42 mmol) and 4-but-2-ynyloxy-benzenesulfonyl chloride provided 0.73 g (92%) of the desired sulfonamide. Electrospray Mass Spec 554.1 $(M+H)^+$.

Step 3

In the same manner as described in Step 3 of Example 215, the sulfonamide (0.64 g, 1.14 mmol) provided 0.54 g (90%) of 1-{[4-(2-butynyloxy)phenyl]sulfonyl}-4-[(3,5-dichloroanilino)carbonyl]-2- piperazinecarboxylic acid. Electrospray Mass Spec 527.9 $(M+H)^+$.

Step 4

In the same manner as described in Step 4 of Example 215, the 1-{[4-2-butynyloxy)phenyl]sulfonyl}-4-[(3,5-dichloroanilino)carbonyl]-2- piperazinecarboxylic acid (0.46 g, 0.88 mmol) provided 0.150 g (31%) of 4-{[4-(2-butynyloxy)phenyl]sulfonyl}-N-1-(3,5-dichlorophenyl)-N-3-hydroxy-1,3-piperazinedicarboxamide as a white powder. Electrospray Mass Spec 540.8 $(M+H)^+$.

Example 224

4-Acetyl-1-(4-But-2-Ynyloxy-Benzenesulfonyl)-Piperazine-2-Carboxylic Acid Hydroxyamide Step 1

To a solution of 0.170 g (0.466 mmol) of 1-(4-but-2-ynyloxy-benzenesulfonyl)-piperazine-2-carboxylic acid ethyl ester in 10 mL of dichloromethane cooled at 0° was added 0.2 mL of triethylamine, 0.05 g of DMAP and 0.3 mL (0.93 mmol) of acetyl chloride. After stirring for 13 h the mixture was diluted with ethyl acetate and washed with saturated aqueous sodium bicarbonate. The organic layer was dried over sodium sulfate, filtered and concentrated in vacuo. The resulting residue was chromatographed on silica gel eluting with ethyl acetate/hexanes (2:1) to provide 0.13 g (68%) of 4-acetyl-1-(4-but-2-ynyloxy-benzenesulfonyl)-piperazine-2-carboxylic acid ethyl ester as a brown oil. Electrospray Mass Spec: 409.3 (M+H)+

Step 2

According to the procedure of Example 54, 0.151 g (0.369 mmol) of of 4-acetyl-1-(4-but-2-ynyloxy-benzenesulfonyl)-piperazine-2-carboxylic acid ethyl ester provided 0.107 g (76%) of the carboxylic acid, 4-acetyl-1-(4-but-2-ynyloxy-benzenesulfonyl)-piperazine-2-carboxylic acid, as a brown oil. Electrospray Mass Spec: 381.3 (M+H)+

Step 3

According to the procedure of Example 25, 0.1157 g (0.304 mmol) of 4-acetyl-1-(4-but-2-ynyloxy-benzenesulfonyl)-piperazine-2-carboxylic acid followed by flash chromatography with methylene chloride/methanol (10:1) provided 0.082 g (68%) of the hydroxamic acid, 4-acetyl-1-(4-but-2-ynyloxy-benzenesulfonyl)-piperazine-2-carboxylic acid hydroxyamide, as a brown solid. Electrospray Mass Spec: 396.3 (M+H)+

Example 225

1-(4-But-2-Ynyloxy-Benzenesulfonyl)-4-Propionyl-Piperazine-2-Carboxylic Acid Hydroxyamide According to the procedure of Example 224, using propionyl chloride in Step 1, 1-(4-but-2-ynyloxy-benzenesulfonyl)-4-propionyl-piperazine-2-carboxylic acid hydroxyamide was obtained as a grey solid. Electrospray Mass Spec: 410.3 (M+H)+

Example 226

1-(4-But-2-Ynyloxy-Benzenesulfonyl)-4-Thiophene-2-Carbonyl)-Piperazine-2-Carboxylic Acid Hydroxyamide According to the procedure of Example 224, using thiophene-2-carbonyl chloride in Step 1, 1-(4-but-2-ynyloxy-benzenesulfonyl)-4-(thiophene-2-carbonyl)-piperazine-2-carboxylic acid hydroxyamide was obtained as a grey solid. Electrospray Mass Spec: 464.3 (M+H)+

Example 227

1-(4-But-2-Ynyloxy-Benzenesulfonyl)-4-Methanesulfonyl-Piperazine-2-Carboxylic Acid Hydroxyamide According to the procedure of Example 224, using methanesulfonyl chloride chloride in Step 1, 1-(4-but-2-ynyloxy-benzenesulfonyl)-4-methanesulfonyl-piperazine-2-carboxylic acid hydroxyamide was obtained as a white powder. Electrospray Mass Spec: 432.1 (M+H)+

Example 228

4-(4-But-2-Ynyloxy-Benzenesulfonyl)-3-Hydroxycarbamoyl-Piperazine-1-Carboxylic Acid Methyl Ester According to the procedure of Example 224, using methyl chloroformate in Step 1, 4-(4-but-2-ynyloxy-benzenesulfonyl)-3-hydroxycarbamoyl-piperazine-1-carboxylic acid methyl ester was obtained as a grey powder. Electrospray Mass Spec: 412.2 (M+H)+

Example 229

{2-[4-(4-But-2-Ynyloxy-Benzenesulfonyl)-3-Hydroxycarbamoyl-Piperazin-1-yl]-2-Oxo-ethyl}-Carbamic Acid Tert-Butyl Ester To a solution of 0.14 g (0.8 mmol) of N-(tert-butoxycarbonyl)glycine dissolved in 3 mL of DMF was added 0.13 g (0.963 mmol) of 1-hydroxybenzotriazole hydrate (HOBT) followed by 0.203 g (1.06 mmol) of 1-(3-dimethylaminopropyl)-3-ethylcarbodiimide hydrochloride (EDC). The resulting mixture was stirred at room temperature for 1 h and 0.191 g (0.522 mmol) of 1-4-but-2-ynyloxy-benzenesulfonyl)piperazine-2-carboxylic acid ethyl ester in 3 mL of DMF was added dropwise. After stirring the reaction for 14 h the solution was diluted with ethyl acetate and washed with water. The organic layer was dried over sodium sulfate, filtered and concentrated in vacuo. The resulting residue was chromatographed on silica gel eluting with ethyl acetate/hexanes (1:1) to provide 0.26 g (95%) of the sulfonamide, ethyl 4-{2-[(tert-butoxycarbonyl)amino]acetyl}- 1-{[4-(2-butynyloxy)phenyl]sulfonyl}-2-piperazine-carboxylate, as a clear oil. Electrospray Mass Spec: 524.2 (M+H)+

Hydrolysis of the carboxylic acid and subsequent conversion into the corresponding hydroxamic acid, as in Example 224, provided {2-[4-(4-but-2-ynyloxy-benzenesulfonyl)-3-hydroxycarbamoyl-piperazin-1-yl]-2-oxo-ethyl}-carbamic acid tert-butyl ester as a grey powder. Electrospray Mass Spec: 511.1 (M+H)+

Example 230

4-Aminoacetyl-1-(4-But-2-Ynyloxy-Benzenesulfonyl)-Piperazine-2-Carboxylic Acid Hydroxyamide To a solution of 0.157 g (0.31 mmol) of the product of Example 229, {2-[4-(4-but-2-ynyloxy-benzenesulfonyl)-3-hydroxycarbamoyl-piperazin-1-yl]-2-oxo-ethyl}-carbamic acid tert-butyl ester, in 4.0 mL of methylene chloride was added 1.0 mL of trifluoroacetic acid. The resulting solution was stirred at room temperature for 1 h and then reduced to dryness. The resulting residue was dissolved in ethyl acetate and washed with saturated aqueous sodium bicarbonate and then brine. The organic layer was dried over sodium sulfate, filtered and concentrated in vacuo to furnish 0.121 g (95%) of 4-aminoacetyl-1-(4but-2-ynyloxy-benzenesulfonyl)-piperazine-2-carboxylic acid hydroxyamide as a yellow solid. Electrospray Mass Spec: 411.1 (M+H)+

Example 231

1-{[4-(2-Butynyloxy)Phenyl]Sulfonyl}-N-hydroxy-4-[(2,2,5-Trimethyl-1,3-Dioxan-5-yl)Carbonyl]-2-Piperazinecarboxamide According to the procedure of Example 229, using 2,2,5-trimethyl-[1,3]dioxane-5-carboxylic acid, the hydroxamic acid 1-{[4-(2-butynyloxy)phenyl]sulfonyl}-N-hydroxy-4-[(2,2,5-trimethyl-1,3-dioxan-5-yl)carbonyl]-2-

Example 232

1-{[4-(2-Butynyloxy)Phenyl]Sulfonyl}-N-Hydroxy-4-[3-Hydroxy-2-(Hydroxymethyl)-2-Methylpropanoyl]-2-Piperazinecarboxamide To a solution of the product of Example 231 in 5 mL of THF was added 0.5 mL of 1.0 M hydrogen chloride in ether. The resulting solution was stirred at room temperature for 20 h and then concentrated in vacuo furnishing 0.054 g (99%) of the diol, 1-{[4-2-butynyloxy)phenyl]sulfonyl}-N-hydroxy-4-[3-hydroxy-2-(hydroxymethyl)-2-methylpropanoyl]-2-piperazinecarboxamide, as a white solid. Electrospray Mass Spec: 470.2 (M+H)+

Example 233

4-(4-Bromo-Benzyl)-1-(4-But-2-Ynyloxy-Benzenesulfonyl)-Piperazine-2-Carboxylic Acid Hydroxyamide To a solution of 0.30 g (0.820 mmol) of 1-(4-but-2-ynyloxy-benzenesulfonyl)-piperazine-2-carboxylic acid ethyl ester (Step 1, Example 220) in 10 mL of DMF was added 0.339 g (2.459 mmol) of potassium carbonate followed by 0.205 g (0.820 mmol) of p-bromobenzyl bromide. The reaction was stirred at room temperature for 15 h, then diluted with ether and water. The organics were washed with water, dried over sodium sulfate, filtered and concentrated in vacuo. The residue was chromatographed on silica gel eluting with ethyl acetate/hexanes (1:1) to provide 0.438 g of 4-(4-bromo-benzyl)-1-(4-but-2-ynyloxy-benzenesulfonyl)-piperazine-2-carboxylic acid ethyl ester as a colorless oil. Electrospray Mass Spec 534.9, 536.8 (M+H)+

Hydrolysis of the carboxylic acid following the procedure of Example 11 and subsequent conversion into the corresponding hydroxamic acid, as in Example 9, provided 4-(4-bromo-benzyl)-1-(4-but-2-ynyloxy-benzenesulfonyl)-piperazine-2-carboxylic acid hydroxyamide as a tan foam. Electrospray Mass Spec: 521.98, 523.91 (M+H)+

Example 234

1-(4-But-2-Ynyloxy-Benzenesulfonyl)-4-Pyridin-3-Ylmethyl-Piperazine-2-Carboxylic Acid Hydroxyamide Following the procedure of Example 233, using 3-picolyl chloride hydrochloride to alkylate 1-(4-but-2-ynyloxy-benzenesulfonyl)-piperazine-2-carboxylic acid ethyl ester, 1-(4-but-2-ynyloxy-benzenesulfonyl)-4-pyridin-3-ylmethyl-piperazine-2-carboxylic acid hydroxyamide was obtained as a white solid. Electrospray Mass Spec: 445.1 (M+H)+

Example 235

(3S)-4-({[4-(2-Butnyloxy)Phenyl]Sulfonyl)-2,2-Dimethyl-Thiomorpholine-3-Carboxylic Acid Hydroxyamide Step 1

A solution of D-penicillamine (0.5 g, 3.35 mmol) in methanol (5 ml) was cooled to 0° C. and crushed sodium hydroxide (0.28 g, 6.87 mmol) was added to give a clear solution. 2-Bromoethanol (0.26 ml. 3.71 mmol) was added and the reaction was stirred at 0° C. for 1 hour and then at room temperature for an additional 1.5 hours. The solvent was evaporated and the oily residue was dissolved in 3 mL water and 6 mL DMF and stirred with sodium carbonate (0.82 g 7.2 mmol) and 4-butynyloxy-benzenesufonyl chloride (0.78 g, 3.18 mmol) at room temperature overnight. After evaporating the solvent, the residue was diluted with ethyl acetate and water. The aqueous layer was acidified to pH~3 with concentrated HCl and extracted with dichloromethane. The organic layer was washed with water and brine, dried over sodium sulfate, filtered and concentrated to obtain 1.2 g of (2S)-2-{[4-(2 butynyloxy)phenyl]sulfonyl}amino)-3-[ (2-hydroxyethyl)sulfanyl]-3-methylbutanoic acid as an oil. Yield 89.6%. Electrospray Mass Spec 400.1 (M–H)⁻.

Step 2

To a solution of (2S)-2-{[4-(2-butynyloxy)phenyl]sulfonyl}amino)-3-[(2-hydroxyethyl)sulfanyl[-3-methylbutanoic acid (1.2 g, 2.99 mmol) in dimethylacetamide (8 mL) was added potassium carbonate (3.3 g, 23.9 mmol), benzyltriethylammonium chloride (0.20 g, 0.90 mmol) and 2-bromo-2-methyl-propane (5.5 mL, 47.9 mmol). The mixture was heated at 50° C. overnight, cooled to room temperature and diluted with ethyl acetate. The organics were washed with water and brine, dried over sodium sulfate, filtered and evaporated to provide 1.10 g of tert-butyl (2S)-2-({[4-(2-butynyloxy)phenyl]sulfonyl})-3-[(2-hydroxyethyl)sulfanyl]-3-methylbutanoate as an oil. Yield ~80.9%. Electrospray Mass Spec 458.2(M+H)+.

Step 3

To a THF solution (15 mL) of tert-butyl (2S)-2-({[4-(2-butynyloxy)phenyl]sulfonyl})-3-[(2-hydroxyethyl)sulfanyl]-3-methylbutanoate (0.59 g, 1.29 mmol) and triphenylphosphine (0.51 g, 1.94 mmol), diethylazodicarboxylate (0.31 mL, 1.94 mmol) was slowly added. The mixture was stirred at room temperature overnight. After removing the solvent, the residue was diluted with ethyl acetate. The organic layer was washed with water and brine, dried over sodium sulfate, filtered and concentrated. The residue was purified by column chromatography on silica gel eluting with hexanes:ethyl acetate (4:1) to give 0.36 g of tert-butyl (3S)-4-({[4-(2-butynyloxy)phenyl]sulfonyl)-2,2-dimethyl-thiomorpholine-3-carboxylate. Yield 64.3%. Electrospray Mass Spec 440.1 (M+H)+.

Step 4

To a solution of tert-butyl 4-({[4-(2-butynyloxy)phenyl]sulfonyl)-2,2-dimethyl-thiomorpholine-3-carboxylate (0.31 g, 0.71 mmol) in dichloromethane (7 mL) was added trifluoroacetic acid (3 mL) and the resulting mixture was stirred at room temperature for 1 hour, after which the solvents were evaporated and toluene was added. The toluene and excess trifloroacetic acid were removed to give 0.25 g of (3S)-4-({[4-(2-butynyloxy)phenyl]sulfonyl)-2,2-dimethyl-thiomorpholine-3-carboxylic acid, which was used for the next step without further purification. Yield:92.6%. mp 129–131° C. %. Electrospray Mass Spec 381.8(M–H)⁻.

Step 5

To a 0° C. solution of 4-({[4-(2-butynyloxy)phenyl] sulfonyl)-2,2-dimethyl-thiomorpholine-3-carboxylic acid (6a) (0.25 g,0.65 mmol) in dichloromethane (5 mL) and DMF (0.1 mL, 1.31 mmol), oxalyl chloride (0.65 mL of 2M in $CH_2Cl_2$; 1.31 mmol) was added dropwise. The reaction mixture was stirred at 0° C. for 10 minutes and at room temperature for 2 hours, then recooled to 0° C. A THF (1 mL) solution of triethylamine (0.34 mL, 2.61 mmol) and hydroxylamine (0.24 mL of 50% hydroxylamine in water, 3.92 mmol) was added in one portion. The reaction was stirred at room temperature overnight. After removing the solvent, the oily residue was diluted with ethyl acetate and water. The organic layer was washed with water and brine, dried over sodium sulfate, filtered and evaporated to give 0.18 g of a solid which was triturated with ether to give 0.14 g of (3S)-4-({[4-(2-butynyloxy)phenyl]sulfonyl)-2,2-dimethyl-thiomorpholine-3-carboxylic acid hydroxyamide as a white solid. Yield 55%. mp 185–186° C. Electrospray Mass Spec 399.1(M+H)⁺

Example 236

9-({[4-(2-Butynyloxy)Phenyl]Sulfonyl}-N-Hydroxy-6Thia-9-Azaspiro[4,5]Decane-10-Carboxamide According to the procedure of Example 235, using alpha-amino-1-mercapto-cyclopentaneacetic acid (Reich, et al. *Bioorg. Med. Chem. Lett.* 4(9) 1167 (1994)), the desired 9-({[4-(2-butynyloxy)phenyl]sulfonyl}-N-hydroxy-6-thia-9-azaspiro[4,5]-decane-10-carboxamide was obtained. mp 206–208° C. Electrospray Mass Spec 425(M+H)⁺.

Example 237

9-({[4-(2-Butynyloxy)Phenyl]Sulfonyl}-N-Hydroxy-1-Thia-4-Azaspiro [5,5]Undecane-5-Carboxamide According to the procedure of Example 235, using alpha-amino-1-mercapto-cyclohexaneacetic acid (Reich, et al. *Bioorg. Med Chem. Lett.* 4(9) 1167 (1994)), the desired 9-({[4-(2-butynyloxy)phenyl]sulfonyl}-N-hydroxy-1-thia-4-azaspiro [5,5]undecane-5-carboxamide was obtained. mp 117–119° C. Electrospray Mass Spec 480(M+H)⁺.

Example 238

4-({[4-(2-Butynyloxy)Phenyl]Sulfonyl)-2,2-Diethyl-Thiomorpholine-3-Carboxylic Acid Hydroxyamide According to the procedure of Example 235, using 3-ethyl-3-sulfanylnorvaline (Reich, et al. *Bioorg. Med Chem. Lett.* 4(9) 1167 (1994)), the desired 4-({[4-(2-butynyloxy)phenyl]sulfonyl)-2,2-diethyl-thiomorpholine-3-carboxylic acid hydroxyamide was obtained. mp 212–214° C. Electrospray Mass Spec 427.1(M+H)⁺.

Example 239

4-({[4-(2-Butynyloxy)Phenyl]Sulfonyl)-N-Hydroxy-Thiomorpholine-3-Carboxamide

According to the procedure of Steps 1 and 2 of Example 235, using D-cysteine, the desired tert-butyl 2-({[4-(2-butynyloxy)phenyl]sulfonyl)amino)-{3-[(2-hydroxyethyl) thio]propanoate was obtained. Electrospray Mass Spec 430.2 (M+H)⁺.

To a solution of tert-butyl 2-({[4-(2-butynyloxy)phenyl] sulfonyl)amino){3-[(2-hydroxyethyl)thio]propanoate (0.5 g, 1.16 mmol) and carbon tetrabromide (0.38 g, 1.16 mmol) in dichloromethane (3 mL), a dichloromethane solution (1 mL) of triphenylphosphine was added dropwise. The reaction mixture was stirred at 0° C. for 10 minutes and at room temperature overnight. After removing the solvent, the oily residue was separated by column chromatography on silica gel eluting with hexane:ethyl acetate (3:2) to give 0.33 g of tert-butyl S-(2-bromoethyl)-N-({[4-(2-butynyloxy)phenyl] sulfonyl)-cysteine. Yield~57.8%. Electrospray Mass Spec 492.1; 494.1 (M+H)⁺.

To a solution of tert-butyl S-(2-bromoethyl)-N-({[4-(2-butynyloxy)phenyl]sulfonyl)-cysteine (0.31 g, 0.63 mmol) dissolved in DMF and cooled in an ice bath was added 3 equivalents of potassium carbonate and the reaction was stirred at room temperature for 1 hour. After removing the solvent, the residue was extracted with ethyl acetate and water. The organic layer was washed with water and brine, dried over sodium sulfate, filtered and concentrated to give 0.25 g of tert-butyl 4-({[4-(2-butynyloxy)phenyl]sulfonyl)-thiomorpholine-3-carboxylate as an oil. Yield ~100%. Electrospray Mass Spec 412.3 (M+H)⁺.

According to the procedures of Steps 4 and 5 of Example 235, tert-butyl 4-({[4-(2-butynyloxy)phenyl]sulfonyl)-thiomorpholine-3-carboxylate was converted into 4-({[4-2-butynyloxy)phenyl]sulfonyl)-N-hydroxy-thiomorpholine-3-carboxamide. mp 150–154° C. Electrospray Mass Spec 371.2 (M+H)⁺.

Example 240

4-([4-(2-Butynyloxy)Phenyl]Sulfonyl}-N-Hydroxy-3-Morpholinecarboxamide

Step 1

To a 0° solution of D-serine methyl ester hydrochloride (0.62 g, 4 mmol) in 5 mL of dichloromethane was added triethylamine (1.67 mL,12 mmol) followed by a dichloromethane (6 mL) solution of 4-(2-butynyloxy)-benzenesufonyl chloride (0.98 g, 4 mmol). The reaction was stirred at room temperature overnight and then the mixture was poured into water. The organic layer was washed with 2N citric acid, water and brine, dried over sodium sulfate, filtered and concentrated to give 1.16 g of methyl 2-({[4-(2-butynyloxy)phenyl]sulfonyl}amino)-3-hydroxypropanoate. Yield~89.2%. mp 72–74° C. Electrospray Mass Spec 328.2 (M+H)⁺.

Step 2

To a THF solution (10 mL) of methyl 2-({[4-(2-butynyloxy)phenyl]-sulfonyl}amino)-3-hydroxypropanoate (0.33 g, 1 mmol) and triphenylphosphine (0.32 g, 1.2 mmol), diethylazodicarboxylate (0.19 mL, 1.2 mmol) was added dropwise. The mixture was stirred at room temperature overnight. After removing the solvent, the residue was extracted with ether. The organic layer was washed with 1N NaHCO₃, water and brine, dried over sodium sulfate, filtered and concentrated. The residue was purified by column chromatography on silica gel eluting with hexane:ethyl acetate (1:1) to provide 0.18 g of 1-({[4-2-butynyloxy) phenyl]sulfonyl}-2-aziridinecarboxylic acid,methyl ester. Yield 58.0%. Electrospray Mass Spec 310.2(M+H)$^+$.

Step 3

To a 0° solution of 1-({[4-(2-butynyloxy)phenyl] sulfonyl}-2-aziridine-carboxylic acid, methyl ester (0.55 g, 1.78 mmol) in 2-bromoethanol (1.26 mL,17.8 mmol) was dropwise added boron trifluoride etherate (0.18 mL). The mixture was stirred at 0° C. for 30 minutes and stirred at room temperature for 6 hours. The reaction was diluted with ethyl acetate. The organic layer was washed with 1N NaHCO$_3$, water and brine, dried over Na$_2$SO$_4$, filtered and concentrated. The residue was purified by column chromatography on silica gel eluting with hexane:ethyl acetate (7:3) to obtain 0.2 g of 3-(2-bromo-ethoxy)-2-(4-[2-butynyloxy]-benzene-sulfonylamino)-propionic acid methyl ester. Yield: 26%. mp 45–46° C. Electrospray Mass Spec 434.1.436.1 (M+H)$^+$.

Step 4

To a solution of 3-(2-bromo-ethoxy)-2-(4-[2-butynyloxy]-benzenesulfonyl-amino)propionic acid methyl ester (0.15 g, 0.35 mmol) dissolved in DMF (2 mL) and cooled in an ice bath was added potassium carbonate (0.16 g, 1.15 mmol) and the reaction was stirred at room temperature for 1 hour. After removing the solvent, the residue was extracted with ethyl acetate and water. The organic layer was washed with water and brine, dried over sodium sulfate, filtered, and concentrated to give 0.09 g of 4-([4-(2-butynyloxy)phenyl]sulfonyl}-morpholine-3-carboxylic acid, methyl ester as an oil. Yield ~73.8%. Electrospray Mass Spec 354.2 (M+H)$^+$.

Step 5

A solution of 4-([4-2-butynyloxy)phenyl]sulfonyl}-morpholine-3-carboxylic acid, methyl ester (0.1 g, 0.28 mmol) in 2.4 mL of THF:methanol:water [4:1:1] was cooled in an ice bath and 2N LiOH (0.3 mL, 0.59 mmol) was added. The reaction was stirred at 0° C. for 30 minutes and at room temperature for 2 hours. After evaporating the solvent, the residue was diluted with ether and filtered. The solid was dissolved in water, neutralized with 1N HCl to pH~3 and extracted with dichloromethane. The organic layer was washed with water and brine, dried over sodium sulfate, filtered and concentrated to give 0.06 g of 4-[4-(2-butynyloxy)phenyl]sulfonyl}-morpholine-3-carboxylic acid. Yield~69.8%. mp 40–42° C. Electrospray Mass Spec 338.1(M−H)$^-$.

Step 6

A solution of 4-([4-2-butynyloxy)phenyl]sulfonyl}-morpholine-3-carboxylic acid (0.52 g, 1.53 mmol) and DMF (0.24 mL, 3.1 mmol) in dichloromethane (6 mL) was cooled in an ice bath and oxalyl chloride (1.54 mL of 2M in CH$_2$Cl$_2$; 3.1 mmol) was added dropwise. The reaction mixture was stirred at 0° C. for 10 minutes and at room temperature for 2 hours and then recooled to 0°. A THF (4.5 mL) solution of triethyl amine (0.86 mL, 6.13 mmol) and hydroxylamine (0.56 mL of 50% hydroxyamine in water, 9 mmol) was added in one portion. The reaction was stirred at room temperature overnight. After removing the solvent, the oily residue was diluted with ethyl acetate and water. The organic layer was washed with water and brine, dried over sodium sulfate, filtered and evaporated to obtain 0.42 g of 4-([4-(2-butynyloxy)phenyl]sulfonyl}-N-hydroxy-3-morpholinecarboxamide. Yield ~77.8%. mp 68–72° C. Electrospray Mass Spec 355.2(M+H)$^+$.

Example 241

9-Benzyl-4-{[4-(2-Butynyloxy)Phenyl]Sulfonyl}-N-Hydroxy-1-Thia-4,9-Diazaspiro[5.5]Undecane-5-Carboxamide Step 1

To a stirred suspension of sodium hydride (4.6 g of 60% oil dispersion, 100 mmol) in dry THF (200 ml) at 0° C. were added simultaneously, in a dropwise manner, ethyl isocyanatoacetate (10.3 g, 100 mmol) and 1-benzyl-4-piperidone (17.5 g, 100 mmol). After the addition reaction mixture was warmed up to room temperature and stirred for 4 h. The reaction mixture was then carefully quenched with saturated ammonium chloride solution. The reaction mixture was extracted with chloroform and washed with saturated brine solution. The organic layer was dried over anhydrous MgSO$_4$, filtered and concentrated. The crude brown oil, ethyl(1-benzyl-4-piperidinylidene)(formylamino)acetate, was pure enough for use in the next step. Yield, 28.9 g (96%); Electrospray Mass Spec: 303 M+H)$^+$.

Step 2

A mixture of ethyl(1-benzyl-4-piperidinylidene) formylamino)acetate (3.0 g, 10.0 mmol), 2-mercaptoethanol (2.7 g, 35 mmol) and sodium methoxide (1 g) was heated at 80° C. for 8 h under nitrogen. The reaction mixture was then cooled to room temperature and quenched with saturated ammonium chloride solution. It was extracted with chloroform, washed twice with brine and dried over anhydrous Na$_2$SO$_4$, filtered and concentrated. The oily residue was purified by silica gel column chromatography eluting with 5% methanol:chloroform to provide ethyl {1-benzyl-4-[(2-hydroxyethyl)sulfanyl]-4-piperidinyl}(formylamino) acetate as a yellow oil; Yield: 2.8 g (73%) Electrospray Mass Spec: 381 (M+H)$^+$.

Step 3

Ethyl{1-benzyl-4-[(2-hydroxyethyl)sulfanyl]-4-piperidinyl}(formylamino)-acetate (2.8 g, 7.3 mmol) was dissolved in 50 ml of ethanol and 5N hydrochloric acid (4 ml) and refluxed for 2 h. The reaction mixture was then concentrated to dryness to provide ethyl amino{1-benzyl-4-[(2-hydroxyethyl)sulfanyl]-4-piperidinyl}acetate as a brown oil which was used for the next step with out purification. Yield: 3.0 g (quantitative); Electrospray Mass Spec: 353 (M+H)$^+$.

Step 4

To a stirred solution of ethyl amino{1-benzyl-4-[(2-hydroxyethyl)sulfanyl]-4-piperidinyl}acetate (2.1 g, 5 mmol) and 4-but-2-ynyloxy benzenesulfonyl chloride (1.24 g, 5.1 mmol) in dichloromethane (200 ml) at 0° C., N,N-diisopropylethylamine (3.0 g, 23.6 mmol) was added slowly. After the addition, the reaction mixture was stirred at room temperature for 4 h and quenched with water. The reaction mixture was washed with water, dried over anhydrous MgSO$_4$, filtered and concentrated. It was purified by silica gel column chromatography eluting with 80% ethyl acetate-:hexane to give ethyl {1-benzyl-4-[(2-hydroxyethyl) sulfanyl]-4-piperidinyl}({[4-(2-butynyloxy)phenyl] sulfonyl}amino)acetate as a brown oil; Yield: 1.0 g (85%); Electrospray Mass Spec: 561 (M+H)+.

Step 5

A mixture of ethyl {1-benzyl-4-[(2-hydroxyethyl) sulfanyl]-4-piperidinyl}({[4-(2-butynyloxy)phenyl] sulfonyl}amino)acetate (5.0 g, 8.9 mmol), tributylphosphine (4.04 g, 20 mmol) and 1,1-(azodicarbonyl)-dipiperidine (5.04 g, 20 mmol) was stirred in dry THF at room temperature for 6 h. The reaction sure was quenched with water, extracted with chloroform and washed well with water. The organic layer was dried over anhydrous $MgSO_4$, filtered and concentrated. The product was purified by silica gel column chromatography eluting with 60% ethyl acetate/hexane to give ethyl-9-benzyl-4-{[4-(2-butynyloxy)phenyl]sulfonyl}-1-thia-4,9-diazaspiro[5.5]undecane-5-carboxylate as a pale yellow oil; Yield: 4.2 g (87.5%); Electrospray Mass Spec: 543 (M+H)+.

Step 6

A mixture of ethyl-9-benzyl-4-{[4-(2-butynyloxy)phenyl] sulfonyl}-1-thia-4,9-diazaspiro[5.5]undecane-5-carboxylate (4.0 g, 7.38 mmol) and 5N sodium hydroxide (20 ml) was refluxed in THF:methanol (1:1, 100 ml) for 8 h. The reaction mixture was concentrated and the residue was carefully neutralized with concentrated hydrochloric acid. The separated sticky mass was extracted with chloroform, washed once with water, dried over anhydrous $MgSO_4$, filtered and concentrated. The brown spongy solid, 9-benzyl-4-{[4-(2-butynyloxy)phenyl]sulfonyl}-1-thia-4,9-diazaspiro[5.5]-undecane-5-carboxylic acid, was used for the next step without purification. Yield: 3.5 g (93%); mp 123–128° C.; Electrospray Mass Spec: 515 (M+H)+.

Step 7

To a stirred suspension of 9-benzyl-4-{[4-(2-butynyloxy) phenyl]sulfonyl}-1-thia-4,9-diazaspiro[5.5]undecane-5-carboxylic acid (3.0 g, 5.8 mmol) in dichloromethane (200 ml)/DMF (5 ml), oxalyl chloride (5.0 g, 39.6 mmol) in dichloromethane (10 ml) was added slowly at 0° C. After the addition, the reaction mixture was stirred at room temperature for 1 h. In a separate flask, hydroxylamine hydrochloride (6.9 g, 100 mmol) was dissolved in DMF/acetonitrile (1:1, 100 ml) and triethylamine (20 g, 200 mmol) was added. It was stirred at room temperature for 1 h and diluted with dichloromethane (50 ml). The acid chloride formed was concentrated to dryness and redissolved in dichloromethane. The hydroxylamine solution was cooled to 0° C., and the acid chloride was added to the hydroxylamine. The reaction mixture was stirred at room temperature for 6 h and concentrated to dryness. It was extracted with chloroform, washed well with water, dried over anhydrous $MgSO_4$, filtered and concentrated. The product was purified by silica gel column chromatography eluting with 5% methanol:chloroform. The hydrochloride salt was prepared by dissolving the free base in methanolic hydrochloric acid to give 9-benzyl-4-{[4-(2-butynyloxy)phenyl]sulfonyl}-N-hydroxy-1-thia-4,9-diazaspiro[5.5]undecane-5-carboxamide hydrochloride as a yellow spongy solid; Yield 1.8 g (58%); mp 151–153° C.; Electrospray Mass Spec: 530 (M+H)+; $H^1$ NMR (DMSO) ☐: 1.8 (s, 3H), 1.9 (m, 2H), 2.3–2.6 (m,4H), 2.7–2.85 (m, 3H), 3.0–3.1 (m,1H), 3.5 (s,2H), 3.8–4.2 (m, 2H), 4.7 (s,1H), 4.8 (s,2H), 7.0 (d, 2H), 7.3–7.5 (m,5H), 7.8 (d,2H), 10.6 (s, 1H), 11.1 (s,1H).

Example 242

9-Methyl-4-{[4-(2-Butynyloxy)Phenyl]Sulfonyl}-N-Hydroxy-1-Thia-4,9-Diazaspirol[5.5]Undecane-5-Carboxamide 9-Methyl-4-{[4-(2-butynyloxy)phenyl]sulfonyl}-N-hydroxy-1-thia-4,9-diazaspiro[5.5]undecane-5-carboxamide was prepared according to the procedure of Example 241. Starting from ethyl isocyanatoacetate and 1-methyl-4-piperidone, 9-methyl4-{[4-(2-butynyloxy) phenyl]sulfonyl}-N-hydroxy-1-thia-4,9-diazaspiro[5.5]-undecane-5-carboxamide was isolated as white solid. mp 195–198; Electrospray Mass Spec: 454 (M+H)+. $H^1$ NMR (DMSO) ☐: 1.8 (s, 3H), 1.9 (m, 2H), 2.3–2.6 (m,4H), 2.7–2.85 (m, 3H), 3.0–3.1 (m,1H), 3.5 (s,2H), 3.8–4.2 (m, 2H), 4.7 (s,1H), 4.8 (s,2H), 7.0 (d, 2H), 7.3–7.5 (m,5H), 7.8 (d,2M, 10.6 (s, 1H), 11.1 (s, 1H).

Example 243

N-Hydroxy-2,2-Dimethyl-4-[(4-{(5-(Tetrahydro-2H-Pyran-2-Yloxy)-2-Pentynyl]Oxy}Phenyl)Sulfonyl]-3-Thiomorpholine Carboxamide Step 1

To a solution of 8.0 mL (51 mmol) of 2-(3-butynyloxy) tetrahydro-2H-pyran in 150 mL of THF under nitrogen atmosphere at −23° C. was added dropwise a solution of 33 mL (53 mmol) of 1.6M butyllithium in hexanes, maintaining the temperature at −23° C. The resulting solution was stirred at 0° C. for 2 h, recooled to −23° C. and 2.4 g (76.5 mmol) of paraformaldehyde was added in several portions. The mixture was stirred at −23° C. for 1 h and let warm to room temperature and stirred for 18 h. The reaction mixture was poured into a large excess of ice water and extracted with ether. The organics were washed with brine until neutral, dried over MgSO4, filtered and concentrated in vacuo. The residue was kugelrohr distilled to provide 7.26 g (77%) of 5-(tetrahydro-2H-pyran-2-yloxy)-2-pentyn-1-ol as a colorless liquid. El Mass Spec: 185.1 (M+H)+

Step 2

To a stirred solution of 5.15 mL (59.8 mmol) of 1,2-dibromoethane in 50 mL of DMF at room temperature was added over 45 min a solution of 10 g (50 mmol) of D-penicillamine methyl ester hydrochloride and 22.5 mL (150.45 mmol) of 1,8-diazabicyclo[5.4.0]undec-7-ene in 100 mL of DMF. The reaction was stirred for 2.5 h, poured into a solution of saturated NaHCO3 and extracted with ethyl acetate. The organics were washed with brine, dried over $MgSO_4$, filtered and concentrated in vacuo to provide 8.24 g (87%) of methyl (3S)-2,2-dimethyl-3-thiomorpholine carboxylate as a pale yellow oil. Electrospray Mass Spec: 190.1 (M+H)+

Step 3

To a solution of 0.5 g (2.6 mmol) of 4-hydroxybenzenesulfonyl chloride (*J. Org. Chem.* 1973, 38, 1047) in 5 mL of chloroform at room temperature was added 0.706 mL (2.86 mmol) of N,O-bis(trimethylsilyl) acetamide. The reaction mixture was stirred for 1 h and added a solution of 0.41 g (2.16 mmol) of methyl (3S)-2,2-dimethyl-3-thiomorpholinecarboxylate in 1 mL of chloroform in one portion, followed by 0.48 mL (4.37 mmol) of N-methylmorpholine. The resulting mixture was stirred for 18 h and 10 mL of methanol was added and the resulting mixture was heated to reflux for 1 h. The reaction was diluted with ethyl acetate, washed with water, 5% HCl and brine, dried over $MgSO_4$ filtered and concentrated in vacuo. The residue was triturated with ether:hexanes (1:2) to provide 0.62 g (83%) of 4-(4-hydroxy-benzenesulfonyl)-2,2-dimethyl-thiomorpholine-3- carboxylic acid methyl ester as a pale yellow solid. Electrospray Mass Spec: 344.4 $(M-H)^-$ Step 4

To a solution of 3.31 g (9.6 mmol) of of 4-(4-hydroxy-benzenesulfonyl)-2,2-dimethyl-thiomorpholine-3- caxboxylic acid methyl ester and 2.12 g (11.5 mmol) of 5-(tetrahydro-2H-pyran-2-yloxy)-2-pentyn-1-ol in 15 mL of THF was added 3.0 g (11.5 mmol) of triphenylphosphine, followed by dropwise addition of 1.8 mL (11.5 mmol) of diethyl azodicarboxylate. The resulting solution was stirred at room temperature for 18 h. The reaction was diluted with ethyl acetate, washed with water and brine, dried over MgSO4, filtered and concentrated in vacuo. The residue was chromatographed on silica gel eluting with ethyl acetate-:hexanes (1:9) to provide 3.03 g (62%) of methyl 2,2-dimethyl-4-[(4-{[5-(tetrahydro-2H-pyran-2-yloxy)-2-pentynyl]oxy}phenyl)sulfonyl]-3-thiomorpholine carboxylate as a colorless oil. Electrospray Mass Spec: 534.4 $(M+Na)^+$ Step 5

A solution of 0.418 g (0.817 mmol) of methyl 2,2-dimethyl-4-[(4-{[5-(tetrahydro-2H-pyran-2-yloxy)-2-pentynyl]oxy}phenyl)sulfonyl]-3-thiomorpholine carboxylate, 4.0 mL (4.08 mmol) of 1N NaOH, 4.0 mL of methanol and 4.0 mL of THF was heated to reflux for 5 h. The reaction was concentrated and the residue was diluted with water, acidified to pH5 and extracted with ethyl acetate. The organics were washed with water and brine, dried over $MgSO_4$, filtered and concentrated in vacuo to provide 0.342 g (84%) of 2,2-dimethyl-4-[(4-{[5-(tetrahydro-2H-pyran-2-yloxy)-2-pentynyl]oxy}phenyl)sulfonyl]-3-thiomorpholine carboxylic acid as a colorless oil. Electrospray Mass Spec: 496.5 $(M-H)^-$ Step 6

To a solution of 0.28 g (0.56 mmol) of 2,2-dimethyl-4-[(4-{[5-(tetrahydro-2H-pyran-2-yloxy)2-pentynyl]oxy}phenyl)sulfonyl]-3-thiomorpholine carboxylic acid and 0.091 g (0.675 mmol) of 1-hydroxybenzotriazole in 2.5 mL of DMF was added 0.151 g (0.788 mmol) of 1-(3-dimethylaminopropyl)-3-ethylcarbodiimide hydrochloride and stirred at room temperature for 1 h. Then 0.173 mL (2.8 mmol) of 50% aqueous hydroxylamine was added and the reaction was stirred for 18 h. The resulting mixture was diluted with ethyl acetate, washed with water, brine, dried over MgSO4, filtered and concentrated in vacuo. The residue was chromatographed on silica gel eluting with 5% methanol/dichloromethane. The product was triturated with ether to provide 0.024 g (8%) of N-hydroxy-2,2-dimethyl-4-[(4-{[5-(tetrahydro-2H-pyran-2-yloxy)-2-pentynyl]oxy}phenyl)sulfonyl]-3-thiomorpholine carboxamide as a white solid. Electrospray Mass Spec: 513.4 $(M+H)^+$ Example 244

N-Hydroxy-4-({4-[(5-Hydroxy-2-Pentynyl)Oxy]Phenyl}Sulfonyl)-2,2-Dimethyl-3-Thiomorpholine Carboxamide To a solution of 0.33 g (0.663 mmol) of 2,2-dimethyl4-[(4-{[5-(tetrahydro-2H-pyran-2-yloxy)-2-pentynyl]oxy}phenyl)sulfonyl]-3-thiomorpholine carboxylic acid (Step 5, Example 243) and 0.108 g (0.796 mmol) of 1-hydroxybenzotriazole in 3 mL of dichloromethane and 1 mL of DMF was added 0.169 g (0.88 mmol) of 1-(3-dimethylaminopropyl)-3-ethylcarbodiimide hydrochloride and the reaction was stirred at room temperature for 1 h. Then 0.203 mL (3.3 1 mmol) of 50% aqueous hydroxylamine was added and the reaction was stirred for 18 h. The reaction was diluted with ethyl acetate, washed with water and brine, dried over MgSO4, filtered and concentrated in vacuo. The residue was dissolved in 10 mL of methanol and 0.028 g (0.11 mmol) of pyridinium p-toluenesulfonate was added and the reaction was heated to reflux for 18 h. The reaction was concentrated in vacuo and the residue was chromatographed on silica get eluting with 2.5% MeOH/$CH_2Cl_2$ to provide 0.59 g (21%) of N-hydroxy-4-({4-[(5-hydroxy-2-pentnyl)oxy]phenyl}sulfonyl)-2,2-dimethyl-3-thiomorpholine carboxamide as a white solid. Electrospray Mass Spec: 429.1 $(M+H)^+$ Example 245

Tert-Butyl 5-[4-({3-[(Hydroxyamino)Carbonyl]-2,2-Dimethyl-4-Thiomorpholinyl}Sulfonyl)Phenoxy]-3-Pentynylcarbamate Step 1

A mixture of 2.61 g (5.1 mmol) of methyl 2,2-dimethyl-4-[(4-{[5-(tetrahydro-2H-pyran-2-yloxy)-2-pentynyl]oxy}phenyl)sulfonyl]-3-thiomorpholine carboxylate and 0.32 g (1.275 mmol) of pyridinium p-toluene sulfonate in 50 mL of methanol was heated to reflux for 18h. The reaction was concentrated in vacuo and the residue was chromatographed on silica gel eluting with ethyl acetate:hexanes (1:4) to provide 2.2 g (100%) of methyl 4-({4-[(5-hydroxy-2-pentynyl)oxy]phenyl}sulfonyl)-2,2-dimethyl-3-thiomorpholine carboxamide as a colorless oil Electrospray Mass Spec: 428.1 (M+H)+

Step 2

To a solution of 2.123 g (8.093 mmol) of triphenylphosphine and 0.373 mL (4.61 mmol) of pyridine in 40 mL of dry THF under nitrogen was added 1.73 g (4.046 mmol) of methyl 4-({4-[(5-hydroxy-2-pentynyl)oxy]phenyl}sulfonyl)-2,2-dimethyl-3-thiomorpholine carboxamide. The solution was cooled in a water bath and 1.34 g (4.046 mmol) of carbon tetrabromide was added and the resulting mixture was stirred for 3h. The resulting suspension was filtered and the filtrate was concentrated in vacuo. The residue was chromatographed on silica gel eluting with ethyl acetate:hexanes (1:8) to provide 1.726 g (87%) of methyl 4-({4-[(5-bromo-2-pentynyl)oxy]phenyl}sulfonyl-2, 2-dimethyl-3-thiomorpholine carboxamide as a pale yellow oil. Electrospray Mass Spec: 492.0 (M+H)+

Step 3

A solution of 1.74 g (3.55 mmol) of methyl 4-({4-[(5-bromo-2-pentynyl)oxy]phenyl}sulfonyl)-2,2-dimethyl-3-thiomorpholine carboxamide and 0.277 g (4.26 mmol) of sodium azide in 15 mL of DMF was stirred at room temperature for 18h. The reaction was diluted with ether, washed with water and brine, dried over MgSO$_4$, filtered and concentrated in vacuo to provide 1.6 g (100%) of methyl 4({4-[(5-azido-2-pentynyl)oxy]phenyl) sulfonyl}2,2-dimethyl-3-thiomorpholine carboxylate as a pale brown oil. Electrospray Mass Spec: 453.2 (M+H)+

Step 4

To a solution of 0.453 g (1.0 mmol) of methyl 4-({4-[(5-azido-2-pentynyl)oxy]phenyl}sulfonyl)-2,2-dimethyl-3-thiomorpholine carboxylate in 7 mL of ether and 1 mL of THF was dropwise added 0.275 mL (1.1 mmol) of tributylphosphine at room temperature. The reaction was stirred for 1h and then cooled to −50° C. (acetonitrile/dry ice bath). A solution of 0.24 g (1.1 mmol) of di-tert-butyldicarbonate in 3.5 mL of ether was added and stirred at −50° C. for 2h. Then 3.5 mL of saturated solution of NaHCO$_3$ was added and the reaction was let warm to room temperature. The resulting mixture was diluted with ethyl acetate, washed with brine, dried over MgSO$_4$, filtered and concentrated in vacuo. The residue was chromatographed on silica gel eluting with ethyl acetate:hexanes (1:6) to provide 0.21 g (40%) of methyl4-{[4-({5-[(tert-butoxycarbonyl)amino]-2-pentynyl}oxy)phenyl]sulfonyl}-2,2-dimethyl-3-thiomorpholine carboxylate as a colorless oil. Electrospray Mass Spec: 527.2 (M+H)+

Step 5

According to the procedure of Step 5 of Example 243, 0.2g (0.38 mmol) of methyl-4-{[4-{5-[(tert-butoxycarbonyl)amino]-2-pentynyl}oxy)phenyl]sulfonyl}-2,2-dimethyl-3-thiomorpholine carboxylate provided 0.159 g (82%) of 4-{[4-{5-[(tert-butoxycarbonyl)amino]-2-pentynyl}oxy)phenyl]sulfonyl}-2,2-dimethyl-3-thiomorpholine carboxylic acid as a colorless oil Electrospray Mass Spec: 513.2 (M+H)+

Step 6

According to the procedure of Step 6 of Example 243, 0.155 g (0.3 mmol) of 4-{[-4-({5-[(tert-butoxycarbonyl)amino]-2-penynyl}oxy)phenyl]sulfonyl}-2,2-dimethyl-3-thiomorpholinecarboxylic acid provided 0.058g (37%) of tert-butyl 5-[4-({3-[(hydroxyamino)carbonyl]-2,2-dimethyl4-thiomorpholinyl)sulfonyl)phenoxy]-3-pentynylcarbamate as a cream solid. Electrospray Mass Spec: 528.1 (M+H)+

Example 246

4-({4-[(5Amino-2-pentynyl)oxy]phenyl}sulfonyl)-N-hydroxy-2,2-dimethyl-3-thiomorpholine carboxamide A solution of 0.071 g (0.135 mmol) of tert-butyl 5-[4-({3-[(hydroxyamino)carbonyl]-2,2-dimethyl-4-thiomorpholinyl}sulfonyl)phenoxy]-3-pentynylcarbamate from Example 245, 1 mL of trifluoroacetic acid and 3mL of dichloromethane was stirred for 1.5h. The solution was concentrated in vacuo and the residue was triturated with ether to provicde 0.058 g (79%) of 4-({4-[(5-amino-2-pentynyl)oxy]phenyl}sulfonyl)-N-hydroxy-2,2-dimethyl-3-thiomorpholine carboxamide as a pale orange solid. Electrospray Mass Spec: 428.3 (M+H)+

Example 247

4-[(4-{[4-(Benzyloxy)-2-butynyl]oxy}phenyl)sulfonyl]-N-hydroxy-2,2-dimethyl-3-thiomorpholine carboxamide Step 1

To a suspension of 1.4 g (34.0 mmol) of 60% sodium hydride in mineral oil in 40 mL of DMF was added 3.44 g (40 mmol) of 2-butyne-1,4-diol and the reaction was stirred at room temperature for 3h. Then 4.04 mL (34.0 mmol) of benzyl bromide was added and the reaction was stirred for 18h. The reaction was quenched with water and extracted with ether. The organics were washed with brine, dried over MgSO$_4$, filtered and concentrated in vacuo. The residue was chromatographed on silica gel eluting with ethyl acetate-:hexanes (1:9) to provide 2.013 g (34%) of the desired product, 4-(benzyloxy)-2-butyn-1-ol, as a colorless oil. CI Mass Spec: 159.1 (M−water+H)+ and 2.47 g (27%) of 1-({[4-(benzyloxy)-2-butynyl]oxy}methyl)benzene as a colorless oil. EI Mass spec: 266.1 (M)+

Step 2

According to the procedure of Step 4 of Example 243, Mitsunobu coupling of 0.345 g (1.0 mmol) of 4-(4-hydroxy-benzenesulfonyl}2,2-dimethyl-thiomorpholine3-carboxylic acid methyl ester and 0.211 g (1.2 mmol) of -(benzyloxy)-2-butyn-1-ol provided 0.211 g (42%) of methyl 4-[(4-{[(benzyloxy)-2-butynyl]oxy)phenyl}-sulfonyl]-2,2-dimethyl-3- thiomorpholine carboxylate as a pale yellow oil. Electrospray Mass Spec: 504.2 (M+H)+

Step 3

According to the procedure of Step 5 of Example 243, 0.2 g (0.397 mmol) of methyl 4-[(4-{[4-(benzyloxy)-2-butynyl]oxy)phenyl}sulfonyl]-2,2-dimethyl-3-thiomorpholine carboxylate provided 0.135g (65%) 4-[(4-{[4-(benzyloxy)-2-butynyl]oxy]phenyl}sulfonyl]-2,2-dimethyl-3-thiomorpholine carboxylate as white solid. Electrospray Mass Spec: 490.1 (N+H)+

Step 4

According to the procedure of Step 6 of Example 243, 0.12 g (0.245 mmol) of 4-[(4-{[4-(benzyloxy)-2-butynyl]oxy}phenylsulonyl]-2,2-dimethyl-3-thiomorpholine carboxylate provided 0.03 g (25%) of 4-[(4-{[4-(benzyloxy)-2-butynyl]oxy}-phenyl)sulfonyl]-N-hydroxy-2,2-dimethyl-3- thiomorpholine carboxamide as a beige solid. Electrospray Mass Spec: 505.2 (M+H)+

Example 248

N-Hydroxy-2,2-dimethyl-4-[(4-{[6-(tetrahydro-2H-pyran-2-yloxy)2-hexynyl]oxy}phenyl)sulfonyl -3-thiomorpholine carboxamide Step 1

To a solution of 1.86 mL (0.02 mol) of 4-pentyn-1-ol and 4.56 mL (0.05 mol) of 3,4-dihydro-2H-pyran in 60 mL of dichloromethane at 0° C. was added 0.038 g (0.2 mmol) of p-toluenesulfonic acid monohydrate. The reaction was stirred at room temperature for 2.5h, then washed with water, saturated solution of $NaHCO_3$, brine, dried over MgSO4, filtered and concentrated in vacuo. The residue was kugelrohr distilled to provide 3.4 g (100%) of the THP-ether of 4-pentyn-1-ol as a colorless liquid. According to the procedure of Step 1 of Example 243, 3.24g (19.26 mmol) of this ether provided 3.51 g (92%) of 6-(tetrahydro-2H-pyran-2-yloxy)-2-hexyn-1-ol as a pale yellow oil. CI Mass Spec: 199.2 $(M+H)^+$ Step 2

According to the procedure of Step 4 of Example 243, Mitsunobu coupling of 3.4 g (9.842 mmol) of 4-(4-hydroxy-benzenesulfonyl)-2,2-dimethyl-thiomorpholine-3-carboxylic acid methyl ester and 2.34 g (11.81 mmol) of 6-(tetrahydro-2H-pyran-2-yloxy)-2-hexyn-1-ol provided 3.33g (64%) of methyl-2,2-dimethyl-4-[(4-{[6-(tetrahydro-2H-pyran-2-yloxy)-2-hexynyl]oxy}phenyl)sulfonyl]-3-thiomorpholine carboxylate as a colorless oil. Electrospray Mass Spec: 526.3 $(M+H)^+$ Step 3

According to the procedure of Step 5 of Example 243, 0.21 g (0.4 mmol) of methyl-2,2-dimethyl-4-[(4-{[6-tetrahydro-2H-pyran-2-yloxy)-2-hexynyl]oxy}phenyl)-sulfonyl]-3-thiomorpholine carboxylate provided 0.163 g (80%) of 2,2-dimethyl4-[(4-{[6-(tetrahydro-2H-pyran-2-yloxy)-2-hexynyl]oxy}phenyl)sulfonyl]-3-thiomorpholine carboxylic acid as a pale yellow oil. Electrospray Mass Spec: 510.2 $(M-H)^-$ Step 4

According to the procedure of Step 6 of Example 243, 0.231 g (0.45 mmol) of 2,2 -dimethyl4 -[(4 -{[6 -(tetrahydro-2 H-pyran-2 -yloxy)-2 -hexynyl]oxy}phenyl)-sulfonyl]-3 -thiomorpholine carboxylic acid provided 0.082 g (35%) of N-hydroxy-2,2 -dimethyl4-[(4 -{[6 -(tetrahydro-2 H-pyran-2 -yloxy)-2 -hexynyl]oxy}phenyl) sulfonyl]-3 -thiomorpholine carboxamide as a beige solid. Electrospray Mass Spec: 527.3 $(M+H)^+$ Example 249

N-Hydroxy-4-({4-[(6-hydroxy-2-hexynyl)oxy] phenyl}sulfonyl)-2,2-dimethyl-3-thiomorpholine carboxamide According to the procedure of Step 1 of Example 245, 0.078 g (0.15 mmol) of N-hydroxy-2,2-dimethyl-4-[(4-{[6-(tetrahydro-2 H-pyran-2 -yloxy)-2-hexynyl]oxy}-phenyl) sulfonyl]-3-thiomorpholine carboxamide provided 0.048 g (74%) of N-hydroxy-4-({4-[(6-hydroxy-2-hexynyl)oxy] phenyl}sulfonyl)-2,2-dimethyl-3-thiomorpholine carboxamide as a beige solid Electrospray Mass Spec: 443.2 $(M+H)^+$ Example 250 tert-Butyl-14-({(3S)-[(hydroxyamino)carbonyl]-2,2-dimethylthiomorpholinyl}sulfonyl)phenoxyl-4-hexynylcarbamate According to the procedures of Steps 1–4 of Example 245, methyl-2,2-dimethyl4-1(4-{[6-(tetrahydro-2H-pyran-2-yloxy)-2-hexynyl]oxy}phenyl)sulfonyl]-3-thiomorpholinecarboxylate (from Example 248 ) provided methyl-4-{[4-({6-[(tert-butoxycarbonyl)amino]-2-hexynyl}oxyphenyl]sulfonyl}-2,2-dimethyl-3-thiomorpholin ecarboxylate as a colorless oil. Electrospray Mass Spec: 541.3(M+H)+

A solution of 0.764 g (1.41 mmol) of methyl4-{[4-({6-[(tert-butoxycarbonyl)amino]-2-hexynyl}oxy)phenyl] sulfonyl}-2,2-dimethyl-3-thiomorpholinecarboxylate and 3.77 g (28.2 mmol) of lithium iodide in 30 mL of ethyl acetate was heated to reflux for 18h. The resulting reaction was acidified, washed with water, an aqueous solution of $Na_2S_2O_3$, brine, dried over $MgSO_4$, filtered and concentrated in vacuo. The residue was chromatographed on silica gel eluting with 0.5% methanol/dichloromethane to provide 0.417 g (56%) of 4-{[4-({6-[(tert-butoxycarbonyl)amino]-2-hexynyl}oxy)phenyl]sulfonyl}-2,2-dimethyl-3-thiomorpholine carboxylic acid as a white solid. Electrospray Mass Spec: 527.2$(M+H)^+$ According to the procedure of Step 6 of Example 243, 0.4 g (0.76 mmol) of 4-{[4-({6-[(tert-butoxycarbonyl)amino]-2-hexynyl}oxy)phenyl]sulfonyl}-2,2-dimethyl-3-thiomorpholinecarboxylic acid provided 0.162 g (39%) of tert-butyl 6-[4-({(3 S)-3-[(hydroxyamino)carbonyl]-2,2-dimethylthiomorpholinyl}sulfonyl)phenoxy]4-hexynylcarbamate as a cream solid. Electrospray Mass Spec: 541.9 (M+H)+

Example 251

(3S)-4-({4-[(6-Amino-2-hexynyl)oxy] phenyl}sulfonyl)-N-hydroxy2,2-dimethyl-3-thiomorpholine carboxamide Hydrogen chloride gas was bubbled into a solution of 0.104 g (0.192 mmol) of tert-butyl 6-[4({(3S)-3-[(hydroxyamino)carbonyl]-2,2-dimethylthiomorpholinyl}sulfonyl)phenoxy]-4-hexynylcarbamate in 6 mL of dichloromethane and 2 mL of methanol for 5 min, and the reaction was stoppered and let stand for 1h and then concentrated in vacuo. The residue was triturated with ether to provide 0.092 g (100%) of (3S)4({4 [(6-amino-2-hexynyl)oxy]phenyl}sulfonyl)N-hydroxy-2,2-dimethyl-3-thiomorpholine carboxamide as a cream solid. Electrospray Mass Spec: 442.1$(N+H)^+$ Example 252 tert-Butyl 7-[4-({(3S)-3-[(hydroxyamino)carbonyl]-2,2-dimethylthiomorpholinyl}sulfonyl)phenoxy]-5heptynylcarbamate According to the procedures of Steps 1 and 2 of Example 248, starting with 5-hexyn-1-ol, methyl 2,2-dimethyl4-[(4-{[7-(tetrahydro-2H-pyran-2-yloxy2-heptynyl]-oxy}phenyl) sulfonyl]-3-thiomorpholine carboxylate was obtained as a pale yellow oil. Electrospray Mass Spec: 562.1 $M+Na)^+$ The tetrahydropyranyl ether of methyl 2,2-dimethyl-4-[(4-{[7-(tetrahydro-2H-pyran-2-yloxy)-2-heptynyl]oxy}phenyl)sulfonyl]-3-thiomorpholinecarboxylate was removed according to the procedure of Step 1 of Example 245 to give methyl 4-({4-[(7-hydroxy-2-heptynyl)oxy] phenyl}sulfonyl)-2,2-dimethyl-3-thiomorpholine carboxylate as a colorless oil. Electrospray Mass Spec: 456.1(M+H)+

According to the procedures of Steps 2–4 of Example 245, methyl 4-({4-[(7-hydroxy-2-heptynyl}oxyphenyl)sulfonyl}-2,2-dimethyl-3-thiomorpholinecarboxylate was converted into the corresponding BOC-protected carbamate, methyl (3 S)4-{[4 ({7-[(tert-butoxycarbonyl)amino]-2-heptynyl) oxy)phenyl]sulfonyl}-2,2-dimethyl-3-thiomorpholine carboxylate obtained as a colorless oil. Electrospray Mass Spec: 555.1 (M+H)$^+$ The methyl ester of methyl (3 S}[4 {[({7-[(tert-butoxycarbonyl)amino]-2-heptynyl}oxy)phenyl]sulfonyl}-2,2-dimethyl-3-thiomorpholine carboxylate was converted into the analogous carboxylic acid using lithium iodide according to the procedure of Example 250 to provide (3 S)-4-{[4-{7-[(tert-butoxycarbonyl)amino]-2-heptynyl)oxy)phenyl]sulfonyl}-2,2- dimethyl-3-thiomorpholine carboxylic acid as a white solid Electrospray Mass Spec: 541.2(M+H)$^+$ According to the procedure of Step 6 of Example 243, 0.3 15 g (0.582 mmol) of (3 S)-4-{[4-({7-[(tert-butoxycarbonyl)amino]-2-heptynyl}oxy)phenyl]sulfonyl)-2,2-dimethyl-3-thiomorpholine carboxylic acid was converted into 0.113 g (36%) of the corresponding hydroxamic acid, tert-butyl 7-[4({(3 S)-3-[(hydroxyamino)carbonyl]-2,2-dimethylthiomorpholinyl)sulfonyl}phenoxy]-5-heptynylcarbamate obtained as a white solid. Electrospray Mass Spec: 556.1(M+H)$^+$ Example 253

(3S)-4-({4-1(7-Amino-2-heptynyloxylphenyl}sulfonyl)-N-hydroxy-2,2-dimethyl-3- thiomorpholine carboxamide According to the procedure of Example 251, 0.106 g (0.19 mmol) of tert-butyl 7-[4-({(3 S)-3-[(hydroxyamino)carbonyl]-2,2-dimethylthiomorpholinyl}-sulfonyl)phenoxy]-5-heptynylcarbamate provided 0.091 g (98%) of (3 S)4-({4-[(7-amino-2-heptynyl)oxy]phenyl}sulfonyl)-N-hydroxy-2,2-dimethyl-3-thiomorpholine carboxamide as a cream solid. Electrospray Mass Spec: 456.2 (M+H)$^+$ Example 254

(3S)-N-Hydroxy-2,2-dimethyl-4-({4-1(3-phenyl-2-propynyl)oxy]phenyl)sulfonyl)-3- thiomorpholine carboxamide Step 1

According to the procedure of Step 2 of Example 248, Mitsunobu coupling of 0.345 g (1.0 mmol) of 4-(4-hydroxy-benzenesulfonyl}2,2-dimethyl-thiomorpholine-3-carboxylic acid methyl ester and 0.159 g (1.2 mmol) of 3-phenyl-2-propyn-1-ol provided 0.254 g (55%) of methyl (3S)-2,2-dimethyl4-({4-[(3-phenyl-2-propynyl)-oxy] phenyl)sulfonyl)-3- thiomorpholine carboxylate as a pale yellow solid. Electrospray Mass Spec: 460.1(M+H)$^+$ Step 2

According to the procedure of Example 250, lithium iodide mediated ester cleavage of 0.282 g (0.61 mmol) of methyl (3S)-2,2-dimethyl-4-({4-[(3-phenyl-2-propynyl)oxy]phenyl)sulfonyl)3- thiomorpholinecarboxylate provided 0.215 g (79%) of (3S)-2,2-dimethyl4-({4-[(3-phenyl-2-propynyl)oxy]phenylsulfonyl)-3-thiomorpholine carboxylic acid as a white solid. Electrospray Mass Spec: 446.0 (M+H)$^+$ Step 3

According to the procedure of Example 9, 0.195 g (0.438 mmol) of (3 S)-2,2-dimethyl-4-({4-[(3-phenyl-2-propynyl)oxy]phenyl}sulfonyl)-3-thiomorpholine-carboxylic acid provided 0.159 g (79%) of (3S)-N-hydroxy-2,2-dimethyl-4-({4-[(3-phenyl-2-propynyl)oxy]phenyl}sulfonyl)-3- thiomorpholine carboxamide as an off white solid. Electrospray Mass Spec: 460.9(M+H)$^+$ Example 255

(3S)-4-{[4-(2-Butynyloxy)phenyl]sulfonyl}-N-hydroxy-2,2-dimethyl-3-thiomorpholine carboxamide 1(S)-oxide Example 266

(3S)-4-{14-(2-Butynyloxy)phenyl]sulfonyl}-N-hydroxy-2,2-dimethyl-3-thiomorpholine carboxamide 1(R)oxide To a 0° C. solution of 2.40 g (6.03 mmol) of the product of Example 235,(3 S)-4-({[4(2-butynyloxy)phenyl]sulfonyl2,2-dimethyl-thiomorpholine-3-carboxylic acid hydroxyamide, in 180 mL of dichloromethane and 36 mL of methanol was added 0.885 g (5.126 mmol) of m-chloroperbenzoic acid in four equal portions, as a solid. Thirty minutes after all of the m-chloroperbenzoic acid had been added, the reaction was diluted with dichloromethane and washed with saturated sodium bicarbonate solution. The organics were dried over sodium sulfate, filtered and concentrated in vacuo. The residue was cbromatographed on silica gel eluting with a gradient of chloroform/methanol (100:1 ) to (10:1 ) to provide 1.48 g of a high $R_f$ sulfoxide diastereomer and 0.22 g of a low $R_f$ sulfoxide diastereomer, both white solids, arbitrarily assigned as (3S)-4-{[4-(2-butynyloxy)phenyl]sulfonyl}-N-hydroxy-2,2-dimethyl-3-thiomorpholine carboxamide l(S)-oxide and (3S)-4-{[4-(2-butynyloxy)phenyl]sulfonyl}-N-hydroxy-2,2-dimethyl-3-thiomorpholine carboxamide l(R)-oxide respectively. Electrospray Mass Spec 415.3 (M+H)$^+$ Example 257

(3S({1[(2-Butynyloxy)phenyl]sulfonyl}-N-hydroxy-2,2-dimethyl-3-thiomorpholine carboxamide 1,1-dioxide To a 0° suspension of 0.200 g (0.503 mmol) of the product of Example 235, (3S)-4-({[4-(2-butynyloxy)phenyl]sulfonyl)-2,2-dimethyl-thiomorpholine-3-carboxylic acid hydroxyamide, in 5 mL of chloroform was added 0.32 mL (43331.508 mmol) of a 32% solution of peracetic acid. The reaction became homogeneous and was allowed to warm to room temperature and stirred for an additional 3h. An additional 0.3 mL of 32% peracetic acid was added and the reaction was stirred overnight at room temperature and then concentrated in vacuo. The residue was diluted with ethyl acetate and the organics were washed with water and saturated sodium bicarbonate solution, dried over sodium sulfate, filtered and concentrated. The residue was chromatographed on silica gel eluting with chloroform/methanol (100:1 ) to provide 0.138 g of (3 S)4-{[4(2-butynyloxy) phenyl]sulfonyl}-N-hydroxy-2,2-dimethyl-3- thiomorpholine carboxamide 1,1-dioxide as a brown solid. Electrospray Mass Spec 431.3 (M+H)+

Example 258

(3S-N-Hydroxy-2,2-dimethyl4-([4(2-propynyloxy) phenyl]sulfonyl)-3-thiomorpholine carboxamide Step 1

To a 0° suspension of 14.92 g (0.10 mmol) of D-penicillamine in 300 mL of dichloroethane and 2.0 mL of DMF was added 22.4 mL of DBU followed by 19.0 mL of trimethylsilyl chloride. The ice bath was removed and the reaction was stirred for 3h, after which an additional 29.9 mL of DBU was added. The reaction was stirred overnight at room temperature and then 10 mL of methanol was added and the reaction was stirred for 1h. The resulting white precipitate was filtered off, washed with 10 mL of methanol and dried in vacuo to provide 16 g of (3 S)-2,2-dimethyl-3-thiomorpholine carboxylic acid as a white solid.

Step 2

To a 0 ° suspension of 32 g (0.18 mol) of the above carboxylic acid in 365 mL of dioxane was added 36.6 mL of concentrated sulfuric acid over 10 minutes followed by 225 mL of isobutylene. The reaction was warmed to room temperature and stirred for 15h with a dry ice/acetone condenser. The reaction was then poured into a mixture of 1L of 2 M sodium bicarbonate solution and 400 mL of ethyl acetate. The organics were dried over sodium sulfate, filtered and concentrated to give 22 g of tert-butyl (3 S)-2,2-dimethyl-3-thiomorpholine carboxylate as a white solid. Electrospray Mass Spec 232.3(M+H)+

Step 3

To a suspension of 20.0 g (0.104 mol) of 4-hydroxybenzenesulfonyl chloride in 200 ml of chloroform was added 28.25 mL (0.114 mol) of bis(trimethylsilyl) acetamide and the reaction was stirred at room temperature for 1h, after which all of the solids have dissolved. To this mixture was added 20.0 g (0.087 mol) of tert-butyl (3S-2, 2-dimethyl-3-thiomorpholine carboxylate followed by 19.2 mL of 4-methylmorpholine and the reaction was sired overnight at room temperature. After the addition of 400 mL of methanol to the reaction, the resulting mixture was stirred overnight at room temperature and then concentrated in vacuo. The residue was diluted with ethyl acetate and the organics were washed with water and 5% HCl solution, dried over magnesium sulfate, filtered and concentrated in vacuo- The resulting white solid was washed with ether/ hexanes (1:2 ) and dried in vacuo to give 28.4 g (85%) of tert-butyl (3S)4-[(4hydroxyphenyl)sulfonyl]-2,2-dimethyl-3-thiomorpholine carboxylate as a white solid. Electrospray Mass Spec 386.5 (M–H)–.

Step 4

According to the procedure of Step 2 of Example 248, Mitsunobu coupling of 0.30 g (0.775 mmol) of tert-butyl (3S)4[(4-hydroxyphenyl)sulfonyl]-2,2-dimethyl-3-thiomorpholinecarboxylate and 0.054 mL (0.93 mmol) of propargyl alcohol gave 0.313 g of tert-butyl (3S-2,2-dimethyl4-{[4-(2-propynyloxy)phenyl]sulfonyl)-3-thiomorpholine carboxylate as a white solid. Electrospray Mass Spec 426.4 (M+H)+

Step 5

Through a solution of 0.271 g (0.638 mmol) of tert-butyl (3 S)-2,2-dimethyl4-{[4-(2-propynyloxy)phenyl]sulfonyl)-3-thiomorpholinecarboxylate in 10 mL of dichloromethane was bubbled hydrogen chloride gas for 10 minutes. The reaction was then stoppered and let sit overnight at room temperature. The solvent was evaporated to give 0.221 g of (3S-2,2-dimethyl-4-{[4-2-propynyloxy)phenyl]sulfonyl)-3-thiomorpholine carboxylic acid as a white solid. Electrospray Mass Spec 368.2 (M–H)–

Step 6

According to the procedure of Example 9, 0.196 g (0.531 mmol) of (3 S)-2,2-dimethyl-4-{[4-(2-propynyloxy)phenyl] sulfonyl}-3-thiomorpholinecarboxylic acid gave 0.192 g of the hydroxamic acid, (3S)-N-hydroxy-2,2-dimethyl4-{[4(2-propynyloxy)phenyl]sulfonyl)-3-thiomorpholine carboxamide as a white solid. Electrospray Mass Spec 385.1 (M+H)+

Example 259

(3S)-N-Hydroxy2,2-dimethyl-4-{[4-(2-pentynyloxy) phenyl]sulfonyl}-3-thiomorpholine carboxamide According to the procedure of Example 258, using 2-pentyn-1-ol in Step 4, (3S)-N-hydroxy-2,2-dimethyl-4-{ [4-(2-pentynyloxy)phenyl]sulfonyl}-3-thiomorpholine carboxamide was obtained as a white solid. Electrospray Mass Spec 413.2(M+H)+

Example 260

(3S)-N-Hydroxy-4-({4-[(4hydroxy-2-butynyl)oxy] phenyl}sulfonyl)-2,2-dimethyl-3-thiomorpholine carboxamide Step 1

According to the procedure of Step 2 of Example 248, Mitsunobu coupling of 2.5 g (6.46 mmol) of tert-butyl (3S)-4-[(4-hydroxyphenyl)sulfonyl]-2,2-dimethyl-3-thiomorpholinecarboxylate and 0.667 g (7.752 mmol) of 2-butyne-1,4-diol gave 1.42 g of tert-butyl (3 S)-4-({4-[(4-hydroxy-2-butynyl)oxy]phenyl)sulfonyl)-2,2-dimethyl-3-thiomorpholine carboxylate as a colorless oil.

Step 2

The alcohol (0.300 g, 0.662 mmol) was dissolved in 3 mL of acetic anhydride and 0.3 mL of pyridine. The reaction was stirred overnight at room temperature and then concentrated in vacuo. The residue was chromatographed on silica gel eluting with ethyl acetate/hexanes (1:3) to provide 0.279 g (85%) of tert-butyl(3 S)4-[(4-{[4-(acetyloxy)-2-butynyl] oxy}phenyl)sulfonyl]-2,2-dimethyl-3-thiomorpholine carboxylate as a colorless oil. Electrospray Mass Spec 498.1 (M+H)+

Step 3

Through a solution of 0.250 g (0.503 mmol) of tert-butyl(3 S)4-[(4-{[4-(acetyloxy)-2-butynyl]oxy}phenyl) sulfonyl]-2,2-dimethyl-3-thiomorpholine carboxylate in 10 mL of dichloromethane was bubbled hydrogen chloride gas for 10 minutes. The reaction was then stoppered and let sit overnight at room temperature The solvent was evaporated to give 0.192 g of (3S)-4-[(4-([4-(acetyloxy)-2-butynyl]oxy) phenyl)sulfonyl]-2,2 dimethyl-3-thiomorpholine carboxylic acid as a colorless oil. Electrospray Mass Spec 440.1 (M–H)–

Step 4

According to the procedure of Example 9, 0.150 g (0.340 mmol) of (3 S)-4-[(4-{[4-(acetyloxy)-2-butynyl]oxy) phenyl)sulfonyl]-2,2-dimethyl-3-thiomorpholine carboxylic acid gave 0.127 g of the hydroxamic acid, (3 S)-N-hydroxy4-({4 [(4-hydroxy-2-butynyl)oxy]phenyl)sulfonyl)-2,2-dimethyl-3-thiomorpholine carboxamide as a white solid. Electrospray Mass Spec 415.2 (M+H)+

Example 261

4-[4-({(3S)-3-[(Hydroxyamino)carbonyl]-2,2-dimethylthiomorpholinyl}sulfonyl)phenoxy]-2-butynyl acetate According to the procedure of Example 25, 0.196 g (0.444 mmol) of (3 S)-4-[(4-{ [4(acetyloxy)-2-butynyl]oxyphenyl) sulfonyl]-2,2-dimethyl-3-thiomorpholine carboxylic acid from Step 3 of Example 260 gave 0.086 g of 4-[4-{(3 S)-3-[(hydroxyamino)carbonyl]-2,2 dimethylthiomorpholinyl)sulfonyl)phenoxy]-2-butynyl acetate as a tan amorphous solid. Electrospray Mass Spec 457.1 (M+H)+

Example 262

(3S)-N-Hydroxy-4-({4-[(6-hydroxy-2,4-hexadiynyl) oxy]phenyl}sulfonyl)-2,2-dimethyl-3-thiomorpholine carboxamide According to the procedures for Example 260, using 2,4-hexadiyn-1,6-diol in Step 1,(3S)-N-hydroxy-4-({4-[(6-hydroxy-2,4-hexadiynyl)oxy]phenyl}sulfonyl)-2,2-dimethyl-3-thiomorpholine carboxamide was obtained as a tan solid. Electrospray Mass Spec 439.1 (M+H)+

Example 263

(3S)-N-Hydroxy-2,2-dimethyl-4-{[4-(2,4-pentadiynyloxy)phenyl]sulfonyl}-3-thiomorpholine carboxamide According to the procedures of Steps 4-6 of Example 258, using 2,4-pentadiyn-1-ol (EP 478,195) in Step 4 (3S)-N-hydroxy-2,2-dimethyl4-{[4(2,4-pentadiynyloxy)phenyl] sulfonyl}-3-thiomorpholine carboxamide was obtained as a white solid. Electrospray Mass Spec 408.9 (M+H)+

Example 264

(3S)-4-({4-[(4-Fluoro-2-butynyl)oxy]phenyl}sulfonyl)-N-hydroxy-2,2-dimethyl-3-thiomorpholine carboxamide To a 0 ° solution of 0.300 g (0.659 mmol) of tert-butyl (3S)-4-({4-[(4-hydroxy-2-butynyl)oxy]phenyl}sulfonyl)-2,2-dimethyl-3-thiomorpholine carboxylate from Step 1 of Example 260 in 75 mL of dichloromethane was added 0.17 mL of (diethylamino)sulfur trifluoride and the reaction was stirred overnight at room temperature. The reaction was quenched with brine and the organic layer was separated and dried over magnesium sulfate, filtered and concentrated in vacuo. The residue was chromatographed on silica gel eluting with ethyl acetate/hexanes (1:10) to give the propargylic fluoride as a brown oil. Electrospray Mass Spec 457.8 (M+H)+

According to the procedures of Steps 3 and 4 of Example 260 the tert-butyl ester was hydrolyzed to the carboxylic acid and then converted into the hydroxamic acid, (3S)-4-({4-[(4-fluoro-2-butynyl)oxy]phenyl}sufonyl)-N-hydroxy-2,2-dimethyl-3-thiomorpholine carboxamide obtained as a light brown solid. Electrospray Mass Spec 417.3 (M+H)+

Example 265

4-({4-[(4-Amino-2-butynyl)oxy]phenyl}sulfonyl)-N-hydroxy-2,2-dimethyl-3- thiomorpholine carboxamide According to the procedure of Step 2 of Example 248, Mitsunobu coupling of 0.10 g (0.288 mmoL) of methyl (3S)-4-[(4-hydroxyphenyl)sulfonyl]-2,2-dimethyl-3-thiomorpholinecarboxylate and 0.031 g (0.363 mmol) of 2-butyne-1,4-diol gave 0.078 g of methyl (3 S)-4-({4-[(4-hydroxy-2-butynyloxy]phenyl)sulfonyl)-2,2-dimethyl-3-thiomorpholine carboxylate as a colorless oil.

Step 2

To a solution of 1.59 g (3.85 mmol) of methyl (3 S)-4-({4-[(4-hydroxy-2-butynyl)oxy]phenyl}sulfonyl)2,2-dimethyl-3-thiomorpholine carboxylate in 50 mL of dichloromethane was added 1.34 mL (9.63 mmol) of triethylamine followed by 0.36 mL (4.62 mmol) of methanesulfonyl chloride. The reaction was stirred at room temperature for 3h and then diluted with ether. The organics were washed with 5% HCl solution and water, dried over magnesium sulfate, filtered and concentrated. The residue was used in the next step without purification.

Step 3

To a solution of the above mesylate (1.06 g, 2.16 mmol) in 12 mL of DMF was added 0.168 g (2.59 mmol) of sodium azide. The reaction was stirred at room temperature for 12h and then diluted with ethyl acetate. The organics were washed with water, dried over magnesium sulfate, filtered and concentrated in vacuo. The residue was chromatographed on silica gel eluting with ethyl acetate/hexanes (1:3) to give 0.823 g of the azide, methyl (3S)-4-({-[(4-azido-2-butynyl)oxy]phenyl}sulfonyl)-2,2-dimethyl-3-thiomorpholine carboxylate.

Step 4

To a solution of 0.811 g (1.852 mmol) of the azide in 13 mL of ether and 3.5 mL of THF was added 0.692 mL (2.777 mmol) of tributylphosphine and the reaction was stirred for 4h. The reaction was then cooled to −40 ° C. and a solution of 0.647 g (2.962 mmol) of di-tert-butyl dicarbonate in 9 mL of ether was added dropwise. The reaction was stirred at 40 ° C. for 1h and then saturated sodium bicarbonate solution was added (10 mL) and the reaction was warmed to room temperature and stirred overnight. The organics were washed with water, dried over magnesium sulfate, filtered and concentrated The residue was chromatographed on silica gel eluting with ethyl acetate/hexanes (1:3) to give 0.301 g of the NH-carbamate methyl ester, methyl 4-{[4-({4 [(tert-butoxycarbonyl)amino]-2-butynyl)oxy)phenyl] sulfonyl)-2,2-dimethyl-3-thiomorpholine carboxylate.

Step 5

According to the procedure of Example 11 0.300 g (0.586 mmol) of the NH-carbamate methyl ester gave 0.149 g of the NH-carbamate carboxylic acid, 4-{[4-{4-[(tert-butoxycarbonyl)amino]-2-butynyl}oxy)phenyl]sulfonyl)-2, 2-dimethyl-3-thiomorpholine carboxylic acid which was subsequently converted into 0.057 g of the hydroxamic acid following the procedure of Example 25. Bubbling hydrogen chloride gas through a dichloromethane solution of the NH-carbamate hydroxamic acid then provided 0.057 g of 4-({4-[(4-amino2-butynyl)oxyphenyl}sulfonyl)-N-hydroxy-2,2-dimethyl-3-thiomorpholine carboxamide hydrochloride. Electrospray Mass Spec 414.4 (M+H)+

Example 266 tert-Butyl 4-[4-({3-(hydroxyamino)carbonyl]-2,2-dimethyl-4-thiomorpholinyl]sulfonyl)phenoxyl-2-butynylcarbamate According to the procedure of Example 25, 0.106 g (0.213 mmol) of 4-{[4-({4-[(tert-butoxycarbonyl)amino]-2-butynyl}oxy)phenyl]sulfonyl}-2,2-dimethyl-3-thiomorpholine carboxylic acid provided 0.052 g of tert-butyl 4-[4-({3-[(hydroxyamino)carbonyl]-2,2-dimethylthiomorpholinyl}sulfonyl)phenoxy]-2-butynylcarbamate as a white solid. Electrospray Mass Spec 514.1 (M+H)+

Example 267 tert-butyl 4-[4-({3-[(hydroxyamino)carbonyl]-2,2-dimethyl-4-thiomorpholinyl)sulfonyl)phenoxy]-2-butynyl(methyl)carbamate Step 1

To a solution of 2.714 g (0.01 mol) of triphenylphosphine in 21 mL of THF and 0.41 mL of pyridine was added 2.137 g (5.174 mmol) of methyl (3S)-4-({4-[(4-hydroxy-2-butynyl)oxy]phenyl}sulfonyl)-2,2-dimethyl-3-thiomorpholine carboxylate (from Step 1 of Example 265) followed by 1.716 g (5.174 mmol) of carbon tetrabromide. The reaction was stirred at room temperature for 4h and then concentrated in vacuo. The residue was chromatographed on silica gel eluting with ethyl acetate/hexanes (1:3) to give 1.523 g (62%) of the propargylic bromide.

Step 2

To a solution of 0.50 g (1.050 mmol) of the propargylic bromide in 5 mL of THF was added 5.25 mL (0.010 mmol) of a 2.0M solution of methylamine in THF followed by 0.020 g of tetrabutylammonium iodide. The reaction was stirred at room temperature for 4h and then diluted with ether. The organics were washed with water, dried over sodium sulfate, filtered and concentrated. The residue chromatographed on silica gel eluting first with ethyl acetate then with chloroform/methanol (9:1 ) to give 0.365 g (82%) of the methylamine, methyl 2,2-dimethyl-4-[(4-{[4-(methylamino)2-butynyl]oxy)phenyl)sulfonyl]-3-thiomorpholinecarboxylate as a colorless oil. Electrospray Mass Spec 427.3(M+H)+

Step 3

To a solution of 0.331 g (0.777 mmol) of methyl 2,2-dimethyl-4-[(4-{[4-(methylamino)-2-butynyl]oxy}phenyl)sulfonyl]-3-thiomorpholinecarboxylate in 5 mL of THF was added 9 mg of 4-dimethylaminopyridine followed by 0. 186 g (0.855 mmol) of di-tert-butyl dicarbonate. The reaction was stirred for 4h and then concentrated in vacuo. The residue chromatographed on silica gel eluting first with ethyl acetate/hexanes (1:10 ) to (1:3 ) to give 0.344 g of methyl 4-{[4-({4-[(tert-butoxycarbonyl)(methyl)amino]-2-butynyl}oxy)phenylsulfonyl}-2,2-dimethyl-3-thiomorpholinecarboxylate as a pale yellow oil. Electrospray Mass Spec 527.6

Step 4

According to the procedures of Example 11 and Example 25, 0.312 g (0.593 mmol) of methyl 4-{[4-({4-[(tert-butoxycarbonyl)(methyl)amino]-2-butynyl}oxy}phenyl]sulfonyl)-2,2-dimethyl-3-thiomorpholinecarboxylate was converted into 0.049 g of the hydroxamic acid, tert-butyl 4-[4-{3-[(hydroxyamino)carbonyl]-2,2-dimethyl-4-thiomorpholinyl)sulfonyl)phenoxy]-2-butynyl(methyl)carbamate obtained as a white solid. Electrospray Mass Spec 528.1(M+H)+

Example 268

7-[4-({(3S)-3-[(Hydroxyamino)carbonyl]-2,2-dimethylthiomorpholinyl}sulfonyl)phenoxy]-5-heptynyl acetate Step 1

According to the procedures of Step I of Example 248, starting with 5-hexyn-1-ol provided 6-(tetrahydro-2H-pyran-2-yloxy)-2-heptyn-1-ol.

According to the procedure of Step 4 of Example 243, Mitsunobu coupling of 0.775 g (2.0 mmol) of tert-butyl (3S)-4[(4-hydroxyphenyl)sulfonyl]-2,2-dimethyl-3-thiomorpholine carboxylate (Step 3, Example 258 ) and 0.510 g (2.4 mmol) of 6-(tetrahydro-2H-pyran-2-yloxy)-2-heptyn-1-ol provided 0.975 g (84%) of tert-butyl (3S)-2,2-dimethyl-4-[(4-{[7-(tetrahydro-2H-pyran-2-yloxy)-2-heptynyloxyphenyl)-sulfonyl]-3-thiomorpholinecarboxylate as a colorless oil. Electrospray Mass Spec: 604.2(M+Na)+

Step 2

According to the procedure of Step 1 of Example 245 the tetrahydropyranyl ether of 0.659 g (1.13 mmol) of tert-butyl (3 S-2,2-dimethyl4-[(4-{[7-tetrahydro-2H-pyran-2-yloxy)-2-heptynyl]oxy}phenyl)sulfonyl]-3-thiomorpholecarboxylate was cleaved to provide 0.472 g (84%) of tert-butyl (3S)-4-({4-[(7-hydroxy-2-heptynyl)oxyphenyl}sulfonyl)2,2-dethyl-3-thiomorpholinecarboxylate as a colorless oil. Electrospray Mass Spec: 498.3(M+H)+

Step 3

A mixture of 0.452 g (0.908 mmol) of tert-butyl (3S)-4-({4-[(7-hydroxy-2-heptynyl)oxy]phenyl}sulfonyl)-2,2-dimethyl-3-thiomorpholinecarboxylate, 2.6 mL (27 mmol) of acetic anhydride and 0.22 mL (2.7 mmol) of pyridine was stirred at room temperature for 6h and concentrated in vacuo. The residue was chromatographed on silica gel eluting with ethyl acetate:hexanes (1:5 ) to provide 0.476 g (97%) of tert-butyl (3S)4-[(4-{[7-(acetyloxy)2-heptynyl]oxy}phenyl)sulfonyl]-2,2-dimethyl-3-thiomorpholinecarboxylate as a colorless oil. Electrospray Mass Spec: 540.0 (M+H)+

Step4

According to the procedure of Example 251, lithium iodide mediated ester cleavage of 0.456 g (0.845 mmol) of tert-butyl (3S)-4-[(4-{[7-acetyloxy)-2-heptynyl]- oxy}phenyl)sulfonyl]-2,2-dimethyl-3-thiomorpholinecarboxylate provided 0.409 g (100%) of (3S)-4-[(4-{[7-(acetyloxy}2-heptynyl]oxy}phenyl)sulfonyl]-2,2-dimethyl-3- thiomorpholinecarboxylic acid as a colorless oil. Electrospray Mass Spec: 446.0 (M+H)+

Step 5

According to the procedure of Example 9, 0.192 g (0.398 mmol) of (3S)-4-[(4-{[7-(acetyloxy)-2-heptynyl]oxy}phenyl)sulfonyl]-2,2-dimethyl-3- thiomorpholinecarboxylic acid provided 0.125 g (63%) of $^7$-[$^4$-{(3S)-3-[(hydroxyamino)carbonyl]-2,2-dimethylthiomorpholinyl)sulfonyl)phenoxy]-5-heptynyl acetate as a white solid. Electrospray Mass Spec: 499.0(M+H)+

Example 269

(3S)-N-Hydroxy(4-1(7-hydroxy-2-heptynyl)oxy]phenyl}sulfonyl)-2,2-dimethyl-3 thiomorpholinecarboxamide A mixture of 0.152 g (0.305 mmol) of 7-[4-({(3S)-3-[(hydroxyamino)-carbonyl]-2,2-dimethylthiomorpholinyl}sulfonyl)phenoxy]-5-heptynyl acetate, 3 mL of aqueous ammonium hydroxide and 3 mL of methanol was stirred at room temperature for 18h and concentrated in vacuo. The residue was chromatographed on silica gel eluting with 1.5% methanol/dichloromethane to provide 0.09 g (65%) of (3S)-N-hydroxy4-((4-[(7-hydroxy-2-heptynyl)oxy]phenyl}sulfonyl)-2,2-dimethyl-3-thiomorpholinecarboxamide as a white solid. Electrospray Mass Spec: 457.0(M+H)+

Example 270

(3S,5S)-4-14(2-Butynyloxy)phenyl)sulfonyl}-N-hydroxy-2,2,5-trimethyl-3-thiomorpholinecarboxamide Step 1

To a stored solution of 0.445 g (2.4 mmol) of 75% 1-bromo-2-propanol in 2 mL of DMF was added a solution of 0.4 g (2.0 mmol) of D-penicillamine hydrochloride and 0.6 mL (4.0 mmol) of 1,8-diazabicyclo[5.4.0 ]undec-7-ene in 4.0 mL of DMF over 15 minutes. The reaction was stirred for 3h and 0.489 g (2.0 mmol) of 4-but-2-ynyloxybenzenesulfonyl chloride and 0.3 mL (2.0 mmol) of 1,8 diazabicyclo[5.4.0]undec-7-ene were added. The reaction was stirred for 18h and diluted with ethyl acetate. The organics were washed with water and brine, dried over MgSO4, filtered and concentrated in vacuo. The residue was chromatographed on silica gel eluting with ethyl acetate-:hexanes (1:5) to provide 0.248 g (29%) of the hydroxy-acid sulfonamide as a colorless oil. Electrospray Mass Spec: 430.0 (M+H)$^+$ Step 2

To a solution of 0.07 g (0.163 mmol) of the above hydroxy-acid sulfonamide in 1.6 mL of THF was added 0.051 g (0.195 mmol) of triphenyphosphine, followed by 0.031 mL (0.195 mmol) of diethylazodicaboxylate. The reaction was stirred at room temperature for 18h and diluted with ethyl acetate. The organics were washed with water and brine, dried over MgSO4, filtered and concentrated in vacuo. The residue was chromatographed by preparative TLC eluting three times with ethyl acetatehexanes (1:5) to provide 0.027 g (39%) of methyl (3S,5S)-4-{[4-(2-butynyloxy)phenyl]sulfonyl}-2,2,5-trimethyl-3- thiomorpholinecarboxylate as a colorless oil [Electrospray Mass Spec: 412.2 (M+H)+] and 0.021 g (31%) of methyl (3S,5R)-4-{[4-(2-butynyloxy)phenyl]sulfonyl}-2,2,5-trimethyl-3-thiomorpholinecarboxylate as a colorless oil [Electrospray Mass Spec: 412.2 M+H)$^+$]

Step 3

Lithium iodide mediated ester cleavage of 0.384 g (0.933 mmol) of methyl (3S,5S)4-{[4-(2-butynyloxy)phenyl]sulfonyl}-2,2,5-trimethyl-3-thiomorpholinecarboxylate according to the procedure of Example 250, provided 0.356 g (96%) of (3S,5S)4-{[4-(2-butynyloxy]phenyl]sulfonyl}-2,2,5-trimethyl-3-thiomorpholinecarboxylic acid as a white solid. Electrospray Mass Spec: 397.9 (M+H)$^+$ Step 4

According to the procedure of Example 9, 0.330 g (0.829 mmol) of (3S,5S)-4-{[4-(2-butynyloxy)phenyl]sulfonyl}-2,2,5-trimethyl-3-thiomorpholinecarboxylic acid provided 0.23 g (67%) of (3S,5S)-4-{[4-(2-butynyloxy)phenyl]sulfonyl}-N-hydroxy-2,2,5-trimethyl-3-thiomorpholinecarboxamide as a white solid. Electrospray Mass Spec: 413.0(+H)$^+$ Example 271

(3S,5R)-4-{[4-(2-Butynyloxy)phenyl]sulfonyl}-N-hydroxy-2,2,5-trimethyl-3-thiomorpholinecarboxamide Step 1

Lithium iodide mediated ester cleavage of 0.335 g (0.814 mmol) of methyl (3S,5R)-4-{[4-(2-butynyloxy)phenyl]sulfonyl}-2,2,5-trimethyl-3-thiomorpholinecarboxylate according to the procedure of Example 250, provided 0.305 g (94%) of (3S,5R)-4-{[4-(2-butynyloxy)phenyl]sulfonyl}-2,2,5-trimethyl-3-thiomorpholinecarboxylic acid as a white solid. Electrospray Mass Spec: 398.0 (M+H)$^+$ Step 2

According to the procedure of Example 9, 0.28 g (0.707 mmol) of (3S,5R)-4-{[4-(2-butynyloxy)phenyl]sulfonyl}-2,2,5-trimethyl-3-thiomorpholinecarboxylic acid provided 0.16 g (55%) of (3S,5R)4-{[4-(2-butynyloxy)phenyl]sulfonyl}-N-hydroxy-2,2,5-trimethyl-3-thiomorpholinecarboxamide as a white solid. Electrospray Mass Spec: 413.2(M+H)+

Example 272

(3S,6S)-4-{[4-(2-Butynyloxy)phenyl]sulfonyl}-N-hydroxy-2,2,6-trimethyl-3-thiomorpholinecarboxamide Step 1

To a solution of 1.47 g (4.53 mmol) of 3,3'-dithiobis[D-valine], dimethyl ester bis hydrochloride in 25 mL of methylene chloride at 0 ° was added 2.5 mL (18.1 mmol) of triethylamine followed by 2.77 g (11.3 mmol) of 4-but-2-ynyloxy-benzenesulfonyl chloride, portionwise. The reaction was stirred at room temperature for 22h and then reduced to dryness. To the resulting residue was added ethyl acetate which was washed with 1M HCl, water and brine. The organic layer was dried over sodium sulfate, filtered, reduced to dryness and chromatographed on silica gel eluting with ethyl acetate (2:1) to provide 1.97 g (59%) of the disulfonamide, 3,3'-dithiobis[N-[[4-(2-butynyloxy)phenyl]sulfonyl]-D-valine] dimethyl ester as a white powder. Electrospray Mass Spec: 741.0 M+H)+

Step 2

To a mixture of 3.474 g (4.70 mmol) of 3,3 '-dithiobis[N-[[4-(2-butynyloxy)phenyl]sulfonyl]-D-valine]dimethyl ester, 6.5 g (46.95 mmol) of potassium carbonate and 30 mL of DMF cooled to 0 ° was added dropwise 4.06 mL (46.95 mmol) of allyl bromide. After stirring overnight at room temperature the mixture was diluted with ethyl acetate and subsequently was washed with water and brine. The organic layer was dried over sodium sulfate, filtered and reduced to dryness. The residue was chromatographed on silica gel eluting with ethyl acetate (3:1 ) to provide 2.97 g (77%) of 3,3'-dithiobis[N-allyl-N-[[4-(2-butynyloxy)phenyl]sulfonyl]-D-valine] dimethyl ester as white foam. Electrospray Mass Spec: 821.0 (M+H)+

Step 3

To a solution of 0.7124 g (0.869 mmol) of 3,3'-dithiobis[N-allyl-N-[[4-(2-butynyloxy)phenyl]sulfonyl]-D-valine] dimethyl ester in 10 mL of THF was added 0.2 mL of water and 3.26 mL (13.04 mmol) of tributylphosphine. This mixture was heated at reflux for 20h, concentrated in vacuo, dissolved in ethyl acetate, washed with 1M citric acid and brine. The organic layer was dried over sodium sulfate, filtered and concentrated in vacuo. The residue was chromatographed on silica gel eluting with ethyl acetate (4:1 ) to provide 0.36 g (50%) of the thiol methyl (2S)-2-allyl{[4-(2-butynyloxy)phenyl]sulfonyl)amino)-3-methyl-3-sulfanylbutanoate as yellow oil. Electrospray Mass Spec: 412.2(M+H)+

Step 4

To a solution of 0.4262 g (1.037 mmol) of methyl (2S)-2-(allyl{[4-(2-butynyloxy)phenyl]sulfonyl}amino)-3-methyl-3-sulfanylbutanoate in 20 mL of cyclohexane was added 50 mg of benzoyl peroxide. The resulting solution was heated at reflux for 3h. After cooling to room temperature and concentrating in vacuo the residue was chromatographed on silica gel eluting with ethyl acetate (4:1 ) to provide 0.222 g (52%) of a 60:40 mixture of C-6 thiomorpholine diastereomers, methyl (3S)-4-{[4-(2-butynyloxy)phenyl]sulfonyl}-2,2,6-trimethyl-3-thiomorpholinecarboxylate, as clear oil. Electrospray Mass Spec: 412.2(M+H)+

Step 5

To a solution of 0.1079 g (0.2625 mmol) of methyl (3S)4-{[4-(2-butynyloxy)phenyl]sulfonyl}-2,2,6-triimethyl-3-thiomorpholinecarboxylate in 2 mL of THF and 2 mL of methanol was added 1.31 mL (1.31. mmol) of 1M sodium hydroxide. The resulting solution was heated at reflux for 6h. After cooling to room temperature the pH was adjusted to 34 by addition of 1N HCl. The mixture was extracted 3 times with a total of 150 ml of chloroform. The combined organic layers were dried over sodium sulfate, filtered and concentrated in vacuo to provide 0.096 g (92%) of the carboxylic acid, (3S)4-{[4-(2-butynyloxy)phenyl]sulfonyl}-2,2,6-trimethyl-3-thiomorpholinecarboxylic acid, as a white powder. Electrospray Mass Spec: 396.2 (M–H)–

Step 6

According to the procedure of Example 25, 0.25 g (0.63 mmol) of (3S)4-{[4-(2-butynyloxy)phenyl]sulfonyl}-2,2,6-trimethyl-3-thiomorpholinecarboxylic acid fished 0.114 g (44%) of the hydroxamic acid, (3S,6S)-4-{[4(2-butynyloxy)phenyl]-sulfonyl)-N-hydroxy-2,2,6-trimethyl-3-thiomorpholinecarboxamide, as a white powder. Electrospray Mass Spec: 413.1(M+H)+

Example 273 tert-Butyl{(2R,5S)-4-{[(2-butynyloxy)phenyl]sulfonyl}-5-[(hydroxyamino)carbonyl]-6,6-dimethylthiomorpholinyl}methylcarbamate Step 1

To a solution of 8.164 g (9.96 mmol) of 3,3'-dithiobis[N-allyl-N-[[4-(2-butynyloxy)-phenyl]sulfonyl]-D-valine] dimethyl ester (from Example 272 ) in 300 mL of methylene chloride at 0 ° was added a solution of 0–51 mL (9.9 mmol) of bromine in 25 mL of dichloromethane dropwise with the exclusion of light. The resulting solution was stirred overnight and was then washed with saturated aqueous sodium thiosulfate and brine. The organic layer was dried over sodium sulfate, filtered and concentrated in vacuo. Flash chromatography of the resulting residue on silica gel eluting with ethyl acetate (4:1 ) provided 7.03 g (72%) of a 2:1 mixture of bromide diastereomers, methyl (3S)-6-(bromomethyl)4-{[4-(2-butynyloxy)phenyl]sulfonyl}-2,2 dimethyl-3-thiomorpholinecarboxylate, as a white foam. Electrospray Mass Spec: 490.0 & 492.0 (M+H)+

Step 2

To a solution of 16.45 g (0.0336 mmol) of methyl (3S)-6-(bromomethyl)4-{[4-(2-butynyloxy)phenyl]sulfonyl}-2,2-dimethyl-3-thiomorpholinecarboxylate in 200 mL of DMSO was added 21.87 g (0.336 mol) of sodium azide. The resulting mixture was heated at 60 ° for 4.5h, cooled to room temperature, diluted with 1L of water and twice extracted with 1L of ether. The organic layer was dried over sodium sulfate, filtered, reduced to dryness and chromatographed on silica gel eluting with ethyl acetate (4:1) to provide 13.35 g (88%) of a 2:1 diastereomeric mixture of azides, methyl (3S)-6-(azidomethyl)4-{[4-(2-butynyloxy)phenyl]sulfonyl}-2,2-dimethyl-3-thiomorpholinecarboxylate as a white foam. . Electrospray Mass Spec: 453.1 (M+H)+

Step 3

To a solution of 13.168 g (0.0291 mol) of methyl (3S)-6-(azidomethyl)4-{[4-(2-butynyloxy)phenyl]sulfonyl)-2,2-dimethyl-3-thiomorpholinecarboxylate in 200 mL of ether was added 8.0 mL (0.03201 mol) of tributylphosphine dropwise over 0.5h. The solution was stirred overnight, cooled to –50 ° and then treated with a solution of 6.99 g (0.032 mol) of di-t-butyldicarbonate in 30 mL of ether dropwise over 0.5h. After 1.5h 50 mL of saturated aqueous sodium bicarbonate was added and the cooling bath was removed. The resulting mixture was twice extracted with 300 mL of ethyl acetate. Combined organic layers were dried over sodium sulfate, filtered, concentrated in vacuo and chromatographed on silica gel eluting with hexanes/ethyl acetate (4: 1 ) to provide 9.91 g (65%) of a 2:1 mixture of carbamates. These diastereomers could be separated by careful iterative gradient flash chromatography eluting with hexanes/ethyl acetate (20:1)–(3:1). The less polar diastereomer (methyl (3S,6R)-6-{[(tert-butoxycarbonyl)amino]methyl}-4-{[4-(2-butynyloxy)phenyl]sulfonyl}-2,2-dimethyl-3-thiomorpholinecarboxylate, Electrospray Mass Spec: 527.2(M+H)+) was eluted first closely followed by (methyl (3S,6S)-6-{[(tert-butoxycarbonyl)amino]methyl)-4-{[4-(2-butynyloxy)phenyl]sulfonyl)-2,2-dimethyl-3-thiomorpholinecarboxylate, Electrospray Mass Spec: 527.1 (M+H)+).

Step 4

To a solution of 3.24 g (6.16 mmol) of methyl (3S,6R)-6-{[(tert-butoxycarbonyl)aminomethyl}4-{(4-(2-butynyloxy)phenyl]sulfonyl)-2,2-dimethyl-3-thiomorpholinecarboxylate in 50 mL of ethyl acetate was added 11 g (82.2 mmol) of lithium iodide. The resulting mixture was heated at reflux for 14h, cooled to room temperature and 10 mL of water was added. The aqueous layer was acidified to pH 3–4 with 1M HCl and back extracted with ethyl acetate. Combined organic layers were washed with water, brine, dried over sodium sulfate, filtered and concentrated in vacuo. The residue was chromatographed on silica gel eluting with -dichloromethane/methanol 10:1 furnishing 2.45 g (78%) of the desired carboxylic acid, (3S,6 R)-6-{[(tert-butoxycarbonyl)amino]methyl)4-[4-(2-butynyloxy)phenyl]sulfonyl}-2,2-dimethyl-3-thiomorpholinecarboxylic acid, as a white foam. Electrospray Mass Spec: 513.3(M+H)+

Step 5

According to the procedure of Example 25, 2.42 g (4.73 mmol) of (3S,6 R)-6-{[(tert-butoxycarbonyl)amino]methyl}4-{[4-(2-butynyloxy)phenyl]sulfonyl}-2,2-dimethyl-3-thiomorpholinecarboxylic acid Finished 0.796 g (32%) of the hydroxamic acid, tert-butyl{(2R,5S)-4-{[4-(2-butynyloxy)phenyl]sulfonyl}-5-[(hydroxyamino)-carbonyl]-6,6-dimethylthiomorpholinyl}methylcarbamate, as a white foam following chromatography on silica gel eluting with dichloromethane/methanol (10:1 ). Electrospray Mass Spec: 528.3 (M+H)+

Example 274 tert-Butyl{(2S,5S)-4-{[4-(2-butynyloxy)phenyl] sulfonyl)-5-[(hydroxyamino)carbonyl]-6,6-dimethylthiomorpholinyl}methylcarbamate Step 1

According to the procedure of Step 4 of Example 273 lithium iodide mediated ester cleavage of 0.83 g (1.58 mmol) of methyl (3S,6S-6-{[(tert-butoxycarbonyl)-amino]methyl)-4-{[4-(2-butynyloxy)phenyl]sulfonyl)-2,2-dimethyl-3-thiomorpholinecarboxylate (Step 3 of Example 273 ) furnished 0.641 g (79%) of the carboxylic acid, (3S,6S)-6-{([tert-butoxycarbonyl)aminomethyl}-4-{[4-2-butynyloxy)phenyl]-sulfonyl}-2,2-dimethyl-3-thiomorpholinecarboxylic acid, as a white foam. Electrospray Mass Spec 513.2: (M+H)+

Step 2

According to the procedure of Example 25, 0.639 g (1.25 mmol) of (3S,6S)-6-{[(tert-butoxycarbonyl)amino]methyl}-4-{[4-(2-butynyloxy)phenyl]sulfonyl -2,2-dimethyl-3-thiomorpholinecarboxylic acid furnished 0.359 g (54%) of the hydroxamic acid, tert-butyl{(2S,5S)-4-{[4-(2-butynyloxy)phenyl]sulfonyl}-5-[(hydroxyamino-carbonyl]-6,6-dimethylthiomorpholinyl)methylcarbamate, as a white foam following chromatography on silica gel eluting with dichloromethane/methanol (10:1 ). Electrospray Mass Spec: 528.3(M+H)+

Example 275

(3S,6R)-Trans-6-(aminomethyl)-4-{14-(2-butynyloxy)phenyl]sulfonyl}-N-hydroxy-2,2-dimethyl-3 thiomorpholinecarboxamide hydrochloride Through a solution of 0.796 g (1.51 mmol) of tert-butyl{(2 R,5S)4-{[4-(2-butynyloxy)phenyl]sulfonyl)-5-[(hydroxyamino)carbonyl]-6,6-dimethyl-thiomorpholinyl}methylcarbamate (Example 273 ) in 30 mL of dichloromethane cooled to 0 ° was bubbled hydrogen chloride gas for 3 minutes. The flask was sealed and stirred at room temperature for 1h. The resulting mixture was concentrated in vacuo to provide 0.674 g (96%) of (3S,6 R)trans-6-aminomethyl)-4-{[4-(2-butynyloxy)phenyl]sulfonyl3-N-hydroxy-2,2-dimethyl-3-thiomorpholinecarboxamide hydrochloride as a brown solid. Electrospray Mass Spec 428.3:(M+H)+

Example 276

(3S,6S)-Cis-6-(aminomethyl)-4-([4(2-butynyloxy) phenyl]sulfonyl}-N-hydroxy-2,2-dimethyl-3-thiomorpholinecarboxamide hydrochloride According to the procedure of Example 275, 0.41 g (0.778 mmol) of the product of Example 274 furnished 0.34 g (94%) of (3S,6S)-cis-6-(aminomethyl)4-{[4-(2-butynyloxy)phenyl]sulfonyl}-N-hydroxy-2,2-dimethyl-3-thiomorpholinecarboxamide hydrochloride as a brown solid. Electrospray Mass Spec: 428.1(M+H)+

Example 277 tert-Butyl{(2S,5S-4-{14-(2-butynyloxy)phenyl] sulfonyl}-5-[(hydroxyamino)carbonyl]-6,6-dimethylthiomorpholinyl}acetate Step 1

To a solution of 21.2 g (0.0285 mol) of 3,3'-dithiobis[N-[[4-(2-butynyloxy)phenyl]sulfonyl]-D-valine]dimethyl ester (Step 1, Example 272 ) in 200 mL of DMF was added 11.8 g (0.0855 mol) potassium carbonate followed by a solution of 18.9 g (0.0855 mol) tert-butyl E)4-bromo-2-butenoate in 30 mL of DME dropwise. The resulting mixture was stirred overnight, diluted with 1L of water and twice extracted with a total of 1L of ether. Combined organic extracts were washed with brine, dried over sodium sulfate, filtered and concentrated in vacuo. The residue was chromatographed on silica gel eluting with ethyl acetate (4:1) to provide 22.87(79%) of 18-(tert-butyl)-9,14-dimethyl(5E,9S,14S,17E)-8,15-bis{[4-(2-butynyloxy)phenyl]-sulfonyl}-2,2,10,10,13,13-hexamethyloxo-3-oxa-11,12-dithia-8,15-diazaoctadeca-5,17-diene-9,14,18-tricarboxylate as a brown oil. Electrospray Mass Spec: 1021.0 (M+H)+

Step 2

To a solution of 22.87 g (0.02241 mol) of 18-(tert-butyl)-9,14-dimethyl(5E,9S,14S,17E)-8,15-bis{[4-(2-butynyloxy)phenyl]sulfonyl)-2,2,10,10,13,13-hexamethyl-4-oxo-3-oxa-11,12-dithia-8,15-diazaoctadeca-5,17-diene-9,14,18-tricarboxylate in 300 mL of THF was added 30 mL of water and 90 mL (0.2241 mol) of tributylphosphine. The resulting mixture was heated at reflux overnight, cooled to room temperature and concentrated in vacuo. The residue was dissolved in ethyl acetate, washed with 1M citric acid, brine, dried over sodium sulfate, -filtered and concentrated in vacuo. The residue was chromatographed on silica gel eluting with ethyl acetate (4:1) to provide 17.63 g (77%) of the thiomorpholine, methyl (3S,6S-6-[2-(tert-butoxy)-2-oxoethyl]-4-{4-[(2-butynyloxy)phenyl]sulfonyl}-2,2-dimethyl-3-thiomorpholinecarboxylate, as a brown oil Electrospray Mass Spec: 512.2 (M+H)+

Step 3

To a solution of 2.273 g (4.45 mmol) of methyl (3S,6S)-6-[2-(tert-butoxy)-2-oxoethyl]-4-{[4-(2-butynyloxy)phenyl]sufonyl}-2,2-dimethyl-3-thiomorpholinecarboxylate in 30 mL of ethyl acetate was added 2.98 g (22.2 mmol) of lithium iodide. This mixture was heated at reflux for 20h and then was cooled to room temperature. Water (100 mL) was added and the aqueous layer was acidified to pH 3–4 with 1M HCl. The mixture was back extracted twice with 200 mL of ethyl acetate. The combined organic layers were washed with water, saturated aqueous sodium thiosulfate and then brine. Sodium sulfate was added to dry the organic layer which was subsequently filtered, concentrated in vacuo and chromatographed on silica gel eluting with dichloromethane/methanol (10:1) to finish 1.535 g (69%) of the mono acid, (3S,6S)-6-[2-(tert-butoxy)-2-oxoethyl]-4-{[4-(2-butynyloxy)phenyl]sulfonyl}-2,2-dimethyl-3-thiomorpholinecarboxylic acid, as a yellow powder. Electrospray Mass Spec: 496.1 (M–H)– and 0.2 g (11%) of the diacid, (3S,6S)4-{[4-(2-butynyloxy)phenyl]sulfonyl-6-(carboxymethyl)-2,2-dimethyl-3-thiomorpholinecarboxylic acid, as a yellow powder. Electrospray Mass Spec: 440 (M–H)–.

Step 4

According to the procedure of Example 25, 0.201 g (0.404 mmol) of (3S,6S) 6-[2-(tert-butoxy)-2-oxoethyl]-4-{[4-(2-butynyloxyphenyl]sulfonyl}-2,2-dimethyl-3-thiomorpholinecarboxylic acid furnished 0.074 g (36%) of the hydroxamic acid, tert-butyl{(2S,5S)4-{[4-(2-butynyloxy)phenylsulfonyl]-5-[(hydroxyamino)carbonyl]-6,6-dimethylthiomorpholinyl}acetate, as a white powder following chromatography on silica gel eluting with dichloromethane/methanol (10:1). Electrospray Mass Spec: 513.1 (M+H)+

Example 278

{(2S,5S)-4-{[4-(2-Butynyloxy)phenyl]sulfonyl)-5-[(hydroxyamino)carbonyl]-6,6-dimethylthiomorpholinyl}acetic acid To a solution of 0.056 g (0.1092 mmol) of tert-butyl{(2S,5S)-4-{[4-(2-butynyloxy)phenyl]sulfonyl}-5-[(hydroxyamino)carbonyl]-6,6-dimethylthiomorpholinyl)acetate (Example 277) in 2 mL of dichloromethane was added 2 mL of trifluoroacetic acid. After 2h the solution was concentrated in vacuo providing 0.052 g (96%) of the carboxylic acid, {(2S,5S)-4-{[4-(2-butynyloxy)phenyl]sulfonyl)-5-[(hydroxyamino)carbonyl]-6,6-dimethylthiomorpholinyl)acetic acid, as a light powder. Electrospray Mass Spec: 457.1 (M+H)+

Example 279

(3S,6S)-4-{[4-(2-Butynyloxy)phenyl]sulfonyl)-N-hydroxy-6-[2-(hydroxyamino)-2-oxoethyl]-2,2-dimethyl-3-thiomorpholinecarboxamide According to the procedure of Example 25, 0.6967 g (1.58 mmol) of the dicarboxylic acid from Example 277,(3S,6S)-4-{[4(2-butynyloxy)phenyl]sulfonyl)-6-(carboxymethyl)-2,2-dimethyl-3-thiomorpholinecarboxylic acid, furnished 0.093 g (12%) of the dihydroxamic acid, (3S,6S)-4-{[4-(2-butynyloxy)phenyl]sulfonyl}-N-hydroxy-6-[2-(hydroxyamino}2-oxoethyl]-2,2-dimethyl-3-thiomorpholinecarboxamide, as a light powder following chromatography on silica gel eluting with dichloromethane/methanol (10:1). Electrospray Mass Spec: 471.9 (M+H)+

Example 280

(3S,6S)-6-(2-Amino-2-oxoethyl)-4-{[4-(2-butynyloxy)phenyl]sulfonyl)-N-hydroxy-2,2-dimethyl-3 thiomorpholinecarboxamide Step 1

According to the procedure of Example 278, 2.33 g (4-55 mmol) of methyl (3S,6S)-6-[2-(tert-butoxy)-2-oxoethyl]-4-{[4-(2-butynyloxy)phenyl]sulfonyl}-2,2-dimethyl-3-thiomorpholinecarboxylate (Step 2, Example 277) finished 1.92 g (93%) of the carboxylic acid, [(2S,5S)4-{([4-(2-butynyloxy)phenyl]sulfonyl}-5-(methoxycarbonyl)6,6-dimethylthiomorpholinyl]acetic acid, as a white solid. Electrospray Mass Spec: 454.1 (M–H)–

Step 2

To a solution of 1.21 g (2.66 mmol) of [(2S,5S)4-{[4-(2-butynyloxy)-phenyl]sulfonyl)-5-(methoxycarbonyl)-6,6-dimethylthiomorpholinyl]acetic acid dissolved in 15 mL of DMF was added 0.884 g (6.64 mmol) of 1-hydroxybenzotriazole hydrate (HOBT) followed by 1.53 g (7.98 mmol) of 1-(3-dimethylaminopropyl)-3-ethylcarbodiimide hydrochloride ADC). The resulting mixture was stirred at room temperature for 1h and then 3 mL of a 28% ammonium hydroxide solution was added. The reaction was stirred overnight and then diluted with ethyl acetate. The organics were washed with 5% HCl solution, water and saturated sodium bicarbonate solution and then dried over sodium sulfate, filtered and concentrated in vacuo to provide 0.83 g (69%) of the amide, methyl(3S,6S-6-(2-amino-2-oxoethyl)4-{[4-(2-butynyloxy)-phenyl]sulfonyl}-2,2-dimethyl-3-thiomorpholinecarboxylate, as a yellow oil. Electrospray Mass Spec 455.1 (M+H)+

Step 3

Lithium iodide mediated ester cleavage, according to the procedure of Step 4 of Example 273, of 0.825 g (1.82 mmol) of methyl(3S,6S)-6-(2-amino-2-oxoethyl)-4-{[4-(2-butynyloxy)phenyl]sufonyl)-2,2-dimethyl-3-thiomorpholinecarboxylate finished 0.65 g (81%) of the carboxylic acid, (3S,6S)-6-(2-amino-2-oxoethyl)-4-{[4-(2-butynyloxy)phenyl]sulfonyl)-2,2-dimethyl-3-thiomorpholinecarboxylic acid, as a viscous oil. Electrospray Mass Spec 441.1 (M+H)+

Step 4

According to the procedure of Example 25 0.077 g (0.175 mmol) of (3S,6S)-6-(2-amino-2-oxoethyl)-4-{[4-(2-butynyloxy)phenyl]sulfonyl}-2,2-dimethyl-3-thiomorpholinecarboxylic acid furnished 0.043 g (54%) of the hydroxamic acid, 3S,6S)-6-(2-amino-2-oxoethyl)4([4-(2-butynyloxy)phenyl]sulfonyl}-N-hydroxy-2,2-dimethyl-3-thiomorpholinecarboxamide, as a light powder following chromatography on silica gel eluting with dichloromethane/methanol (10:1 ). Electrospray Mass Spec: 455.1 (M+H)+

Example 281

(3S,6S)4-{[4-(2-Butynyloxy)phenyl]sulfonyl)-6-12-(dimethylamino)-2-oxoethyl]-N-hydro-2,2-dimethyl-3-thiomorpholinecarboxamide Step 1

To a solution of 1.535 g (3.09 mmol) of (3S,6S)-6-[2-(tert-butoxy)-2-oxoethyl]4-{[4-(2-butynyloxy)phenyl]sulfonyl)-2,2-ethyl-3-thiomorpholinecarboxylic acid (Example 277 ) in 15 mL of dichloromethane was added sequentially 0.43 mL (3.09 mmol) of triethylamine, 0.905 g (3.55 mmol) of bis(2-oxo-3-oxazolidinyl)phosphinic chloride, 0.493 g (3.09 mmol) of O-benzyl hydroxylamine and an additional 1.29 mL (9.27 mmol) of triethylamine. After stirring overnight the mixture was concentrated in vacuo and partitioned between ethyl acetate and saturated aqueous sodium bicarbonate. The organic layer was washed consecutively with water and brine. Sodium sulfate was added to dry the organic layer which was subsequently filtered, concentrated in vacuo and chromatographed on silica gel eluting with hexanes/ethyl acetate (4:1 ) to furnish 1.5 g (81%) of tert-butyl((2S,5S)-5-{[(benzyloxy)amino]carbonyl}-4-{[4-2-butynyloxy)phenyl]sulfonyl}-6,6-dimethylthiomorpholinyl)acetate as a white solid. Electrospray Mass Spec: 603.1 (M+H)+

Step 2

According to the procedure of Example 278 0.3237 g (0.538 mmol) of tert-butyl((2S,5S)-5-{[(benzyloxy)amino]carbonyl}-4-{[4-(2-butynyloxy)phenyl]sulfonyl}-6,6-dimethylthiomorpholinyl)acetate finished 0–294 g (100%) of the carboxylic acid, ((2S,5S)-5-{[(benzyloxy)amino]carbonyl}A{[4-(2-butynyloxy)phenyl]sulfonyl)-6,6-dimethylthiomorpholinyl)acetic acid, as a white solid. Electrospray Mass Spec: 547.0 (M+H)+

Step 3

To a solution of 0.283 g (0.518 mmol) of((2S,5S)-5-{[(benzyloxy)amino]carbonyl}-4-{[4-(2-butynyloxy)phenyl]sulfonyl}-6,6-dimethylthiomorpholinyl)acetic acid dissolved in 15 mL of DMF was added 0.083 g (0.662 mmol) of 1-hydroxybenzotriazole hydrate (DOBT) followed by 0.132 g (0.689 mmol) of 1-(3-dimethylaminopropyl)-3-ethylcarbodiimide hydrochloride (EDC). The resulting mixture was stirred at room temperature for 1h and then 3 mL of a 3 M solution of dimethylamine in THF was added. The reaction was then stirred overnight and then diluted with ethyl acetate. The organics were washed with 5% HCl solution, water and saturated sodium bicarbonate solution and then dried over sodium sulfate, filtered and concentrated in vacuo to provide 0.14 g (47%) of the amide, (3S,6S)-N-(benzyloxy)-4-{[4-(2-butynyloxy)phenyl]sulfonyl)-6-[2-(dimethylamino)-2-oxoethyl]-2,2-dimethyl-3-thiomorpholinecarboxamide, as a clear oil. Electrospray Mass Spec 574.1 (M+H)+

Step 4

To a solution of 0.064 g (0.1116 mmol) of (3S,6S)-N-(benzyloxy)4-{[4-(2-butynyloxy)phenyl]sulfonyl}-6-[2-(dimethylamino)-2-oxoethyl]-2,2-dimethyl-3-thiomorpholinecarboxamide in 0.8 mL of triflouroacetic acid cooled at 0 ° was added 0.335 mL (0.335 mmol) of a 1.0 M solution of boron tris(trifluoroacetate). The resulting solution was stirred for 2h, concentrated in vacuo and purified by chromatography on silica gel eluting with dichloromethane/methanol (10:1 ) to provide 0.051 g (94%) of the hydroxamic acid, (3S,6S)4-{[4-(2-butynyloxy)phenyl]sulfonyl)-6-[2-(dimethylamino)-2-oxoethyl]-N-hydroxy-2,2-dimethyl-3-thiomorpholinecarboxamide, as a brown powder. Electrospray Mass Spec 484.1 (M+H)+

Example 282

(3S,6S)-4-{[4-(2-Butynyloxy)phenyl]sulfonyl)-N-hydroxy-2,2-dimethyl-6-[2-(4-morpholinyl}2-oxoethyl]-3-thiomorpholinecarboxamide Step 1

To a solution of 0.179 g (0.327 mmol) of the product of Step 2 of Example 281, ((2S,5S)-5-{[(benzyloxy)amino]carbonyl)}-4-[4-(2-butynyloxy)phenyl]sulfonyl}-6,6-dimethylthiomorpholinyl)acetic acid, dissolved in 5 mL of DMF was added 0.096 mL (0.69 mmol) of triethylamine, 50 mg of DMAP, 0.031 mL (0.36 mmol) of morpholine and 0.078 mL (0.36 mmol) of diphenylphosphoryl azide. After stirring for 12h the solution was partitioned between ethyl acetate and water. The organic phase was washed with brine, dried over sodium sulfate, filtered and concentrated in vacuo. The residue was purified by chromatography on silica gel eluting with hexaneslethyl acetate (1:1) to furnish 0.1586 g (79%) of (3S,6S)-N-(benzyloxy)4-{[4-(2-butynyloxy)phenyl]sulfonyl)-2,2-dimethyl-6-[2-(4-morpholinyl)-2-oxoethyl]-3-thiomorpholinecarboxamide as a light solid. Electrospray Mass Spec 616.4 (M+H)+

Step 2

According to the procedure of Step 4 of Example 281 0.1431 g (0.233 mmol) of (3S,6S)-N-(benzyloxy)4-{[4-(2-butynyloxy)phenyl]sulfonyl)-2,2-dimethyl-6-[2-(4-morpholinyl)-2-oxoethyl]-3-thiomorpholinecarboxamide furnished 0.1014 g (83%) of the hydroxamic acid, (3S,6S)-4-{[4-(2-butynyloxy)phenyl]sulfonyl)-N-hydroxy-2,2-dimethyl-6-[2-(4-morpholinyl)-2-oxoethyl]-3-thiomorpholinecarboxamide, as a brown solid. Electrospray Mass Spec 523.8 (M–H)–

Example 283

(3S,6S)-4-{[4-(2-Butynyloxy)phenyl]sulfonyl}-N-hydroxy-2,2-dimethyl-6-[2-(4-methyl-1-piperazinyl)2-oxoethyl]-3-thiomorpholinecarboxamidehydrochloride Step 1

According to the procedure of Step 1 of Example 282, 0.234 g (0.428 mmol) of the product of Step 2 of Example 281,((2S,5S)-5-{[(benzyloxy)amino]carbonyl)-4-{[4-(2-butynyloxy)phenyl]sulfonyl}-6,6-dimethylthiomorpholinyl)acetic acid and 0.052 mL (0.47 mmol) of 1-methylpiperazine furnished 0.23 g (86.1%) of (3S,6S)-N-(benzloxy)4-{[4-(2-butynyloxy)phenyl]sulfonyl)-2,2-dimethyl-6-[2-(4-methyl-1-piperazinyl)-2-oxoethyl]-3-thiomorpholinecarboxamide as a white solid after chromatography on silica gel eluting with dichloromethane/methanol (20:1 ). Electrospray Mass Spec 629.1 (M+H)+

Step 2

To a solution of 0.2 g (0.3185 mmol) of (3S,6S)-N-(benzyloxy)4-{[4-(2-butynyloxy)phenyl]sulfonyl}-2,2-dimethyl-6-[2-(4-methyl-1-piperazinyl)-2-oxoethyl]-3-thiomorpholinecarboxamide in 3 mL of triflouroacetic acid cooled at 0 ° was added 0.96 mL (0.96 mmol) of a 1.0 M solution of boron tris(trifluoroacetate). The resulting solution was stirred for 2h, concentrated in vacuo and then purified by chromatography on silica gel eluting with dichloromethane/ methanol (10:1 ) to provide the free base which was then dissolved in 3 mL of methanol. Through this solution cooled to 0 ° was bubbled HCl gas for 2 minutes. The solution was 25 concentrated in vacuo yielding 0.12 g (66%) of (3S,6S)4-{[4-(2-butynyloxy)phenyl]sulfonyl}-N-hydroxy-2,2-dimethyl-6-[2-(4-methyl-1-piperazinyl)-2-oxoethyl]-3-thiomorpholinecarboxamide hydrochloride as a brown powder. Electrospray Mass Spec 539.0 (M+H)+

Example 284

(3S,6S)-4-{[4-(2-Butynyloxy)phenyl]sulfonyl}-6-(2-{[2-(dimethylamino)ethyl]amino}-2-oxoethyl)-N-hydroxy-2,2-dimethyl-3-thiomorpholinecarboxamide Step 1

According to the procedure of Step 1 of Example 282, 0.234 g (0.428 mmol) of ((2S,5S)-5-{[(benzloxy)amino]carbonyl}-4-{[4-(2-butynyloxy)phenyl]sulfonyl}-6,6-dimethylthiomorpholinyl)acetic acid and 0.052 mL (0.47 mmol) of N, N-dimethylethylenediamine furnished 0.129 g (49%) of (3S,6S)-N-(benzyloxy)4-{[4-(2-butynyloxy)phenyl]sulfonyl}-6-2-{[2-(dimethylamino)ethyl]amino}-2-oxoethyl)2,2-dimethyl-3-thiomorpholinecarboxamide after chromatography on silica gel eluting with dichloromethane/ methanol (20:1) as a white solid. Electrospray Mass Spec 617.0 (M+H)+

Step 2

According to the procedure of Step 2 of Example 283 0.111 g (0.18 mmol) of (3S,6S)-N-(benzyloxy)4-{[4-(2-butynyloxy)phenyl]sulfonyl}-6-(2-{[2-(dimethylamino)ethyl]amino}-2-oxoethyl)-2,2-dimethyl-3-thiomorpholinecarboxamide and furnished 0.051 g (50%) of desired hydrochloride salt, (3S,6S)-4-{[4-(2-butynyloxy)phenyl]sulfonyl}-6-(2-{[2-(dimethylamino)ethyl]amino}-2-oxoethyl)-N-hydroxy-2,2-dimethyl-3-thiomorpholinecarboxamide hydrochloride, as a brown powder. Electrospray Mass Spec 527.0 (M+H)+

Example 285

Methyl (3S,6S)-6-{[(tert-butoxycarbonyl)amino]methyl}-4-{[4-(2-butynyloxy)phenyl]sulfonyl}-2,2-dimethyl-3-thiomorpholinecarboxylate To a solution of 0.6138 g (1.35 mmol) of the product of Step I of Example 280, [(2S,5S)4-{[4-(2-butynyloxy)phenyl]sulfonyl)-5-(methoxycarbonyl)-6,6-dimethylthiomorpholinyl]acetic acid, in 10 ml of t-butanol was added 0.188 mL (1.35 mmol) of triethylamine and 0.291 ml (1.35 mmol) of diphenylphosphoryl azide. The solution was heated at reflux for 12h, cooled to room temperature, concentrated in vacuo and chromatographed on silica gel eluting with hexanes/ethyl acetate (4:1 ) to provide 0.414 g (58%) of the carbamate, methyl (3S,6S)-6-{[(tert-butoxycarbonyl)amino]methyl)}-4-[4-(2-butynyloxyphenylsulfonyl}-2,2-dimethyl-3-thiomorpholinecarboxylate. Electrospray Mass Spec: 527.1 (M+H)+.

Example 286

(4S)-3-{4-(2-Butynyloxy)phenyl]sulfonyl)-N-hydroxy-5,5-dimethyl-1,3-thiazolidine-4-carboxamide Step 1

To a room temperature solution of 4.3 g (32.3 mmol) of 5,5-dimethyl-1,3-thiazolidine4-carboxylic acid (J. Med. Chem. 1989, 32(2 ), 466–472) in 30 ml of dioxane:water (2:1) containing 4.9 mL (35.5 mmol) of triethylamine was added 7.9 g (32.3 mmol) of 4-butynyloxybenzenesulfonyl chloride. The mixture was stirred at 25 ° C. for 18h. The resulting mixture was diluted with ethyl acetate and washed with 1N aqueous hydrochloric acid (3×). The organic phase was dried over anhydrous magnesium sulfate and concentrated in vacuo to afford a foam which was chromatographed on silica gel eluting with methanol/dichloromethane to give (4S)-3-{[4-(2- butynyloxy)phenyl]sulfonyl}-5,5-dimethyl-1,3-thiazolidine4-carboxylic acid as a white solid. Electrospray Mass Spec 368.1 (M–H)–

Step 2

To oxalyl chloride (4.5 mL of a 2 M solution in dichloromethane) in dichloromethane at 0° C. was added DMF (0.69 mL). After 15 min a solution of (4S)-3-{[4-(2-butynyloxy)phenyl]sulfonyl}-5,5-dimethyl-1,3-tbiazolidine-4-carboxylic acid (1.58 g, 4.5 mmol) in DMF was added and the resulting reaction mixture was stirred at room temperature for 1h.

In a separate flask, 9.4 mL of triethylamine was added to a 0° C. mixture of 3.13 g of hydroxylamine hydrochloride in 97 nm of tetrahydrofuran and 24 mL of water. After this mixture had been stirred for 15 min at 0° C., the acid chloride solution was added to it in one portion and the resulting solution was allowed to warm to room temperature and stirred for another 18h. Ethyl acetate and aqueous sodium bicarbonate were then added to the reaction flask.

The organic phase was washed with aqueous sodium bicarbonate and dried over anhydrous potassium carbonate. Concentration in vacuo and trituration with ether/dichloromethane gave (4S)-3-{[4-(2-butynyloxy)phenyl]sulfonyl}-N-hydroxy-5,5-dimethyl-1,3-thiazolidine-4-carboxamide as a white powder (1.2 g). Electrospray Mass Spec 385.3 (M+H)+

Example 287 tert-Butyl 4-({[4-(2-butynyloxy)phenyl]sulfonyl}amino)-4-[(hydroxyamino)carbonyl]-1-piperidinecarboxylate Step 1

4-Amino-1-(tert-butoxycarbonyl)-4-piperidinecarboxylic acid (1.0 g, 4.09 mmol) in dioxane (5 mL) and water (2.5 mL) was treated with triethylamine (0.63 mL, 4.5 mmol) and 0.8 mL of 5 N aqueous sodium hydroxide and 4-(2-butynyloxy)phenyl sulfonyl chloride (1.0 g, 4.09 mmol) was then added. After 40h, ethyl acetate and 1N aqueous hydrochloric acid was added. The organic phase was washed an additional 2x with 1N aqueous hydrochloric acid and once with brine, then dried over anhydrous magnesium sulfate to give an oil (0.98 g) which was chromatographed on silica gel eluting with dichloromethane/methanol to give 1-(tert-butoxycarbonyl)4-({[4-(2-butynyloxy)phenyl]sulfonyl}amino)-4-piperidinecarboxylic acid as a white powder (0.36 g). Electrospray Mass Spec 453.1(+H)+.

Step 2

To oxalyl chloride (0.70 mL of a 2 M solution in dichloromethane) in dichloromethane (1 mL) at 0° C. was added dimethylformamide (0.11 mL). After 15 min a solution of 1-(tert-butoxycarbonyl)-4-({[4-(2-butynyloxy)phenyl]sulfonyl}-amino)-4-piperidinecarboxylic acid (0.315 g, 0.70 mmol) in dimethylformamide was added and the resulting reaction mixture was stirred at room temperature for 1h In a separate flask, 1.46 mL of triethylamine was added to a 0 ° C. mixture of 0.486 g of hydroxylamine hydrochloride in 15 mL of tetrahydrofuran and 3.7 mL of water. After this mixture stirred for 15 min at 0° C., the acid chloride solution was added to it in one portion and the resulting solution was allowed to warm to room temperature and stirred for another 18 h. Ethyl acetate and aqueous sodium bicarbonate were then added to the reaction flask. The organic phase was washed with aqueous sodium bicarbonate (3x) and dried over anhydrous potassium carbonate. Concentration in vacuo gave tert-butyl 4-({[4-(2-butynyloxy)phenyl]sulfonyl}amino)-4-[(hydroxyamino)carbonyl]-1-piperidinecarboxylate as a hard foam (0.142 g). Electrospray mass spec 468.2 (M+H)+.

Example 288

4-({[4-(2-Butynyloxy)phenyl]sulfonyl}amino)-N-hydroxy-4-piperidinecarboxamide

To a solution of tert-butyl 4-({[4-(2-butynyloxy)phenyl]sulfonyl}amino)4-[(hydroxyamino)carbonyl]-1-piperidinecarboxylate (0.114 g) from Example 287, in dioxane (1 mL) was added 4N hydrochloric acid in dioxane (2 mL). After 4 hours the reaction mixture was concentrated in vacuo. Trituration with dichloromethane and diethyl ether gave 4-({[4-(2-butynyloxy)phenyl]sulfonyl)amino)-N-hydroxy-4-piperidinecarboxamide as an off-white powder. Electrospray Mass Spec 368.2 (M+H)+.

Example 289

1-Benzoyl-4-{[4(2-butynyloxy)phenyl]sulfonyl}-N-hydroxy-1,4-diazepane-5-carboxamide Step 1

To a solution of tert-butyl 1,4-diazepane-5-carboxylate (WO 98/08823 )(4.5 g, 22.5 mmol) in dioxane (225 mL) was added water (200 mL) and 1N aqueous sodium hydroxide (22.5 mL). Di-tert-butyl dicarbonate (4.91 g, 22.5 mmol) was then added. After 18hours triethylamine (9.4 mL, 67 mmol), 4-dimethylaminopyridine (0.274 g, 2.25 mmol) and 4-(2-butynyloxy)phenyl]sulfonyl chloride (6.61 g, 27 mmol) were added. After stirring overnight 1 N aqueous hydrochloric acid (100 mL) was added and the mixture was extracted with dichloromethane. The combined organic extracts were dried over anhydrous potassium carbonate and concentrated in vacuo. Chromatography on silica gel eluting with dichloromethane/methanol gave a yellow glass (4.52 g). Chromatography of this material on silica gel with hexane/ethyl acetate gave di(tert-butyl) 4-{[4-(2-butynyloxy)phenyl]sufonyl)-1,4-diazepane-1,5-dicarboxylate as a glass (0.83 g). Electrospray Mass Spec 509.3 M+H)+

Step 2

Treatment of di(tert-butyl) 4-{[4-(2-butynyloxy)phenyl]sulfonyl)-1,4-diazepane-1,5-dicarboxylate (0.83 g, 1.63 mmol) with 2 N hydrochloric acid in dioxane (30 mL) at 25 ° C. for 2hours gave, after concentration in vacuo, a quantitative yield of tert-butyl 4-{[4-(2-butynyloxy)phenyl]sulfonyl)-1,4-diazepane-5-carboxylate. Electrospray Mass Spec 409.3 (M+H)

Step 3 tert-Butyl 4-{[4-(2-butynyloxy)phenyl]sulfonyl)-1,4-diazepane-5-carboxylate (0.425 g, 0.96 mmol) in dichloromethane at 25° C. (10 mL) was treated with triethylamine (0.28 mL, 2.02 mmol) followed by benzoyl chloride (0.12 mL, 1.06 mmol) and dimethylaminopyridine (10 mg). After 18 hours aqueous workup gave tert-butyl 1-benzoyl-4-{[4-(2-butynyloxy)phenyl]sulfonyl}-1,4-diazepane-5-carboxylate. $^1$H NMR (dmso-d6, 300 MH): 1.24 (s, 9H, t-bu), 1.82(s, 3H, CH3 ), 2.0–4.0 (m, 81, CH2 ), 4.65 (s, 1H, CM, 4.85 (s. 21H, CH2 ), 7.0–7.9 (m, 9H, ArH). Treatment with trifluoroacetic acid (4 mL) in dichoromethane (10 mL) for 6hours gave, after concentration in vacuo followed by chromatography on silica gel eluting with dichloromethane/methanol, 1-benzoyl4-{[4-(2-butynyloxy)phenyl]sulfonyl}-1,4-diazepane-5-carboxylic acid as a foam (0.328 g).

Step 4

To oxalyl chloride (0.72 mL of a 2 M solution in dichloromethane) in dichloromethane (1 mL) at 0° C. was added dimethylformamide (0.11 mL). After 15 min a solution of 1-benzoyl-4-{[4-(2-butynyloxy)phenyl]sulfonyl}-1,4-diazepane-5-carboxylic acid (0.328 g, 0.718 mmol) in dimethylformamide was added and the resulting reaction mixture was stirred at room temperature for 1h In a separate flask, 1.5 mL of triethylamine was added to a 0° C. mixture of 0.50 g of hydroxylamine hydrochloride in 15.4 mL of tetrahydrofuran and 3.8 mL of water. After this mixture stirred for 15 min at 0° C., the acid chloride solution was added to it in one portion and the resulting solution was allowed to warm to room temperature and stirred for another 18h. Ethyl acetate and aqueous sodium bicarbonate were then added to the reaction flask The organic phase was washed with aqueous sodium bicarbonate (3×) and dried over anhydrous potassium carbonate. Concentration in vacuo gave a thick gum (0.35 g) which was chromatographed on silica gel eluting with dichloromethane/methanol to give an off-white foam (0.22 g) which was triturated with diethyl ether to give 1-benzoyl-{[4-{[4-(2-butynyloxy)phenyl]sulfonyl}-N-hydroxy-1,4-diazepane-5-carboxamide as an off white powder (0.173 g). Electrospray Mass Spec 472.3(M+H)+.

Example 290

1-Benzyl-4-{[4-(2-butynyloxy)phenyl]sulfonyl}-N-hydroxy-1,4-diazepane-5-carboxamide Step 1

To 10 mL of a methanolic solution of the product of Step 2 of Example 289, tert-butyl 4-{[4-(2-butynyloxy)phenyl]sulfonyl}-1,4-diazepane-5-carboxylate, (0.37 g, 0.84 mmol) was added triethylamine (0.25 mL, 1.8 mmol), benzyl bromide (0.11 mL, 0.92 mmol) and a catalytic amount of tetrabutylammonium iodide. After 18hours 5% aqueous sodium bicarbonate was added and the mixture extracted with dichlormethane (4×). The combined organic extracts were dried over anhydrous magnesium sulfate and concentrated in vacuo to give an oil (0.51 g). Chromatography on silica gel gave tert-butyl 1-benzyl-4-{[4-(2-butynyloxy)phenyl]sulfonyl)-I,4-diazepane-5-carboxylate as a clear colorless oil (0.34 g).

Step 2

To a solution of tert-butyl 1-benzyl4-{[4(2-butynyloxy)phenyl-1-sulfonyl)-1,4-diazepane-5-carboxylate (0–34 g 0.68 mmol) in dicloromethane (2 mL) at 0 ° C. was added trifluoroacetic acid (1.23 mL). After 2.5h the reaction mixture was allowed to warm to 25 ° C. whereupon an additional 1 mL of trifluoroacetic acid was added. After 18h the reaction mixture was concentrated in vacuo to provide 1-benzyl4-{[4(2-butynyloxy)phenyl]sulfonyl)-1,4-diazepane-5-carboxylic acid as a white powder. Electrospray Mass Spec 443.4 M+H)+

Step 3

In a manner analogous to that described in Step 4 of Example 289, 1-benzyl-4-{([(2-butynyloxy)phenyl]sulfonyl}-1,4-diazepane-5-carboxylic acid (0.68 mmol) was converted into 1-benzyl-4-{[4-2-butynyloxy)phenyl]sulfonyl)-N-hydroxy-1,4-diazepane-5-carboxamide (0.169 g), obtained as a white solid. Electrospray Mass Spec 458.2 (M+H)+

Example 291 tert-Butyl 4-{[4-(2-butynyloxy)phenyl]sulfonyll}-1(hydroxyamino)carbonyl]-1,4-diazepane-1-carboxylate Step 1

In a manner analogous to that described in Step 2 of Example 290, 2.86 g (5.78 mmol) of di(tert-butyl) 4-{[4-(2-butynyloxy)phenyl]sulfonyl}-1,4-diazepane-1,5-dicarboxylate (from Step 1 of Example 289 ) was converted into 4-{[4(2-butynyloxyphenyl]sulfonyl}-1,4-diazepane-5-carboxylic acid which was purified by chromatography on silica gel to give a yellow solid. Electrospray Mass Spec 353.1 (M+H)+

Step 2

To a solution of 4-{[4-(2-butynyloxy)phenyl]sulfonyl}-1,4-diazepane-5-carboxylic acid (2.9 mmol) in dioxane (30 mL) and water (30 mL) was added 1N aqueous sodium hydroxide (9 mL). Di-tert-butyl dicarbonate (0.63 g, 2.9 mmol) was then added. After 18h 1 N aqueous hydrochloric acid (15 mL) was added and the mixture was extracted with dichloromethane (3×). The combined organic extracts were dried over anhydrous sodium sulfate and concentrated in vacuo to give tert-butyl 4-{[4-(2-butynyloxy)phenyl]sulfonyl}-1,4-diazepane-5-carboxylic acid -1-carboxylate as a brown foam (1.24 g).

Step 3

To a solution of tert-butyl 4-{[4-(2-butynyloxy)phenyl]sulfonyl)-1,4-diazepane-5-carboxylic acid-1-carboxylate (0.74 & 1.6 mmol) in dimethylformamide (8 mL) at 0° C. was added 1-hydroxybenzotriazole (0.39 g, 2.9 mmol) and 1-(3-dimethylaminopropyl)-3-ethylcarbodiimide (0.56 g, 2.9 mmol). After 45 min 50% aqueous hydroxyl amine (0.26 mL) was added. After 2hours the reaction mixture was diluted with ethyl acetate and water. The aqueous phase was extracted with ethyl acetate 3×. The combined organic phases were washed with aqueous sodium bicarbonate 3× and with water 4×. The organic phase was dried over anhydrous sodium sulfate and concentrated m vacuo to give tert-butyl 4-{[4-(2-butynyloxy)phenyl]sulfonyl]-5-[(hydroxyamino)carbonyl]-1,4-diazepane-1-carboxylate (0.62 g). Electrospray Mass Spec 468.1 (M+H)+

Example 292

4-{[4-(2-Butynyloxy)phenyl]sulfonyl}-N-hydroxy-1,4-diazepane-5-carboxamide

To the product of Example 291, tert-butyl 4-{[4-(2-butynyloxy)phenyl]-sulfonyl}-5-[hydroxyamino)carbonyl]-1,4-diazepane-1-carboxylate (0.32 g, 0.68 mmol), was added 4N hydrochloric acid in dioxane (9 mL). After 10 min the reaction mixture was concentrated in vacuo. Trituration of the residue with diethyl ether gave 4-{[4-(2-butynyloxy)phenyl]sulfonyl)-N-hydroxy-1,4-diazepane-5-carboxamide as an off-white powder (0.27 g). Electrospray Mass Spec 368.2(M+H)+

Example 293

4-{[4-(2-Butynyloxy)phenyl]sulfonyl}-N-hydroxy-l-methyl-1,4-diazepane-5-carboxamide Triethylamine (0.08 mL) was added to a suspension of the product of Example 292, 4-{[4-(2-butynyloxy)phenyl]

sulfonyl}-N-hydroxy-1,4-diazepane-5-carboxamide (0.10 g), in methanol (6 mL) to give a solution which was cooled to 0° C. Iodomethane (0.025 mL) was then added. After 30 min the reaction mixture was allowed to warm to 25 ° C. After 20 min additional iodomethane (0.02 mL) was added followed by additional triethylamine (0.015 mL). After 18hours the reaction mixture was diluted with dichloromethane and water. The aqueous phase was washed with dichloromethane (3×). The combined organic extracts were dried over anhydrous sodium sulfate and concentrated in vacuo. The material obtained was combined with material from a previous reaction run on the same scale and chromatographed on silica gel to give 4-{[4-(2-butynyloxy) phenyl]sulfonyl}-N-hydroxy-1-methyl-1,4-diazepane-5-carboxamide (0.067 g). Electrospray Mass Spec 382.2 (N+H)+

Example 294

4-{[4-(2-Butynyloxy)phenyl]sulfonyl}-N-hydroxy-1,4-thiazepine-5-carboxamide

Step 1

To D,L-homocysteine (6.69 g, 49.4 mmol) was added 2N aqueous potassium hydroxide (32 mL) and the resulting solution was cooled to 0° C. 2-Bromoethanol (4.2 mL, 59.3 mmol) in ethanol (56 mL) was then added dropwise and the reaction mixture was allowed to warm to 25° C. After 18 h the reaction mixture was acidified to pH 5 and concentrated to give 2-(amino)4-[(2-hydroxyethyl)sulfanyl]butanoic acid (WO 9808823 ) as a white paste. To this material was added water (110 mL) and dioxane (110 mL) and triethylanine (20.7 mL, 148 mmol) and to the resulting solution was added 4-(2-butynyloxy)phenylsulfonyl chloride (14.2 g, 54.3 mmol). After 20h the reaction mixture was acidified to pH 1 with 1N aqueous hydrochloric acid and extracted with dichloromethane (3+). The combined organic extracts were dried over anhydrous sodium sulfate and concentrated in vacuo to give 2-({[4-(2-butynyloxy)phenyl]sulfonyl}amino) 4-[(2-hydroxyethyl)sulfanyl]butanoic acid as an oil (20.8 g). Electrospray Mass Spec 385.8 (M–H)–.

Step 2

To a solution of 2-{[4-(2-butynyloxy)phenyl] sulfonyl}amino)-4-[(2-hydroxyethyl)sulfanyl]butanoic acid (20.8 g) in ether and methanol was dropwise added trimethylsilyldiazomethane (25 mL. 2.0 M in hexanes). The reaction mixture was concentrated in vacuo and the resulting oil was chromatographed on silica gel eluting with hexane/ ethyl acetate to give methyl 2-({[4-(2-butynyloxy)phenyl]-sulfonyl)amino)-4-[(2-hydroxyethyl)sulfanyl] butanoate as a light yellow oil (6.68 g). Electrospray Mass Spec 401.9 (M+H)+.

Step 3

To methyl 2-({[4-2-butynyloxy)phenyl]sulfonyl}amino) 4-[(2-hydroxyethyl)-sulfanyl]butanoate (5.5 g, 13.7 mmol) in tetrahydrofuran (100 mL) was added triphenylphosphine (4.3 g, 16.4 mmol). Diethyl azodicarboxylate (2.4 mL, 15.1 mmol) was then added dropwise. After 2h the reaction mixture was concentrated in vacuo to give an oil which was chromatographed on silica gel eluting with hexane/ethyl acetate to give methyl 4-{[4-(2-butynyloxy) phenylsulfonyl}-1,4-thiazepine-5-carboxylate as a white solid (4.04 g). mp 95–98 ° C. Electrospray Mass Spec 384.0 (M+H)+.

Step 4

To methyl 4-{ [4-(2-butynyloxy)phenyl]sulfonyl}-I,4-thiazepine-5-carboxylate (0.27 g, 0.7 mmol) was added 5 N aqueous sodium hydroxide (7 mL) and methanol (7 mL). The reaction mixture was heated at reflux for 5 minutes. Upon cooling to 25° C. the reaction mixture was acidified to pH 1 with 1N aqueous hydrochloric acid. The mixture was extracted with dichloromethane (3×) and the combined organic extracts were dried over anhydrous sodium sulfate. Concentration in vacuo gave 4-{[4-(2-butynyloxy)phenyl] sulfonyl}-1,4-thiazepine-5-carboxylic acid as a white powder (0.26 g). Electrospray Mass Spec 370.0(M+H)+.

Step 5

A solution of 4-{[4-(2-butynyloxy)phenyl]sulfonyl}-1,4-thiazepine-5-carboxylic acid (0.23 g, 0.62 mL) in dimethylformamide (3.5 mL) at 0° C. was treated with 1-hydroxybenzotriazole (0.15 g, 1.1 mmol) and 13-dimethylaminopropyl)-3-ethylcarbodiimide (0.21 g, 1.1 mmol). After 45 min 50% aqueous hydroxylamine (0.2 mL) was added dropwise and the reaction mixture was allowed to warm to 25 ° C. After 72 h ethyl acetate and water were added and the organic phase washed with ethyl acetate (3×). The combined organic extracts were dried over anhydrous sodium sulfate and concentrated in vacuo to give 4-{[4-(2-butynyloxy)phenyl]sulfonylI-N-hydroxy-1,4-thiazepine-5-carboxamide as a hard white foam (0.20 g). Electrospray Mass Spec 385 (M+H)+.

Example 328

(2R)-5-(acetylamino)-2-(([4-(but-2-ynyloxy)phenyl] sulfonyl}amino)N-hydroxypentanamide Step A. (2R)-5-(tert-butyloxycarbonylamino)-2-({ [4-(but-2-ynyloxy)phenyl]-sulfonyl}amino)-N-hydroxypentanoic acid D-Orn(Boc) (4.0 g, 17.2 mmol) was dissolved in dioxane (20 mL) and water (20 mL) and 4-but-2-ynyloxy-benzenesulfonyl chloride (4.0 & 16.4 mmol) and triethylamine (4.4 mL, 31.6 mmol) were added. The mixture was stirred at room temperature for 18 hours. The solvent was evaporated and the residue dissolved in ethyl acetate and washed with brine and dried over MgSO$_4$ and concentrated. The crude product was used directly in Step B.

Step B

Coupling of sulfonylated amino acid to hydroxylamine resin.

4-O-Methylhydroxylamine-phenoxymethyl-copoly (styrene-1%-divinylbenzene)-resin[1] (20.0 g, 1.1 meq/g) was placed in a 250 mL solid phase synthesis vessel (Chem Glass) and suspended in DMF (100 mL). D-2-(4-but-2-ynyloxy-benzenesulfonylamino)-5-tert-butoxycarbonylaminopentanoic acid (9 g, 1.0 eq.) HOBt (16.2 g, 6.0 eq.) and DIC (12.5 mL, 4.0 eq.) were added. The reaction was shaken on an orbital shaker at room temperature for 16hours. The reaction was filtered and washed with DMF (3×50 mL), DCM (3×50 mL), MeOH (2×50 mL), and DCM (2×50 mL) The resin was dried in vacuo at room temperature.

Step C

Removal of the Boc group

The dried resin from Step B was placed in a 250 mL solid phase synthesis vessel and 2,6-lutidine (1.5 M solution in DCM, 50 mL) followed by trimethylsilyltriflate (1.0 M solution in DCM, 50 mL) were added. The reaction was shaken for 30 minutes, then filtered and the resin washed with DCM (2×50 mL). 2,6 Lutidine (1.5 M solution in DM 50 mL) followed by trimethylsilyltriflate (1.0 M solution in DCM, 50 mL) were again added and the reaction was shaken for a further 30 minutes, then filtered and the resin washed with DCM (2×50 mL), DMF (3×50 mL), DCM (3×50 mL), MeOH (2×50 mL), and DCM (2×50 mL) The resin was dried in vacuo at room temperature.

Step D

Acylation of ornitine side chain.

The resin from Step C was split into 24 empty 25 mL SPE column (Jones Chromatography USA, Inc. Part #120-102-H) and suspended in DMF (4 mL). To the first tube was added acetic acid (76 uL, 2.0 eq.) HOBt (541 mg, 6.0 eq.) and DIC (417 uL, 4.0 eq.) were added. The reaction was shaken on an orbital shaker at room temperature for 16hours. The reaction was filtered and washed with DMF (3×20 mL), DCM (3×20 mL), MEOH (2×20 mL), and DCM (2×20 mL).

Step E

Cleavage of the product from resin

The resin prepared in Step D was suspended in DCM (1.0 mL) and TFA (1.0 mL) was added. The reaction was shaken for 1 hour at room temperature. The reaction was filtered and the resin washed with DCM (2×1 mL). The filtrate and the washing were combined and concentrated to dryness on a Savant SpeedVac. MEOH (1 mL) was added and the mixture concentrated. The crude product was purified by reverse phase HPLC under the under the conditions described for Example 62B.

The hydroxamic acid compounds described in Table 2 below are synthesized according to the procedures of Example 328 using either D-Orn(Boc) or D-Lys(Boc) and the following acids in Step D: acetic acid, 5-benzimidazole carboxylic acid, benzoic acid, 4-bromobenzoic acid, butyric acid, 3-chlorothiophene-2-carboxylic acid, 4-chlorobenzoic acid, cyclohexane carboxylic acid, 3,4-dichlorophenyl acetic acid, 2,5-dimethyl-3-furoic acid, 3,5-dimethylisoxazole-carboxylic acid, hydrocinnamic acid, isocotinic acid, nicotinic acid, o-anisic acid, p-anisic acid, p-nitrophenyl acetic acid, phenylacetic acid, 3-quinoline carboxylic acid, 3-thiophenecarboxylic acid, transcinnamic acid, and oleic acid.

TABLE 2

| Example | R | HPLC retention time[5] (min.) | MS[3] (M + H) |
|---|---|---|---|
| 328 | D-Orn(Ac) | 1.91 | 398 |
| 329 | D-Orn(5-benzimidazolyl) | 1.98 | 500 |
| 330 | D-Orn(benzoyl) | 2.33 | 460 |
| 331 | D-Orn(4-bromobenzoyl) | 2.59 | 539 |
| 332 | D-Orn(butyryl) | 2.12 | 426 |
| 333 | D-Orn(3-chlorothiophene-2-carbonyl) | 2.43 | 501 |

TABLE 2-continued

| Example | R | HPLC retention time[5] (min.) | MS[3] (M + H) |
|---|---|---|---|
| 334 | D-Orn(4-chlorobenzoyl) | 2.55 | 494 |
| 335 | D-Orn(cyclohexylcarbonyl) | 2.44 | 466 |
| 336 | D-Orn(2,5-dimethyl-3-furoyl) | 2.74 | 543 |
| 337 | D-Orn(3,4-dichlorophenyl acetyl) | 2.45 | 478 |
| 338 | D-Orn(3,5-dimethylisoxazole-4-carbonyl) | 2.18 | 479 |
| 339 | D-Orn(hydrocinnamoyl) | 2.48 | 488 |
| 340 | D-Orn(isonicotinyl) | 1.78 | 461 |
| 341 | D-Orn(nicotinyl) | 1.81 | 461 |
| 342 | D-Orn(o-methoxybenzoyl) | 2.41 | 490 |
| 343 | D-Orn(p-methoxybenzoyl) | 2.36 | 490 |
| 344 | D-Orn(p-nitrobenzoyl) | 2.45 | 519 |
| 345 | D-Orn(phenylacetyl) | 2.38 | 474 |
| 346 | D-Orn(3-quinoline carbonyl) | 2.06 | 511 |
| 347 | D-Orn(3-thiophene carbonyl) | 2.28 | 466 |
| 348 | D-Orn(cinnamoyl) | 2.52 | 486 |
| 349 | D-Lys(5-benzimidazolyl) | 2.01 | 514 |
| 350 | D-Lys(benzoyl) | 2.39 | 474 |
| 351 | D-Lys(4-bromobenzoyl) | 2.65 | 553 |
| 352 | D-Lys(3-chlorothiophene-2-carbonyl) | 2.5 | 515 |
| 353 | D-Lys(4-chlorobenzoyl) | 2.61 | 509 |
| 354 | D-Lys(cyclohexylcarbonyl) | 2.49 | 480 |
| 355 | D-Lys(3,4-dichlorophenyl acetyl) | 2.63 | 557 |
| 356 | D-Lys(2,5-dimethyl-3-furoyl) | 2.51 | 492 |
| 357 | D-Lys(3,5-dimethylisoxazole-4-carbonyl) | 2.22 | 493 |
| 358 | D-Lys(hydrocinnamoyl) | 2.51 | 502 |
| 359 | D-Lys(isonicotinyl) | 2.01 | 475 |
| 360 | D-Lys(o-methoxybenzoyl) | 2.47 | 504 |
| 361 | D-Lys(p-methoxybenzoyl) | 2.41 | 504 |
| 362 | D-Lys(p-nitrobenzoyl) | 2.5 | 533 |
| 363 | D-Lys(phenylacetyl) | 2.42 | 458 |
| 364 | D-Lys(3-quinoline carbonyl) | 2.1 | 525 |
| 365 | D-Lys(3-thiophene carbonyl) | 2.33 | 480 |
| 366 | D-Lys(cinnamoyl) | 2.57 | 500 |
| 367 | D-Orn(Z-octadec-9-enoyl) | 4.35 | 620 |

[5]LC conditions: Hewlett Packard 1100; YMC ODS-A 4.6 mm + 50 mm 5 u column at 23° C.; 10 μL injection; Solvent A: 0.05% TFA/water; Solvent B:0.05% TFA/acetonitrile; Gradient: Time 0:98% A; 0.5 min: 98% A; 4.5 min: 5% A, 5.0 min: 5% A. Flow rate 2.5 mL/min; Detection: 220 and 254 nm DAD.

Example 368

N-[(4R)-4-({[4-(But-2-ynyloxy)phenyl]sulfonyl}amino)-5-(hydroxyamino)-5-oxopentyl]thiophene-2-carboxamide Step A (2R)-2-(4-But-2-ynyloxy-benzenesulfonylamino)-5-tert-butoxycarbonylaminopentanoic acid O-tert-butylhydroxyamide (2R)-2-(4-but-2-ynyloxy-benzenesulfonylamimo)-5-tert-butoxycarbonylaminopentanoic acid (10 g, 22.7 prepared as described in Example 328Step A was dissolved in DCM (100 mL) and HOBt (3.7 g, 27.4 mmol), O-tert-Butyl hydroxylamine hydrochloride (4.2 g, 33.4 mmol) triethylamine (9.4 mL, 67 mmol) and EDC (5 g& 32.2 mmol) were added in that order. The reaction was stirred at room temperature for 16 hours, then diluted with ethyl acetate and washed with water, dried over MgSO$_4$ and concentrated.

Step B: (2 R-2-(4-But-2-ynyloxy-benzenesulfonylamino)-5-amnopentanoic acid O-tert-butylhydroxyamide The residue from Step A was dissolved in 2,6-lutidine (1.5 M in DCM, 33 mL, 50 mmol) and trimethylsilyltfiflate (1.0

M in DCM, 33 mL, 33 mmol) was added. The reaction was stirred for 2 hours then diluted with ethyl acetate and washed with water and saturated aqueous sodium bicarbonate. The organic phase was dried over $MgSO_4$ and concentrated.

Step C: N-[(4 R)-4-({[4-(But-2-ynyloxy)phenyl] sulfonyl)amino)-5-(O-tert-butylhydroxyamino)-5-oxopentyl]thiophene-2-carboxamide The residue from Step B (102 mg 0.25 mmol) was dissolved in DCM (2 mL). Triethylamine (104 uL, 0.75 mmol), DMAP (0.3 mg, 0.025 mmol) and thiophene-2-carbonyl chloride (55 mg, 0.37 mmol) were added. The reaction was shaken on an orbital shaker for 16hours then concentrated to dryness.

Step D: N-[(4R)-4-({[4-(But-2-ynyloxy)phenyl] sulfonyl)amino)-5-(hydroxyamino)-5-oxopentyl]-thiophene-2-carboxanide The residue from Step C was dissolved in DCM (1 mL) and TFA (1 mL) was added. The solution was shaken at 40° C. for 5hours, then concentrated. The residue was dissolved in MeOH and purified by reverse phase HPLC under the conditions described below to give Example 368(8.5 mg) Electrospray Mass Spec 466(M+H)+; HPLC retention times 3.06 minutes. Flow Rate: 22.5 mL/minute.

Example 369

(2R)-2-({[4-(But-2-ynyloxy)phenyl]sulfonyl) amino)-5-{[(ethylamino)carbonyl]amino)-N-hydroxypentanamide Step A:

The residue from Example 368Step B (102 mg, 0.25 mmol) was dissolved in DCM (2 mL) and triethylamine (69 uL, 0.5 mmol) and ethyl isocyanate (22 uL, 0.27 mmol) were added. The reaction was shaken on an orbital shaker for 16hours then concentrated to dryness.

Step B:

The procedure used in Example 368,Step D was used to give Example 369(7.2 mg) Electrospray Mass Spec 427(M+H)+; HPLC retention time[5] 2.26 minutes.

Example 370

(2R)-5-[(Anilinocarbonyl)amino]-2-({[4(but-2-yuyloxy)phenyl]sulfonyl}amino)N-hydroxypentanamide Step A:

The residue from Example 368Step B (102 mg, 0.25 mmol) was dissolved in DCM (2 mL) and triethylamine (69 uL, 0.5 mmol) and phenyl isocyanate (2230 uL, 0.27 mmol) were added. The reaction was shaken on an orbital shaker for 16hours then concentrated to dryness.

Step B:

The procedure used in Example 368Step D was used to give Example 370(21.3 mg) Electrospray Mass Spec 475 (M+H)+; HPLC retention time[5] 2.7 minutes.

Example 371

Octyl (4R-4-({[4-but-2-ynylexy) phenyllsufonyllamino)-5-(hydroxyamino)-oxopentylcarbamate Step A:

The residue from Example 368Step B (102 m& 0.25 mmol) was dissolved in DCM (2 mL) and diisopropylethylamine (87 uL, 0.5 mmol) and octyl chloroformate (54 uL, 0.27 mmol) were added. The reaction was shaken on an orbital shaker for 16hours then concentrated to dryness.

Step B:

The procedure used in Example 368Step D was used to give Example 371 (5.2 mg) Electrospray Mass Spec 512 (M+H)+; HPLC retention time[5] 2.52 minutes.

Example 372

4-Methoxyphenyl (4R)-4-({[4-but-2-ynyloxeyphenyl]sulfonylamino)-5-(hydroxyamino)-5-oxopentylcarbamate Step A:

The residue from Example 368Step B (102 mg 0.25 mmol) was dissolved in DCM (2 mL) and diisopropylethylamine (87 uL, 0.5 mmol) and 4 methoxyphenyl chloroformate (41 uL, 0.27 mmol) were added. The reaction was shaken on an orbital shaker for 16 hours then concentrated to dryness.

Step B:

The procedure used in Example 368Step D was used to give Example 372(14.7 mg) Electrospray Mass Spec 506 N+H)+; BPLC retention time[5] 2.82 minutes.

Example 373

(2R)-2-({[4-(But-2-ynylosy)phenyl] sulfonyl}amino)-5-{[(diethylamino)carbonyl] amino}-N-hydroxypentanamide Step A:

The residue from Example 368 Step B (102 mg, 0.25 mmol) was dissolved in DCM (2 mL) and triethylamime amine (69 uL, 0.5 mmol) and diethyl carbamoyl chloride (35 uL, 0.27 mmol) were added. The reaction was shaken on an orbital shaker for 16 hours then concentrated to dryness.

Step B:

The procedure used in Example 368Step D was used to give Example 373(19.7 mg) Electrospray Mass Spec 455 (M+H)+; HPLC retention time[5] 2.52 minutes.

Example 374

(2R-2-({[4-(But-2-ynyloxy)phenyl]sulfonyl}amino) N-hydroxy-5-{[(methylanilino)carbonyl] amino}pentanamide Step A:

The residue from Example 368Step B (102 mg, 0.25 mmol) was dissolved in DCM (2 mL) and triethylamime amine (69 uL, 0.5 mmol) and methylphenyl carbamoyl chloride (46 mg, 0.27 mmol) were added. The reaction was shaken on an orbital shaker for 16 hours then concentrated to dryness.

Step B:

The procedure used in Example 368 Step D was used to give Example 374(28 mg) Electrospray Mass Spec 489 (+H)+; HPLC retention time[5] 2.73 minutes.

Example 375

(2R-2-({[4-(But-2-ynylox)phenyl]sulfonyl}amino)-N-hydroxy-5-{[(1-methyl-1H-imidazol-4-yl)sulfonyl]amino}pentanamide Step A:

The residue from Example 368 Step B (102 mg, 0.25 mmol) was dissolved in DCM (2 mL) and diisopropylethylamine (87 uL, 0.5 mmol) and 1-methylimidazole4-sulfonyl chloride (50 mg 0.27 mmol) were added. The reaction was shaken on an orbital shaker for 16hours then concentrated to dryness.

Step B:

The procedure used in Example 368Step D was used to give Example 375(9.5 mg) Electrospray Mass Spec 500 (M+H)+; HPLC retention time[5] 2.28 minutes.

Example 376

(2R)-2-({[4-(But-2-ynyloxy)phenyl]sulfonyl}amino) N-hydroxy-5-1(2-morpholin-4-ylacetyl)amino]pentanamide Step A:

The residue from Example 368 Step B (102 mg, 0.25 mmol) was dissolved in DCM (2 ml) and triethylamime amine (87 uL, 0.5 mmol), DMAP (0.3 mg, 0.025 mmol) and chloroacetyl chloride (30 uL, 0.27 mmol) were added. The reaction was shaken on an orbital shaker for 16 hours then concentrated to dryness.

Step B:

The residue from Step A was dissolved in DCM (2 mL) and morpholine (87 uL, 1.0 mmol) was added. The reaction was shaken at room temperature for 16 hours, then concentrated to dryness.

Step C:

The procedure used in Example 368Step D was used to give Example 376(23.1 mg) Electrospray Mass Spec 483 (M+H)+; HPLC retention time[5] 1.92 minutes.

Example 377

(2R)-2-({14-(But-2 ynyloxyphenyl]sulfonyl amino)-N-hydroxy-5-{[2-(4-methylpiperazin-1-yl)acetyl]amino}pentanamide Step A:

The residue from Example 376Step A was dissolved in DCM (2 mL) and N-methyl piperazine (110 uL, 1. mmol) was added. The reaction was shaken at room temperature for 16hours, then concentrated to dryness.

Step B:

The procedure used in Example 368Step D was used to give Example 377(16.8 mg) Electrospray Mass Spec 496 (M+H)+; HPLC retention time[5] 1.89 minutes.

Example 378

(2R)-5-{[2-(Benzylamino)acetyl]amino}-2-({[4-(but-2-ynyloxy)phenyl]sulfonyl}amino)N-hydroxypentanamide Step A:

The residue from Example 376Step A was dissolved in DCM (2 mL) and benzylamine (110 uL, 1.0 mmol) was added. The reaction was shaken at room temperature for 16hours, then concentrated to dryness.

Step B:

The procedure used in Example 368,Step D was used to give Example 378(20.2 mg) Electrospray Mass Spec 503 (M+H)+; HPLC retention time[5] 3.64 minutes.

Example 379

(3S)([14-(2-Butynyloxy)phenyl]sulfonyl}-N-hydroxy-2,2-dimethyl-3,4 dihydro-2H-1,4-thiazine-3 carboxamide Step 1

The product of Step 3 of Example 243, 4-(4-hydroxybenzenesulfonyl)-2,2-dimethylthiomorpholine-3-carboxylic acid methyl ester (2.00 g, 5.746 mmol), and 2-butyn-1-1-ol (0.52 mL, 6.916 mmol) underwent Mitsunobu coupling according to the procedure of Step 4 of Example 243 to provide 1.68 g of methyl (3S)4-({[4-(2-butynyloxy)-phenyl]sulfonyl}-2,2-dimethyl-thiomorpholine-3-carboxylate as a white solid.

Step2

To a 0° C. solution of 1.68 g (4.23 mmol) of methyl (3S)-4-({[4-(2-butynyloxy)phenyl]sulfonyl)-2,2-dimethyl-thiomorpholine-3-carboxylate in 100 mL of dichloromethane and 16 mL of methanol was added 0.730 g of m-chloroperbenzoic acid in four equal portions, as a solid. Thirty minutes after all of the m-chloroperbenzoic acid had been added, the reaction was diluted with dichloromethane and washed with saturated sodium bicarbonate solution. The organics were dried over sodium sulfate, filtered and concentrated in vacuo. The residue was chromatographed on silica gel eluting with a gradient of ethyl acetate/hexanes (1:1 ) to ethyl acetate to provide 1.50 g of a 3:1 mixture of sulfoxide diastereomers, methyl (3S)-4-({[4-(2-butynyloxy)phenyl]sulfonyl)2,2-dimethyl-thiomorpholine-3-carboxylate-1-oxide, which was used for the next step.

Step 3

A solution of 1.50 g (3.632 mmol) of methyl (3S)A({[4-(2-butynyloxy)-phenyl]sulfonyl)2,2-dimethyl-thiomorpholine-3-carboxylate-1-oxide in 20 mL of acetic anhydride was heated to reflux for 4h and then concentrated in vacuo. The residue was chromatographed on silica gel eluting with ethyl acetate/hexanes (1:10 ) to provide 0.985 g of methyl(3S)-4-{[4-(2-butynyloxy)phenyl]sulfonyl)-2,2-dimethyl-3,4-dihydro-2H-1,4-thiazine-3-carboxylate as a colorless oil. Electrospray Mass Spec 396.1 (M+H)+.

Step 4

Lithium iodide (0.770 & 5.75 mmol) mediated ester cleavage of 0.227 g (0.575 mmol) of methyl(3S)-4-{[4-(2-butynyloxy)phenyl]sulfonyl}-2,2-dimethyl-3,4-dihydro-2H-1,4-thiazine-3-carboxylate according to the procedure of Example 250 provided 0.205 g of (3S)-4-{[4(2-butynyloxy) phenyl]sulfonyl)-2,2-dimethyl-3,4-dihydro-2H-1,4-thiazine-3-carboxylic acid as a white solid. Electrospray Mass Spec 382.0 (+H)+.

Step 5

According to the procedure of Example 9, 0.200 g (0.525 mmol) of (3S)-4-{[4-(2-butynyloxy)phenyl]sulfonyl}-2,2-dimethyl-3,4-dihydro-2H-1,4-thiazine-3-carboxylic acid was converted into 0.173 g of the corresponding hydroxamic acid, (3S)-4-{[4-(2-butynyloxy)phenyl]sulfonyl)-N-hydroxy-2,2-dimethyl-3,4-dihydro-2H-1,4-thiazine-3-carboxamide, obtained as a white solid. Electrospray Mass Spec 396.9 (M+H)+.

Pharmacology

Representative compounds of his invention were evaluated as inhibitors of the enzymes MMP-1, MMP-9, MMP-13 and TNF-a converting enzyme (TACE). The standard pharmacological test procedures used, and results obtained which establish this biological profile are shown below.

Test Procedures for Measuring MMP-1, MMP-9, and MMP-13 Inhibition

These standard pharmacological test procedures are based on the cleavage of a thiopeptide substrates such as Ac-ProLeu-Gly(2-mercapt-4-methyl-pentanoyl)-Leu-Gly-OEt by the matrix metalloproteinases MMP-1, MMP-13 (collagenases) or MMP-9(gelatinase), which results in the release of a substrate product that reacts colorimetrically with DTNB (5,5'-dithiobis(2-nitro-benzoic acid)). The enzyme activity is measured by the rate of the color increase. The thiopeptide substrate is made up fresh as a 20 mM stock in 100% DMSO and the DTNB is dissolved in 100% DMSO as a 100 mM stock and stored in the dark at room temperature. Both the substrate and DTNB are diluted together to 1 mM with substrate buffer (50 mM HEPES pH 7.5, 5 mM $CaCl_2$) before use. The stock of enzyme is diluted with buffer (50 mM HEPES, pH 7.5, 5 mM $CaCl_2$, 0.02% Brij) to the desired final concentration. The buffer, enzyme, vehicle or inhibitor, and DTNB/substrate are added in this order to a 96 well plate (total reaction volume of 200 μl) and the increase in color is monitored spectrophotometrically for 5 minutes at 405 nm on a plate reader and the increase in color over time is plotted as a linear line.

Alternatively, a fluorescent peptide substrate is used. In this test procedure, the peptide substrate contains a fluorescent group and a quenching group. Upon cleavage of the substrate by an MMP, the fluorescence that is generated is quantitated on the fluorescence plate reader. The assay is run in HCBC assay buffer (50 mM HEPES, pH 7.0, 5 mM $Ca^{+2}$, 0.02% Brij, 0.5% Cysteine), with human recombinant MMP-1, MMP-9, or MMP-13. The substrate is dissolved in methanol and stored frozen in 1 mM aliquots. For the assay, substrate and enzymes are diluted in HCBC buffer to the desired concentrations. Compounds are added to the 96 well plate containing enzyme and the reaction is started by the addition of substrate. The reaction is read (excitation 340 nm, emission 444 nm) for 10 min. and the increase in fluorescence over time is plotted as a linear line.

For either the thiopeptide or fluorescent peptide test procedures, the slope of the line is calculated and represents the reaction rate. The linearity of the reaction rate is confirmed ($r^2>0.85$). The mean (x±sem) of the control rate is calculated and compared for statistical significance ($p<0.05$) with drug-treated rates using Dunnett's multiple comparison test. Dose-response relationships can be generated using multiple doses of drug and $IC_{50}$ values with 95% CI are estimated using linear regression Test Procedure for Measuring TACE Inhibition Using 96-well black microtiter plates, each well receives a solution composed of 10 μL TACE (final concentration 1 μg/mL), 70 μL Tris buffer, pH 7.4 containing 10% glycerol (final concentration 10 mM, and 10 μL of test compound solution in DMSO (final concentration 1 μM, DMSO concentration <1%) and incubated for 10 minutes at room temperature. The reaction is initiated by addition of a fluorescent peptidyl substrate (final concentration 100 μM to each well and then shaking on a shaker for 5 sec.

The reaction is read (excitation 340 nm, emission 420 nm) for 10 min. and the increase in fluorescence over time is plotted as a linear line. The slope of the line is calculated and represents the reaction rate.

The linearity of the reaction rate is confirmed ($r^2>0.85$). The mean (x±sem) of the control rate is calculated and compared for statistical significance ($p<0.05$) with drug-treated rates using Dunnett's multiple comparison test. Dose-response relationships can be generate using multiple doses of drug and $IC_{50}$ values with 95% CI are estimated using linear regression.

Human Monocytic THP-1 Cell Differentiation Assay For Soluble Proteins (THP-1 Soluble Protein Assay)

Mitogenic stimulation of THP-1 cells cause differentiation into macrophage like cells with concomitant secretion of tumor necrosis factor (TNF-a) and TNF receptor (TNF-R p75/80 and TNF-R p55160 ) and Interleukin-8(IL-8 ), among other proteins. In addition, non-stimulated THP-1 cells shed both the p75/80 and the p55/60 receptors over time. The release of membrane bound TNF-a and possibly TNF-R p75/80 and TNF-R p55/60, but not EL-8, is mediated by an enzyme called TNF-a converting enzyme or TACE. This assay can be used to demonstrate either an inhibitory or a stimulatory compound effect on this TACE enzyme and any cytotoxic consequence of such a compound.

THP-1 cells (from ATCC) are a human monocytic cell line which were obtained from the peripheral blood of a one year old male with acute monocytic leukemia They can be grown in culture and differentiated into macrophage like cells by stimulation with mitogens.

For the assay, THP-1 cells are seeded from an ATCC stock which was previously grown and frozen back at 5×10/ml/ vial. One vial is seeded into a T25-flask with 16 mls of RPMI-1640 with glutamax (Gibco) media containing 10% fetal bovine serum, 100 units/ml penicillin, 100 jig/ml streptomycin, and $5×10^{-5}$ M 2-mercapto-ethanol (THP-1 media). Each vial of cells are cultured for about two weeks prior to being used for an assay and then are used for only 4 to 6 weeks to screen compounds. Cells are subcultured on Mondays and Thursdays to a concentration of 1×105/ml. To perform an assay, the THP-1 cells are co-incubated in a 24 well plate with 50 ml/well of a 24 mg/ml stock of Lipopolysacharide (LPS) (Calbiochem Lot# B13189 ) at 37° C. in 5% $CO_2$ at a concentration of $1.091×10^6$ cells/ml (1.1 ml/well) for a total of 24hours. At the same time, 50 ml/well of drug, vehicle or THP-1 media is plated in appropriate wells to give a final volume of 1.2 ml/well. Standard and test compounds are dissolved in DMSO at a concentration of 36 mM and diluted from here to the appropriate concentrations in THP-1 media and added to the wells at the beginning of the incubation period to give final concentrations of 100 mM, 30 mM, 10 mM, 3 mM, 1 mM, 300 nM, and 100 nM. Cell exposure to DMSO was limited to 0.1% final concentration. Positive control wells were included in the experiment which had mitogen added but no drug. Vehicle control wells were included as well, which were identical to the positive control wells, except that DMSO was added to give a final concentration of 0.083%. Negative control wells were included in the experiment which had vehicle but no mitogen or drug added to the cells. Compounds can be evaluated for their effect on basal (non-stimulated) shedding of the receptors by replacing the LPS with 50 ml/well of THP-1 media. Plates are placed into an incubator set at 5% $CO_2$ and at 37° C. After 4 hours of incubation, 300 ml/well of tissue culture supernatant (TCS) is removed for use in an TNF-a ELISA Following 24hours of incubation, 700 ml/well of TCS is removed and used for analysis in TNF-R p75180, TNF-R p55160 and IL-8 ELISAs.

In addition, at the 24hours timepoint, and the cells for each treatment group are collected by resuspension in 500 $\mu$l/well of THP-1 media and transferred into a FACS tube. Two ml/tube of a 0.5 mg/ml stock of propidium iodide (PI) (Boerhinger Mannheim cat. #1348639 ) is added. The samples are run on a Becton Dickinson FaxCaliber FLOW cytometry machine and the amount of dye taken up by each cell is measured in the high red wavelength (FL3 ). Only cells with compromised membranes (dead or dying) can take up PI. The percent of live cells is calculated by the number of cells not stained with PI, divided by the total number of cells in the sample. The viability values calculated for the drug treated groups were compared to the viability value calculated for the vehicle treated mitogen stimulated group ("vehicle positive control") to determine the "percent change from control". This "percent change from control" value is an indicator of drug toxicity.

The quantity of soluble TNF-a, TNF-R p75180 and TNF-R p55160 and IL-8 in the TCS of the TBP-1 cell cultures are obtained with commercially available ELISAs from R&D Systems, by extrapolation from a standard curve generated with kit standards. The number of cells that either take up or exclude PI are measured by the FLOW cytometry machine and visualized by histograms using commercially available Cytologic software for each treatment group including all controls. Biological variability in the magnitude of the response of TBP-1 cell cultures requires that experiments be compared on the basis of percent change from "vehicle positive control" for each drug concentration. Percent change in each soluble protein evaluated from the "vehicle positive control" was calculated for each compound concentration with the following formula:

$$\% \text{ Change} = \frac{\text{pg/ml(compound)} - \text{pg/ml (veh pos control)}}{\text{pg/ml (veh pos control)} - \text{pg/ml(veh neg control)}} \times 100$$

For the soluble protein (TNF-a, p75180, p5560, IL-8 ) studies under stimulated conditions, the mean pg/ml of duplicate wells were determined and the results expressed as percent change from "vehicle positive control". For the soluble protein (p75/80 and p55160 receptors) studies under non-stimulated conditions, the mean pg/ml of duplicate wells were determined and the results expressed as percent change from "vehicle positive control" utilizing the following formula:

% Change =

$$\frac{\text{pg/ml (compound neg control)} - \text{pg/ml (veh neg control)}}{\text{pg/ml (veh neg control)}} \times 100$$

IC50 values for each compound are calculated by nonlinear regression analysis using customized software utilizing the JUMP statistical package.

For the cell viability studies, the viabilities (PI exclusion) of pooled duplicate wells were determined and the results expressed as % change from "vehicle positive control". The viability values calculated for the compound treated groups were compared to the viability value calculated for the "vehicle positive control" to determine "percent change from control" as below. This value "percent change from control" is an indicator of drug toxicity.

$$\% \text{ Change} = \frac{\% \text{ live cells (compound)}}{\% \text{ live cells (veh pos control)}} - 1 \times 100$$

References:

Bjornberg, F., Lantz, M., Olsson, I., and Gullberg, U. Mechanisms involved in the processing of the p55 and the p75 tumor necrosis factor (TNF) receptors to soluble receptor forms. Lymphokine Cytokine Res. 13:203–211, 1994.

Gatanaga, T., Hwang, C., Gatanaga, M., Cappuccini, F., Yamamoto, R, and Granger, G. The regulation of TNF mRNA synthesis, membrane expression, and release by PMA- and LPS-stimulated human monocytic THP-1 cells in vitro. Cellular Immun. 138:1–10, 1991.

Tsuchiya, S., Yamabe, M., Yamagugbi, Y., Kobayashi, Y., Konno, T., and Tada, K. Establishment and characterization of a human acute monocytic leukemia cell line (THP-1 ). Int. J. Cancer. 26:1711–176,1980.

Results of the above in vitro matrix metalloproteinase inhibition, TACE inhibition and TBP standard pharmacological test procedures are given in Tables 1-15 below.

TABLE 1

| Example # | R | MMP-1[a] | MMP-9[a] | MMP-13[a] | TACE[a] | THP[b] |
|---|---|---|---|---|---|---|
| 25 | H | 47% (10) | 753 | 185 | 4.8 | 39 |
| 30 | Me | | 4385 | 262 | 40 | 6.0 | 60 |
| 27 | iPr | 2965 | 42 | 18 | 32 | 75 |
| 105 | iBu | 1743 | 213 | 52 | 6.8 | 87 |
| 106 | tBu | 880 | 224 | 41 | 17 | 91 |
| 129 | $C_6H_{10}$-4-OH | 1037 | 192 | 28 | 7.4 | 92 |
| 35 | $Me_2$ | 10,000 | 1377 | 396 | 12.9 | 9 |
| 139 | —$(CH_2)_4$— | >10,000 | 3695 | 1272 | 37 | 26 |
| 138 | —$(CH_2)_5$— | 5167 | 2174 | 619 | 27 | 19 |
| 287 | —$(CH_2)_2$N(BOC)—$(CH_2)_2$— | >10,000 | — | 530 | 37 | 60 |
| 288 | —$(CH_2)_2$NH—$(CH_2)_2$— | >10,000 | — | >10,000 | 50 | 25 |
| 167 | $CH_2SCH_3$ | 1739 | 228 | 40 | 3.5 | 77 |
| 158 | $C(Me)_2SCH_3$ | 1024 | 164 | 30 | 25 | 78 |
| 159 | $C(Me)_2SEt$ | 852 | 424 | 42 | 12 | 76 |
| 160 | $C(Me)_2SPr$ | 1401 | 1007 | 65 | 15 | 67 |
| 169 | $CH_2SCH_2$-3-Pyridyl | 1908 | 160 | 28 | 2.9 | 77 |
| 161 | $C(Me)_2SCH_2$-3-Pyridyl | 476 | 130 | 7.9 | 6.4 | 81 |
| 168 | $CH_2SCH_2Ph$ | 1970 | 141 | 16 | 4.5 | 62 |
| 162 | $C(Me)_2SCH_2Ph$ | 310 | 138 | 8.3 | 19 | 49 |
| 163 | $C(Me)_2SCH_2$-3-Me-2-Imidazole | 1719 | 306 | 47 | 18 | 77 |
| 164 | $C(Me)_2S(CH_2)_2N[(CH_2)_2]_2O$ | 1570 | 204 | 20 | 64 | 70 |
| 170 | $CH_2S(CH_2)_{10}CH=CHEt$ | >10,000 | 1574 | 322 | 272 | 7 |
| 165 | $C(Me)_2SCH_2CO_2tBu$ | 2431 | 587 | 177 | 69 | 84 |
| 166 | $C(Me)_2SCH_2CO_2H$ | 1897 | 2942 | 241 | — | 55 |
| 171 | $C(Me)_2S(CH_2)_3$—OH | 2140 | — | 36 | 25 | 67 |
| 172 | $CH_2S(CH_2)_3$—OH | >1,000 | — | 169 | 11 | 70 |

[a]$IC_{50}$ (nM)
[b]% Inhibiton @ 3 μM

TABLE 2

| Example # | $R_1$ | $R_2$ | MMP-1[a] | MMP-9[a] | MMP-13[a] | TACE[a] | THP[b] |
|---|---|---|---|---|---|---|---|
| 17 | H | Me | 1895 | 309 | 99 | 6.8 | 33 |
| 23 | H | $CH_2$-3-Pyridyl | 1156 | 40 | 20 | 7.2 | 63 |
| 124 | H | $(CH_2)_2N[(CH_2)_2]_2O$ | 1768 | 211 | 54 | 13 | 24 |
| 107 | Me | Me | 330 | 68 | 28 | 4.5 | 83 |
| 33 | Me | $CH_2$-3-Pyridyl | 239 | 65 | 26 | 5.0 | 80 |
| 135 | Me | $CH_2CCCH_2N[(CH_2)_2]_2NMe$ | 921 | 142 | 66 | 21 | 76 |
| 9 | iPr | Me | 40 | 11 | 4.5 | 7.4 | 94 |
| 108 | iPr | Et | 92 | 119 | 67 | 33 | 76 |
| 109 | iPr | $CH_2CCH$ | 210 | 233 | 53 | 55 | 85 |
| 110 | iPr | Pr | 196 | 477 | 153 | 66 | 47 |
| 111 | iPr | $(CH_2)_3Ph$ | 308 | 1423 | 303 | 481 | 35 |
| 112 | iPr | $CH_2$-o-Pr | 189 | 397 | 142 | 57 | 50 |
| 113 | iPr | $CH_2CH(CH_3)_2$ | 299 | 918 | 309 | 107 | 0 |
| 123 | iPr | $(CH_2)_2N[(CH_2)_2]_2O$ | 244 | 628 | 89 | 102 | 35 |
| 118 | iPr | $(CH_2)_3NEt_2$ | 121 | 86 | 45 | 154 | 77 |
| 119 | iPr | $(CH_2)_3N[(CH_2)_2]_2O$ | 129 | 94 | 46 | 124 | 61 |
| 120 | iPr | $(CH_2)_3N[(CH_2)_2]_2NMe$ | 111 | 211 | 161 | 149 | 61 |
| 121 | iPr | $(CH_2)_4NEt_2$ | 120 | 256 | 114 | 177 | 65 |
| 122 | iPr | $(CH_2)_4N[(CH_2)_2]_2NMe$ | 86 | 135 | 50 | 126 | 69 |
| 114 | iPr | $CH_2$-3-Pyridyl | 236 | 193 | 94 | 93 | 75 |
| 125 | iPr | $CH_2CCCH_2N[(CH_2)_2]_2NMe$ | 505 | 846 | 151 | 108 | 72 |
| 126 | iPr | $CH_2CCCH_2NEt_2$ | 212 | 149 | 36 | 73 | 93 |
| 127 | iPr | $CH_2CCCH_2NHMe$ | 187 | 53 | 37 | 104 | 83 |
| 137 | —$(CH_2)_5$— | $CH_2$-3-Pyridyl | 482 | 79 | 48 | 191 | 0 |

TABLE 2-continued

Structure: HO-NH-C(=O)-C(R1)(R1)-N(R1)-S(=O)2-C6H4-O-CH2-C≡C-CH3

| Example # | R1 | R2 | MMP-1[a] | MMP-9[a] | MMP-13[a] | TACE[a] | THP[b] |
|---|---|---|---|---|---|---|---|
| 115 | $C_6H_{11}$ | Me | 94 | 14 | 6.6 | 31 | 89 |
| 116 | $C_6H_{11}$ | $CH_2$-3-Pyridyl | 218 | 336 | 53 | 204 | 75 |
| 117 | $C_6H_{11}$ | $CH_2PhO(CH_2)_2N[(CH_2)_2]_2NH$ | 74 | 76 | 33 | 274 | 88 |
| 130 | $C_6H_{10}$-4-OH | Me | 169 | 30 | 15 | 23 | 92 |
| 136 | —$(CH_2)_5$— | Me | 682 | 3753 | 1629 | 574 | 0 |
| 128 | $C_6H_{10}$-4-$NEt_2$ | Me | 2368 | 184 | 212 | 376 | 51 |
| 213 | $(CH_2)_3SPh$-p-Cl | Me | 453 | — | 9.0 | 210 | 87 |

[a] $IC_{50}$ (nM)
[b] % Inhibition @ 3 μM

TABLE 3

Structure: HO-NH-C(=O)-C(R2)(H)-N(R3)-S(=O)2-C6H4-O-CH2-C≡C-CH3

| Example # | R2 | R3 | MMP-1[a] | MMP-9[a] | MMP-13[a] | TACE[a] | THP[b] |
|---|---|---|---|---|---|---|---|
| 154 | $CH_2SCH_3$ | Me | 47 | 19 | 5.4 | 3.3 | 90 |
| 149 | $C(Me)_2SCH_3$ | Me | 17 | 13 | 4.6 | 29 | 88 |
| 150 | $C(Me)_2SEt$ | Me | 25 | 20 | 9.3 | 51 | 86 |
| 151 | $C(Me)_2SPr$ | Me | 24 | 31 | 14 | 31 | 82 |
| 156 | $CH_2SCH_2Ph$ | Me | 70 | 11 | 4.5 | 4.8 | 75 |
| 157 | $CH_2SCH_2Ph$ | $CH_3$-3-Pyridyl | 111 | 32 | 3.8 | 98 | 79 |
| 153 | $C(Me)_2SCH_2Ph$ | Me | 13 | 5.5 | 2.0 | 160 | 46 |
| 155 | $CH_2SCH_2$-3-Pyridyl | Me | 61 | 14 | 4.8 | 5.9 | 93 |
| 152 | $C(Me)_2SCH_2$-3-Pyridyl | Me | 8.7 | 3.7 | 1.7 | 74 | 85 |
| 140 | $C(Me)_2S(CH_2)_2$—$N[(CH_2)_2]_2O$ | Me | 45 | 103 | 9.2 | 86 | 80 |
| 141 | $C(Me)_2S(CH_2)_2$—$N[(CH_2)_2]_2NMe$ | Me | 17 | 8.3 | 7.6 | 101 | 86 |
| 142 | $C(Me)_2S(CH_2)_2$—$NEt_2$ | Me | 72 | 10 | 14 | 131 | 89 |
| 144 | $C(Me)_2S(CH_2)_2$-1-Imidazolyl | Me | 16 | 26 | 5.9 | 60 | 89 |
| 145 | $C(Me)_2S(CH_2)_2$-NProlineEt | Me | 18 | 7.1 | 2.5 | 109 | 83 |
| 143 | $C(Me)_2S(CH_2)_3$—$NC_4H_8$ | Me | 72 | 9.5 | 16 | 219 | 86 |
| 146 | $C(Me)_2S(CH_2)_3$—$N[(CH_2)_2]_2O$ | Me | 13 | 5.3 | 3.6 | 132 | 84 |
| 147 | $C(Me)_2S(CH_2)_3$—$N[(CH_2)_2]_2NMe$ | Me | 21 | 5.3 | 5.3 | 157 | 89 |
| 149 | $C(Me)_2S(CH_2)_3$—$NEt_2$ | Me | 25 | 4.8 | 5.2 | 88 | 87 |

[a] $IC_{50}$ (nM)
[b] % Inhibition @ 3 μM

TABLE 4

Structure: HO-NH-C(=O)-C(R2)(H)-N(R3)-S(=O)2-pyridyl(Y)-X-R1

| Example # | X | Y | R1 | R2 | R3 | MMP-1[a] | MMP-9[a] | MMP-13[a] | TACE[a] | THP[b] |
|---|---|---|---|---|---|---|---|---|---|---|
| 17 | O | CH | $CH_2CCCH_3$ | H | Me | 1895 | 309 | 99 | 6.8 | 33 |
| 133 | NH | CH | $CH_2CCH$ | H | Me | ~10,000 | 1511 | 751 | 120 | 8 |
| 134 | S | CH | $CH_2CCCH_3$ | H | Me | 4948 | 111 | 84 | 38 | 14 |

TABLE 4-continued

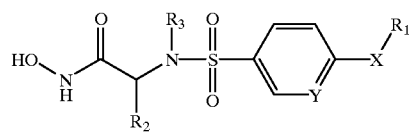

| Example # | X | Y | R$_1$ | R$_2$ | R$_3$ | MMP-1[a] | MMP-9[a] | MMP-13[a] | TACE[a] | THP[b] |
|---|---|---|---|---|---|---|---|---|---|---|
| 131 | O | N | CH$_2$CCCH$_3$ | H | Me | ~10,000 | 402 | 428 | 29 | 18 |
| 132 | O | — | CH$_2$CCPh-4-Cl | H | Me | >10,000 | 2373 | 1121 | 1100 | 27 |

[a]IC$_{50}$ (nM)
[b]% Inhibition @ 3 μM

TABLE 5

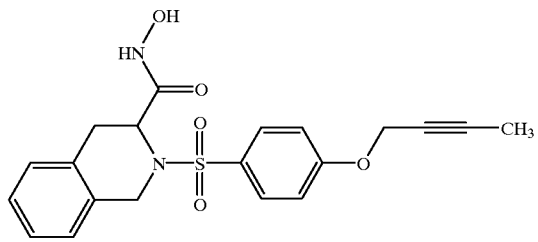

| Example # | MMP-1[a] | MMP-9[a] | MMP-13[a] | TACE[a] | THP[b] |
|---|---|---|---|---|---|
| 41 | 121 | 24 | 10 | 7.0 | 93 |

[a]IC$_{50}$ (nM)
[b]% Inhibition @ 3 μM

TABLE 6

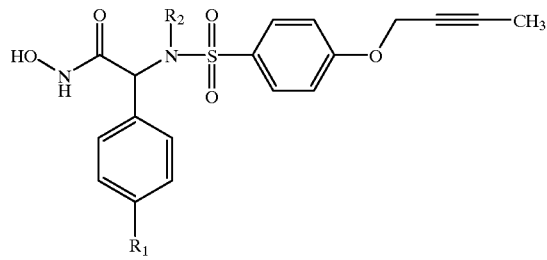

| Example # | R$_1$ | R$_2$ | MMP-1[a] | MMP-9[a] | MMP-13[a] | TACE[a] | THP[b] |
|---|---|---|---|---|---|---|---|
| 211 | H | Me | 496 | 43 | 20 | 8.0 | — |
| 176 | OH | H | ~10,000 | 898 | 103 | 4.0 | 89 |
| 178 | OMe | Me | 482 | 43 | 14 | 23 | 91 |
| 177 | OCH$_2$CCH | H | <10,000 | 310 | 57 | 4.8 | 64 |
| 180 | O(CH$_2$)$_2$NHBOC | Me | 599 | 34 | 9.3 | 265 | 89 |
| 199 | O(CH$_2$)$_2$NHBOC | H | ~10,000 | 862 | 139 | 42 | 84 |
| 201 | O(CH$_2$)$_2$NHAc | H | ~10,000 | 569 | 73 | 9.4 | 77 |
| 181 | O(CH$_2$)$_2$NH$_2$ | Me | 645 | 26 | 24 | 16 | 92 |
| 200 | O(CH$_2$)$_2$NH$_2$ | H | ~10,000 | 518 | 176 | 15 | 78 |
| 191 | O(CH$_2$)$_2$N(Me)BOC | Me | 1154 | 37 | 60 | 64 | 90 |
| 192 | O(CH$_2$)$_2$NHMe | Me | 927 | 11 | 27 | 26 | 95 |
| 203 | O(CH$_2$)$_2$N(Me)BOC | H | >10,000 | 859 | 126 | 49 | 73 |
| 204 | O(CH$_2$)$_2$NHMe | H | ~10,000 | 349 | 146 | 18 | 73 |
| 182 | O(CH$_2$)$_2$NMe$_2$ | Me | 487 | 22 | 15 | 16 | 92 |
| 207 | O(CH$_2$)$_2$NMe$_2$ | H | >10,000 | — | 112 | 53 | 51 |
| 208 | O(CH$_2$)$_2$-4-Thiazolyl-5-Me | H | >10,000 | — | 230 | 69 | 74 |
| 212 | Cl | Me | 798 | — | 36 | 62 | 86 |

[a]IC$_{50}$ (nM)
[b]% Inhibition @ 3 μM

TABLE 7

| Example # | R₁ | R₂ | MMP-1[a] | MMP-9[a] | MMP-13[a] | TACE[a] | THP[b] |
|---|---|---|---|---|---|---|---|
| 179 | O(CH$_2$)$_2$N[(CH$_2$)$_2$]$_2$O | Me | 546 | 29 | 11 | 52 | 97 |
| 206 | O(CH$_2$)$_2$N[(CH$_2$)$_2$]$_2$O | H | >10,000 | — | 147 | 33 | 70 |
| 185 | O(CH$_2$)$_2$N[(CH$_2$)$_2$]$_2$NBOC | Me | 839 | 53 | 27 | 309 | 89 |
| 186 | O(CH$_2$)$_2$N[(CH$_2$)$_2$]$_2$NH | Me | 568 | 32 | 21 | 31 | 93 |
| 183 | O(CH$_2$)$_2$NC$_4$H$_8$ | Me | 497 | 55 | 42 | 40 | 93 |
| 205 | O(CH$_2$)$_2$NC$_4$H$_8$ | H | ~10,000 | — | 146 | 24 | 66 |
| 188 | O(CH$_2$)$_3$NH$_2$ | Me | 469 | 48 | 41 | 25 | 94 |
| 187 | O(CH$_2$)$_3$NHBOC | Me | 910 | 46 | 13 | 199 | 91 |
| 184 | O(CH$_2$)$_2$NC(=O)C$_3$H$_6$ | Me | 434 | 55 | 11 | 35 | 94 |
| 189 | O-3-β-PyrolidineBOC | Me | 2437 | 297 | 120 | 231 | 92 |
| 190 | O-3-β-PyrolidineNH | Me | 527 | 37 | 29 | 32 | 94 |
| 194 | O(CH$_2$)$_3$NHAc | Me | 592 | — | 15 | 61 | 94 |
| 197 | O(CH$_2$)$_3$NHSO$_2$CH$_3$ | Me | 569 | — | 24 | 25 | 94 |
| 196 | O(CH$_2$)$_3$NHCO$_2$CH$_2$Ph | Me | 25% @ 1 | — | 31 | 109 | 87 |
| 193 | O(CH$_2$)$_3$NHCO$_2$Et | Me | ~1000 | — | 29.3 | 61 | 91 |
| 198 | O(CH$_2$)$_3$NHCONHPh | Me | 834 | — | 11 | 62 | 92 |
| 195 | O(CH$_2$)$_3$NHCO$_2$nBu | Me | >1,000 | — | 28 | 122 | 90 |
| 202 | O(CH$_2$)$_2$N[(CH$_2$)$_2$]$_2$NBOC | H | >10,000 | — | 345 | 113 | 45 |
| 209 | O(CH$_2$)$_2$O(CH$_2$)$_2$O(CH$_2$)$_2$OMe | H | ~10,000 | — | 132 | 39 | 75 |
| 210 | O(CH$_2$)$_2$O(CH$_2$)$_2$OMe | H | >10,000 | — | 278 | 17 | — |

[a]IC$_{50}$ (nM)
[b]% Inhibition @ 3 μM

TABLE 8

| Example # | R | MMP-1[a] | MMP-9[a] | MMP-13[a] | TACE[a] | THP[b] |
|---|---|---|---|---|---|---|
| 214 | H | 676 | 14 | 7.6 | 23 | 71 |
| 56 | Me | 3344 | 667 | 158 | 41 | 32 |
| 233 | CH$_2$Ph-4-Br | 2833 | 69 | 55 | 184 | 33 |
| 234 | CH$_2$-3-Py | 3197 | 108 | 49 | 28 | 25 |
| 224 | Ac | 357 | 88 | 22 | 13 | 81 |
| 225 | COEt | 1002 | 727 | 230 | 17 | 76 |
| 230 | COCH$_2$NH$_2$ | 8497 | 1225 | 410 | 127 | 27 |
| 229 | COCH$_2$NHBOC | 1009 | 322 | 85 | 64 | 85 |
| 226 | CO-2-Thienyl | 498 | 251 | 119 | 12 | 86 |
| 228 | COOCH$_3$ | 201 | 71 | 9.2 | 9.0 | 81 |
| 58 | BOC | 456 | 24 | 17 | 21 | 79 |
| 215 | CON[(CH$_2$)$_2$]$_2$O | 695 | 60 | 39 | 35 | 51 |
| 216 | CONEt$_2$ | 1752 | 221 | 97 | 28 | 59 |
| 218 | CON(iPr)$_2$ | 3291 | 822 | 213 | 49 | 56 |
| 217 | CONC$_4$H$_8$ | 1248 | 209 | 83 | 28 | 73 |
| 227 | SO$_2$CH$_3$ | 96 | 51 | 6.4 | 7.3 | 81 |
| 220 | CON(Me)Ph | 1640 | 561 | 62 | 20 | 60 |
| 231 | COCH[(CH$_2$O)$_2$CH(CH$_3$)$_2$] | 2448 | 1115 | 355 | 59 | 73 |
| 232 | COCH(CH$_2$OH)$_2$ | 1677 | 785 | 289 | 44 | 72 |
| 221 | CONHPh-4-OMe | 1511 | 576 | 182 | 69 | 58 |
| 222 | CONHPh-4-F | 941 | 173 | 75 | 30 | 61 |
| 219 | CO$_2$CH$_2$Ph | 176 | 45 | 10 | — | 87 |
| 223 | CONHPh-3,5-Cl | 1717 | 642 | 153 | 83 | 42 |

TABLE 8-continued

[Structure: piperazine with CONHOH, N-sulfonyl-phenyl-O-CH2-C≡C-CH3, and N-R]

| Example # | R | MMP-1[a] | MMP-9[a] | MMP-13[a] | TACE[a] | THP[b] |
|---|---|---|---|---|---|---|

[a]IC$_{50}$ (nM)
[b]% Inhibition @ 3 μM

TABLE 9

[Structure: thiomorpholine/morpholine ring with R2 substituents, CONHOH, N-sulfonyl-phenyl-O-R1]

| Example # | X | R$_1$ | R$_2$ | MMP-1[a] | MMP-9[a] | MMP-13[a] | TACE[a] | THP[b] |
|---|---|---|---|---|---|---|---|---|
| 240 | O | CH$_2$CCCH$_3$ | H | 162 | 170 | 28 | 4.5 | 80 |
| 239 | S | CH$_2$CCCH$_3$ | H | 148 | 21 | 12 | 2.9 | 84 |
| 258 | S | CH$_2$CCH | Me | 0.8 | — | 0.8 | 19 | 91 |
| 235, 38 | S | CH$_2$CCCH$_3$ | Me | 6.6 | 12 | 3.0 | 8.4 | 94 |
| 256 | S=O | CH$_2$CCCH$_3$ | Me | 43 | 145 | 48 | 25 | 92 |
| 255 | S=O | CH$_2$CCCH$_3$ | Me | 46 | 29 | 8.7 | 24 | 95 |
| 257 | SO$_2$ | CH$_2$CCCH$_3$ | Me | 24 | 64 | 23 | 24 | 91 |
| 259 | S | CH$_2$CCCH$_2$CH$_3$ | Me | 5.9 | — | 5.0 | 28 | 92 |
| 40 | S | CH$_2$CC(CH$_2$)$_3$CH$_3$ | Me | 29 | 7.8 | 6.6 | 23 | 82 |
| 236 | S | CH$_2$CCCH$_3$ | —(CH$_2$)$_4$— | 24 | — | 11 | 43 | 94 |
| 237 | S | CH$_2$CCCH$_3$ | —(CH$_2$)$_5$— | 62 | — | 12 | 212 | 90 |
| 241 | S | CH$_2$CCCH$_3$ | —(CH$_2$)$_2$NBn(CH$_2$)$_2$— | 3.1 | — | 0.5 | 786 | 94 |
| 238 | S | CH$_2$CCCH$_3$ | Et | 38 | — | 6.8 | 228 | 73 |
| 242 | S | CH$_2$CCCH$_3$ | —(CH$_2$)$_2$NMe(CH$_2$)$_2$— | — | — | — | 868 | 73 |

[a]IC$_{50}$ (nM)
[b]% Inhibition @ 3 μM

TABLE 10

[Structure: gem-dimethyl thiomorpholine with CONHOH, N-sulfonyl-phenyl-O-R1]

| Example # | R$_1$ | MMP-1[a] | MMP-9[a] | MMP-13[a] | TACE[a] | THP[b] |
|---|---|---|---|---|---|---|
| 254 | CH$_2$CCPh | 13 | — | 11 | 173 | 77 |
| 263 | CH$_2$CCCCH | 5.7 | — | 11 | 42 | 88 |
| 264 | CH$_2$CCCH$_2$F | 11 | — | 2.5 | 35 | 94 |
| 61 | CH$_2$CCCH$_2$OH | 24 | 70 | 13 | 40 | 89 |
| 260 | CH$_2$CCCH$_2$OH | 33 | — | 8.1 | 20 | 95 |
| 261 | CH$_2$CCCH$_2$OAc | 103 | — | 1.1 | 45 | 92 |
| 247 | CH$_2$CCCH$_2$OCH$_2$Ph | 53 | 108 | 2.5 | 160 | 57 |
| 265 | CH$_2$CCCH$_2$NH$_2$ | 97 | 8.7 | 7.5 | 67 | 40 |
| 266 | CH$_2$CCCH$_2$NHBOC | 26 | 31 | 4.0 | 74 | 79 |
| 267 | CH$_2$CCCH$_2$N(Me)BOC | 364 | 1265 | 37 | 112 | 15 |
| 244 | CH$_2$CC(CH$_2$)$_2$OH | 35 | 72 | 14 | 62 | 57 |
| 246 | CH$_2$CC(CH$_2$)$_2$NH$_2$ | 1052 | 41 | 27 | 138 | 4 |
| 245 | CH$_2$CC(CH$_2$)$_2$NHBOC | 300 | 2384 | 6.6 | 112 | 37 |
| 243 | CH$_2$CC(CH$_2$)$_2$OTHP | 194 | 178 | 4.1 | 87 | 52 |
| 248 | CH$_2$CC(CH$_2$)$_3$OTHP | 98 | 48 | 7.3 | 92 | 21 |

TABLE 10-continued

[Structure: thiomorpholine with gem-dimethyl, CONHOH, N-sulfonyl-phenyl-OR₁]

| Example # | R₁ | MMP-1[a] | MMP-9[a] | MMP-13[a] | TACE[a] | THP[b] |
|---|---|---|---|---|---|---|
| 249 | $CH_2CC(CH_2)_3OH$ | 159 | 377 | 86 | 40 | 51 |
| 251 | $CH_2CC(CH_2)_3NH_2$ | 226 | 28 | 8.7 | 28 | 22 |
| 250 | $CH_2CC(CH_2)_3NHBOC$ | 42 | 160 | 1.7 | 153 | 27 |
| 262 | $CH_2CCCCCH_2OH$ | 9.9 | — | 14 | 39 | 81 |
| 252 | $CH_2CC(CH_2)_4NHBOC$ | 87 | — | 4.3 | 199 | 70 |
| 253 | $CH_2CC(CH_2)_4NH_2$ | 92 | — | 7.3 | 40 | 37 |
| 268 | $CH_2CC(CH_2)_4OAc$ | 29 | — | 2.9 | 78 | 76 |
| 269 | $CH_2CC(CH_2)_4OH$ | 101 | — | 17 | 53 | 77 |

[a]$IC_{50}$ (nM)
[b]% Inhibition @ 3 μM

TABLE 11

[Structure: thiomorpholine with gem-dimethyl, CONHOH, N-sulfonyl-phenyl-O-CH₂-C≡C-CH₃, with R₁ and R₂ substituents]

| Example # | R₁ | R₂ | MMP-1[a] | MMP-9[a] | MMP-13[a] | TACE[a] | THP[b] |
|---|---|---|---|---|---|---|---|
| 272 | Me(cis) | H | 7.8 | 166 | 8.7 | 24 | 92 |
| 273 | β-$CH_2NHBOC$ | H | 16 | 61 | 9.2 | 87 | 90 |
| 274 | α-$CH_2NHBOC$ | H | 24 | 107 | 16 | 59 | 84 |
| 275 | β-$CH_2NH_2$ | H | 30 | 22 | 16 | 128 | 82 |
| 276 | α-$CH_2NH_2$ | H | 21 | 64 | 24 | 57 | 94 |
| 277 | α-$CH_2CO_2tBu$ | H | 7.8 | — | 7.6 | 234 | 69 |
| 278 | α-$CH_2CO_2H$ | H | 17 | — | 6.7 | 20 | 89 |
| 280 | α-$CH_2CONH_2$ | H | 35 | — | 29 | 42 | 91 |
| 281 | α-$CH_2CON(CH_3)_2$ | H | 50 | — | 23 | 130 | 76 |
| 282 | α-$CH_2CON[(CH_2)_2]_2O$ | H | 25 | — | 20 | 95 | 91 |
| 279 | α-$CH_2CONHOH$ | H | 21 | — | 4.5 | 46 | 87 |
| 271 | H | α-Me | 47 | — | 88 | 45 | 82 |
| 270 | H | β-Me | 32 | — | 61 | 86 | 62 |
| 379 | C | C | 316 | — | 271 | 16 | 85 |
| 283 | α-$CH_2CON[(CH_2)_2]_2NMe$ | H | 28 | — | 23 | 143 | 90 |
| 284 | α-$CH_2CONH(CH_2)_2NMe_2$ | H | 31 | — | 76 | 125 | 88 |

[a]$IC_{50}$ (nM)
[b]% Inhibition @ 3 μM

TABLE 12

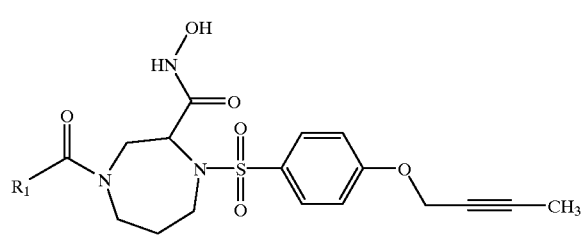

| Example # | R₁ | MMP-1[a] | MMP-9[a] | MMP-13[a] | TACE[a] | THP[b] |
|---|---|---|---|---|---|---|
| 49 | Ph | 362 | 75 | 65 | 17 | 32 |

[a]$IC_{50}$ (nM)
[b]% Inhibition @ 3 μM

TABLE 13
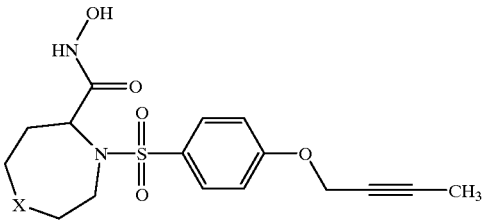
| Example # | X | MMP-1[a] | MMP-9[a] | MMP-13[a] | TACE[a] | THP[b] |
|---|---|---|---|---|---|---|
| 290 | NCH₂Ph | 287 | 25 | 7.5 | 83 | 45 |
| 292 | NH | 274 | — | 33 | 24 | 83 |
| 293 | NMe | 238 | — | 21 | 23 | 82 |
| 291 | NBOC | 92 | — | 5.4 | 74 | 75 |
| 289 | NCOPh | 113 | 12 | 4.0 | 10 | 93 |
| 294 | S | — | — | — | 13 | 87 |
[a]IC$_{50}$ (nM)
[b]% Inhibition @ 3 μM
TABLE 14
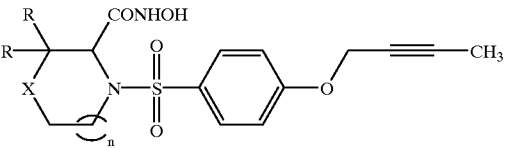
| Example # | X | n | R | MMP-1[a] | MMP-9[a] | MMP-13[a] | TACE[a] | THP[b] |
|---|---|---|---|---|---|---|---|---|
| 288 | S | 0 | Me | 3036 | 1794 | 852 | 20 | 73 |
| 173 | S | 2 | Me | 20 | — | 16 | 111 | 80 |
| 174 | S | 2 | H | 408 | — | 36 | 20 | 80 |
| 175 | SO₂ | 2 | H | 1027 | — | 50 | 28 | 83 |
[a]IC$_{50}$ (nM)
[b]% Inhibition @ 3 μM
TABLE 15
In Vitro Inhibition of TACE
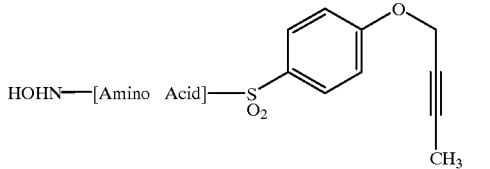
| Example | % Inhibition at 1 uM | IC 50 nM |
|---|---|---|
| 62B | 46.2 | |
| 63 | 47.6 | |
| 64 | 67.4 | 420 ± 50 |
| 65 | 102 | 398 ± 136 |
| 66 | 45.6 | |
| 67 | 46.2 | |
| 68 | 70.4 | 885 |
| 69 | 48.5 | |
| 70 | 21.1 | |
| 71 | 86.7 | 402 ± 55 |
| 72 | 57.4 | 550 |
| 73 | 79 | 451 ± 31 |
TABLE 15-continued
In Vitro Inhibition of TACE
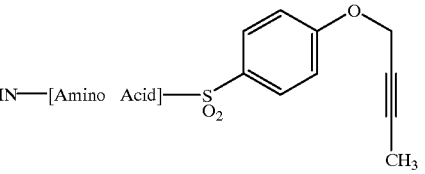
| Example | % Inhibition at 1 uM | IC 50 nM |
|---|---|---|
| 74 | 73.8 | 297 ± 119 |
| 75 | 55.8 | 387 |
| 76 | 29.7 | |
| 77 | 105 | 6.9 ± 3.3 |
| 78 | 101 | 11.8 ± 4.6 |
| 79 | 107 | 5.7 ± 2.5 |
| 80 | 105 | 10.8 ± 3.7 |
| 81 | 106 | 4.99 ± 1.1 |
| 82 | 98.4 | 7.1 |
| 83 | 105 | 45.1 ± 9.5 |
| 84 | 100.7 | 7.8 ± 0.4 |
| 85 | 102 | 8.3 ± 2.7 |
| 86 | 37.5 | |
| 87 | 47.8 | |
| 88 | 8.4 | |
| 89 | 56.8 | |
| 90 | 58.9 | 462 ± 58 |
| 91 | 95 | 328 ± 38 |
| 92 | 101.5 | 490 ± 139 |
| 93 | 61.7 | 546 |
| 94 | 38.2 | |
| 95 | 98.6 | 120 |
| 96 | 22 | |
| 97 | 67.5 | 283 ± 42 |
| 98 | 2.5 | |
| 99 | 28.5 | |
| 100 | 15.4 | |
| 101 | 30.2 | |
| 102 | 27.3 | |
| 103 | 52.8 | |
| 104 | 38.5 | |
| 295 | | 29.3 |
| 296 | | 10.9 |
| 297 | | 10.9 |
| 298 | 40 | |
| 299 | | 10.4 |
| 300 | | 11 |
| 301 | | 24.6 |
| 302 | 3 | |
| 303 | | 27.4 |
| 304 | | 28.9 |
| 305 | | 13.4 |
| 306 | | 8.7 |
| 307 | | 29.4 |
| 308 | | 29.5 |
| 309 | | 11.4 |
| 310 | | 27.9 |
| 311 | | 15.7 |
| 312 | | 4.7 |
| 313 | | 6.3 |
| 314 | | 25 |
| 315 | | 5.7 |
| 316 | | 4 |
| 317 | | 6.5 |
| 318 | | 11.9 |
| 319 | | 10.5 |
| 320 | | 7.4 |
| 321 | | 4.7 |
| 322 | | 11.8 |
| 323 | | 17.6 |
| 324 | | 14.7 |
| 325 | | 6.9 |
| 326 | | 58.6 |
| 327 | | 5.5 |
| 328 | | 6.26 |

TABLE 15-continued

In Vitro Inhibition of TACE

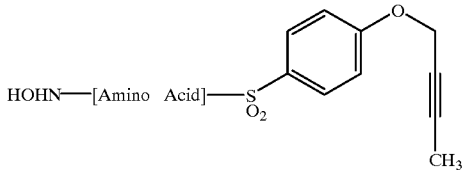

| Example | % Inhibition at 1 uM | IC 50 nM |
|---|---|---|
| 329 | | 6.88 |
| 330 | | 3.58 |
| 331 | | 5.32 |
| 332 | | 5.13 |
| 333 | | 4.21 |
| 334 | | 4.7 |
| 335 | | 6.5 |
| 336 | | 6.11 |
| 337 | | 4.2 |
| 338 | | 3.73 |
| 339 | | 4.6 |
| 340 | | 6.67 |
| 341 | | 4.88 |
| 342 | | 4.54 |
| 343 | | 3.54 |
| 344 | | 5.24 |
| 345 | | 4.43 |
| 346 | | 4.63 |
| 347 | | 3.15 |
| 348 | | 6.25 |
| 349 | | 9.41 |
| 350 | | 6.28 |
| 351 | | 9.57 |
| 352 | | 4.96 |
| 353 | | 6.1 |
| 354 | | 5.89 |
| 355 | | 12.38 |
| 356 | | 9.36 |
| 357 | | 14.13 |
| 358 | | 8.84 |
| 359 | | 9.28 |
| 360 | | 4.97 |
| 361 | | 6.32 |
| 362 | | 4.55 |
| 363 | | 3.39 |
| 364 | | 7.79 |
| 365 | | 14.63 |
| 366 | | 106 |
| 367 | | 38 |
| 368 | | 151 |
| 369 | | 14.2 |
| 370 | | 2.4 |
| 371 | | 377 |
| 372 | | 8.4 |
| 373 | | 16.9 |
| 374 | | 18.2 |
| 375 | | 24.6 |
| 376 | | 21.9 |
| 377 | | 26.5 |
| 378 | | 22.8 |

Based on the results obtained in the standard pharmacological test procedures described above, the compounds of this invention were shown to be inhibitors of the enzymes MMP-1, MMP-9, MMP-13 and TNF-a converting enzyme (TACE) and are therefore useful in the treatment of disorders such as arthritis, tumor metastasis, tissue ulceration, abnormal wound healing, periodontal disease, graft rejection, insulin resistance, bone disease and HIV infection.

The compounds of this invention are also useful in treating or inhibiting pathological changes mediated by matrix metalloproteinases such as atherosclerosis, atherosclerotic plaque formation, reduction of coronary thrombosis from atherosclerotic plaque rupture, restenosis, MMP-mediated osteopenias, inflammatory diseases of the central nervous system, skin aging, angiogenesis, tumor metastasis, tumor growth, osteoarthritis, rheumatoid arthritis, septic arthritis, corneal ulceration, proteinuria, aneurysmal aortic disease, degenerative cartilage loss following traumatic joint injury, demyelinating diseases of the nervous system, cirrhosis of the liver, glomerular disease of the kidney, premature rupture of fetal membranes, inflammatory bowel disease, age related macular degeneration, diabetic retinopathy, proliferative vitreoretinopathy, retinopathy of prematurity, ocular inflammation, keratoconus, Sjogren's syndrome, myopia, ocular tumors, ocular angiogenesis/neovascularization and corneal graft rejection.

Compounds of this invention may be administered neat or with a pharmaceutical carrier to a patient in need thereof. The pharmaceutical carrier may be solid or liquid.

Applicable solid carriers can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such a solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g., cellulose derivatives, preferable sodium carboxymethyl cellulose solution), alcohols (including monohydric alcohols and polyhydric alcohols, e.g., glycols) and their derivatives, and oils (e.g., fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

The compounds of this invention may be administered rectally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may also be administered transdermally through the use of a transdermal patch containing the active compound and a carrier that is inert to the active compound, is non-toxic to the skin, and allows delivery of the agent for systemic absorption into the blood stream via the skin. The carrier may take any number of forms such as creams and ointments, pastes, gels, and occlusive devices. The creams and ointments may be viscous liquid or semi-solid emulsions of either the oil in water or water in oil type. Pastes comprised of absorptive powders dispersed in petroleum or hydrophilic petroleum containing the active ingredient may also be suitable. A variety of occlusive devices may be used to release the active ingredient into the blood stream such as a semipermeable membrane covering a reservoir containing the active ingredient with or without a carrier, or a matrix containing the active ingredient. Other occlusive devices are known in the literature.

The dosage to be used in the treatment of a specific patient suffering a MMP or TACE dependent condition must be subjectively determined by the attending physician. The variables involved include the severity of the dysfunction, and the size, age, and response pattern of the patient. Treatment will generally be initiated with small dosages less than the optimum dose of the compound. Thereafter the dosage is increased until the optimum effect under the circumstances is reached. Precise dosages for oral, parenteral, nasal, or intrabronchial administration will be determined by the administering physician based on experience with the individual subject treated and standard medical principles.

Preferably the pharmaceutical composition is in unit dosage form, e.g., as tablets or capsules. In such form, the composition is sub-divided in unit dose containing appropriate quantities of the active ingredient; the unit dosage form can be packaged compositions, for example packed powders, vials, ampoules, prefilled syringes or sachets containing liquids. The unit dosage form can be, for example, a capsule or tablet itself, or it can be the appropriate number of any such compositions in package form.

What is claimed:

1. Compounds having the formula:

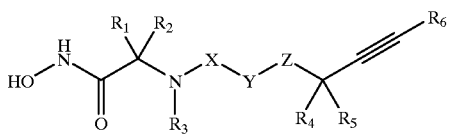

wherein:

X is $SO_2$ or $-P(O)-R_{10}$;

Y is aryl or heteroaryl, with the proviso that X and Z may not be bonded to adjacent atoms of Y;

Z is O, NH, CH, or S;

$R_2$ is hydrogen, aryl, aralkyl, heteroaryl, heteroaralkyl, cycloalkyl of 3–6 carbon atoms, piperidinyl, piperazinyl, morpholinyl, tetrahydropyranyl, tetrahydrofuranyl, pyrrolidinyl, alkyl of 1–6 carbon atoms, alkenyl of 2–6 carbon atoms, alkynyl of 2–6 carbon atoms;

$R_1$ and $R_3$, together with the atoms to which they are attached, may form a 6 membered ring wherein $R_1$ and $R_3$ represent divalent moieties of the formula:

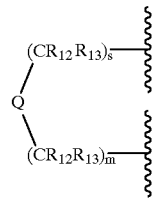

wherein Q is a carbon-carbon single or double bond, O, S, SO, $SO_2$, $-N-R_{11}$, or $-CONR_{14}$:

m=2–3 s is 0–2; provided that Q, s, and m, taken together represent 4 atoms;

$R_4$ and $R_5$ are each, independently, hydrogen or alkyl of 1–6 carbon atoms, $-CN$, or $-CCH$;

$R_6$ is hydrogen, aryl, heteroaryl, alkyl of 1–6 carbon atoms, alkenyl of 2–6 carbon atoms, alkynyl of 2–6 carbon atoms, cycloalkyl of 3–6 carbon atoms, piperidinyl piperazinyl, morpholinyl, tetrahydropyranyl, tetrahydrofuranyl, pyrolidinyl;

$R_8$ and $R_9$ are each, independently, hydrogen, alkyl of 1–6 carbon atoms, alkenyl of 2–6 carbon atoms, alkynyl of 2–6 carbon atoms, cycloalkyl of 3–6 carbon atoms, aryl, aralkyl, heteroaryl, heteroaralkyl, piperidinyl, piperazinyl, morpholinyl, tetrahydropyranyl, tetrahydrofuranyl, pyrrolidinyl;

$R_{10}$ is alkyl of 1–6 carbon atoms, cycloalkyl of 3–6 carbon atoms, aryl or heteroaryl;

$R_{11}$ is hydrogen, alkyl of 1–6 carbon atoms, cycloalkyl of 3–6 carbon atoms, aryl, heteroaryl, $-S(O)_nR_8$, $-COOR_8$, $-CONRR_8R_9$, $-SO_2 NR_8R_9$ or $-COR_8$;

$R_{12}$ and $R_{13}$ are independently selected from H, $-OR_8$, $-NR_8R_9$, alkyl of 1–6 carbon atoms, alkenyl of 2–6 carbon atoms, alkynyl of 2–6 carbon atoms, cycloalkyl of 3–6 carbon atoms, aryl, heteroaryl, $-COOR_8$; $-CONR_8R_9$; or $R_{12}$ and $R_{13}$ together form a $-C_3-C_6$-cycloalkyl of 3–6 carbon atoms or a $-C_5-C_8$-cycloheteroalkyl ring; or $R_{12}$ and $R_{13}$, together with the carbon to which they are attached, form a carbonyl group;

$R_{14}$ is hydrogen, aryl, heteroaryl, alkyl of 1–6 carbon atoms or cycloalkyl of 3–6 carbon atoms;

and n is 0–2;

or a pharmaceutically acceptable salt thereof.

2. A compound according to claim 1 wherein Y is a phenyl ring substituted at the 1- and 4-positions by X and Z, respectively, or a pharmaceutically acceptable salt thereof.

3. A compound according to claim 1 wherein Y is a phenyl ring substituted at the 1- and 4-positions by X and Z, respectively, and X is $SO_2$, or a pharmaceutically acceptable salt thereof.

4. A compound according to claim 1 wherein Y is a phenyl ring substituted at the 1- and 4-positions by X and Z, respectively, X is $SO_2$, and Z is oxygen, or a pharmaceutically acceptable salt thereof.

5. A compound according to claim 1 wherein Y is a phenyl ring substituted at the 1- and 4-positions by X and Z, respectively, X is SO$_2$, Z is oxygen and R$_4$ and R$_5$ are hydrogen, or a pharmaceutically acceptable salt thereof.

6. A compound according to claim 1 wherein Y is a phenyl ring substituted at the 1- and 4-positions by X and Z, respectively, X is SO$_2$, Z is oxygen, R$_4$ and R$_5$ are hydrogen, and R$_6$ is —CH$_2$OH or methyl, or a pharmaceutically acceptable salt thereof.

7. A compound according to claim 1 wherein R$_1$ and R$_3$, together with the atoms to which they are attached, form a piperazine, piperidine, tetrahydroisoquinoline, morpholine, thiomorpholine, or diazepine ring.

8. A compound according to claim 7 wherein Y is a phenyl ring substituted at the 1- and 4-positions by X and Z, respectively, X is SO$_2$, and Z is oxygen, or a pharmaceutically acceptable salt thereof.

9. A compound according to claim 8 wherein R$_2$ is hydrogen such that structure B has the absolute stereochemistry shown below:

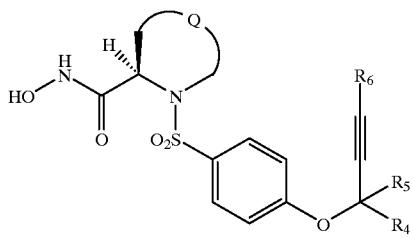

or a pharmaceutically acceptable salt thereof.

10. A method of inhibiting pathological changes mediated by TNF-α converting enzyme (TACE) in a mammal in need thereof which comprises administering to said mammal a therapeutically effective amount of a compound having the formula:

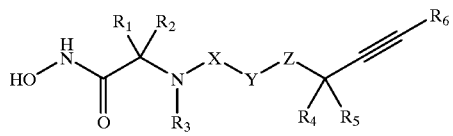

wherein:

X is SO$_2$ or —P(O)—R$_{10}$;

Y is aryl or heteroaryl, with the proviso that X and Z may not be bonded to adjacent atoms of Y;

Z is O, NH, CH$_2$ or S;

R$_2$ is hydrogen, aryl, aralkyl, heteroaryl, heteroaralkyl, cycloalkyl of 3–6 carbon atoms, piperidinyl, piperazinyl, morpholinyl, tetrahydropyranyl, tetrahydrofuranyl, pyrrolidinyl, alkyl of 1–6 carbon atoms, alkenyl of 2–6 carbon atoms, alkynyl of 2–6 carbon atoms;

R$_1$ and R$_3$, together with the atoms to which they are attached, may form a 6 membered ring wherein R$_1$ and R$_3$ represent divalent moieties of the formula:

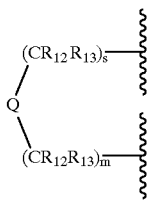

wherein Q is a carbon-carbon single or double bond, O, S, SO, SO2, —N—R$_{11}$, or —CONR$_{14}$;

m=2–3 s is 0-2; provided that Q, s, and m, taken together represent 4 atoms;

R$_4$ and R$_5$ are each, independently, hydrogen or alkyl of 1–6 carbon atoms, —CN, or —CCH;

R$_6$ is hydrogen, aryl, heteroaryl, alkyl of 1–6 carbon atoms, alkenyl of 2–6 carbon atoms, alkynyl of 2–6 carbon atoms, cycloalkyl of 3–6 carbon atoms, piperidinyl, piperazinyl, morpholinyl, tetrahydropyranyl, tetrahydrofuranyl, pyrrolidinyl;

R$_8$ and R$_9$ are each, independently, hydrogen, alkyl of 1–6 carbon atoms, alkenyl of 2–6 carbon atoms, alkynyl of 2–6 carbon atoms, cycloalkyl of 3–6 carbon atoms, aryl, aralkyl, heteroaryl, heteroaralkyl, piperidinyl, piperazinyl, morpholinyl, tetrahydropyranyl, tetrahydrofuranyl, pyrrolidinyl;

R$_{10}$ is alkyl of 1–6 carbon atoms, cycloalkyl of 3–6 carbon atoms, aryl or heteroaryl;

R$_{11}$ is hydrogen, alkyl of 1–6 carbon atoms, cycloalkyl of 3-6 carbon atoms, aryl, heteroaryl, —S(O)$_n$R, —COOR$_8$, —CONR$_8$R$_9$, —SO$_2$NR$_{R9}$ or —COR$_8$;

R$_{12}$ and R$_{13}$ are independently selected from H, —OR, —NR$_8$R$_9$, alkyl of 1–6 carbon atoms, alkenyl of 2–6 carbon atoms, alkynyl of 2–6 carbon atoms, cycloalkyl of 3–6 carbon atoms, aryl, heteroaryl, —COOR$_8$; —CONR$_8$R$_9$; or R$_{12}$ and R$_{13}$ together form a —C$_3$–C$_6$-cycloalkyl of 3–6 carbon atoms or a —C$_5$–C$_8$-cycloheteroalkyl ring; or R$_{12}$ and R$_{13,}$ together with the carbon to which they are attached, form a carbonyl group;

R$_{14}$ is hydrogen, aryl, heteroaryl, alkyl of 1–6 carbon atoms or cycloalkyl of 3–6 carbon atoms;

and n is 0–2;

or a pharmaceutically acceptable salt thereof.

11. The method according to claim 10 wherein the condition treated is rheumatoid arthritis, graft rejection, cachexia, inflammation, fever, insulin resistance, septic shock, congestive heart failure, inflammatory disease of the central nervous system, inflammatory bowel disease or HIV infection.

12. A pharmaceutical composition comprising a compound having the formula:

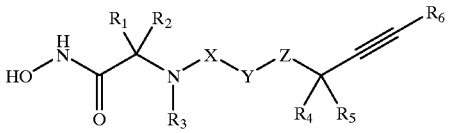

wherein:

X is SO$_2$ or —P(O)—R$_{10}$;

Y is aryl or heteroaryl, with the proviso that X and Z may not be bonded to adjacent atoms of Y;

Z is O, NH, $CH_2$ or S;

$R_2$ is hydrogen, aryl, aralkyl, heteroaryl, heteroaralkyl, cycloalkyl of 3–6 carbon atoms, piperidinyl, piperazinyl, morpholinyl, tetrahydropyranyl, tetrahydrofuranyl, pyrrolidinyl, alkyl of 1–6 carbon atoms, alkenyl of 2–6 carbon atoms, alkynyl of 2–6 carbon atoms;

$R_1$ and $R_3$, together with the atoms to which they are attached, may form a 6 membered ring wherein $R_1$ and $R_3$ represent divalent moieties of the formula:

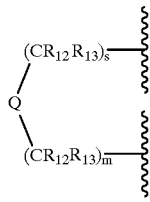

wherein Q is a carbon-carbon single or double bond, O, S, SO, SO2, —N—$R_{11}$, or —CON$R_{14}$;

m=2–3 s is 0–2; provided that Q, s, and m, taken together represent 4 atoms;

$R_4$ and $R_5$ are each, independently, hydrogen or alkyl of 1–6 carbon atoms, —CN, or —CCH;

$R_6$ is hydrogen, aryl, heteroaryl, alkyl of 1–6 carbon atoms, alkenyl of 2–6 carbon atoms, alkynyl of 2–6 carbon atoms, cycloalkyl of 3–6 carbon atoms, piperidinyl, piperazinyl, morpholinyl, tetrahydropyranyl, tetrahydrofuranyl, pyrrolidinyl;

$R_8$ and $R_9$ are each, independently, hydrogen, alkyl of 1–6 carbon atoms, alkenyl of 2–6 carbon atoms, alkynyl of 2–6 carbon atoms, cycloalkyl of 3–6 carbon atoms, aryl, aralkyl, heteroaryl, heteroaralkyl, piperidinyl, piperazinyl, morpholinyl, tetrahydropyranyl, tetrahydrofuranyl, pyrrolidinyl;

$R_{10}$ is alkyl of 1–6 carbon atoms, cycloalkyl of 3–6 carbon atoms, aryl or heteroaryl;

$R_{11}$ is hydrogen, alkyl of 1–6 carbon atoms, cycloalkyl of 3–6 carbon atoms, aryl, heteroaryl, —S(O)$_n$$R_8$, —COO$R_8$, —CON$R_8$$R_9$, —SO$_2$N$R_8$$R_9$ or —CO$R_8$;

$R_{12}$ and $R_{13}$ are independently selected from H, —O$R_8$, —N$R_8$$R_9$, alkyl of 1–6 carbon atoms, alkenyl of 2–6 carbon atoms, alkynyl of 2–6 carbon atoms, cycloalkyl of 3–6 carbon atoms, aryl, heteroaryl, —COO$R_8$; —CON$R_8$$R_9$; or $R_{12}$ and $R_{13}$ together form a —$C_3$–$C_6$-cycloalkyl of 3–6 carbon atoms or a —$C_5$–$C_8$-cycloheteroalkyl ring; or $R_{12}$ and $R_{13}$, together with the carbon to which they are attached, form a carbonyl group;

$R_{14}$ is hydrogen, aryl, heteroaryl, alkyl of 1–6 carbon atoms or cycloalkyl of 3–6 carbon atoms;

and n is 0–2;

or a pharmaceutically acceptable salt thereof.

13. A compound according to claim 1 which is selected from the group consisting of: 4-(4-But-2-ynyloxy-benzenesulfonyl)-2,2-dimethyl-thiomorpholine-3-carboxylic acid hydroxyamide;

4-(4-Hept-2-ynyloxy-benzenesulfonyl)-2,2-dimethyl-thiomorpholine-3-carboxylic acid hydroxyamide;

1-(4-But-2-ynyloxy-benzenesulfonyl)-4-methyl-piperazine-2-carboxylic acid hydroxyamide hydrochloride;

4-[4-(4-Hydroxy-but-2-ynyloxy)-benzenesulfonyl]-2,2-dimethyl-thiomorpholine-3-carboxylic acid hydroxyamide;

4-(4-But-2-ynyloxy-benzenesulfonyl)-3-hydroxycarbamoyl-piperazine-1-carboxylic acid tert-butyl ester;

1-(4-But-2-ynyloxy-benzenesulfonyl)-piperazine-2-carboxylic acid hydroxyamide;

1-(4-But-2-ynyloxy-benzenesulfonyl)-4-(morpholine-4-carbonyl)-piperazine-2-carboxylic acid hydroxyamide;

4-(4-But-2-ynyloxy-benzenesulfonyl)-piperazine-1,3-dicarboxylic acid 1-diethylamide 3-hydroxyamide;

1-(4-But-2-ynyloxy-benzenesulfonyl)-4-(pyrrolidine-1-carbonyl)-piperazine-2-carboxylic acid hydroxyamide;

4-(4-But-2-ynyloxy-benzenesulfonyl)-piperazine-1,3-dicarboxylic acid 1-diisopropylamide 3-hydroxyamide;

Benzyl 4-{[4-(2-butynyloxy)phenyl]sulfonyl )-3-[(hydroxyamino)carbonyl]-1-piperazinecarboxylate;

4-(4-But-2-ynyloxy-benzenesulfonyl)-piperazine-1,3-dicarboxylic acid 3-hydroxyamide 1-(methyl-phenyl-amide);

4-{[4-(2-Butynyloxy)phenyl]sulfonyl}-N-3-hydroxy-N-1-(4-methoxyphenyl)-1,3-piperazinedicarboxamide;

4-{[4-(2-Butynyloxy)phenyl]sulfonyl}-N-1-(4-fluorophenyl)-N-3-hydroxy- 1,3-piperazinedicarboxamide;

4-{[4-(2-Butynyloxy)phenyl]sulfonyl }-N- 1-(3,5-dichlorophenyl)-N-3-hydroxy- 1,3-piperazinedicarboxamide;

4-Acetyl-1-(4-but-2-ynyloxy-benzenesulfonyl)-piperazine-2-carboxylic acid hydroxyamide;

1-(4-But-2-ynyloxy-benzenesulfonyl)-4-propionyl-piperazine-2-carboxylic acid hydroxyamide;

1-(4-But-2-ynyloxy-benzenesulfonyl)-4-(thiophene-2-carbonyl)-piperazine-2-carboxylic acid hydroxyamide;

1-(4-But-2-ynyloxy-benzenesulfonyl)-4-methanesulfonyl-piperazine-2-carboxylic acid hydroxyamide;

4-(4-But-2-ynyloxy-benzenesulfonyl)-3-hydroxycarbamoyl-piperazine- 1-carboxylic acid methyl ester;

{-2-[4-(4-But-2-ynyloxy-benzenesulfonyl)-3-hydroxycarbamoyl-piperazin-1-yl]-2-oxo-ethyl}-carbamic acid tert-butyl ester;

4-Aminoacetyl-1-(4-but-2-ynyloxy-benzenesulfonyl)-piperazine-2-carboxylic acid hydroxyamide;

1-{[4-(2-Butynyloxy)phenylsulfonyl}-N-hydroxy-4-[(2,2,5-trimethyl- 1,3-dioxan-5-yl)carbonyl]-2-piperazinecarboxamide;

1-{[4-(2-Butynyloxy)phenyl]sulfonyl}-N-hydroxy-4-[3-hydroxy-2-(hydroxymethyl)-2-methylpropanoyl-2-piperazinecarboxamide;

4-(4-Bromo-benzyl)-1-(4-but-2-ynyloxy-benzenesulfonyl)-piperazine-2-carboxylic acid hydroxyamide;

1-(4-But-2-ynyloxy-benzenesulfonyl)-4-pyridin-3-ylmethyl-piperazine-2-carboxylic acid hydroxyamide;

(3S)4-({[4-(2-Butynyloxy)phenyl]sulfonyl)2,2-dimethyl-thiomorpholine-3-carboxylic acid hydroxyamide;

9-({[4-(2-Butynyloxy)phenyl]sulfonyl )-N-hydroxy-6-thia-9-azaspiro[4,5-]decane-10-carboxamide;

9-({[4-(2-Butynyloxy)phenyl]sulfonyl)-N-hydroxy-1-thia-4 azaspiro[5,5]undecane-5-carboxamide;

4-({[4(2-Butynyloxy)phenyl]sulfonyl)2,2-diethyl-thiomorpholine-3-carboxylic acid hydroxyamide;

4-({[4-(2-Butynyloxy)phenyl]sulfonyl)-N-hydroxy-thiomorpholine-3-carboxamide; 4-([4(2-Butynyloxy)phenyl]sulfonyl}-N-hydroxy-3-morpholinecarboxamide;

9-Benzyl-4-{[4-(2-butynyloxy)phenyl]sulfonyl}-N-hydroxy-1-thia-4,9-diazaspiro[5.5]undecane-5-carboxamide;

9-Methyl-4-{[4-(2-butynyloxy)phenyl]sulfonyl}-N-hydroxy-1-thia-4,9-diazaspiro[5.5 ]undecane-5-carboxamide;

N-Hydroxy-2,2-dimethyl-4-[(4-{[5-(tetrahydro-2H-pyran-2-yloxy)-2-pentynyl]oxy)phenyl)sulfonyl]-3-thiomorpholine carboxamide;

N-Hydroxy-4-({4-[(5-hydroxy-2-pentynyl)oxy]phenyl}sulfonyl)-2,2-dimethyl-3-thiomorpholine carboxamide;

tert-Butyl 5-[4-({3-[(hydroxyamino)carbonyl]-2,2-dimethyl-4-thiomorpholinyl}-sulfonyl)phenoxyl-3-pentynylcarbamate;

4-((4-[(5-Amino-2-pentynyl)oxy]phenyl]sulfonyl)-N-hydroxy-2,2-dimethyl-3-thiomorpholine carboxamide;

4-[(4-{[4-(Benzyloxy)-2-butynyloxy)phenyl)sulfonyl]-N-hydroxy-2,2-dimethyl-3- thiomorpholine carboxamide;

N-Hydroxy-2,2-dimethyl-4-[(4-{[6-(tetrahydro-2H-pyran-2-yloxy)-2-hexynyl]oxy}phenyl)sulfonyl]-3-thiomorpholine carboxamide;

N-Hydroxy-4-({4-[(6-hydroxy-2-hexynyl)oxy]phenyl}sulfonyl)-2,2-dimethyl-3-thiomorpholine carboxamide;

tert-Butyl 6-[4-({(3S)-3-[(hydroxyamino)carbonyl]-2,2-dimethylthiomorpholinyl)sulfonyl)phenoxy]-4-hexynylcarbamate;

(3S)-4-({4-[(6 Amino-2-hexynyl)oxy]phenyl ) sulfonyl)-N-hydroxy-2,2-dimethyl-3- thiomorpholine carboxamide;

tert-Butyl 7-[4-({(3S)-3-[(hydroxyammo)carbonyl-2,2-dimethylthiomorpholinyl}sulfonyl)phenoxy]-5-heptynylcarbamate;

(3S)-4-(4-[(7-Amino-2-heptynyl)oxy]phenyl}sulfonyl)-N-hydroxy-2,2-dimethyl-3-thiomorpholine carboxamide;

(3S)-N-Hydroxy-2,2-dimethyl-4-({4-[(3-phenyl-2-propynyl)oxy]-phenyl}sulfonyl)-3-thiomorpholine carboxamide;

(3S)-4-{[4-(2-Butynyloxy)phenyl]sulfonyl}-N-hydroxy-2,2-dimethyl-3-thiomorpholine carboxamide (1S)-oxide;

(3S)-4-{[4-(2-Butynyloxy)phenyl]sulfonyl}-N-hydroxy-2,2-dimethyl-3-thiomorpholine carboxamide (1R)-oxide;

(3S)-4-{ [4-(2-Butynyloxy)phenyl]sulfonyl}-N-hydroxy-2,2-dimethyl-3-thiomorpholine carboxamide 1,1-dioxide;

(3S)-N-Hydroxy-2,2-dimethyl-4-{[4-(2-propynyloxy)phenyl]sulfonyl}-3-thiomorpholine carboxamide;

(3S)-N-Hydroxy-2,2-dimethyl-4-{[(2-pentynyloxy)phenyl]sulfonyl}-3-thiomorpholine carboxamide;

(3S)-N-Hydroxy-4-({[4-(4-hydroxy-2-butynyl)oxy]phenyl}sulfonyl)-2,2-dimethyl-3-thiomorpholine carboxamide;

4-[4-({(3S)-3-[(Hydroxyamino)carbonyl]-2,2-dimethylthiomorpholinyl}-sulfonyl)phenoxy]-2-butynyl acetate;

(3S)-N-Hydroxy-({4-[(6-hydroxy-2,4-hexadiynyl)oxy]phenyl)sulfonyl)-2,2-dimethyl-3-thiomorpholine carboxamide;

(3S)-N-Hydroxy-2,2-dimethyl-4-{[4-(2,4-pentadiynyloxy)phenyl]sulfonyl}-3-thiomorpholine carboxamide;

(3S)-4-(({4-[(4-Fluoro-2-butynyl)oxy]phenyl}sulfonyl)-N-hydroxy-2,2-dimethyl-3-thiomorpholine carboxamide;

4-({4-[(4-Amino-2-butynyl)oxy]phenyl)sulfonyl)-N-hydroxy-2,2-dimethyl-3-thiomorpholine carboxamide;

tert-Butyl-4-[4-({3-[(hydroxyamino)carbonyl]-2,2-dimethyl-4-thiomorpholinyl}sulfonyl)phenoxyl-2-butynylcarbamate;

tert-Butyl 4-[4-({3-[(hydroxyamino)carbonyl]-2,2-dimethyl-4 thiomorpholinyl}sulfonyl)phenoxy]-2-butynyl(methyl)carbamate;

7-[4-({(3S)-3-[(Hydroxyamino)carbonyl]-2,2-dimethylthiomorpholinyl]-sulfonyl)phenoxy]-5-heptynyl acetate;

(3S)-N-Hydroxy-4-({4-[(7-hydroxy-2-heptynyl)oxy]phenyl}sulfonyl-2,2-dimethyl-3- thiomorpholinecarboxamide;

(3S,5S)-4-([4-(2-Butynyloxy)phenyl]sulfonyl}-N-hydroxy-2,2,5-trimethyl-3-thiomorpholinecarboxamide;

(3S,5 R)-4-{[4-(2-Butynyloxy)phenyl]sulfonyl3-N-hydroxy-2,2,5-trimethyl-3-thiomorpholinecarboxamide;

(3S,6S)-4-{[4(2-Butynyloxy)phenyl]sulfonyl}-N-hydroxy-2,2,6-trimethyl-3-thiomorphominecarboxanide;

tert-Butyl{-(2R,5S)-4-{[4-(2-butynyloxy)phenyl]sulfonyl}-5-[(hydroxyamino)carbonyl]-6,6-dimethylthiomorpholinyl}methylcarbamate;

tert-Butyl{-(2S,5S)-4-{[4-(2-butynyloxy)phenyl]sulfonyl}-5-[(hydroxyamino)carbonyl]-6,6-dimethylthiomorpholinyl}methylcarbamate;

(3S,6R)-Trans-6-(aminomethyl)-4-{[4-(2-butynyloxy)phenyl]sulfonyl}-N-hydroxy-2,2-dimethyl-3-thiomorpholinecarboxamide hydrochloride;

(3S,6S)-Cis-6-(aminomethyl)-4-{ [4-(2-butynyloxy)phenyl]sulfonyl}-N-hydroxy-2,2-dimethyl-3-thiomorphohinecarboxamide hydrochloride;

tert-Butyl{(2S,5S)4-{[4-(2-butynyloxy)phenyl]sulfonyl}-5-[(hydroxyamino)carbonyl]-6,6-dimethylthiomorpholinyl} acetate;

{(2S,5S)-4-{[4(2-Butynyloxy)phenyl]sulfonyl)-5-[(hydroxyamino)carbonyl]-6,6-dimethylthiomorpholinyl acetic acid;

(3S,6S)-4-{([4(2-Butynyloxy)phenyl]sulfonyl)-N-hydroxy-6-[2-(hydroxyamino)-2-oxoethyl]-2,2-dimethyl-3-thiomorpholinecarboxamide;

(3S,6S)-6-(2-Amino-2-oxoethyl)-4-{[4-(2-butynyloxy)phenyl]sulfonyl}-N-hydroxy-2,2-dimethyl-3-thiomorpholinecarboxamide;

(3S,6S)-4-{[4(2-Butynyloxy)phenyl]sulfonyl}-6-[2-(dimethylamino)-2-oxoethyl]-N-hydroxy-2,2-dimethyl-3-thiomorpholinecarboxamide;

(3S,6S)-4-{[4-(2-Butynyloxy)phenylsulfonyl}-N-hydroxy-2,2-dimethyl-6-[2-(4-morpholinyl)-2-oxoethyl]-3-thiomorpholinecarboxamide;

(3S,6S)-4-{[(2-Butynyloxy)phenyl]sulfonyl}-N-hydroxy-2,2-dimethyl-6-[2-(4-methyl-1-piperazinyl)-2-oxoethyl]-3-thiomorpholinecarboxamide hydrochloride;

(3S,6S)-4-{(4-(2-Butynyloxy)phenyl]sulfonyl}-6-(2-{[2-(dimethylamino)ethyl]-amino)-2-oxoethyl)-N-hydroxy-2,2-dimethyl-3-thiomorpholinecarboxamide;

or a pharmaceutical salt thereof.

* * * * *